US008420389B2
US 8,420,389 B2

(12) United States Patent
Audonnet

(10) Patent No.: US 8,420,389 B2
(45) Date of Patent: Apr. 16, 2013

(54) NIPAH VIRUS VACCINES

(75) Inventor: Jean Christophe Francis Audonnet, Lyons (FR)

(73) Assignee: Merial Limited, Duluth, GA (US)

(*) Notice: Subject to any disclaimer, the term of this patent is extended or adjusted under 35 U.S.C. 154(b) by 269 days.

(21) Appl. No.: 12/839,556

(22) Filed: Jul. 20, 2010

(65) Prior Publication Data

US 2010/0278862 A1 Nov. 4, 2010

Related U.S. Application Data

(63) Continuation of application No. 11/404,534, filed on Apr. 14, 2006, now Pat. No. 7,803,612.

(60) Provisional application No. 60/674,583, filed on Apr. 25, 2005.

(51) Int. Cl.
*C12N 15/33* (2006.01)
*C07H 21/04* (2006.01)

(52) U.S. Cl.
USPC .................................. 435/320.1; 536/23.72

(58) Field of Classification Search .................... None
See application file for complete search history.

(56) References Cited

U.S. PATENT DOCUMENTS 5,766,598 A 6/1998 Paoletti
5,843,456 A 12/1998 Paoletti

OTHER PUBLICATIONS

Genbank entry for AF238467, Jun. 2000, 2 pages.*
Tamin, A. et al., "Function properties of the fusion and attachment glycoprotiens of Nipah Virus", Virology 2002, vol. 296: pp. 190-200.
Guillaume V. et al., "Nipah virus: vaccination and passive protection studies in a hamster model", J. Virol. 2004, 78 (2):834-40.
Paoletti E., et al., "Highly attenuated poxvirus vectors" NYVAC, ALVAC and TROVAC, Dev. Biol. Stand., 1995, 84: 159-63.
Weingartl HM., et al., "Recombinant Nipah virus vaccines protect pigs against challenge", J. Virol. 2006, 80(16): 7929-38.
GenBank entry for accession No. AF238466, Jun. 2000.
Harcourt, B., et al., "Molecular characterization of Nipah virus, a newly emergent paramyxovirus", Virology, 2000, 271: 334-349.
Harcourt, B, et al., "Molecular characterization of the polymerase gene and genomic termini of Nipah virus", 2001, Virology, 287: 192-201.

* cited by examiner

*Primary Examiner* — Michael Burkhart
(74) *Attorney, Agent, or Firm* — Judy Jarecki-Black; Ruoying Chen; Merial Limited

(57) ABSTRACT

The present invention relates to recombinant anti-Nipah virus vaccines and the administration of such vaccines to animals, advantageously pigs. Advantageously, the anti-Nipah virus vaccine may comprise a recombinant avipox virus containing a Nipah virus glycoprotein gene. The invention encompasses methods of vaccinating animals, advantageously pigs, by administration of anti-Nipah virus vaccines that may comprise a recombinant avipox virus that may contain a Nipah virus glycoprotein gene.

6 Claims, 39 Drawing Sheets

Nipah virus, complete genome:
```
   1 accaaacaag ggagaatatg gatacgttaa aatatataac gtattttaa aacttaggaa
  61 ccaagacaaa cacttttggt cttggtattg gatcctcaag aaatatatca tcatgagtga
 121 tatctttgaa gaggcggcta gttttaggag ttatcaatct aagttaggga gagatgggag
 181 ggctagtgca gcaactgcta ctttgacaac caagataagg atatttgtac cagctactaa
 241 tagtccagag ctcagatggg aactaacatt gtttgcactt gatgtgatta gatctccgag
 301 tgctgccgag tcaatgaaag ttggagctgc tttcacactc atctctatgt attcagagag
 361 acccggggct ctcattagaa gtctcctcaa tgacccagac attgaagctg taataataga
 421 tgttggatca atggtcaacg gaataccagt aatggagagg agaggagaca aggctcagga
 481 ggagatggaa ggcttgatga gaatcctcaa aactgctcga gacagcagca agggaaaaac
 541 accttttgtt gacagccgag cttacggcct acggataaca gacatgagca cctggtctc
 601 tgcagttatc accatcgagg cccagatctg gatactgatc gctaaagcag ttacagctcc
 661 cgacactgcc gaggaaagtg aaactagaag atgggctaaa tacgtccaac aaaagagagt
 721 caatccgttc tttgctctaa ctcaacaatg gctaacagaa atgaggaatc tgctctccca
 781 gagtctatca gtaaggaagt tcatggttga gatcctcata gaagtcaaga aggaggatc
 841 tgctaaaggc agagcagtag aaataatctc agacatcgga aactatgtcg aggaaactgg
 901 tatggcagga ttcttcgcaa ccatcagatt cgggttggag acaaggtatc cagcacttgc
 961 actcaacgaa ttccagagtg acctcaacac catcaaaagc ttgatgctac tctacagaga
1021 aattggccca agagcccctt atatggtgct tcttgaagaa tcaattcaga ctaaatttgc
1081 ccctggaggt tacccattat tgtggagctt gccatgggt gtggctacta ctattgacag
1141 gtctatgggg gcattgaata tcaatcgtgg ttatcttgag cctatgtatt tcagactagg
1201 ccaaaaatca gcacgtcacc atgctggagg aattgatcag aacatggcaa atagactggg
1261 actaagttca gatcaagttg cagaactcgc tgctgcagtt caggaaacat cagcaggaag
1321 gcaagagagt aatgttcagg ctagagaggc aaaatttgct gcaggaggtg tgctcattgg
1381 aggcagtgat caagatatcg atgaagggga agaacctata gaacagagtg gcagacagtc
1441 agttaccttc aaaagggaga tgagtatttc atcccttgct aacagtgtgc cgagcagttc
1501 tgtgagcaca tccggtggga ccagattgac taattcatta ctaaacctca gatcaagact
1561 ggctgcaaaa gcagcaaaag aagccgcctc atccaatgca acagatgatc cagcaatcag
1621 caacagaact caaggggaat cagagaagaa gaataatcaa gacctcaaac ctgctcaaaa
1681 tgaccttgat ttcgtcagag ctgatgtgtg acgtctattt ccaatattct acagtatcca
1741 aaaatctttc tatagtacac tatcataata cgacactaag ggatcaacca tatcaaagtt
1801 acgaatcgtt ttaattatat taatcaaatg atactctttt atgggcaaac cgaagaacca
1861 atgtctacat gtaaattgag ctttggtatt gcaatctaat acttgctcaa aatcttgaac
1921 tattagtgta atttctatca tcatagagtt atcaagattt tattatataa gttggtgcag
1981 atctttggac atgaattaca cactacactc taatgaagac aaaatttaca ttacatattt
2041 aaggactatt tcctatcctt tcaatggtac ttggttatga aggtttctta atttaactaa
2101 gctactgtct ttgcactgga atatacaata cctcttacct catttcttac tttaatatca
2161 tgttatttt ttgataagtc acttaacttg accaaggtct accaggtaat gctcgcacaa
2221 gtgaactgca atctcaactt agattaaaca taatcatgca aaatcactat tttgtactac
2281 taactcatta agaaaaactt aggatccaag agatttactc taggatctcc tattaagctt
2341 agcagtcatt agttgagagt tcaacttgca aaactctaac cttcactcta ataacaattc
2401 atccaatgga taaattggaa ctagtcaatg atggcctcaa tattattgac tttattcaga
2461 agaaccaaaa agaaatacag aagacatacg gacgatcaag tattcaacaa cccagcatca
2521 aagatcaaac aaaagcctgg gaagattttc tgcagtgcac cagtggagaa tctgaacaag
2581 ttgagggggg aatgtctaag gatgatgagt atgttgaaag aagaaacttg gaggatctat
2641 ccagtacttc tcccacagat ggaactattg aaagagagt gtcgaacacc cgtgactggg
2701 cagaaggttc agatgacata caactggacc cagtggttac agacttgta taccatgatc
2761 atgggggaga atgtaccgga tatggattta cttcaagccc tgagagaggg tggagtgatt
2821 acacatcagg agcaaacaat gggaatgtat gtcttgtatc tgatgcaaag atgctgtcct
2881 atgctcccga aattgcagtt tctaaagaag atcgggaaac tgatctagtt catcttgaga
2941 ataaactatc tactacagga ctgaatccca gcagtacc gttcactctg agaaacctgt
3001 ctgatcctgc aaaagactct cctgtgattg ctgaacacta ctacggacta ggagttaaag
3061 agcaaaacgt tggccctcag actagcagaa atgtcaattt ggacagcatc aaattgtaca
3121 catcagatga cgaagaggca gatcagcttg aattcgaaga tgagtttgca ggaagctcaa
```

FIG. 1A

```
3181 gtgaagtgat agtcggcatt tctcctgaag atgaagagcc ttcaagtgtt ggcggaaaac
3241 ccaatgaatc cattggacgt acaatcgaag gccaatcaat ccgagacaac cttcaagcca
3301 aggacaacaa atcaacagat gtaccaggag caggaccgaa agattcagca gtgaaggaag
3361 aaccacccca gaagaggcta cctatgttag ctgaagaatt tgagtgctct ggatcggaag
3421 acccaatcat tcgggagctg ctgaaggaga actcactcat aaattgtcag caagggaaag
3481 atgctcagcc tccatatcat tggagcatcg agaggtcaat aagcccggat aaaactgaga
3541 tcgtcaacgg tgctgtgcaa actgctgaca ggcaaagacc aggaactccg atgccaaagt
3601 cccgaggtat tccattaaaa aagggcacag acgcgaaata tccatctgct gggacggaaa
3661 acgtgcctgg gtcgaagagt ggtgcaaccc ggcatgttcg aggatcaccc ccctaccaag
3721 aaggcaagag tgtcaatgcg gagaatgtcc aactgaatgc ttccactgcg gttaaggaaa
3781 ctgataagtc agaagtaaac cccgtagacg acaacgactc acttgatgat aaatacatca
3841 tgccttcaga tgatttctca aacactttct tcccgcacga cactgatcgc ttgaattatc
3901 acgcagatca tttaggtgat tatgaccttg aaaccctgtg tgaagagtcg gttctaatgg
3961 gagtgatcaa ctctataaaa ttaattaatc tggatatgcg cttaaatcac attgaagaac
4021 aagttaaaga gatcccaaag atcatcaata agcttgagtc cattgacaga gttctggcca
4081 agactaacac cgcactctca accattgaag gacacctggt ttccatgatg ataatgatac
4141 cagggaaagg gaaaggagaa agaaagggga aaaataatcc tgagcttaaa ccagtgatag
4201 gaagagacat tctagagcag caatctcttt tttcttttga caatgtcaag aatttcagag
4261 atggatcgtt gacaaacgaa ccgtatgggg cagctgtaca gttgagagaa gatcttattc
4321 ttcctgaact taattttgag gagacaaatg catctcaatt tgttcctatg cagatgatt
4381 catccagaga tgttatcaag acattgataa ggactcacat taaagataga gagttgagat
4441 cagaactgat tggttacctg aataaagcgg aaaatgatga ggaaattcag gagatagcga
4501 acactgtcaa tgacatcatt gacggtaata tttgatcact gaattgtcag cagaaataca
4561 atgatctaac aacaatctcc cacaagtaga caatggtttc aggtcaataa taacaacctc
4621 aatactaatc tttcacataa gcattactca ttccagccct cagacgataa cacaatactt
4681 gatacatgtt tattgaagtg tatgtagcat gattgaacta ttcaataact gtatttctca
4741 ctcttgctct tagttagtca ttgtgtctaa taattattat tacagtacaa ggtattatga
4801 attcaaagat acgcaataaa tctgatatca gcatagagta gaaaattgtt gtttttgtca
4861 tgatcattcg aagatttaac aatgatgtca actttcatac ctaaacataa taacataaaa
4921 tggtcgattt gtattgtaga tctctcacgc attttagtgt catgaattag tgtttcaaat
4981 cagttgcata tcaattaaga aaaacttagg agacaggtat agaacctctc tttcagataa
5041 ctggtcaatt aaggacagaa attctgtttc tcaaatccgc tagcctttgt caaagaggac
5101 acaagcaatg gagccggaca tcaagagtat ttcaagtgag tcaatggaag gagtatctga
5161 tttcagccct agttcttggg agcatggtgg gtatcttgat aaggttgaac cagaaattga
5221 tgaaaatggc agtatgattc caaaatacaa gatctatacc ccaggagcta acgagaggaa
5281 atacaacaac tacatgtacc ttatatgtta cggctttgtt gaagatgttg agagaacccc
5341 agagacaggg aaacgcaaga agatcaggac aattgctgcc taccctctgg gtgttggtaa
5401 gagtgcctct catcccaag atcttctgga ggaactctgt tccctcaaag ttactgtgag
5461 aagaacagct ggatcaactg agaaaattgt gtttggatca tctggccctc taaatcacct
5521 cgttccgtgg aagaaagtac tgactagtgg ttcaattttt aatgcagtca aggtttgtcg
5581 gaacgttgat cagatacagc ttgacaagca tcaagctctg agaatatttt ttctcagtat
5641 cacaaagctc aatgattctg aatctacat gattccacga accatgcttg agttcaggag
5701 aaacaatgcc attgccttca atcttctagt gtacttgaag attgatgctg atttatccaa
5761 aatggggatc cagggaagcc tcgataaaga tggcttcaag gttgcctcct tcatgctaca
5821 cttggggaac tttgtccgtc gtgcaggaa gtattactct gttgattatt gtaggaggaa
5881 gattgatagg atgaaattgc agttttcact gggttccata gcggactaa gtctccacat
5941 taagatcaat ggtgtaatca gcaaacggct gtttgctcaa atgggattcc aaaaaaacct
6001 ttgtttctct tgatggaca tcaatccttg gctcaacaga ttgacctgga caacagttg
6061 tgagatcagc cgagtagcag ctgtgttgca gccttctatt ccaagagagt tcatgatcta
6121 tgatgatgtc ttcattgaca atacagggag aattctaaag ggctaaacag aattcttcta
6181 aaatttaatc agtcatgagt ttagtaatca tacctagtca taatacatca cacaggacta
6241 tttacaaaag acagttaaaa aatggaataa tcatgtagta gtaattgaga acattattag
6301 aatagtataa ctaaatgta gtttttttga gtatttgatt taaaattaga taactattac
6361 aaaaaactta ggagccaagc tcttgcctcg ttcagaaggt taaacaagca ttcttaccat
```

FIG. 1A (Continued)

```
6_1  tggatcaaca aaaggattgg ttttatcgtc taagaaattt attgaaaggc aagaaattc
6481 ctggttttat gttgaatgag gtgtatcaaa ctaaggagac cttctaacag ccaggtcata
6541 ggaatataaa taaaaataag aataaaattg attccatcgg aagattcatt tcaagaagtg
6601 atcaaatcaa agcggttggc agacctacca atcatatacc acaagactcg acaatggtag
6661 ttatacttga caagagatgt tattgtaatc ttttaatatt gattttgatg atctcggagt
6721 gtagtgttgg gattctacat tatgagaaat tgagtaaaat tggacttgtc aaggagtaa
6781 caagaaaata caagattaaa agcaatcctc tcacaaaaga cattgttata aaaatgattc
6841 cgaatgtgtc gaacatgtct cagtgcacag ggagtgtcat ggaaaattat aaaacacgat
6901 taaacggtat cttaacacct ataagggagc gttagagat ctacaaaaac aacactcatg
6961 accttgtcgg tgatgtgaga ttagccggag ttataatggc aggagttgct attgggattg
7021 caaccgcagc tcaaatcact gcaggtgtag cactatatga ggcaatgaag aatgctgaca
7081 acatcaacaa actcaaaagc agcattgaat caactaatga agctgtcgtt aaacttcaag
7141 agactgcaga aagacagtc tatgtgctga ctgctctaca ggattacatt aatactaatt
7201 tagtaccgac aattgacaag ataagctgca acagacaga actctcacta gatctggcat
7261 tatcaaagta cctctctgat ttgcttttg tatttggccc caaccttcaa gacccagttt
7321 ctaattcaat gactatacag gctatatctc aggcattcgg tggaaattat gaaacactgc
7381 taagaacatt gggttacgct acagaagact ttgatgatct tctagaaagt gacagcataa
7441 caggtcaaat catctatgtt gatctaagta gctactatat aattgtcagg gtttattttc
7501 ctattctgac tgaaattcaa caggcctata tccaagagtt gttaccagtg agcttcaaca
7561 atgataattc agaatggatc agtattgtcc caaatttcat attggtaagg aatacattaa
7621 tatcaaatat agagattgga ttttgcctaa ttacaaagag gagcgtgatc tgcaaccaag
7681 attatgccac acctatgacc aacaacatga gagaatgttt aacgggatcg actgagaagt
7741 gtcctcgaga gctggttgtt tcatcacatg ttcccagatt tgcactatct aacggggttc
7801 tgtttgccaa ttgcataagt gttacatgtc agtgtcaaac aacaggcagg gcaatctcac
7861 aatcaggaga acaaactctg ctgatgattg acaacaccac ctgtcctaca gccgtactcg
7921 gtaatgtgat tatcagctta gggaaatatc tggggtcagt aaattataat tctgaaggca
7981 ttgctatcgg tcctccagtc tttacagata agttgatat atcaagtcag atatccagca
8041 tgaatcagtc cttacaacag tctaaggact atatcaaaga ggctcaacga ctccttgata
8101 ctgttaatcc atcattaata agcatgttgt ctatgatcat actgtatgta ttatcgatcg
8161 catcgttgtg tataggggttg attacattta tcagttttat cattgttgag aaaaagagaa
8221 acacctacag cagattagag gataggagag tcagacctac aagcagtggg gatctctact
8281 acattgggac atagtgtatt cagattgatg aaattatgtt agagaaatca gaaaacttct
8341 gactttcaga aatggattgt atacaattag ttagatcatc ctgaataatc gaggtgagaa
8401 cattgcaact ataaaatcag atcatgtaaa tagttgtaaa aaattaaaag cttcttttaa
8461 ttcttttgaa caataattta attaatatat aacatattct ctcacacgag cgctaaccta
8521 tacactctct actaatattt tatactcata attaatgata taatgacaaa taaggattca
8581 aattggatta tgatatagtt tcatactaca atagcatttc gaccaagaaa atatccttac
8641 aattatacaa tgtacttaac cgtgaatatg taattgataa tttcccttta gaaatttaat
8701 aaaaaactta ggacccaggt ccataactca ttggatactt aactgtatct ttctaagcta
8761 tcacatatca aaggagagat tgaatgcttt tttggagatc tagatcatta ctatatgtgt
8821 ctcctataat cacatcatag gagtgaacca taatacacat ctttgggtag gggaaggaaa
8881 gtattgttga cgtactgatt gatctgcttg agtcaaataa tcagtcataa caattcaaga
8941 aaatgccggc agaaaacaag aaagttagat tcgaaaatac tacttcagac aaagggaaaa
9001 ttcctagtaa agttattaag agctactacg gaaccatgga cattaagaaa ataaatgaag
9061 gattattgga cagcaaaata ttaagtgctt tcaacacagt aatagcattg cttggatcta
9121 tcgtgatcat agtgatgaat ataatgatca tccaaaatta cacaagatca acagacaatc
9181 aggccgtgat caaagatgcg ttgcaggta tccaacagca gatcaaaggg cttgctgaca
9241 aaatcggcac agagatagg cccaaagtat cactgattga cacatccagt accattacta
9301 tcccagctaa cattgggctg ttaggttcaa agatcagcca gtcgactgca agtataaatg
9361 agaatgtgaa tgaaaaatgc aaattcacac tgcctccctt gaaaatccac gaatgtaaca
9_1  tttcttgtcc taacccactc ccttttagag agtataggcc acagacagaa ggggtgagca
9481 atctagtagg attacctaat aatatttgcc tgcaaaagac atctaatcag atattgaagc
9541 caaagctgat tcatacact ttacccgtag tcggtcaaag tggtacctgt atcacagacc
9601 cattgctggc tatggacgag ggctattttg catatagcca cctggaaaga atcggatcat
```

FIG. 1A (Continued)

```
 9661 gttcaagagg ggtctccaaa caaagaataa taggagttgg agaggtacta gacagaggtg
 9721 atgaagttcc ttctttattt atgaccaatg tctggacccc accaaatcca aacaccgttt
 9781 accactgtag tgctgtatac aacaatgaat tctattatgt actttgtgca gtgtcaactg
 9841 ttggagaccc tattctgaat agcacctact ggtccggatc tctaatgatg acccgtctag
 9901 ctgtgaaacc caagagtaat ggtgggggtt acaatcaaca tcaacttgcc ctacgaagta
 9961 tcgagaaagg gaggtatgat aaagttatgc cgtatggacc ttcaggcatc aaacagggtg
10021 acaccctgta ttttcctgct gtaggatttt tggtcaggac agagtttaaa tacaatgatt
10081 caaattgtcc catcacgaag tgtcaataca gtaaacctga aaattgcagg ctatctatgg
10141 ggattagacc aaacagccat tatatccttc gatctggact attaaaatac aatctatcag
10201 atggggagaa ccccaaagtt gtattcattg aaatatctga tcaaagatta tctattggat
10261 ctcctagcaa aatctatgat tctttgggtc aacctgtttt ctaccaagcg tcattttcat
10321 gggatactat gattaaattt ggagatgttc taacagtcaa ccctctggtt gtcaattggc
10381 gtaataacac ggtaatatca agacccggc aatcacaatg cctagattc aatacatgtc
10441 cagagatctg ctgggaagga gtttataatg atgcattcct aattgacaga tcaattgga
10501 taagcgcggg tgtattcctt gacagcaatc agaccgcaga aaatcctgtt tttactgtat
10561 tcaaagataa tgaaatactt tatagggcac aactggcttc tgaggacacc aatgcacaaa
10621 aaacaataac taattgtttt ctcttgaaga ataagatttg gtgcatatca ttggttgaga
10681 tatatgacac aggagacaat gtcataagac ccaaactatt cgcggttaag ataccagagc
10741 aatgtacata aaaatcaacc tcataattta atggattgat ctaatataat gataataatc
10801 gtacaaagac atgtgatgta aacaaaattg ttgtaattaa ataagtcctc agctgaatac
10861 ttttttaaga ttagcaatag catgttttc cagttattgg atagttgata atataattct
10921 gaaactgggt taataaataa tcttgatcgg tgatctttga gaacaatgat atcatatagt
10981 tcatcaagtg ataatcaatt ctttatatgt cactttaga gtatattttg agacttagta
11041 ttttcggccc gaatgttaaa tttaatagtt catacataac ctaaactcaa gttctaagca
11101 taatgataac aattaatgcg aacttgtctt gatgtaagga agatttgata ttaactgaga
11161 ctccacttga tatagtagag ctgaatcttg taaataaatt ataatgaata gtttattcaa
11221 agattatcat tcatattagt gtaaattaag aaaaacttag gacccaggtc cttgattatg
11281 ccaattttct cgagaaatca ttcaattgac catagactga aagcgttgtt acctagttct
11341 tcagaagaga tcttattaga attaatttat atgatctaat tcccttaaaa actgaatacc
11401 aaaaaacaaa aatggccgat gaattatcaa tatccgacat catttaccct gaatgtcatt
11461 tggatagtcc tatagtctct ggtaaactaa tatcagctat tgaatatgct caattgagac
11521 acaatcagcc cagtgatgat aaaagactgt ctgagaatat taggttaaac cttcacggga
11581 aaagaaagag tctatacata ttaagacaat ccaaacaggg tgattacatt agaaacaaca
11641 taaaaaacct aaaggaattc atgcatattg cgtacctga atgcaataac attctattct
11701 ccatcacatc ccaaggcatg actagcaaac ttgataacat catgaaaaag tcattcaaag
11761 catacaatat cattagtaag aaagtaattg ggatgctgca aaatatcact agaaatctca
11821 taactcaaga tagaagagat gaaataatta atatacatga gtgtaggcga ttagggatt
11881 tagggaagaa tatgagtcaa tctaaatggt atgagtgttt tttgttttgg tttactatca
11941 aaacagagat gcgagcagtg atcaagaatt cgcaaaagcc gaaattccgt tcagattcat
12001 gcataataca catgcgagac aaaagtactg aaataatcct aaatccgaat cttatctgca
12061 ttttcaaatc agacaaaact ggaaagaagt gttattatct tacacccgaa atggttctaa
12121 tgtattgtga tgtcctagag ggaaggatga tgatggagac aacagtcaaa tcggatatca
12181 agtaccaacc tctaatctcg agatccaatg ccctctgggg gctaattgat cccttgttcc
12241 ctgtcatggg aaacagaatt tacaatatag tgtctatgat agagccttta gttcttgcac
12301 tactccaact caaggatgag gctaggatcc tgagggtgc atttctgcat cactgcataa
12361 aggaaatgca tcaagaattg agtgagtgtg gttttacaga tcagaagatt cggtctatgt
12_1 ttattgatga tcttttatcc attctaaata tcgataatat acatctgttg gcagagttct
12480 tttctttctt tcgtacgttt ggccatccta ttcttgaggc taaagttgct gcagaaaaag
12541 tgagagaaca tatgttggca gataaagttc ttgaatatgc ccctataatg aaagcacatg
12601 ctatattctg cgggactata ataaatgggt atagggatag acacggagga gcctggcctc
12661 ctctttacct ccccgcacat gcatctaaac atataatccg tttgaaaaat ctggggaat
12721 ctttgaccat tgatgactgt gtcaagaatt gggaatcatt ctgtgggatt caatttgatt
12781 gtttcatgga gctgaaattg gacagtgatc tgagtatgta tatgaaagat aaagctttat
12841 ctccaatcaa agacgaatgg gacagtgtat accacgtga agtgttgagc tataccccac
```

FIG. 1A (Continued)

```
12901 cgaagtcaac cgagccaaga agattggttg acgttttgt aaatgatgaa aactttgatc
12961 catacaacat gctggaatat gtcttatccg gtgcttatct cgaggatgaa caattcaatg
13021 tttcttatag cttgaaggag aaagagacga agcaagctgg acgattgttc gcaaagatga
13081 cctacaaaat gcgtgcatgt caagtcatag cagaggccct gatagcctca ggtgtcggta
13141 aatattttaa ggagaacggg atggttaagg atgagcacga acttttgaag acactcttcc
13201 aattgtctat ttcctcagtt cctcgaggga acagtcaggg taatgatcct caatccatca
13261 ataatataga aagagatttc caatacttta aagggtcac taccaatgtg aaagacaaaa
13321 agaataactc ttttaataag gttaaatctg ctctcaataa tccgtgccaa gctgacggag
13381 tccatcataa catgtcaccc aatacacgaa atcgttataa gtgtagtaat acaagtaagt
13441 cttttctcga ttatcatacc gagtttaatc ctcacaatca ctataaatca gacaatacag
13501 aggcggccgt actgtccagg tatgaggaca acactgggac aaaatttgat acagtaagtg
13561 catttcttac aactgatctt aagaaattct gtctcaattg gagatacgaa tcaatggcta
13621 tatttgctga acgtctggat gagatatacg gtttacctgg attttttaat tggatgcaca
13681 aacgactaga aagatctgtt atctatgttg cagaccctaa ttgcccccct aatattgaca
13741 aacatatgga actagaaaaa actcctgaag atgatatatt cattcattat cctaaaggcg
13801 gtattgaagg atatagccaa aaaacatgga ctatagcaac tatcccottt ttattcttga
13861 gtgcctatga gacaaacacg aggattgctg caattgtcca aggagacaat gaatcaattg
13921 ctatcactca aaaagttcat cctaatcttc cctacaaggt aaagaaagag atctgtgcaa
13981 agcaagctca gctttatttt gaaaggttaa ggatgaactt aagagccctc ggccacaatc
14041 ttaaagctac agaaactatc atcagtacac atcttttat ttattcgaag aaaattcatt
14101 atgatggtgc tgtgctgtct caggcactca aatcaatgtc aagatgttgc ttttggtcag
14161 agactctggt ggatgaaact agatcagctt gtagtaacat cagcactaca atagctaaag
1_21 ctatagaaaa tgggttgtca agaaatgtcg gctattgcat caatattttg aaagtaattc
1_81 agcagcttct catatcaact gagtttagta ttaacgagac attgacactg gatgtgacat
14341 ctcccatttc aaataattta gattggctta taacagctgc attaatcccg gcacctattg
14401 gaggattcaa ttaccttaat ttgtctagaa ttttttgttag aaatataggt gatccggtta
14461 cagcatcttt ggctgatctt aagagaatga ttgatcacag tattatgact gaaagcgtat
14521 tacaaaaagt tatgaatcaa gaacctggtg atgcgagttt cttggactgg gccagtgatc
14581 catactcggg caacttgcct gactcacaaa gcatcactaa aacaattaaa aatatcacag
14641 caaggactat actgaggaac tcaccgaacc caatgctaaa aggtttattt catgacaaat
14701 ctttgatga agatcttgaa ctagctagct tcttaatgga caggagggtt atattaccta
14761 gagccgctca tgagatactg gataattcat tgacaggtgc cagagaggaa attgctggtt
14821 tattagatac aactaaaggc ttgatcagat cagggctaag aaagagtgga cttcagccaa
14881 agttagtttc tagattatct catcatgatt ataatcaatt tttaatactg aacaaacttc
14941 tatcaaacag aagacaaaat gacttgatat catcaaatac ttgctcagtt gacttggcac
15001 gagcattgag atctcacatg tggagggaat tagcgttagg tagagtaata tacggtcttg
15061 aggtaccaga tgcacttgag gctatggtgg gaaggtatat aacagggagc ttagagtgcc
15121 aaatttgtga gcaggaaaac acgatgtatg ggtggttctt tgtacctagg gattcccaat
15181 tggatcaggt agatagagag cactcatcaa taagagtacc ttatgtagga tcaagtacgg
15241 atgaaagatc ggatatcaaa ctagggaatg tcaaaagacc aactaaggcc ttgcgttctg
15301 ctatcagaat tgcgacagta tatacttggg cctatgggga caatgaagag tgttggtatg
15361 aagcttggta cctagcgtct cagagggtaa acatagactt agatgtattg aaagctataa
15_1 ccccagtttc cacttcaaac aatttatccc atagattgag agataaatcc acacaattta
15481 agtttgcagg gagtgtactc aacagagttt ctagatatgt aacataagc aatgacaatc
15541 tagatttcag aattgaggga aaaagtag atacgaatct tatttatcaa caagcaatgc
15601 tattaggggtt atcggtattg gaaggtaaat tcagattgag attagaaact gatgattaca
15661 acgggatata tcacttacac gtaaaggata ttgttgtgt caaagaagtg gctgatgtag
15721 gccaagtaga cgctgagttg cctatcccag aatatactga agtggataac aatcatctta
15781 tatatgatcc agaccccgtt tcagaaatag attgcagccg tctttctaat caggagtcca
15841 aatcaagaga attagactt cctttatggt caactgagga acttcatgat gtcctagcta
15901 agactgttgc tcagaccgtt cttgagatta aacaaaggc tgacaaggat gttttaaagc
15961 aacaccttgc aatagactct gacgataaca tcaacagctt aatcacagaa tttctaatag
16021 ttgatcctga actgtttgca ctttatctag gacaatctat atcaataaaa tgggccttttg
16081 aaattcatca taggcgtcct agaggaagac atactatggt cgacctattg tcagatcttg
```

FIG. 1A (Continued)

```
16141 tatcaaatac atcaaagcac acttacaaag tgttgtcaaa tgccttgtca catcctagag
16201 tattcaagag atttgtaaac tgtggcttgc tattgcctac acagggtcct taccttcatc
16261 aacaagattt tgaaaagttg tctcaaaacc ttcttgtaac atcttatatg atttatctaa
16321 tgaactggtg tgacttcaag aaatccccct ttttaatcgc cgaacaggat gaaactgtga
16381 taagtctacg agaggatata ataacatcca aacatctctg tgttataatt gacttatatg
16441 caaatcacca taaacctcct tggataatag atctaaaccc acaagaaaaa atatgtgtac
16501 tgcgtgactt tatttctaaa tctaggcatg tggacacgtc ctccagatca tggaatactt
16561 ctgacctgga ttttgtaata ttctatgcat ctttgactta tttgagaaga ggtataataa
16621 aacaattaag gataagacaa gttactgagg ttatagatac cacaacaatg ttaagggaca
16681 atataattgt agagaatcct cctattaaaa caggagtgtt agacatcaga ggttgtataa
16741 tatacaattt agaggaaatc ctgtctatga acacaaaatc agcatcaaaa aagatcttta
16801 atcttaatag taggccgtca gtggagaatc ataaatatag aaggataggt ctcaactcat
16861 catcttgtta caaggcatta aatctatcac ctctgattca aaggtatttg ccgtcgggag
16921 ctcaaaggtt gtttatagga gaaggttctg ggagcatgat gttattatat cagtctacat
16981 tggggcaatc aatttctttt tacaattcag gtatagatgg agattatata ccaggtcaaa
17041 gagaactgaa actatttccc tctgaatact caattgctga ggaagaccca tctctgacgg
17101 ggaaattgaa aggactagtg gtgcccctat tcaatggaag accagaaaca acatggatcg
17161 ggaatttaga ctcctacgag tatatcataa ataggacagc ggggcgaagt ataggtcttg
17221 tccattctga catggagtct gggattgaca aaaatgtaga ggagatacta gtagaacatt
17281 cccatctaat atctatcgcg ataaatgtta tgatggagga cggactatta gtatccaaga
17341 tagcatacac ccctggattc ccaatctcaa gattatttaa catgtacaga tcatatttcg
17401 gactagtact ggtgtgtttc ccagtatata gtaatccaga ttctactgaa gtatatcttc
17461 tttgcttaca gaagacggtc aagactattg ttccccgca aaaagtcctt gagcactcta
17521 atttgcacga tgaagtcaat gaccagggaa taacatcagt gattttttaaa atcaagaatt
17581 cacagtctaa gcagttccac gatgatctaa agaagtacta tcagattgac caacctttt
17641 ttgtaccaac taaaatcact agtgatgaac aagtacttct ccaagcaggg ctgaaactca
17701 atgggccaga aattcttaag agtgaaatca gttatgatat cggttcagat atcaatacat
17761 taagagacac catcataatt atgttaaatg aggctatgaa ttattttgat gacaacagat
17821 caccttcaca ccacctagaa ccctatccag ttttggagag aactagaatt aaaacaataa
17881 tgaattgtgt gactaaaaaa gtgattgtct actcacttat caagttcaag gacaccaaaa
17941 gctcagaact ttatcacatc aaaaataaca tcagaagaaa agttctaatc ttagatttca
18001 gatcgaagct catgacaaag actctaccta aagggatgca agagagaaga gaaaaaaacg
18061 gtttcaaaga agtttggata gtagatttat cgaatcgaga agttaaaatc tggtggaaga
18121 taatcggata catatctatt atctgattta accttccaaa tccaagacca actgataact
18181 tatgttgatc taaggttcag ttattaagaa aaacttaata acgattcttc tttacccttg
18241 ttcggt (SEQ ID NO: 1)
```

FIG. 1A (Continued)

Nucleocapsid protein:
MSDIFEEAASFRSYQSKLGRDGRASAATATLTTKIRIFVPATNSPELRWELTLFALDVIRSPSAAESMKVGAAFTLI
SMYSERPGALIRSLLNDPDIEAVIIDVGSMVNGIPVMERRGDKAQEEMEGLMRILKTARDSSKGKTPFVDSRAYGLR
ITDMSTLVSAVITIEAQIWILIAKAVTAPDTAEESETRRWAKYVQQKRVNPFFALTQQWLTEMRNLLSQSLSVRKFM
VEILIEVKKGGSAKGRAVEIISDIGNYVEETGMAGFFATIRFGLETRYPALALNEFQSDLNTIKSLMLLYREIGPRA
PYMVLLEESIQTKFAPGGYPLLWSFAMGVATTIDRSMGALNINRGYLEPMYFRLGQKSARHHAGGIDQNMANRLGLS
SDQVAELAAAVQETSAGRQESNVQAREAKFAAGGVLIGGSDQDIDEGEEPIEQSGRQSVTFKREMSISSLANSVPSS
SVSTSGGTRLTNSLLNLRSRLAAKAAKEAASSNATDDPAISNRTQGESEKKNNQDLKPAQNDLDFVRADV (SEQ
ID NO: 2)

Phosphoprotein:
MDKLELVNDGLNIIDFIQKNQKEIQKTYGRSSIQQPSIKDQTKAWEDFLQCTSGESEQVEGGMSKDDGDVERRNLED
LSSTSPTDGTIGKRVSNTRDWAEGSDDIQLDPVVTDVVYHDHGGECTGYGFTSSPERGWSDYTSGANNGNVCLVSDA
KMLSYAPEIAVSKEDRETDLVHLENKLSTTGLNPTAVPFTLRNLSDPAKDSPVIAEHYYGLGVKEQNVGPQTSRNVN
LDSIKLYTSDDEEADQLEFEDEFAGSSSEVIVGISPEDEEPSSVGGKPNESIGRTIEGQSIRDNLQAKDNKSTDVPG
AGPKDSAVKEEPPQKRLPMLAEEFECSGSEDPIIRELLKENSLINCQQGKDAQPPYHWSIERSISPDKTEIVNGAVQ
TADRQRPGTPMPKSRGIPIKKGTDAKYPSAGTENVPGSKSGATRHVRGSPPYQEGKSVNAENVQLNASTAVKETDKS
EVNPVDDNDSLDDKYIMPSDDFSNTFFPHDTDRLNYHADHLGDYDLETLCEESVLMGVINSIKLINLDMRLNHIEEQ
VKEIPKIINKLESIDRVLAKTNTALSTIEGHLVSMMIMIPGKGKGERKGKNNPELKPVIGRDILEQQSLFSFDNVKN
FRDGSLTNEPYGAAVQLREDLILPELNFEETNASQFVPMADDSSRDVIKTLIRTHIKDRELRSELIGYLNKAENDEE
IQEIANTVNDIIDGNI (SEQ ID NO: 3)

V protein:
MDKLELVNDGLNIIDFIQKNQKEIQKTYGRSSIQQPSIKDQTKAWEDFLQCTSGESEQVEGGMSKDDGDVERRNLED
LSSTSPTDGTIGKRVSNTRDWAEGSDDIQLDPVVTDVVYHDHGGECTGYGFTSSPERGWSDYTSGANNGNVCLVSDA
KMLSYAPEIAVSKEDRETDLVHLENKLSTTGLNPTAVPFTLRNLSDPAKDSPVIAEHYYGLGVKEQNVGPQTSRNVN
LDSIKLYTSDDEEADQLEFEDEFAGSSSEVIVGISPEDEEPSSVGGKPNESIGRTIEGQSIRDNLQAKDNKSTDVPG
AGPKDSAVKEEPPQKRLPMLAEEFECSGSEDPIIRELLKENSLINCQQGKDAQPPYHWSIERSISPDKTEIVNGAVQ
TADRQRPGTPMPKSRGIPIKKGHRREISICWDGKRAWVEEWCNPACSRITPLPRRQECQCGECPTECFHCG (SEQ
ID NO: 4)

C protein:
MMASILLTLFRRTKKKYRRHTDDQVFNNPASKIKQKPGKIFCSAPVENLNKLRGECLRMMEMLKEETWRIYPVLLPQ
MELLERECRTPVTGQKVQMTYNWTQWLQTLYTMIMEENVPDMDLLQALREGGVITHQEQTMGMYVLYLMQRCCPMLP
KLQFLKKIGKLI (SEQ ID NO: 5)

Matrix protein:
MEPDIKSISSSESMEGVSDFSPSSWEHGGYLDKVEPEIDENGSMIPKYKIYTPGANERKYNNYMYLICYGFVEDVERT
PETGKRKKIRTIAAYPLGVGKSASHPQDLLEELCSLKVTVRRTAGSTEKIVFGSSGPLNHLVPWKKVLTSGSIFNAV
KVCRNVDQIQLDKHQALRIFFLSITKLNDSGIYMIPRTMLEFRRNNAIAFNLLVYLKIDADLSKMGIQGSLDKDGFK
VASFMLHLGNFVRRAGKYYSVDYCRRKIDRMKLQFSLGSIGGLSLHIKINGVISKRLFAQMGFQKNLCFSLMDINPW
LNRLTWNNSCEISRVAAVLQPSIPREFMIYDDVFIDNTGRILKG (SEQ ID NO: 6)

Fusion protein:
MVVILDKRCYCNLLILILMISECSVGILHYEKLSKIGLVKGVTRKYKIKSNPLTKDIVIKMIPNVSNMSQCTGSVME
NYKTRLNGILTPIKGALEIYKNNTHDLVGDVRLAGVIMAGVAIGIATAAQITAGVALYEAMKNADNINKLKSSIEST
NEAVVKLQETAEKTVYVLTALQDYINTNLVPTIDKISCKQTELSLDLALSKYLSDLLFVFGPNLQDPVSNSMTIQAI
SQAFGGNYETLLRTLGYATEDFDDLLESDSITGQIIYVDLSSYYIIVRVYFPILTEIQQAYIQELLPVSFNNDNSEW
ISIVPNFILVRNTLISNIEIGFCLITKRSVICNQDYATFMTNNMRECLTGSTEKCPRELVVSSHVPRFALSNGVLFA
NCISVTCQCQTTGRAISQSGEQTLLMIDNTTCPTAVLGNVIISLGKYLGSVNYNSEGIAIGPPVFTDKVDISSQISS
MNQSLQQSKDYIKEAQRLLDTVNPSLISMLSMIILYVLSIASLCIGLITFISFIIVEKKRNTYSRLEDRRVRPTSSG
DLYYIGT (SEQ ID NO: 7)

FIG. 1B

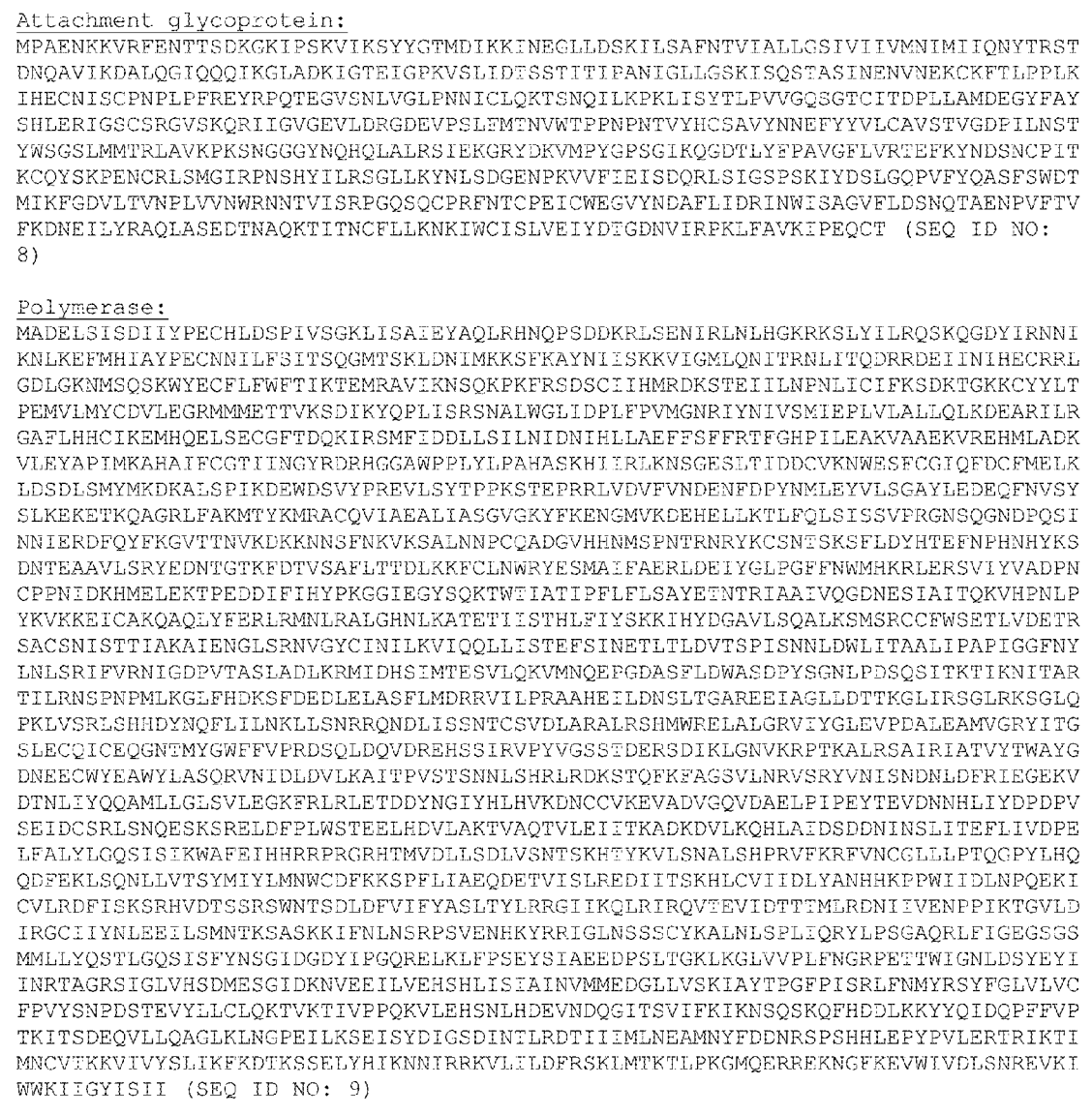

Attachment glycoprotein:

MPAENKKVRFENTTSDKGKIPSKVIKSYYGTMDIKKINEGLLDSKILSAFNTVIALLGSIVIIVMNIMIIQNYTRST
DNQAVIKDALQGIQQQIKGLADKIGTEIGPKVSLIDTSSTITIPANIGLLGSKISQSTASINENVNEKCKFTLPPLK
IHECNISCPNPLPFREYRPQTEGVSNLVGLPNNICLQKTSNQILKPKLISYTLPVVGQSGTCITDPLLAMDEGYFAY
SHLERIGSCSRGVSKQRIIGVGEVLDRGDEVPSLFMTNVWTPPNPNTVYHCSAVYNNEFYYVLCAVSTVGDPILNST
YWSGSLMMTRLAVKPKSNGGGYNQHQLALRSIEKGRYDKVMPYGPSGIKQGDTLYFPAVGFLVRTEFKYNDSNCPIT
KCQYSKPENCRLSMGIRPNSHYILRSGLLKYNLSDGENPKVVFIEISDQRLSIGSPSKIYDSLGQPVFYQASFSWDT
MIKFGDVLTVNPLVVNWRNNTVISRPGQSQCPRFNTCPEICWEGVYNDAFLIDRINWISAGVFLDSNQTAENPVFTV
FKDNEILYRAQLASEDTNAQKTITNCFLLKNKIWCISLVEIYDTGDNVIRPKLFAVKIPEQCT (SEQ ID NO: 8)

Polymerase:

MADELSISDIIYPECHLDSPIVSGKLISAIEYAQLRHNQPSDDKRLSENIRLNLHGKRKSLYILRQSKQGDYIRNNI
KNLKEFMHIAYPECNNILFSITSQGMTSKLDNIMKKSFKAYNIISKKVIGMLQNITRNLITQDRRDEIINIHECRRL
GDLGKNMSQSKWYECFLFWFTIKTEMRAVIKNSQKPKFRSDSCIIHMRDKSTEIILNPNLICIFKSDKTGKKCYYLT
PEMVLMYCDVLEGRMMMETTVKSDIKYQPLISRSNALWGLIDPLFPVMGNRIYNIVSMIEPLVLALLQLKDEARILR
GAFLHHCIKEMHQELSECGFTDQKIRSMFIDDLLSILNIDNIHLLAEFFSFFRTFGHPILEAKVAAEKVREHMLADK
VLEYAPIMKAHAIFCGTIINGYRDRHGGAWPPLYLPAHASKHIIRLKNSGESLTIDDCVKNWESFCGIQFDCFMELK
LDSDLSMYMKDKALSPIKDEWDSVYPREVLSYTPPKSTEPRRLVDVFVNDENFDPYNMLEYVLSGAYLEDEQFNVSY
SLKEKETKQAGRLFAKMTYKMRACQVIAEALIASGVGKYFKENGMVKDEHELLKTLFQLSISSVPRGNSQGNDPQSI
NNIERDFQYFKGVTTNVKDKKNNSFNKVKSALNNPCQADGVHHNMSPNTRNRYKCSNTSKSFLDYHTEFNPHNHYKS
DNTEAAVLSRYEDNTGTKFDTVSAFLTTDLKKFCLNWRYESMAIFAERLDEIYGLPGFFNWMHKRLERSVIYVADPN
CPPNIDKHMELEKTPEDDIFIHYPKGGIEGYSQKTWTIATIPFLFLSAYETNTRIAAIVQGDNESIAITQKVHPNLP
YKVKKEICAKQAQLYFERLRMNLRALGHNLKATETIISTHLFIYSKKIHYDGAVLSQALKSMSRCCFWSETLVDETR
SACSNISTTIAKAIENGLSRNVGYCINILKVIQQLLISTEFSINETLTLDVTSPISNNLDWLITAALIPAPIGGFNY
LNLSRIFVRNIGDPVTASLADLKRMIDHSIMTESVLQKVMNQEPGDASFLDWASDPYSGNLPDSQSITKTIKNITAR
TILRNSPNPMLKGLFHDKSFDEDLELASFLMDRRVILPRAAHEILDNSLTGAREEIAGLLDTTKGLIRSGLRKSGLQ
PKLVSRLSHHDYNQFLILNKLLSNRRQNDLISSNTCSVDLARALRSHMWRELALGRVIYGLEVPDALEAMVGRYITG
SLECQICEQGNTMYGWFFVPRDSQLDQVDREHSSIRVPYVGSSTDERSDIKLGNVKRPTKALRSAIRIATVYTWAYG
DNEECWYEAWYLASQRVNIDLDVLKAITPVSTSNNLSHRLRDKSTQFKFAGSVLNRVSRYVNISNDNLDFRIEGEKV
DTNLIYQQAMLLGLSVLEGKFRLRLETDDYNGIYHLHVKDNCCVKEVADVGQVDAELPIPEYTEVDNNHLIYDPDPV
SEIDCSRLSNQESKSRELDFPLWSTEELHDVLAKTVAQTVLEIITKADKDVLKQHLAIDSDDNINSLITEFLIVDPE
LFALYLGQSISIKWAFEIHHRRPRGRHTMVDLLSDLVSNTSKHTYKVLSNALSHPRVFKRFVNCGLLLPTQGPYLHQ
QDFEKLSQNLLVTSYMIYLMNWCDFKKSPFLIAEQDETVISLREDIITSKHLCVIIDLYANHHKPPWIIDLNPQEKI
CVLRDFISKSRHVDTSSRSWNTSDLDFVIFYASLTYLRRGIIKQLRIRQVTEVIDTTTMLRDNIIVENPPIKTGVLD
IRGCIIYNLEEILSMNTKSASKKIFNLNSRPSVENHKYRRIGLNSSSCYKALNLSPLIQRYLPSGAQRLFIGEGSGS
MMLLYQSTLGQSISFYNSGIDGDYIPGQRELKLFPSEYSIAEEDPSLTGKLKGLVVPLFNGRPETTWIGNLDSYEYI
INRTAGRSIGLVHSDMESGIDKNVEEILVEHSHLISIAINVMMEDGLLVSKIAYTPGFPISRLFNMYRSYFGLVLVC
FPVYSNPDSTEVYLLCLQKTVKTIVPPQKVLEHSNLHDEVNDQGITSVIFKIKNSQSKQFHDDLKKYYQIDQPFFVP
TKITSDEQVLLQAGLKLNGPEILKSEISYDIGSDINTLRDTIIIMLNEAMNYFDDNRSPSHHLEPYPVLERTRIKTI
MNCVTKKVIVYSLIKFKDTKSSELYHIKNNIRRKVLILDFRSKLMTKTLPKGMQERREKNGFKEVWIVDLSNREVKI
WWKIIGYISII (SEQ ID NO: 9)

FIG. 1B (Continued)

```
                  P/V/C
           N      P/V/C         M       F       G                 L                    3'-trailer
5'-leader
                    Nipah virus (AF212302)
                          18246 bp                G Vaccine antigen
```

FIG. 2A

```
              Nru I    H6p              M   P   A   E   N   K   K   V
11470.SL  5'  ATCGCGATATCCGTTAAGTTTGTATCGTAATGCCGGCAGAAAACAAGAAAGTT

V   K   I   P   E   Q   C   T   *   Xho I   (SEQ ID NO: 10)
              GTTAAGATACCAGAGCAATGTACATAACTCGAGCG              (SEQ ID NO: 11)
11471.SL  3'  CAATTCTATGGTCTCGTTACATGTATTGAGCTCGC              (SEQ ID NO: 13)
```

FIG. 2B

```
                       → C5R
  1   GCGGCCGCAT TCTGAATGTT AAATGTTATA CTTTGGATGA AGCTATAAAT ATGCATTGGA
      CGCCGGCGTA AGACTTACAA TTTACAATAT GAAACCTACT TCGATATTTA TACGTAACCT

61   AAAATAATCC ATTTAAAGAA AGGATTCAAA TACTACAAAA CCTAAGCGAT AATATGTTAA
      TTTTATTAGG TAAATTTCTT TCCTAAGTTT ATGATGTTTT GGATTCGCTA TTATACAATT

121   CTAAGCTTAT TCTTAACGAC GCTTTAAATA TACACAAATA AACATAATTT TTGTATAACC
      GATTCGAATA AGAATTGCTG CGAAATTTAT ATGTGTTTAT TTGTATTAAA AACATATTGG

181   TAACAAATAA CTAAACATA AAAATAATAA AAGGAAATGT AATATCGTAA TTATTTTACT
      ATTGTTTATT GATTTGTAT TTTTATTATT TTCCTTTACA TTATAGCATT AATAAAATGA

241   CAGGAATGGG GTTAAATATT TATATCACGT GTATATCTAT ACTGTTATCG TATACTCTTT
      GTCCTTACCC CAATTATAA ATATAGTGCA CATATAGATA TGACAATAGC ATATGAGAAA

301   ACAATTACTA TTACGAATAT GCAAGAGATA ATAAGATTAC GTATTTAAGA GAATCTTGTC
      TGTTAATGAT AATGCTTATA CGTTCTCTAT TATTCTAATG CATAAATTCT CTTAGAACAG
              ← 7927.DC

361   ATGATAATTG GGTACGACAT AGTGATAAAT GCTATTTCGC ATCGTTACAT AAAGTCAGTT
      TACTATTAAC CCATGCTGTA TCACTATTTA CGATAAAGCG TAGCAATGTA TTTCAGTCAA

_1   GGAAGATGG ATTTGACAGA TGTAACTTAA TAGGTGCAAA AATGTTAAAT AACAGCATTC
      CCTTTCTACC TAAACTGTCT ACATTGAATT ATCCACGTTT TTACAATTTA TTGTCGTAAG

7696.CXL →
481   TATCGGAAGA TAGGATACCA GTTATATTAT ACAAAAATCA CTGGTTGGAT AAAACAGATT
      ATAGCCTTCT ATCCTATGGT CAATATAATA TGTTTTTAGT GACCAACCTA TTTTGTCTAA

541   CTGCAATATT CGTAAAAGAT GAAGATTACT GCGAATTTGT AAACTATGAC AATAAAAAGC
      GACGTTATAA GCATTTTCTA CTTCTAATGA CGCTTAAACA TTTGATACTG TTATTTTTCG

601   CATTTATCTC AACGACATCG TGTAATTCTT CCATGTTTTA TGTATGTGTT TCAGATATTA
      GTAAATAGAG TTGCTGTAGC ACATTAAGAA GGTACAAAAT ACATACACAA AGTCTATAAT

661   TGAGATTACT ATAAACTTTT TGTATACTTA TATTCCGTAA ACTATATTAA TCATGAAGAA
      ACTCTAATGA TATTTGAAAA ACATATGAAT ATAAGGCATT TGATATAATT AGTACTTCTT

721   AATGAAAAAG TATAGAAGCT GTTCACGAGC GGTTGTTGAA ACAACAAAA TTATACATTC
      TTACTTTTTC ATATCTTCGA CAAGTGCTCG CCAACAACTT TGTTGTTTT AATATGTAAG
                                          ← 7926.DC

781   AAGATGGCTT ACATATACGT CTGTGAGGCT ATCATGGATA ATGACAATGC ATCTCTAAAT
      TTCTACCGAA TGTATATGCA GACACTCCGA TAGTACCTAT TACTGTTACG TAGAGATTTA

841   AGGTTTTTGG ACAATGGATT CGACCCTAAC ACGGAATATG GTACTCTACA ATCTCCTCTT
      TCCAAAAACC TGTTACCTAA GCTGGGATTG TGCCTTATAC CATGAGATGT TAGAGGAGAA

901   GAAATGGCTG TAATGTTCAA GAATACCGAG GCTATAAAAA TCTTGATGAG GTATGGAGCT
      CTTTACCGAC ATTACAAGTT CTTATGGCTC CGATATTTTT AGAACTACTC CATACCTCGA
```

FIG. 2D

```
                         7697.CXL →
 961   AAACCTGTAG TTACTGAATG CACAACTTCT TGTCTGCATG ATGCGGTGTT GAGAGACGAC
       TTTGGACATC AATGACTTAC GTGTTGAAGA ACAGACGTAC TACGCCACAA CTCTCTGCTG

1021   TACAAAATAG TGAAAGATCT GTTGAAGAAT AACTATGTAA ACAATGTTCT TTACAGCGGA
       ATGTTTTATC ACTTTCTAGA CAACTTCTTA TTGATACATT TGTTACAAGA AATGTCGCCT

1081   GGCTTTACTC CTTTGTGTTT GGCAGCTTAC CTTAACAAAG TTAATTTGGT TAAACTTCTA
       CCGAAATGAG GAAACACAAA CCGTCGAATG GAATTGTTTC AATTAAACCA ATTTGAAGAT

1141   TTGGCTCATT CGGCGGATGT AGATATTTCA AACACGGATC GGTTAACTCC TCTACATATA
       AACCGAGTAA GCCGCCTACA TCTATAAAGT TTGTGCCTAG CCAATTGAGG AGATGTATAT
                                                      ← 7925.DC

1201   GCCGTATCAA ATAAAAATTT AACAATGGTT AAACTTCTAT TGAACAAAGG TGCTGATACT
       CGGCATAGTT TATTTTTAAA TTGTTACCAA TTTGAAGATA ACTTGTTTCC ACGACTATGA

1261   GACTTGCTGG ATAACATGGG ACGTACTCCT TTAATGATCG CTGTACAATC TGGAAATATT
       CTGAACGACC TATTGTACCC TGCATGAGGA AATTACTAGC GACATGTTAG ACCTTTATAA

1321   GAAATATGTA GCACACTACT TAAAAAAAAT AAAATGTCCA GAACTGGGAA AAATTGATCT
       CTTTATACAT CGTGTGATGA ATTTTTTTTA TTTTACAGGT CTTGACCCTT TTTAACTAGA

1381   TGCCAGCTGT AATTCATGGT AGAAAAGAAG TGCTCAGGCT ACTTTTCAAC AAAGGAGCAG
       ACGGTCGACA TTAAGTACCA TCTTTTCTTC ACGAGTCCGA TGAAAAGTTG TTTCCTCGTC

1441   ATGTAAACTA CATCTTTGAA AGAAATGGAA AATCATATAC TGTTTTTGGAA TTGATTAAAG
       TACATTTGAT GTAGAAACTT TCTTTACCTT TTAGTATATG ACAAAAACCTT AACTAATTTC

7792.SL →
1501   AAAGTTACTC TGAGACACAA AAGAGGTAGC TGAAGTGGTA CTCTCAAAGG TACGTGACTA
       TTTCAATGAG ACTCTGTGTT TTCTCCATCG ACTTCACCAT GAGAGTTTCC ATGCACTGAT

1561   ATTAGCTATA AAAAGGATCC GGGTTAATTA ATTAGTCATC AGGCAGGGCG AGAACGAGAC
       TAATCGATAT TTTTCCTAGG CCCAATTAAT TAATCAGTAG TCCGTCCCGC TCTTGCTCTG

⇒ H6p
1621   TATCTGCTCG TTAATTAATT AGAGCTTCTT TATTCTATAC TTAAAAAGTG AAAATAAATA
       ATAGACGAGC AATTAATTAA TCTCGAAGAA ATAAGATATG AATTTTTCAC TTTTATTTAT

1681   CAAAGGTTCT TGAGGGTTGT GTTAAATTGA AAGCGAGAAA TAATCATAAA TTATTTCATT
       GTTTCCAAGA ACTCCCAACA CAATTTAACT TTCGCTCTTT ATTAGTATTT AATAAAGTAA

⇒ Nipah G
                               Met ProAlaGlu AsnLysLys ValArgPheGlu·
1741   ATCGCGATAT CCGTTAAGTT TGTATCGTAA TGCCGGCAGA AAACAAGAAA GTTAGATTCG
       TAGCGCTATA GGCAATTCAA ACATAGCATT ACGGCCGTCT TTTGTTCTTT CAATCTAAGC ..AsnThrThr SerAspLys GlyLysIlePro SerLysVal IleLysSer TyrTyrGlyThr·
1801   AAAATACTAC TTCAGACAAA GGGAAAATTC CTAGTAAAGT TATTAAGAGC TACTACGGAA
       TTTTATGATG AAGTCTGTTT CCCTTTTAAG GATCATTTCA ATAATTCTCG ATGATGCCTT
                       ← 11472.SL
```

FIG. 2D (Continued)

```
              ..MetAspIle LysLysIle AsnGluGlyLeu LeuAspSer LysIleLeu SerAlaPheAsn·
1861          CCATGGACAT TAAGAAAATA AATGAAGGAT TATTGGACAG CAAAATATTA AGTGCTTTCA
              GGTACCTGTA ATTCTTTTAT TTACTTCCTA ATAACCTGTC GTTTTATAAT TCACGAAAGT

..ThrValIle AlaLeuLeu GlySerIleVal IleIleVal MetAsnIle MetIleIleGln·
1921          ACACAGTAAT AGCATTGCTT GGATCTATCG TGATCATAGT GATGAATATA ATGATCATCC
              TGTGTCATTA TCGTAACGAA CCTAGATAGC ACTAGTATCA CTACTTATAT TACTAGTAGG

..AsnTyrThr ArgSerThr AspAsnGlnAla ValIleLys AspAlaLeu GlnGlyIleGln·
1981          AAAATTACAC AAGATCAACA GACAATCAGG CCGTGATCAA AGATGCGTTG CAGGGTATCC
              TTTTAATGTG TTCTAGTTGT CTGTTAGTCC GGCACTAGTT TCTACGCAAC GTCCCATAGG

..GlnGlnIle LysGlyLeu AlaAspLysIle GlyThrGlu IleGlyPro LysValSerLeu·
2041          AACAGCAGAT CAAAGGGCTT GCTGACAAAA TCGGCACAGA GATAGGGCCC AAAGTATCAC
              TTGTCGTCTA GTTTCCCGAA CGACTGTTTT AGCCGTGTCT CTATCCCGGG TTTCATAGTG

..IleAspThr SerSerThr IleThrIlePro AlaAsnIle GlyLeuLeu GlySerLysIle·
2101          TGATTGACAC ATCCAGTACC ATTACTATCC CAGCTAACAT TGGGCTGTTA GGTTCAAAGA
              ACTAACTGTG TAGGTCATGG TAATGATAGG GTCGATTGTA ACCCGACAAT CCAAGTTTCT

11473.SL →
              ..SerGlnSer ThrAlaSer IleAsnGluAsn ValAsnGlu LysCysLys PheThrLeuPro·
2161          TCAGCCAGTC GACTGCAAGT ATAAATGAGA ATGTAATGA AAAATGCAAA TTCACACTGC
              AGTCGGTCAG CTGACGTTCA TATTTACTCT TACATTACT TTTTACGTTT AAGTGTGACG

..ProLeuLys IleHisGlu CysAsnIleSer CysProAsn ProLeuPro PheArgGluTyr·
2221          CTCCCTTGAA AATCCACGAA TGTAACATTT CTTGTCCTAA CCCACTCCCT TTTAGAGAGT
              GAGGGAACTT TTAGGTGCTT ACATTGTAAA GAACAGGATT GGGTGAGGGA AAATCTCTCA
                    ← 11474.SL

..ArgProGln ThrGluGly ValSerAsnLeu ValGlyLeu ProAsnAsn IleCysLeuGln·
2281          ATAGGCCACA GACAGAAGGG GTGAGCAATC TAGTAGGATT ACCTAATAAT ATTTGCCTGC
              TATCCGGTGT CTGTCTTCCC CACTCGTTAG ATCATCCTAA TGGATTATTA TAAACGGACG

..LysThrSer AsnGlnIle LeuLysProLys LeuIleSer TyrThrLeu ProValValGly·
2341          AAAAGACATC TAATCAGATA TTGAAGCCAA AGCTGATTTC ATACACTTTA CCCGTAGTCG
              TTTTCTGTAG ATTAGTCTAT AACTTCGGTT TCGACTAAAG TATGTGAAAT GGGCATCAGC

..GlnSerGly ThrCysIle ThrAspProLeu LeuAlaMet AspGluGly TyrPheAlaTyr·
2401          GTCAAAGTGG TACCTGTATC ACAGACCCAT TGCTGGCTAT GGACGAGGGC TATTTTGCAT
              CAGTTTCACC ATGGACATAG TGTCTGGGTA ACGACCGATA CCTGCTCCCG ATAAAACGTA

..SerHisLeu GluArgIle GlySerCysSer ArgGlyVal SerLysGln ArgIleIleGly·
2461          ATAGCCACCT GGAAAGAATC GGATCATGTT CAAGAGGGGT CTCCAAACAA AGAATAATAG
              TATCGGTGGA CCTTTCTTAG CCTAGTACAA GTTCTCCCCA GAGGTTTGTT TCTTATTATC

11475.SL →
              ..ValGlyGlu ValLeuAsp ArgGlyAspGlu ValProSer LeuPheMet ThrAsnValTrp·
2521          GAGTTGGAGA GGTACTAGAC AGAGGTGATG AAGTTCCTTC TTTATTTATG ACCAATGTCT
              CTCAACCTCT CCATGATCTG TCTCCACTAC TTCAAGGAAG AAATAAATAC TGGTTACAGA

..ThrProPro AsnProAsn ThrValTyrHis CysSerAla ValTyrAsn AsnGluPheTyr·
2581          GGACCCCACC AAATCCAAAC ACCGTTTACC ACTGTAGTGC TGTATACAAC AATGAATTCT
              CCTGGGGTGG TTTAGGTTTG TGGCAAATGG TGACATCACG ACATATGTTG TTACTTAAGA
```

FIG. 2D (Continued)

```
          ..TyrValLeu CysAlaVal SerThrValGly AspProIle LeuAsnSer ThrTyrTrpSer·
2641      ATTATGTACT TTGTGCAGTG TCAACTGTTG GAGACCCTAT TCTGAATAGC ACCTACTGGT
          TAATACATGA AACACGTCAC AGTTGACAAC CTCTGGGATA AGACTTATCG TGGATGACCA
                              ← 11476.SL
          ..GlySerLeu MetMetThr ArgLeuAlaVal LysProLys SerAsnGly GlyGlyTyrAsn·
2701      CCGGATCTCT AATGATGACC CGTCTAGCTG TGAAACCCAA GAGTAATGGT GGGGGTTACA
          GGCCTAGAGA TTACTACTGG GCAGATCGAC ACTTTGGGTT CTCATTACCA CCCCCAATGT

..GlnHisGln LeuAlaLeu ArgSerIleGlu LysGlyArg TyrAspLys ValMetProTyr·
2761      ATCAACATCA ACTTGCCCTA CGAAGTATCG AGAAAGGGAG GTATGATAAA GTTATGCCGT
          TAGTTGTAGT TGAACGGGAT GCTTCATAGC TCTTTCCCTC CATACTATTT CAATACGGCA

..GlyProSer GlyIleLys GlnGlyAspThr LeuTyrPhe ProAlaVal GlyPheLeuVal·
2821      ATGGACCTTC AGGCATCAAA CAGGGTGACA CCCTGTATTT TCCTGCTGTA GGATTTTTGG
          TACCTGGAAG TCCGTAGTTT GTCCCACTGT GGGACATAAA AGGACGACAT CCTAAAAACC

..ArgThrGlu PheLysTyr AsnAspSerAsn CysProIle ThrLysCys GlnTyrSerLys·
2881      TCAGGACAGA GTTTAAATAC AATGATTCAA ATTGTCCCAT CACGAAGTGT CAATACAGTA
          AGTCCTGTCT CAAATTTATG TTACTAAGTT TAACAGGGTA GTGCTTCACA GTTATGTCAT

11477.SL →
          ..ProGluAsn CysArgLeu SerMetGlyIle ArgProAsn SerHisTyr IleLeuArgSer·
2941      AACCTGAAAA TTGCAGGCTA TCTATGGGGA TTAGACCAAA CAGCCATTAT ATCCTTCGAT
          TTGGACTTTT AACGTCCGAT AGATACCCCT AATCTGGTTT GTCGGTAATA TAGGAAGCTA

..GlyLeuLeu LysTyrAsn LeuSerAspGly GluAsnPro LysValVal PheIleGluIle·
3001      CTGGACTATT AAAATACAAT CTATCAGATG GGGAGAACCC CAAAGTTGTA TTCATTGAAA
          GACCTGATAA TTTTATGTTA GATAGTCTAC CCCTCTTGGG GTTTCAACAT AAGTAACTTT
                              ← 11478.SL

..SerAspGln ArgLeuSer IleGlySerPro SerLysIle TyrAspSer LeuGlyGlnPro·
3061      TATCTGATCA AGATTATCT ATTGGATCTC CTAGCAAAAT CTATGATTCT TTGGGTCAAC
          ATAGACTAGT TTCTAATAGA TAACCTAGAG GATCGTTTTA GATACTAAGA AACCCAGTTG

..ValPheTyr GlnAlaSer PheSerTrpAsp ThrMetIle LysPheGly AspValLeuThr·
3121      CTGTTTTCTA CCAAGCGTCA TTTTCATGGG ATACTATGAT TAAATTTGGA GATGTTCTAA
          GACAAAAGAT GGTTCGCAGT AAAAGTACCC TATGATACTA ATTTAAACCT CTACAAGATT

..ValAsnPro LeuValVal AsnTrpArgAsn AsnThrVal IleSerArg ProGlyGlnSer·
3181      CAGTCAACCC TCTGGTTGTC AATTGGCGTA ATAACACGGT AATATCAAGA CCCGGGCAAT
          GTCAGTTGGG AGACCAACAG TTAACCGCAT TATTGTGCCA TTATAGTTCT GGGCCCGTTA

..GlnCysPro ArgPheAsn ThrCysProGlu IleCysTrp GluGlyVal TyrAsnAspAla·
3241      CACAATGCCC TAGATTCAAT ACATGTCCAG AGATCTGCTG GGAAGGAGTT TATAATGATG
          GTGTTACGGG ATCTAAGTTA TGTACAGGTC TCTAGACGAC CCTTCCTCAA ATATTACTAC

11479.SL →
          ..PheLeuIle AspArgIle AsnTrpIleSer AlaGlyVal PheLeuAsp SerAsnGlnThr·
3301      CATTCCTAAT TGACAGAATC AATTGGATAA GCGCGGGTGT ATTCCTTGAC AGCAATCAGA
          GTAAGGATTA ACTGTCTTAG TTAACCTATT CGCGCCCACA TAAGGAACTG TCGTTAGTCT

..AlaGluAsn ProValPhe ThrValPheLys AspAsnGlu IleLeuTyr ArgAlaGlnLeu·
3361      CCGCAGAAAA TCCTGTTTTT ACTGTATTCA AAGATAATGA AATACTTTAT AGGGCACAAC
          GGCGTCTTTT AGGACAAAAA TGACATAAGT TTCTATTACT TTATGAAATA TCCCGTGTTG
```

FIG. 2D (Continued)

```
                ..AlaSerGlu AspThrAsn AlaGlnLysThr IleThrAsn CysPheLeu LeuLysAsnLys·
     3_1        TGGCTTCTGA GGACACCAAT GCACAAAAAA CAATAACTAA TTGTTTTCTC TTGAAGAATA
                ACCGAAGACT CCTGTGGTTA CGTGTTTTTT GTTATTGATT AACAAAAGAG AACTTCTTAT
                     ← 11480.SL

..IleTrpCys IleSerLeu ValGluIleTyr AspThrGly AspAsnVal IleArgProLys·
     3481       AGATTTGGTG CATATCATTG GTTGAGATAT ATGACACAGG AGACAATGTC ATAAGACCCA
                TCTAAACCAC GTATAGTAAC CAACTCTATA TACTGTGTCC TCTGTTACAG TATTCTGGGT

..LeuPheAla ValLysIle ProGluGlnCys Thr (SEQ ID NO: 14)
     3541       AACTATTCGC GGTTAAGATA CCAGAGCAAT GTACATAACT CGAGTCTAGA ATCGATCCCG
                TTGATAAGCG CCAATTCTAT GGTCTCGTTA CATGTATTGA GCTCAGATCT TAGCTAGGGC

→ C5L
     3601       GGTTTTTATG ACTAGTTAAT CACGGCCGCT TATAAAGATC TAAAATGCAT AATTCTAAA
                CCAAAAATAC TGATCAATTA GTGCCGGCGA ATATTTCTAG ATTTTACGTA TTAAAGATTT

7928.DC →
     3661       TAATGAAAAA AAGTACATCA TGAGCAACGC GTTAGTATAT TTTACAATGG AGATTAACGC
                ATTACTTTTT TTCATGTAGT ACTCGTTGCG CAATCATATA AAATGTTACC TCTAATTGCG

3721       TCTATACCGT TCTATGTTTA TTGATTCAGA TGATGTTTTA GAAAGAAAG TTATTGAATA
                AGATATGGCA AGATACAAAT AACTAAGTCT ACTACAAAAT CTTTCTTTC AATAACTTAT
                     ← 7793.SL

3781       TGAAAACTTT AATGAAGATG AAGATGACGA CGATGATTAT TGTTGTAAAT CTGTTTTAGA
                ACTTTTGAAA TTACTTCTAC TTCTACTGCT GCTACTAATA ACAACATTTA GACAAAATCT

3841       TGAAGAAGAT GACGCGCTAA AGTATACTAT GGTTACAAAG TATAAGTCTA TACTACTAAT
                ACTTCTTCTA CTGCGCGATT TCATATGATA CCAATGTTTC ATATTCAGAT ATGATGATTA

3901       GGCGACTTGT GCAAGAAGGT ATAGTATAGT GAAAATGTTG TTAGATTATG ATTATCAAAA
                CCGCTGAACA CGTTCTTCCA TATCATATCA CTTTTACAAC AATCTAATAC TAATACTTTT

3961       ACCAAATAAA TCAGATCCAT ATCTAAAGGT ATCTCCTTTG CACATAATTT CATCTATTCC
                TGGTTTATTT AGTCTAGGTA TAGATTTCCA TAGAGGAAAC GTGTATTAAA GTAGATAAGG

4021       TAGTTTAGAA TACCTGCAGC CAAGCTTGGC ACTGGCCGTC GTTTTAC (SEQ ID NO: 15)
                ATCAAATCTT ATGGACGTCG GTTCGAACCG TGACCGGCAG CAAAATG (SEQ ID NO: 16)
                                                      ← M13F
```

FIG. 2D (Continued)

```
              Nru I     H6p                  M  P  A  E  N  K  K  V
11470.SL  5' ATCGCGATATCCGTTAAGTTTGTATCGTAATGCCGGCAGAAAACAAGAAAGTT

V  K  I  P  E  Q  C  T  *   Xho I  (SEQ ID NO: 10)
          GTTAAGATACCAGAGCAATGTACATAACTCGAGCG   (SEQ ID NO: 11)
11471.SL  3' CAATTCTATGGTCTCGTTACATGTATTGAGCTCGC  (SEQ ID NO: 13)
```

```
          M13F →                                               ⇒ F8R
  1   GTAAAACGAC GGCCAGTGAA TTGTAATACG ACTCACTATA GGGCGAATTG GGTGACCCTT
      CATTTTGCTG CCGGTCACTT AACATTATGC TGAGTGATAT CCCGCTTAAC CCACTGGGAA

61   TACAAGAATA AAAGAAGAAA CAACTGTGAA ATAGTTTATA AATGTAATTC GTATGCAGAA
      ATGTTCTTAT TTTCTTCTTT GTTGACACTT TATCAAATAT TTACATTAAG CATACGTCTT

121   AACGATAATA TATTTTGGTA TGAGAAATCT AAAGGAGACA TAGTTTGTAT AGACATGCGC
      TTGCTATTAT ATAAAACCAT ACTCTTTAGA TTTCCTCTGT ATCAAACATA TCTGTACGCG

181   TCTTCCGATG AGATATTCGA TGCTTTTCTA ATGTATCATA TAGCTACAAG ATATGCCTAT
      AGAAGGCTAC TCTATAAGCT ACGAAAAGAT TACATAGTAT ATCGATGTTC TATACGGATA

241   CATGATGATG ATATATATCT ACAAATAGTG TTATATTATT CTAATAATCA AAATGTTATA
      GTACTACTAC TATATATAGA TGTTTATCAC AATATAATAA GATTATTAGT TTTACAATAT

301   TCTTATATTA CGAAAAATAA ATACGTTAAG TATATAAGAA ATAAAACTAG AGACGATATT
      AGAATATAAT GCTTTTTATT TATGCAATTC ATATATTCTT TATTTTGATC TCTGCTATAA

361   CATAAAGTAA AAATATTAGC TCTAGAAGAC TTTACAACGG AAGAAATATA TTGTTGGATT
      GTATTTCATT TTTATAATCG AGATCTTCTG AAATGTTGCC TTCTTTATAT AACAACCTAA

1   AGTAATATAT AACAGCGTAG CTGCACGGTT TTGATCATTT TCCAACAATA TAAACCAATG
      TCATTATATA TTGTCGCATC GACGTGCCAA AACTAGTAAA AGGTTGTTAT ATTTGGTTAC
            7864.SL →
481   AAGGAGGACG ACTCATCAAA CATAAATAAC ATTCACGGAA AATATTCAGT ATCAGATTTA
      TTCCTCCTGC TGAGTAGTTT GTATTTATTG TAAGTGCCTT TTATAAGTCA TAGTCTAAAT
             ← 7876.SL

541   TCACAAGATG ATTATGTTAT TGAATGTATA GACGGATCTT TTGATTCGAT CAAGTATAGA
      AGTGTTCTAC TAATACAATA ACTTACATAT CTGCCTAGAA AACTAAGCTA GTTCATATCT

601   GATATAAAGG TTATAATAAT GAAGAATAAC GGTTACGTTA ATTGTAGTAA ATTATGTAAA
      CTATATTTCC AATATTATTA CTTCTTATTG CCAATGCAAT TAACATCATT TAATACATTT

661   ATGCGGAATA AATACTTTTC TAGATGGTTG CGTCTTTCTA CTTCTAAAGC ATTATTAGAC
      TACGCCTTAT TTATGAAAAG ATCTACCAAC GCAGAAAGAT GAAGATTTCG TAATAATCTG

721   ATTTACAATA ATAAGTCAGT AGATAATGCT ATTGTTAAAG TCTATGGTAA AGGTAAGAAA
      TAAATGTTAT TATTCAGTCA TCTATTACGA TAACAATTTC AGATACCATT TCCATTCTTT

781   CTTATTATAA CAGGATTTTA TCTCAAACAA AATATGATAC GTTATGTTAT TGAGTGGATA
      GAATAATATT GTCCTAAAAT AGAGTTTGTT TTATACTATG CAATACAATA ACTCACCTAT

841   GGGGATGATT TTACAAACGA TATATACAAA ATGATTAATT TCTATAATGC GTTATTCGGT
      CCCCTACTAA AATGTTTGCT ATATATGTTT TACTAATTAA AGATATTACG CAATAAGCCA

7865.SL →
901   AACGATGAAT TAAAAATAGT ATCCTGTGAA AACACTCTAT GCCCGTTTAT AGAACTTGGT
      TTGCTACTTA ATTTTTATCA TAGGACACTT TTGTGAGATA CGGGCAAATA TCTTGAACCA
                                                 ← 7875.SL

961   AGATGCTATT ATGGTAAAAA ATGTAAGTAT ATACACGGAG ATCAATGTGA TATCTGTGGT
      TCTACGATAA TACCATTTTT TACATTCATA TATGTGCCTC TAGTTACACT ATAGACACCA
```

FIG. 3C

```
1021   CTATATATAC TACACCCTAC CGATATTAAC CAACGAGTTT CTCACAAGAA AACTTGTTTA
       GATATATATG ATGTGGGATG GCTATAATTG GTTGCTCAAA GAGTGTTCTT TTGAACAAAT

1081   GTAGATAGAG ATTCTTTGAT TGTGTTTAAA AGAAGTACCA GTAAAAAGTG TGGCATATGC
       CATCTATCTC TAAGAAACTA ACACAAATTT TCTTCATGGT CATTTTTCAC ACCGTATACG

1141   ATAGAAGAAA TAAACAAAAA ACATATTTCC GAACAGTATT TTGGAATTCT CCCAAGTTGT
       TATCTTCTTT ATTTGTTTTT TGTATAAAGG CTTGTCATAA AACCTTAAGA GGGTTCAACA

1201   AAACATATTT TTTGCCTATC ATGTATAAGA CGTTGGGCAG ATACTACCAG AAATACAGAT
       TTTGTATAAA AAACGGATAG TACATATTCT GCAACCCGTC TATGATGGTC TTTATGTCTA

1261   ACTGAAAATA CGTGTCCTGA ATGTAGAATA GTTTTTCCTT TCATAATACC CAGTAGGTAT
       TGACTTTTAT GCACAGGACT TACATCTTAT CAAAAAGGAA AGTATTATGG GTCATCCATA

1321   TGGATAGATA ATAAATAATGA TAAAAAAATA TTATATAATA GATATAAGAA AATGATTTTT
       ACCTATCTAT TATTTATACT ATTTTTTTAT AATATATTAT CTATATTCTT TTACTAAAAA

1381   ACAAAAATAC CTATAAGAAC AATAAAAATA TAATTACATT TACGGAAAAT AGCTGGTTTT
       TGTTTTTATG GATATTCTTG TTATTTTAT ATTAATGTAA ATGCCTTTTA TCGACCAAAA

7866.SL →
1441   AGTTTACCAA CTTAGAGTAA TTATCATATT GAATCTATAT TGCTAATTAG CTAATAAAAA
       TCAAATGGTT GAATCTCATT AATAGTATAA CTTAGATATA ACGATTAATC GATTATTTT
                   ← 7874.SL

1501   CCCGGGTTAA TTAATTAGTC ATCAGGCAGG GCGAGAACGA GACTATCTGC TCGTTAATTA
       GGGCCCAATT AATTAATCAG TAGTCCGTCC CGCTCTTGCT CTGATAGACG AGCAATTAAT

⇒ H6p
1561   ATTAGAGCTT CTTTATTCTA TACTTAAAAA GTGAAAATAA ATACAAAGGT TCTTGAGGGT
       TAATCTCGAA GAAATAAGAT ATGAATTTTT CACTTTTATT TATGTTTCCA AGAACTCCCA

1621   TGTGTTAAAT TGAAAGCGAG AAATAATCAT AAATTATTTC ATTATCGCGA TATCCGTTAA
       ACACAATTTA ACTTTCGCTC TTTATTAGTA TTTAATAAAG TAATAGCGCT ATAGGCAATT

⇒ Nipah G
                        MetProAla GluAsnLys LysValArgPhe GluAsnThr ThrSerAsp
1681   GTTTGTATCG TAATGCCGGC AGAAAACAAG AAAGTTAGAT TCGAAAATAC TACTTCAGAC
       CAAACATAGC ATTACGGCCG TCTTTTGTTC TTTCAATCTA AGCTTTTATG ATGAAGTCTG LysGlyLysIle ProSerLys ValIleLys SerTyrTyrGly ThrMetAsp IleLysLys
1741   AAAGGGAAAA TTCCTAGTAA AGTTATTAAG AGCTACTACG GAACCATGGA CATTAAGAAA
       TTTCCCTTTT AAGGATCATT TCAATAATTC TCGATGATGC CTTGGTACCT GTAATTCTTT
                       ← 11472.SL IleAsnGluGly LeuLeuAsp SerLysIle LeuSerAlaPhe AsnThrVal IleAlaLeu
1801   ATAAATGAAG GATTATTGGA CAGCAAAATA TTAAGTGCTT TCAACACAGT AATAGCATTG
       TATTTACTTC CTAATAACCT GTCGTTTTAT AATTCACGAA AGTTGTGTCA TTATCGTAAC LeuGlySerIle ValIleIle ValMetAsn IleMetIleIle GlnAsnTyr ThrArgSer
1861   CTTGGATCTA TCGTGATCAT AGTGATGAAT ATAATGATCA TCCAAAATTA CACAAGATCA
       GAACCTAGAT AGCACTAGTA TCACTACTTA TATTACTAGT AGGTTTTAAT GTGTTCTAGT
```

FIG. 3C (Continued)

```
      ThrAspAsnGln AlaValIle LysAspAla LeuGlnGlyIle GlnGlnGln IleLysGly
1921  ACAGACAATC AGGCCGTGAT CAAAGATGCG TTGCAGGGTA TCCAACAGCA GATCAAAGGG
      TGTCTGTTAG TCCGGCACTA GTTTCTACGC AACGTCCCAT AGGTTGTCGT CTAGTTTCCC

LeuAlaAspLys IleGlyThr GluIleGly ProLysValSer LeuIleAsp ThrSerSer
1981  CTTGCTGACA AAATCGGCAC AGAGATAGGG CCCAAAGTAT CACTGATTGA CACATCCAGT
      GAACGACTGT TTTAGCCGTG TCTCTATCCC GGGTTTCATA GTGACTAACT GTGTAGGTCA

11473.SL →
      ThrIleThrIle ProAlaAsn IleGlyLeu LeuGlySerLys IleSerGln SerThrAla
2041  ACCATTACTA TCCCAGCTAA CATTGGGCTG TTAGGTTCAA AGATCAGCCA GTCGACTGCA
      TGGTAATGAT AGGGTCGATT GTAACCCGAC AATCCAAGTT TCTAGTCGGT CAGCTGACGT

SerIleAsnGlu AsnValAsn GluLysCys LysPheThrLeu ProProLeu LysIleHis
2101  AGTATAAATG AGAATGTGAA TGAAAAATGC AAATTCACAC TGCCTCCCTT GAAAATCCAC
      TCATATTTAC TCTTACACTT ACTTTTTACG TTTAAGTGTG ACGGAGGGAA CTTTTAGGTG
                                                      ← 11474.SL

GluCysAsnIle SerCysPro AsnProLeu ProPheArgGlu TyrArgPro GlnThrGlu
2161  GAATGTAACA TTTCTTGTCC TAACCCACTC CCTTTTAGAG AGTATAGGCC ACAGACAGAA
      CTTACATTGT AAAGAACAGG ATTGGGTGAG GGAAAATCTC TCATATCCGG TGTCTGTCTT

GlyValSerAsn LeuValGly LeuProAsn AsnIleCysLeu GlnLysThr SerAsnGln
2221  GGGGTGAGCA ATCTAGTAGG ATTACCTAAT AATATTTGCC TGCAAAAGAC ATCTAATCAG
      CCCCACTCGT TAGATCATCC TAATGGATTA TTATAAACGG ACGTTTTCTG TAGATTAGTC

IleLeuLysPro LysLeuIle SerTyrThr LeuProValVal GlyGlnSer GlyThrCys
2281  ATATTGAAGC CAAAGCTGAT TCATACACT TTACCCGTAG TCGGTCAAAG TGGTACCTGT
      TATAACTTCG GTTTCGACTA AGTATGTGA AATGGGCATC AGCCAGTTTC ACCATGGACA

IleThrAspPro LeuLeuAla MetAspGlu GlyTyrPheAla TyrSerHis LeuGluArg
2341  ATCACAGACC CATTGCTGGC TATGGACGAG GGCTATTTTG CATATAGCCA CCTGGAAAGA
      TAGTGTCTGG GTAACGACCG ATACCTGCTC CCGATAAAAC GTATATCGGT GGACCTTTCT

IleGlySerCys SerArgGly ValSerLys GlnArgIleIle GlyValGly GluValLeu
2401  ATCGGATCAT GTTCAAGAGG GGTCTCCAAA CAAAGAATAA TAGGAGTTGG AGAGGTACTA
      TAGCCTAGTA CAAGTTCTCC CCAGAGGTTT GTTTCTTATT ATCCTCAACC TCTCCATGAT

11475.SL →
      AspArgGlyAsp GluValPro SerLeuPhe MetThrAsnVal TrpThrPro ProAsnPro
2461  GACAGAGGTG ATGAAGTTCC TTCTTTATTT ATGACCAATG TCTGGACCCC ACCAAATCCA
      CTGTCTCCAC TACTTCAAGG AAGAAATAAA TACTGGTTAC AGACCTGGGG TGGTTTAGGT

AsnThrValTyr HisCysSer AlaValTyr AsnAsnGluPhe TyrTyrVal LeuCysAla
2521  AACACCGTTT ACCACTGTAG TGCTGTATAC AACAATGAAT TCTATTATGT ACTTGTGCA
      TTGTGGCAAA TGGTGACATC ACGACATATG TTGTTACTTA AGATAATACA TGAAACACGT

ValSerThrVal GlyAspPro IleLeuAsn SerThrTyrTrp SerGlySer LeuMetMet
2581  GTGTCAACTG TTGGAGACCC TATTCTGAAT AGCACCTACT GGTCCGGATC TCTAATGATG
      CACAGTTGAC AACCTCTGGG ATAAGACTTA TCGTGGATGA CCAGGCCTAG AGATTACTAC
             ← 11476.SL
```

FIG. 3C (Continued)

```
              ThrArgLeuAla ValLysPro LysSerAsn GlyGlyGlyTyr AsnGlnHis GlnLeuAla
2641   ACCCGTCTAG CTGTGAAACC CAAGAGTAAT GGTGGGGGTT ACAATCAACA TCAACTTGCC
       TGGGCAGATC GACACTTTGG GTTCTCATTA CCACCCCCAA TGTTAGTTGT AGTTGAACGG

LeuArgSerIle GluLysGly ArgTyrAsp LysValMetPro TyrGlyPro SerGlyIle
2701   CTACGAAGTA TCGAGAAAGG GAGGTATGAT AAAGTTATGC CGTATGGACC TTCAGGCATC
       GATGCTTCAT AGCTCTTTCC CTCCATACTA TTTCAATACG GCATACCTGG AAGTCCGTAG

LysGlnGlyAsp ThrLeuTyr PheProAla ValGlyPheLeu ValArgThr GluPheLys
2761   AAACAGGGTG ACACCCTGTA TTTTCCTGCT GTAGGATTTT TGGTCAGGAC AGAGTTTAAA
       TTTGTCCCAC TGTGGGACAT AAAAGGACGA CATCCTAAAA ACCAGTCCTG TCTCAAATTT

TyrAsnAspSer AsnCysPro IleThrLys CysGlnTyrSer LysProGlu AsnCysArg
2821   TACAATGATT CAAATTGTCC CATCACGAAG TGTCAATACA GTAAACCTGA AAATTGCAGG
       ATGTTACTAA GTTTAACAGG GTAGTGCTTC ACAGTTATGT CATTTGGACT TTTAACGTCC

11477.SL →
              LeuSerMetGly IleArgPro AsnSerHis TyrIleLeuArg SerGlyLeu LeuLysTyr
2881   CTATCTATGG GGATTAGACC AAACAGCCAT TATATCCTTC GATCTGGACT ATTAAAATAC
       GATAGATACC CCTAATCTGG TTTGTCGGTA ATATAGGAAG CTAGACCTGA TAATTTTATG

AsnLeuSerAsp GlyGluAsn ProLysVal ValPheIleGlu IleSerAsp GlnArgLeu
2941   AATCTATCAG ATGGGGAGAA CCCCAAAGTT GTATTCATTG AAATATCTGA TCAAAGATTA
       TTAGATAGTC TACCCCTCTT GGGGTTTCAA CATAAGTAAC TTTATAGACT AGTTTCTAAT
              ← 11478.SL

SerIleGlySer ProSerLys IleTyrAsp SerLeuGlyGln ProValPhe TyrGlnAla
3001   TCTATTGGAT CTCCTAGCAA AATCTATGAT TCTTTGGGTC AACCTGTTTT CTACCAAGCG
       AGATAACCTA GAGGATCGTT TTAGATACTA AGAAACCCAG TTGGACAAAA GATGGTTCGC

SerPheSerTrp AspThrMet IleLysPhe GlyAspValLeu ThrValAsn ProLeuVal
3061   TCATTTTCAT GGGATACTAT GATTAAATTT GGAGATGTTC TAACAGTCAA CCCTCTGGTT
       AGTAAAAGTA CCCTATGATA CTAATTTAAA CCTCTACAAG ATTGTCAGTT GGGAGACCAA

ValAsnTrpArg AsnAsnThr ValIleSer ArgProGlyGln SerGlnCys ProArgPhe
3121   GTCAATTGGC GTAATAACAC GGTAATATCA AGACCCGGGC AATCACAATG CCCTAGATTC
       CAGTTAACCG CATTATTGTG CCATTATAGT TCTGGGCCCG TTAGTGTTAC GGGATCTAAG

AsnThrCysPro GluIleCys TrpGluGly ValTyrAsnAsp AlaPheLeu IleAspArg
3181   AATACATGTC CAGAGATCTG CTGGGAAGGA GTTTATAATG ATGCATTCCT AATTGACAGA
       TTATGTACAG GTCTCTAGAC GACCCTTCCT CAAATATTAC TACGTAAGGA TTAACTGTCT

11479.SL →
              IleAsnTrpIle SerAlaGly ValPheLeu AspSerAsnGln ThrAlaGlu AsnProVal
3241   ATCAATTGGA TAAGCGCGGG TGTATTCCTT GACAGCAATC AGACCGCAGA AAATCCTGTT
       TAGTTAACCT ATTCGCGCCC ACATAAGGAA CTGTCGTTAG TCTGGCGTCT TTTAGGACAA

PheThrValPhe LysAspAsn GluIleLeu TyrArgAlaGln LeuAlaSer GluAspThr
3301   TTTACTGTAT TCAAAGATAA TGAAATACTT TATAGGGCAC AACTGGCTTC TGAGGACACC
       AAATGACATA AGTTTCTATT ACTTTATGAA ATATCCCGTG TTGACCGAAG ACTCCTGTGG
                                                     ← 11480.SL
```

FIG. 3C (Continued)

```
          AsnAlaGlnLys ThrIleThr AsnCysPhe LeuLeuLysAsn LysIleTrp CysIleSer
   3361   AATGCACAAA AAACAATAAC TAATTGTTTT CTCTTGAAGA ATAAGATTTG GTGCATATCA
          TTACGTGTTT TTTGTTATTG ATTAACAAAA GAGAACTTCT TATTCTAAAC CACGTATAGT

LeuValGluIle TyrAspThr GlyAspAsn ValIleArgPro LysLeuPhe AlaValLys
   3_1    TTGGTTGAGA TATATGACAC AGGAGACAAT GTCATAAGAC CCAAACTATT CGCGGTTAAG
          AACCAACTCT ATATACTGTG TCCTCTGTTA CAGTATTCTG GGTTTGATAA GCGCCAATTC

⇒ FSL
          IleProGluGln CysThr (SEQ ID NO: 17)
   3481   ATACCAGAGC AATGTACATA ACTCGAGTTT TTATTGACTA GTTAATCATA AGATAAATAA
          TATGGTCTCG TTACATGTAT TGAGCTCAAA AATAACTGAT CAATTAGTAT TCTATTTATT

7867.SL →
   3541   TATACAGCAT TGTAACCATC GTCATCCGTT ATACGGGGAA TAATATTACC ATACAGTATT
          ATATGTCGTA ACATTGGTAG CAGTAGGCAA TATGCCCCTT ATTATAATGG TATGTCATAA
                            ← 7873.SL

3601   ATTAAATTTT CTTACGAAGA ATATAGATCG GTATTTATCG TTAGTTTATT TTACATTTAT
          TAATTTAAAA GAATGCTTCT TATATCTAGC CATAAATAGC AATCAAATAA AATGTAAATA

3661   TAATTAAACA TGTCTACTAT TACCTGTTAT GGAAATGACA AATTTAGTTA TATAATTTAT
          ATTAATTTGT ACAGATGATA ATGGACAATA CCTTTACTGT TTAAATCAAT ATATTAAATA

3721   CATAAAATTA AGATAATAAT AATGAAATCA AATAATTATG TAAATGCTAC TAGATTATGT
          GTATTTTAAT TCTATTATTA TTACTTTAGT TTATTAATAC ATTTACGATG ATCTAATACA

3781   GAATTACGAG GAAGAAAGTT TACGAACTGG AAAAAATTAA GTGAATCTAA AATATTAGTC
          CTTAATGCTC CTTCTTTCAA ATGCTTGACC TTTTTTAATT CACTTAGATT TTATAATCAG

3841   GATAATGTAA AAAAAATAAA TGATAAAACT AACCAGTTAA AAACGGATAT GATTATATAC
          CTATTACATT TTTTTTATTT ACTATTTTGA TTGGTCAATT TTTGCCTATA CTAATATATG

3901   GTTAAGGATA TTGATCATAA AGGAAGAGAT ACTTGCGGTT ACTATGTACA CCAAGATCTG
          CAATTCCTAT AACTAGTATT TCCTTCTCTA TGAACGCCAA TGATACATGT GGTTCTAGAC

7868.SL →
   3961   GTATCTTCTA TATCAAATTG GATATCTCCG TTATTCGCCG TTAAGGTAAA TAAAATTATT
          CATAGAAGAT ATAGTTTAAC CTATAGAGGC AATAAGCGGC AATTCCATTT ATTTTAATAA
                            ← 7872.SL

4021   AACTATTATA TATGTAATGA ATATGATATA CGACTTAGCG AAATGGAATC TGATATGACA
          TTGATAATAT ATACATTACT TATACTATAT GCTGAATCGC TTTACCTTAG ACTATACTGT

4081   GAAGTAATAG ATGTAGTTGA TAAATTAGTA GGAGGATACA ATGATGAAAT AGCAGAAATA
          CTTCATTATC TACATCAACT ATTTAATCAT CCTCCTATGT TACTACTTTA TCGTCTTTAT

4141   ATATATTTGT TTAATAAATT TATAGAAAAA TATATTGCTA ACATATCGTT ATCAACTGAA
          TATATAAACA AATTATTTAA ATATCTTTTT ATATAACGAT TGTATAGCAA TAGTTGACTT

_01    TTATCTAGTA TATTAAATAA TTTTATAAAT TTAATAAAA AATACAATAA CGACATAAAA
          AATAGATCAT ATAATTTATT AAAATATTTA AAATTATTTT TTATGTTATT GCTGTATTTT
```

FIG. 3C (Continued)

```
  _61  GATATTAAAT CTTTAATTCT TGATCTGAAA AACACATCTA TAAAACTAGA TAAAAAGTTA
       CTATAATTTA GAAATTAAGA ACTAGACTTT TTGTGTAGAT ATTTTGATCT ATTTTTCAAT

4321  TTCGATAAAG ATAATAATGA ATCGAACGAT GAAAAATTGG AAACAGAAGT TGATAGCTA
       AAGCTATTTC TATTATTACT TAGCTTGCTA CTTTTTAACC TTTGTCTTCA ACTATTCGAT

4381  ATTTTTTTCA TCTAAATAGT ATTATTTTAT TGAAGTACGA AGTTTTACGT TAGATAAATA
       TAAAAAAGT AGATTTATCA TAATAAAATA ACTTCATGCT TCAAAATGCA ATCTATTTAT

4441  ATAAAGGTCG ATTTTTATTT TGTTAAATAT CAAATATGTC ATTATCTGAT AAAGATACAA
       TATTTCCAGC TAAAAATAAA ACAATTTATA GTTATACAG TAATAGACTA TTTCTATGTT

7869.SL →
 4501  AAACACACGG TGATTATCAA CCATCTAACG AACAGATATT ACAAAAAATA CGTCGGACTA
       TTTGTGTGCC ACTAATAGTT GGTAGATTGC TTGTCTATAA TGTTTTTTAT GCAGCCTGAT
                    ← 7871.SL

4561  TGGAAAACGA AGCTGATAGC CTCAATAGAA GAAGCATTAA AGAAATTGTT GTAGATGTTA
       ACCTTTTGCT TCGACTATCG GAGTTATCTT CTTCGTAATT TCTTTAACAA CATCTACAAT

4621  TGAAGAATTG GGATCATCCT CTCAACGAAG AAATAGATAA AGTTCTAAAC TGGAAAAATG
       ACTTCTTAAC CCTAGTAGGA GAGTTGCTTC TTTATCTATT TCAAGATTTG ACCTTTTTAC

4681  ATACATTAAA CGATTTAGAT CATCTAAATA CAGATGATAA TATTAAGGAA ATCATACAAT
       TATGTAATTT GCTAAATCTA GTAGATTTAT GTCTACTATT ATAATTCCTT TAGTATGTTA

4741  GTCTGATTAG AGAATTTGCG TTTAAAAAGA TCAATTCTAT TATGTATAGT TATGCTATGG
       CAGACTAATC TCTTAAACGC AAATTTTTCT AGTTAAGATA ATACATATCA ATACGATACC

4801  TAAAACTCAA TTCAGATAAC GAAACATTGA AAGATAAAAT TAAGGATTAT TTTATAGAAA
       ATTTGAGTT AAGTCTATTG CTTTGTAACT TTCTATTTA ATTCCTAATA AAATATCTTT

4861  CTATTCTTAA AGACAAACGT GGTTATAAAC AAAAGCCATT ACCCTAGAGC GGCCGCCACC
       GATAAGAATT TCTGTTTGCA CCAATATTTG TTTTCGGTAA TGGGATCTCG CCGGCGGTGG

4921  GCGGTGGAGC TCCAGCTTTT GTTCCCTTTA GTGAGGGTTA ATTTCGAGCT TGGCGTAATC
       CGCCACCTCG AGGTCGAAAA CAAGGGAAAT CACTCCCAAT TAAAGCTCGA ACCGCATTAG

4981  ATGGTCATAG CTGTTTCC (SEQ ID NO: 18)
       TACCAGTATC GACAAAGG (SEQ ID NO: 19)
           ← M13R
```

FIG. 3C (Continued)

```
                    P/V/C
            N       P/V/C
5'-leader                      M    F      G              L              3'-trailer ↓     Nipah virus (AF212302)
                                           18246 bp
                                  F
                                        Vaccine antigen
```

FIG. 4A

```
              Nru I   H6p                    M  V  V  I  L  D  K  R
11458.SL   5' TA TCGCGA TATCCGTTAAGTTTGTATCGT AATGGTAGTTATACTTGACAAGAGA

D  L  L  F  V  F  G  P  N  L
              GATTTGCTTTTTGTATTTGGCCCCAACCTT
                        ↓
11456.SL   5' GATTTGCTATTCGTATTTGGGCCCAACCTT
11457.SL   3' CTAAACGATAAGCATAAA CCCGGG TTGGAA
                                  Apa I

G  D  L  Y  Y  I  G  T  *  (SEQ ID NO: 20)
              GGGGATCTCTACTACATTGGGACATAG   (SEQ ID NO: 21)
11459.SL   3' CCCCTAGAGATGATGTAACCCTGTATC GGGCCC TAGGCG (SEQ ID NO: 22)
                                           XmaI BamH I
```

FIG. 4B

```
         M13F→                                                    ⇒F8R
  1  GTAAAACGAC GGCCAGTGAA TTGTAATACG ACTCACTATA GGGCGAATTG GGTGACCCTT
     CATTTTGCTG CCGGTCACTT AACATTATGC TGAGTGATAT CCCGCTTAAC CCACTGGGAA

61  TACAAGAATA AAAGAAGAAA CAACTGTGAA ATAGTTTATA AATGTAATTC GTATGCAGAA
     ATGTTCTTAT TTTCTTCTTT GTTGACACTT TATCAAATAT TTACATTAAG CATACGTCTT

121  AACGATAATA TATTTTGGTA TGAGAAATCT AAAGGAGACA TAGTTTGTAT AGACATGCGC
     TTGCTATTAT ATAAAACCAT ACTCTTTAGA TTTCCTCTGT ATCAAACATA TCTGTACGCG

181  TCTTCCGATG AGATATTCGA TGCTTTTCTA ATGTATCATA TAGCTACAAG ATATGCCTAT
     AGAAGGCTAC TCTATAAGCT ACGAAAAGAT TACATAGTAT ATCGATGTTC TATACGGATA

241  CATCATGATG ATATATATCT ACAAATAGTG TTATATTATT CTAATAATCA AAATGTTATA
     GTACTACTAC TATATATAGA TGTTTATCAC AATATAATAA GATTATTAGT TTTACAATAT

301  TCTTATATTA CGAAAAATAA ATACGTTAAG TATATAAGAA ATAAAACTAG AGACGATATT
     AGAATATAAT GCTTTTTATT TATGCAATTC ATATATTCTT TATTTTGATC TCTGCTATAA

361  CATAAAGTAA AAATATTAGC TCTAGAAGAC TTTACAACGG AAGAAATATA TTGTTGGATT
     GTATTTCATT TTTATAATCG AGATCTTCTG AAATGTTGCC TTCTTTATAT AACAACCTAA

1  AGTAATATAT AACAGCGTAG CTGCACGGTT TTGATCATTT TCCAACAATA TAAACCAATG
     TCATTATATA TTGTCGCATC GACGTGCCAA AACTAGTAAA AGGTTGTTAT ATTTGGTTAC

7864.SL →
481  AAGGAGGACG ACTCATCAAA CATAAATAAC ATTCACGGAA ATATTCAGT ATCAGATTTA
     TTCCTCCTGC TGAGTAGTTT GTATTTATTG TAAGTGCCTT TTATAAGTCA TAGTCTAAAT
          ← 7876.SL

541  TCACAAGATG ATTATGTTAT TGAATGTATA GACGGATCTT TTGATTCGAT CAAGTATAGA
     AGTGTTCTAC TAATACAATA ACTTACATAT CTGCCTAGAA AACTAAGCTA GTTCATATCT

601  GATATAAAGG TTATAATAAT GAAGAATAAC GGTTACGTTA ATTGTAGTAA ATTATGTAAA
     CTATATTTCC AATATTATTA CTTCTTATTG CCAATGCAAT TAACATCATT TAATACATTT

661  ATGCGGAATA AATACTTTTC TAGATGGTTG CGTCTTTCTA CTTCTAAAGC ATTATTAGAC
     TACGCCTTAT TTATGAAAAG ATCTACCAAC GCAGAAAGAT GAAGATTTCG TAATAATCTG

721  ATTTACAATA ATAAGTCAGT AGATAATGCT ATTGTAAAG TCTATGGTAA AGGTAAGAAA
     TAAATGTTAT TATTCAGTCA TCTATTACGA TAACAATTTC AGATACCATT TCCATTCTTT

781  CTTATTATAA CAGGATTTTA TCTCAAACAA AATATGATAC GTTATGTTAT TGAGTGGATA
     GAATAATATT GTCCTAAAAT AGAGTTTGTT TTATACTATG CAATACAATA ACTCACCTAT

841  GGGGATGATT TTACAAACGA TATATACAAA ATGATTAATT TCTATAATGC GTTATTCGGT
     CCCCTACTAA AATGTTTGCT ATATATGTTT TACTAATTAA AGATATTACG CAATAAGCCA

7865.SL →
901  AACGATGAAT TAAAAATAGT ATCCTGTGAA AACACTCTAT GCCCGTTTAT AGAACTTGGT
     TTGCTACTTA ATTTTTATCA TAGGACACTT TTGTGAGATA CGGGCAAATA TCTTGAACCA
                               ←7875.SL
```

FIG. 4D

```
 961  AGATGCTATT ATGGTAAAAA ATGTAAGTAT ATACACGGAG ATCAATGTGA TATCTGTGGT
      TCTACGATAA TACCATTTTT TACATTCATA TATGTGCCTC TAGTTACACT ATAGACACCA

1021  CTATATATAC TACACCCTAC CGATATTAAC CAACGAGTTT CTCACAAGAA AACTTGTTTA
      GATATATATG ATGTGGGATG GCTATAATTG GTTGCTCAAA GAGTGTTCTT TTGAACAAAT

1081  GTAGATAGAG ATTCTTTGAT TGTGTTTAAA AGAAGTACCA GTAAAAAGTG TGGCATATGC
      CATCTATCTC TAAGAAACTA ACACAAATTT TCTTCATGGT CATTTTTCAC ACCGTATACG

1141  ATAGAAGAAA TAAACAAAAA ACATATTTCC GAACAGTATT TTGGAATTCT CCCAAGTTGT
      TATCTTCTTT ATTTGTTTTT TGTATAAAGG CTTGTCATAA AACCTTAAGA GGGTTCAACA

1201  AAACATATTT TTTGCCTATC ATGTATAAGA CGTTGGGCAG ATACTACCAG AAATACAGAT
      TTTGTATAAA AAACGGATAG TACATATTCT GCAACCCGTC TATGATGGTC TTTATGTCTA

1261  ACTGAAAATA CGTGTCCTGA ATGTAGAATA GTTTTTCCTT TCATAATACC CAGTAGGTAT
      TGACTTTTAT GCACAGGACT TACATCTTAT CAAAAAGGAA AGTATTATGG GTCATCCATA

1321  TGGATAGATA ATAAATATGA TAAAAAAATA TTATATAATA GATATAAGAA AATGATTTTT
      ACCTATCTAT TATTTATACT ATTTTTTTAT AATATATTAT CTATATTCTT TTACTAAAAA

1381  ACAAAAATAC CTATAAGAAC AATAAAAATA TAATTACATT TACGGAAAAT AGCTGGTTTT
      TGTTTTTATG GATATTCTTG TTATTTTTAT ATTAATGTAA ATGCCTTTTA TCGACCAAAA

7866.SL →
1441  AGTTTACCAA CTTAGAGTAA TTATCATATT GAATCTATAT TGCTAATTAG CTAATAAAAA
      TCAAATGGTT GAATCTCATT AATAGTATAA CTTAGATATA ACGATTAATC GATTATTTTT
            ← 7874.SL

1501  CCCGGGTTAA TTAATTAGTC ATCAGGCAGG GCGAGAACGA GACTATCTGC TCGTTAATTA
      GGGCCCAATT AATTAATCAG TAGTCCGTCC CGCTCTTGCT CTGATAGACG AGCAATTAAT

⇒ H6p
1561  ATTAGAGCTT CTTTATTCTA TACTTAAAAA GTGAAAATAA ATACAAAGGT TCTTGAGGGT
      TAATCTCGAA GAAATAAGAT ATGAATTTTT CACTTTTATT TATGTTTCCA AGAACTCCCA

NruI
1621  TGTGTTAAAT TGAAAGCGAG AAATAATCAT AAATTATTTC ATTATCGCGA TATCCGTTAA
      ACACAATTTA ACTTTCGCTC TTTATTAGTA TTTAATAAAG TAATAGCGCT ATAGGCAATT

⇒Nipah F
                 MetValVal IleLeuAsp LysArgCysTyr CysAsnLeu LeuIleLeu
1681  GTTTGTATCG TAATGGTAGT TATACTTGAC AAGAGATGTT ATTGTAATCT TTTAATATTG
      CAAACATAGC ATTACCATCA ATATGAACTG TTCTCTACAA TAACATTAGA AAATTATAAC IleLeuMetIle SerGluCys SerValGly IleLeuHisTyr GluLysLeu SerLysIle
1741  ATTTTGATGA TCTCGGAGTG TAGTGTTGGG ATTCTACATT ATGAGAAATT GAGTAAAATT
      TAAAACTACT AGAGCCTCAC ATCACAACCC TAAGATGTAA TACTCTTTAA CTCATTTTAA
                 ← 11468.SL GlyLeuValLys GlyValThr ArgLysTyr LysIleLysSer AsnProLeu ThrLysAsp
1801  GGACTTGTCA AAGGAGTAAC AAGAAAATAC AAGATTAAAA GCAATCCTCT CACAAAAGAC
      CCTGAACAGT TTCCTCATTG TTCTTTTATG TTCTAATTTT CGTTAGGAGA GTGTTTTCTG
```

FIG. 4D (Continued)

```
             IleValIleLys MetIlePro AsnValSer AsnMetSerGln CysThrGly SerValMet
1861         ATTGTTATAA AAATGATTCC GAATGTGTCG AACATGTCTC AGTGCACAGG GAGTGTCATG
             TAACAATATT TTTACTAAGG CTTACACAGC TTGTACAGAG TCACGTGTCC CTCACAGTAC

GluAsnTyrLys ThrArgLeu AsnGlyIle LeuThrProIle LysGlyAla LeuGluIle
1921         GAAAATTATA AAACACGATT AAACGGTATC TTAACACCTA TAAAGGGAGC GTTAGAGATC
             CTTTTAATAT TTTGTGCTAA TTTGCCATAG AATTGTGGAT ATTTCCCTCG CAATCTCTAG

TyrLysAsnAsn ThrHisAsp LeuValGly AspValArgLeu AlaGlyVal IleMetAla
1981         TACAAAAACA ACACTCATGA CCTTGTCGGT GATGTGAGAT TAGCCGGAGT TATAATGGCA
             ATGTTTTTGT TGTGAGTACT GGAACAGCCA CTACACTCTA ATCGGCCTCA ATATTACCGT

11460.SL →
             GlyValAlaIle GlyIleAla ThrAlaAla GlnIleThrAla GlyValAla LeuTyrGlu
2041         GGAGTTGCTA TTGGGATTGC AACCGCAGCT CAAATCACTG CAGGTGTAGC ACTATATGAG
             CCTCAACGAT AACCCTAACG TTGGCGTCGA GTTTAGTGAC GTCCACATCG TGATATACTC

AlaMetLysAsn AlaAspAsn IleAsnLys LeuLysSerSer IleGluSer ThrAsnGlu
2101         GCAATGAAGA ATGCTGACAA CATCAACAAA CTCAAAAGCA GCATTGAATC AACTAATGAA
             CGTTACTTCT TACGACTGTT GTAGTTGTTT GAGTTTTCGT CGTAACTTAG TTGATTACTT
                                                              ← 11465.SL

AlaValValLys LeuGlnGlu ThrAlaGlu LysThrValTyr ValLeuThr AlaLeuGln
2161         GCTGTCGTTA AACTTCAAGA GACTGCAGAA AAGACAGTCT ATGTGCTGAC TGCTCTACAG
             CGACAGCAAT TTGAAGTTCT CTGACGTCTT TTCTGTCAGA TACACGACTG ACGAGATGTC

AspTyrIleAsn ThrAsnLeu ValProThr IleAspLysIle SerCysLys GlnThrGlu
2221         GATTACATTA ATACTAATTT AGTACCGACA ATTGACAAGA TAAGCTGCAA ACAGACAGAA
             CTAATGTAAT TATGATTAAA TCATGGCTGT TAACTGTTCT ATTCGACGTT TGTCTGTCTT

11456.SL →      ApaI
             LeuSerLeuAsp LeuAlaLeu SerLysTyr LeuSerAspLeu LeuPheVal PheGlyPro
2281         CTCTCACTAG ATCTGGCATT ATCAAAGTAC CTCTCTGATT TGCTATTCGT ATTTGGGCCC
             GAGAGTGATC TAGACCGTAA TAGTTTCATG GAGAGACTAA ACGATAAGCA TAAACCCGGG
                                                              ← 11457.SL

AsnLeuGlnAsp ProValSer AsnSerMet ThrIleGlnAla IleSerGln AlaPheGly
2341         AACCTTCAAG ACCCAGTTTC TAATTCAATG ACTATACAGG CTATATCTCA GGCATTCGGT
             TTGGAAGTTC TGGGTCAAAG ATTAAGTTAC TGATATGTCC GATATAGAGT CCGTAAGCCA

GlyAsnTyrGlu ThrLeuLeu ArgThrLeu GlyTyrAlaThr GluAspPhe AspAspLeu
2401         GGAAATTATG AAACACTGCT AAGAACATTG GGTTACGCTA CAGAAGACTT TGATGATCTT
             CCTTTAATAC TTTGTGACGA TTCTTGTAAC CCAATGCGAT GTCTTCTGAA ACTACTAGAA

11461.SL →
             LeuGluSerAsp SerIleThr GlyGlnIle IleTyrValAsp LeuSerSer TyrTyrIle
2461         CTAGAAAGTG ACAGCATAAC AGGTCAAATC ATCTATGTTG ATCTAAGTAG CTACTATATA
             GATCTTTCAC TGTCGTATTG TCCAGTTTAG TAGATACAAC TAGATTCATC GATGATATAT

IleValArgVal TyrPhePro IleLeuThr GluIleGlnGln AlaTyrIle GlnGluLeu
2521         ATTGTCAGGG TTTATTTTCC TATTCTGACT GAAATTCAAC AGGCCTATAT CCAAGAGTTG
             TAACAGTCCC AAATAAAAGG ATAAGACTGA CTTTAAGTTG TCCGGATATA GGTTCTCAAC
                                                              ← 11464.SL
```

FIG. 4D (Continued)

```
         LeuProValSer PheAsnAsn AspAsnSer GluTrpIleSer IleValPro AsnPheIle
   2581  TTACCAGTGA GCTTCAACAA TGATAATTCA GAATGGATCA GTATTGTCCC AAATTTCATA
         AATGGTCACT CGAAGTTGTT ACTATTAAGT CTTACCTAGT CATAACAGGG TTTAAAGTAT

LeuValArgAsn ThrLeuIle SerAsnIle GluIleGlyPhe CysLeuIle ThrLysArg
   2641  TTGGTAAGGA ATACATTAAT ATCAAATATA GAGATTGGAT TTGCCTAAT TACAAAGAGG
         AACCATTCCT TATGTAATTA TAGTTTATAT CTCTAACCTA AACGGATTA ATGTTTCTCC

SerValIleCys AsnGlnAsp TyrAlaThr ProMetThrAsn AsnMetArg GluCysLeu
   2701  AGCGTGATCT GCAACCAAGA TTATGCCACA CCTATGACCA ACAACATGAG AGAATGTTTA
         TCGCACTAGA CGTTGGTTCT AATACGGTGT GGATACTGGT TGTTGTACTC TCTTACAAAT

ThrGlySerThr GluLysCys ProArgGlu LeuValValSer SerHisVal ProArgPhe
   2761  ACGGGATCGA CTGAGAAGTG TCCTCGAGAG CTGGTTGTTT CATCACATGT TCCCAGATTT
         TGCCCTAGCT GACTCTTCAC AGGAGCTCTC GACCAACAAA GTAGTGTACA AGGGTCTAAA

AlaLeuSerAsn GlyValLeu PheAlaAsn CysIleSerVal ThrCysGln CysGlnThr
   2821  GCACTATCTA ACGGGGTTCT GTTTGCCAAT TGCATAAGTG TTACATGTCA GTGTCAAACA
         CGTGATAGAT TGCCCCAAGA CAAACGGTTA ACGTATTCAC AATGTACAGT CACAGTTTGT

11462.SL →
         ThrGlyArgAla IleSerGln SerGlyGlu GlnThrLeuLeu MetIleAsp AsnThrThr
   2881  ACAGGCAGGG CAATCTCACA ATCAGGAGAA CAAACTCTGC TGATGATTGA CAACACCACC
         TGTCCGTCCC GTTAGAGTGT TAGTCCTCTT GTTTGAGACG ACTACTAACT GTTGTGGTGG

CysProThrAla ValLeuGly AsnValIle IleSerLeuGly LysTyrLeu GlySerVal
   2941  TGTCCTACAG CCGTACTCGG TAATGTGATT ATCAGCTTAG GAAATATCT GGGGTCAGTA
         ACAGGATGTC GGCATGAGCC ATTACACTAA TAGTCGAATC CCTTTATAGA CCCCAGTCAT
              ← 11463.SL

AsnTyrAsnSer GluGlyIle AlaIleGly ProProValPhe ThrAspLys ValAspIle
   3001  AATTATAATT CTGAAGGCAT TGCTATCGGT CCTCCAGTCT TTACAGATAA AGTTGATATA
         TTAATATTAA GACTTCCGTA ACGATAGCCA GGAGGTCAGA AATGTCTATT TCAACTATAT

SerSerGlnIle SerSerMet AsnGlnSer LeuGlnGlnSer LysAspTyr IleLysGlu
   3061  TCAAGTCAGA TATCCAGCAT GAATCAGTCC TTACAACAGT CTAAGGACTA TATCAAAGAG
         AGTTCAGTCT ATAGGTCGTA CTTAGTCAGG AATGTTGTCA GATTCCTGAT ATAGTTTCTC

AlaGlnArgLeu LeuAspThr ValAsnPro SerLeuIleSer MetLeuSer MetIleIle
   3121  GCTCAACGAC TCCTTGATAC TGTTAATCCA TCATTAATAA GCATGTTGTC TATGATCATA
         CGAGTTGCTG AGGAACTATG ACAATTAGGT AGTAATTATT CGTACAACAG ATACTAGTAT

LeuTyrValLeu SerIleAla SerLeuCys IleGlyLeuIle ThrPheIle SerPheIle
   3181  CTGTATGTAT TATCGATCGC ATCGTTGTGT ATAGGGTTGA TTACATTTAT CAGTTTTATC
         GACATACATA ATAGCTAGCG TAGCAACACA TATCCCAACT AATGTAAATA GTCAAAATAG

IleValGluLys LysArgAsn ThrTyrSer ArgLeuGluAsp ArgArgVal ArgProThr
   3241  ATTGTTGAGA AAAAGAGAAA CACCTACAGC AGATTAGAGG ATAGGAGAGT CAGACCTACA
         TAACAACTCT TTTTCTCTTT GTGGATGTCG TCTAATCTCC TATCCTCTCA GTCTGGATGT

SerSerGlyAsp LeuTyrTyr IleGlyThr           BamHI (SEQ ID NO: 23)
   3301  AGCAGTGGGG ATCTCTACTA CATTGGGACA TAGCCCGGGA TCCCTCGAGT TTTTATTGAC
         TCGTCACCCC TAGAGATGAT GTAACCCTGT ATCGGGCCCT AGGGAGCTCA AAAATAACTG
```

FIG. 4D (Continued)

```
                    => F8L                              7867.SL →
3361  TAGTTAATCA  TAAGATAAAT  AATATACAGC  ATTGTAACCA  TCGTCATCCG  TTATACGGGG
      ATCAATTAGT  ATTCTATTTA  TTATATGTCG  TAACATTGGT  AGCAGTAGGC  AATATGCCCC
                                                          ← 7873.SL

3_1   AATAATATTA  CCATACAGTA  TTATTAAATT  TTCTTACGAA  GAATATAGAT  CGGTATTTAT
      TTATTATAAT  GGTATGTCAT  AATAATTTAA  AAGAATGCTT  CTTATATCTA  GCCATAAATA

3481  CGTTAGTTTA  TTTTACATTT  ATTAATTAAA  CATGTCTACT  ATTACCTGTT  ATGGAAATGA
      GCAATCAAAT  AAAATGTAAA  TAATTAATTT  GTACAGATGA  TAATGGACAA  TACCTTTACT

3541  CAAATTTAGT  TATATAATTT  ATGATAAAAT  TAAGATAATA  ATAATGAAAT  CAAATAATTA
      GTTTAAATCA  ATATATTAAA  TACTATTTTA  ATTCTATTAT  TATTACTTTA  GTTTATTAAT

3601  TGTAAATGCT  ACTAGATTAT  GTGAATTACG  AGGAACAAAG  TTTACGAACT  GGAAAAAATT
      ACATTTACGA  TGATCTAATA  CACTTAATGC  TCCTTGTTTC  AAATGCTTGA  CCTTTTTAA

3661  AAGTGAATCT  AAAATATTAG  TCGATAATGT  AAAAAAAATA  AATGATAAAA  CTAACCAGTT
      TTCACTTAGA  TTTTATAATC  AGCTATTACA  TTTTTTTTAT  TTACTATTTT  GATTGGTCAA

3721  AAAAACGGAT  ATGATTATAT  ACGTTAAGGA  TATTGATCAT  AAAGGAAGAG  ATACTTGCGG
      TTTTTGCCTA  TACTAATATA  TGCAATTCCT  ATAACTAGTA  TTTCCTTCTC  TATGAACGCC

7868.SL →
3781  TTACTATGTA  CACCAAGATC  TGGTATCTTC  TATATCAAAT  TGGATATCTC  CGTTATTCGC
      AATGATACAT  GTGGTTCTAG  ACCATAGAAG  ATATAGTTTA  ACCTATAGAG  GCAATAAGCG
                                                          ← 7872.SL

3841  CGTTAAGGTA  AATAAAATTA  TTAACTATTA  TATATGTAAT  GAATATGATA  TACGACTTAG
      GCAATTCCAT  TTATTTTAAT  AATTGATAAT  ATATACATTA  CTTATACTAT  ATGCTGAATC

3901  CGAAATGGAA  TCTGATATGA  CAGAAGTAAT  AGATGTAGTT  GATAAATTAG  TAGGAGGATA
      GCTTTACCTT  AGACTATACT  GTCTTCATTA  TCTACATCAA  CTATTTAATC  ATCCTCCTAT

3961  CAATGATGAA  ATAGCAGAAA  TAATATATTT  GTTAATAAA   TTATAGAAA   AATATATTGC
      GTTACTACTT  TATCGTCTTT  ATTATATAAA  CAATTATTT   AATATCTTT   TTATATAACG

4021  TAACATATCG  TTATCAACTG  AATTATCTAG  TATATTAAAT  AATTTTATAA  ATTTTAATAA
      ATTGTATAGC  AATAGTTGAC  TTAATAGATC  ATATAATTTA  TTAAAATATT  TAAAATTATT

4081  AAAATACAAT  AACGACATAA  AGATATTAA   ATCTTTAATT  CTTGATCTGA  AAAACACATC
      TTTTATGTTA  TTGCTGTATT  TTCTATAATT  TAGAAATTAA  GAACTAGACT  TTTTGTGTAG

4141  TATAAAACTA  GATAAAAAGT  TATTCGATAA  AGATAATAAT  GAATCGAACG  ATGAAAAATT
      ATATTTTGAT  CTATTTTTCA  ATAAGCTATT  TCTATTATTA  CTTAGCTTGC  TACTTTTTAA

_01   GGAAACAGAA  GTTGATAAGC  TAATTTTTTT  CATCTAAATA  GTATTATTTT  ATGAAGTAC
      CCTTTGTCTT  CAACTATTCG  ATTAAAAAAA  GTAGATTTAT  CATAATAAAA  TACTTCATG

_61   GAAGTTTTAC  GTTAGATAAA  TAATAAAGGT  CGATTTTTAT  TTGTTAAAT   ATCAAATATG
      CTTCAAAATG  CAATCTATTT  ATTATTTCCA  GCTAAAAATA  AACAATTTA   TAGTTTATAC
```

FIG. 4D (Continued)

```
                           7869.SL →
4321  TCATTATCTG ATAAAGATAC AAAAACACAC GGTGATTATC AACCATCTAA CGAACAGATA
      AGTAATAGAC TATTTCTATG TTTTTGTGTG CCACTAATAG TTGGTAGATT GCTTGTCTAT
                            ← 7871.SL
4381  TTACAAAAAA TACGTCGGAC TATGGAAAAC GAAGCTGATA GCCTCAATAG AAGAAGCATT
      AATGTTTTTT ATGCAGCCTG ATACCTTTTG CTTCGACTAT CGGAGTTATC TTCTTCGTAA

4441  AAAGAAATTG TTGTAGATGT TATGAAGAAT TGGGATCATC CTCTCAACGA AGAAATAGAT
      TTTCTTTAAC AACATCTACA ATACTTCTTA ACCCTAGTAG GAGAGTTGCT TCTTTATCTA

4501  AAAGTTCTAA ACTGGAAAAA TGATACATTA AACGATTTAG ATCATCTAAA TACAGATGAT
      TTTCAAGATT TGACCTTTTT ACTATGTAAT TTGCTAAATC TAGTAGATTT ATGTCTACTA

4561  AATATTAAGG AAATCATACA ATGTCTGATT AGAGAATTTG CGTTTAAAAA GATCAATTCT
      TTATAATTCC TTTAGTATGT TACAGACTAA TCTCTTAAAC GCAAATTTTT CTAGTTAAGA

4621  ATTATGTATA GTTATGCTAT GGTAAAACTC AATTCAGATA ACGAAACATT GAAAGATAAA
      TAATACATAT CAATACGATA CCATTTGAG TTAAGTCTAT TGCTTTGTAA CTTTCTATTT

4681  ATTAAGCATT ATTTTATACA AACTATTCTT AAAGACAAAC GTGGTTATAA ACAAAAGCCA
      TAATTCGTAA TAAAATATCT TTGATAAGAA TTTCTGTTTG CACCAATATT TGTTTTCGGT

4741  TTACCCTAGA GCGGCCGCCA CCGCGGTGGA GCTCCAGCTT TGTTCCCTT TAGTGAGGGT
      AATGGGATCT CGCCGGCGGT GGCGCCACCT CGAGGTCGAA ACAAGGGAA ATCACTCCCA

4801  TAATTTCGAG CTTGGCGTAA TCATGGTCAT AGCTGTTTCC  (SEQ ID NO: 24)
      ATTAAAGCTC GAACCGCATT AGTACCAGTA TCGACAAAGG  (SEQ ID NO: 25)
                           ← M13R
```

FIG. 4D (Continued)

```
            Nru I   H6p                     M  V  V  I  L  D  K  R
11458.SL  5' TATCGCGATATCCGTTAAGTTTGTATCGTAATGGTAGTTATACTTGACAAGAGA

D  L  L  F  V  F  G  P  N  L
          GATTTGCTTTTTGTATTTGGCCCCAACCTT
                    ↓
11456.SL  5' GATTTGCTATTCGTATTTGGGCCCAACCTT
11457.SL  3' CTAAACGATAAGCATAAACCCGGGTTGGAA
                                 Apa I

G  D  L  Y  Y  I  G  T  *   (SEQ ID NO: 20)
          GGGGATCTCTACTACATTGGGACATAG   (SEQ ID NO: 21)
11459.SL  3' CCCCTAGAGATGATGTAACCCTGTATCGGGCCCTAGGCG (SEQ ID NO: 22)
                                        XmaI BamH I
```

FIG. 5A

```
         M13R →                                     ⇒ C5R
     1   GGAAACAGCT ATGACCATGA TTACGAATTG CGGCCGCAAT TCTGAATGTT AAATGTTATA
         CCTTTGTCGA TACTGGTACT AATGCTTAAC GCCGGCGTTA AGACTTACAA TTTACAATAT

61   CTTTGGATGA AGCTATAAAT ATGCATTGGA AAAATAATCC ATTTAAAGAA AGGATTCAAA
         GAAACCTACT TCGATATTTA TACGTAACCT TTTTATTAGG TAAATTTCTT TCCTAAGTTT

121   TACTACAAAA CCTAAGCGAT AATATGTTAA CTAAGCTTAT TCTTAACGAC GCTTTAAATA
         ATGATGTTTT GGATTCGCTA TTATACAATT GATTCGAATA AGAATTGCTG CGAAATTTAT

181   TACACAAATA AACATAATTT TTGTATAACC TAACAAATAA CTAAAACATA AAAATAATAA
         ATGTGTTTAT TTGTATTAAA AACATATTGG ATTGTTTATT GATTTTGTAT TTTTATTATT

241   AAGGAAATGT AATATCGTAA TTATTTTACT CAGGAATGGG GTTAAATATT TATATCACGT
         TTCCTTTACA TTATAGCATT AATAAAATGA GTCCTTACCC CAATTTATAA ATATAGTGCA

301   GTATATCTAT ACTGTTATCG TATACTCTTT ACAATTACTA TTACGAATAT GCAAGAGATA
         CATATAGATA TGACAATAGC ATATGAGAAA TGTTAATGAT AATGCTTATA CGTTCTCTAT
                                                 ← 7927.DC

361   ATAAGATTAC GTATTTAAGA GAATCTTGTC ATGATAATTG GGTACGACAT AGTGATAAAT
         TATTCTAATG CATAAATTCT CTTAGAACAG TACTATTAAC CCATGCTGTA TCACTATTTA

1   GCTATTTCGC ATCGTTACAT AAAGTCAGTT GGAAAGATGG ATTTGACAGA TGTAACTTAA
         CGATAAAGCG TAGCAATGTA TTTCAGTCAA CCTTTCTACC TAAACTGTCT ACATTGAATT

7696.CXL →
   481   TAGGTGCAAA AATGTTAAAT AACAGCATTC TATCGGAAGA TAGGATACCA GTTATATTAT
         ATCCACGTTT TTACAATTTA TTGTCGTAAG ATAGCCTTCT ATCCTATGGT CAATATAATA

541   ACAAAAATCA CTGGTTGGAT AAAACAGATT CTGCAATATT CGTAAAAGAT GAAGATTACT
         TGTTTTTAGT GACCAACCTA TTTTGTCTAA GACGTTATAA GCATTTTCTA CTTCTAATGA

601   GCGAATTTGT AAACTATGAC AATAAAAAGC CATTTATCTC AACGACATCG TGTAATTCTT
         CGCTTAAACA TTTGATACTG TTATTTTTCG GTAAATAGAG TTGCTGTAGC ACATTAAGAA

661   CCATGTTTTA TGTATGTGTT TCAGATATTA TGAGATTACT ATAAACTTTT TGTATACTTA
         GGTACAAAAT ACATACACAA AGTCTATAAT ACTCTAATGA TATTTGAAAA ACATATGAAT

721   TATTCCGTAA ACTATATTAA TCATGAAGAA AATGAAAAAG TATAGAAGCT GTTCACGAGC
         ATAAGGCATT TGATATAATT AGTACTTCTT TTACTTTTTC ATATCTTCGA CAAGTGCTCG
                                                          ← 7926.DC

781   GGTTGTTGAA AACAACAAAA TTATACATTC AAGATGGCTT ACATATACGT CTGTGAGGCT
         CCAACAACTT TTGTTGTTTT AATATGTAAG TTCTACCGAA TGTATATGCA GACACTCCGA

841   ATCATGGATA ATGACAATGC ATCTCTAAAT AGGTTTTTGG ACAATGGATT CGACCCTAAC
         TAGTACCTAT TACTGTTACG TAGAGATTTA TCCAAAAACC TGTTACCTAA GCTGGGATTG

901   ACGGAATATG GTACTCTACA ATCTCCTCTT GAAATGGCTG TAATGTTCAA GAATACCGAG
         TGCCTTATAC CATGAGATGT TAGAGGAGAA CTTTACCGAC ATTACAAGTT CTTATGGCTC
```

FIG. 5C

```
                                                                7697.CXL →
 961  GCTATAAAAA TCTTGATGAG GTATGGAGCT AAACCTGTAG TTACTGAATG CACAACTTCT
      CGATATTTTT AGAACTACTC CATACCTCGA TTTGGACATC AATGACTTAC GTGTTGAAGA

1021  TGTCTGCATG ATGCGGTGTT GAGAGACGAC TACAAAATAG TGAAAGATCT GTTGAAGAAT
      ACAGACGTAC TACGCCACAA CTCTCTGCTG ATGTTTTATC ACTTTCTAGA CAACTTCTTA

1081  AACTATGTAA ACAATGTTCT TTACAGCGGA GGCTTTACTC CTTTGTGTTT GGCAGCTTAC
      TTGATACATT TGTTACAAGA AATGTCGCCT CCGAAATGAG GAAACACAAA CCGTCGAATG

1141  CTTAACAAAG TTAATTTGGT TAAACTTCTA TTGGCTCATT CGGCGGATGT AGATATTTCA
      GAATTGTTTC AATTAAACCA ATTTGAAGAT AACCGAGTAA GCCGCCTACA TCTATAAAGT

1201  AACACGGATC GGTTAACTCC TCTACATATA GCCGTATCAA ATAAAAATTT AACAATGGTT
      TTGTGCCTAG CCAATTGAGG AGATGTATAT CGGCATAGTT TATTTTTAAA TTGTTACCAA
                       ← 7925.DC

1261  AAACTTCTAT TGAACAAAGG TGCTCATACT GACTTGCTGG ATAACATGGG ACGTACTCCT
      TTTGAAGATA ACTTGTTTCC ACGAGTATGA CTGAACGACC TATTGTACCC TGCATGAGGA

1321  TTAATGATCG CTGTACAATC TGGAAATATT GAAATATGTA GCACACTACT TAAAAAAAAT
      AATTACTAGC GACATGTTAG ACCTTTATAA CTTTATACAT CGTGTGATGA ATTTTTTTTA

1381  AAAATGTCCA GAACTGGGAA AAATTGATCT TGCCAGCTGT AATTCATGGT AGAAAAGAAG
      TTTTACAGGT CTTGACCCTT TTTAACTAGA ACGGTCGACA TTAAGTACCA TCTTTTCTTC

1441  TGCTCAGGCT ACTTTTCAAC AAAGGAGCAG ATGTAAACTA CATCTTTGAA AGAAATGGAA
      ACGAGTCCGA TGAAAAGTTG TTTCCTCGTC TACATTTGAT GTAGAAACTT TCTTTACCTT

7792.SL →
1501  AATCATATAC TGTTTTGGAA TTGATTAAAG AAAGTTACTC TGAGACACAA AAGAGGTAGC
      TTAGTATATG ACAAAACCTT AACTAATTTC TTTCAATGAG ACTCTGTGTT TTCTCCATCG

1561  TGAAGTGGTA CTCTCAAAGG TACGTGACTA ATTAGCTATA AAAAGGATCC GGGTTAATTA
      ACTTCACCAT GAGAGTTTCC ATGCACTGAT TAATCGATAT TTTTCCTAGG CCCAATTAAT

⇒ 86p
1621  ATTAGTCATC AGGCAGGGCG AGAACGAGAC TATCTGCTCG TTAATTAATT AGAGCTTCTT
      TAATCAGTAG TCCGTCCCGC TCTTGCTCTG ATAGACGAGC AATTAATTAA TCTCGAAGAA

1681  TATTCTATAC TTAAAAAGTG AAAATAAATA CAAAGGTTCT TGAGGGTTGT GTTAAATTGA
      ATAAGATATG AATTTTTCAC TTTTATTTAT GTTTCCAAGA ACTCCCAACA CAATTTAACT

Nipah F ⇒
                                                             Met·
1741  AAGCGAGAAA TAATCATAAA TTATTTCATT ATCGCGATAT CCGTTAAGTT TGTATCGTAA
      TTCGCTCTTT ATTAGTATTT AATAAAGTAA TAGCGCTATA GGCAATTCAA ACATAGCATT ..ValValIle LeuAspLys ArgCysTyrCys AsnLeuLeu IleLeuIle LeuMetIleSer·
1801  TGGTAGTTAT ACTTGACAAG AGATGTTATT GTAATCTTTT AATATTGATT TTGATGATCT
      ACCATCAATA TGAACTGTTC TCTACAATAA CATTAGAAAA TTATAACTAA AACTACTAGA
```

FIG. 5C (Continued)

```
                ..GluCysSer ValGlyIle LeuHisTyrGlu LysLeuSer LysIleGly LeuValLysGly·
    1861        CGGAGTGTAG TGTTGGGATT CTACATTATG AGAAATTGAG TAAAATTGGA CTTGTCAAAG
                GCCTCACATC ACAACCCTAA GATGTAATAC TCTTTAACTC ATTTTAACCT GAACAGTTTC
                    ← 11468.SL

..ValThrArg LysTyrLys IleLysSerAsn ProLeuThr LysAspIle ValIleLysMet·
    1921        GAGTAACAAG AAAATACAAG ATTAAAGCA ATCCTCTCAC AAAAGACATT GTTATAAAAA
                CTCATTGTTC TTTTATGTTC TAATTTTCGT TAGGAGAGTG TTTTCTGTAA CAATATTTTT

..IleProAsn ValSerAsn MetSerGlnCys ThrGlySer ValMetGlu AsnTyrLysThr·
    1981        TGATTCCGAA TGTGTCGAAC ATGTCTCAGT GCACAGGGAG TGTCATGGAA AATTATAAAA
                ACTAAGGCTT ACACAGCTTG TACAGAGTCA CGTGTCCCTC ACAGTACCTT TTAATATTTT

..ArgLeuAsn GlyIleLeu ThrProIleLys GlyAlaLeu GluIleTyr LysAsnAsnThr·
    2041        CACGATTAAA CGGTATCTTA ACACCTATAA AGGGAGCGTT AGAGATCTAC AAAAACAACA
                GTGCTAATTT GCCATAGAAT TGTGGATATT TCCCTCGCAA TCTCTAGATG TTTTTGTTGT

..HisAspLeu ValGlyAsp ValArgLeuAla GlyValIle MetAlaGly ValAlaIleGly·
    2101        CTCATGACCT TGTCGGTGAT GTGAGATTAG CCGGAGTTAT AATGGCAGGA GTTGCTATTG
                GAGTACTGGA ACAGCCACTA CACTCTAATC GGCCTCAATA TTACCGTCCT CAACGATAAC

11460.SL →
                ..IleAlaThr AlaAlaGln IleThrAlaGly ValAlaLeu TyrGluAla MetLysAsnAla·
    2161        GGATTGCAAC CGCAGCTCAA ATCACTGCAG GTGTAGCACT ATATGAGGCA ATGAAGAATG
                CCTAACGTTG GCGTCGAGTT TAGTGACGTC CACATCGTGA TATACTCCGT TACTTCTTAC

..AspAsnIle AsnLysLeu LysSerSerIle GluSerThr AsnGluAla ValValLysLeu·
    2221        CTGACAACAT CAACAAACTC AAAAGCAGCA TTGAATCAAC TAATGAAGCT GTCGTTAAAC
                GACTGTTGTA GTTGTTTGAG TTTTCGTCGT AACTTAGTTG ATTACTTCGA CAGCAATTTG
                                                ← 11465.SL

..GlnGluThr AlaGluLys ThrValTyrVal LeuThrAla LeuGlnAsp TyrIleAsnThr·
    2281        TTCAAGAGAC TGCAGAAAAG ACAGTCTATG TGCTGACTGC TCTACAGGAT TACATTAATA
                AAGTTCTCTG ACGTCTTTTC TGTCAGATAC ACGACTGACG AGATGTCCTA ATGTAATTAT

..AsnLeuVal ProThrIle AspLysIleSer CysLysGln ThrGluLeu SerLeuAspLeu·
    2341        CTAATTTAGT ACCGACAATT GACAAGATAA GCTGCAAACA GACAGAACTC TCACTAGATC
                GATTAAATCA TGGCTGTTAA CTGTTCTATT CGACGTTTGT CTGTCTTGAG AGTGATCTAG

11456.SL →       ApaI
                ..AlaLeuSer LysTyrLeu SerAspLeuLeu PheValPhe GlyProAsn LeuGlnAspPro·
    2401        TGGCATTATC AAAGTACCTC TCTGATTGC TATTCGTATT TGGGCCCAAC CTTCAAGACC
                ACCGTAATAG TTTCATGGAG AGACTAAACG ATAAGCATAA ACCCGGGTTG GAAGTTCTGG
                                                ← 11457.SL

..ValSerAsn SerMetThr IleGlnAlaIle SerGlnAla PheGlyGly AsnTyrGluThr·
    2461        CAGTTTCTAA TTCAATGACT ATACAGGCTA TATCTCAGGC ATTCGGTGGA AATTATGAAA
                GTCAAAGATT AAGTTACTGA TATGTCCGAT ATAGAGTCCG TAAGCCACCT TTAATACTTT

..LeuLeuArg ThrLeuGly TyrAlaThrGlu AspPheAsp AspLeuLeu GluSerAspSer·
    2521        CACTGCTAAG AACATTGGGT TACGCTACAG AAGACTTTGA TGATCTTCTA GAAAGTGACA
                GTGACGATTC TTGTAACCCA ATGCGATGTC TTCTGAAACT ACTAGAAGAT CTTTCACTGT
```

FIG. 5C (Continued)

```
              11461.SL →
       ..IleThrGly GlnIleIle TyrValAspLeu SerSerTyr TyrIleIle ValArgValTyr·
2581   GCATAACAGG TCAAATCATC TATGTTGATC TAAGTAGCTA CTATATAATT GTCAGGGTTT
       CGTATTGTCC AGTTTAGTAG ATACAACTAG ATTCATCGAT GATATATTAA CAGTCCCAAA

..PheProIle LeuThrGlu IleGlnGlnAla TyrIleGln GluLeuLeu ProValSerPhe·
2641   ATTTTCCTAT TCTGACTGAA ATTCAACAGG CCTATATCCA AGAGTTGTTA CCAGTGAGCT
       TAAAAGGATA AGACTGACTT TAAGTTGTCC GGATATAGGT TCTCAACAAT GGTCACTCGA
                             ← 11464.SL

..AsnAsnAsp AsnSerGlu TrpIleSerIle ValProAsn PheIleLeu ValArgAsnThr·
2701   TCAACAATGA TAATTCAGAA TGGATCAGTA TTGTCCCAAA TTTCATATTG GTAAGGAATA
       AGTTGTTACT ATTAAGTCTT ACCTAGTCAT AACAGGGTTT AAAGTATAAC CATTCCTTAT

..LeuIleSer AsnIleGlu IleGlyPheCys LeuIleThr LysArgSer ValIleCysAsn·
2761   CATTAATATC AAATATAGAG ATTGGATTTT GCCTAATTAC AAAGAGGAGC GTGATCTGCA
       GTAATTATAG TTTATATCTC TAACCTAAAA CGGATTAATG TTTCTCCTCG CACTAGACGT

..GlnAspTyr AlaThrPro MetThrAsnAsn MetArgGlu CysLeuThr GlySerThrGlu·
2821   ACCAAGATTA TGCCACACCT ATGACCAACA ACATGAGAGA ATGTTTAACG GGATCGACTG
       TGGTTCTAAT ACGGTGTGGA TACTGGTTGT TGTACTCTCT TACAAATTGC CCTAGCTGAC

..LysCysPro ArgGluLeu ValValSerSer HisValPro ArgPheAla LeuSerAsnGly·
2881   AGAAGTGTCC TCGAGAGCTG GTTGTTTCAT CACATGTTCC CAGATTTGCA CTATCTAACG
       TCTTCACAGG AGCTCTCGAC CAACAAAGTA GTGTACAAGG GTCTAAACGT GATAGATTGC

..ValLeuPhe AlaAsnCys IleSerValThr CysGlnCys GlnThrThr GlyArgAlaIle·
2941   GGGTTCTGTT TGCCAATTGC ATAAGTGTTA CATGTCAGTG TCAAACAACA GGCAGGGCAA
       CCCAAGACAA ACGGTTAACG TATTCACAAT GTACAGTCAC AGTTTGTTGT CCGTCCCGTT

11462.SL →
       ..SerGlnSer GlyGluGln ThrLeuLeuMet IleAspAsn ThrThrCys ProThrAlaVal·
3001   TCTCACAATC AGGAGAACAA ACTCTGCTGA TGATTGACAA CACCACCTGT CCTACAGCCG
       AGAGTGTTAG TCCTCTTGTT TGAGACGACT ACTAACTGTT GTGGTGGACA GGATGTCGGC
                                                         ← 11463.SL

..LeuGlyAsn ValIleIle SerLeuGlyLys TyrLeuGly SerValAsn TyrAsnSerGlu·
3061   TACTCGGTAA TGTGATTATC AGCTTAGGGA AATATCTGGG GTCAGTAAAT TATAATTCTG
       ATGAGCCATT ACACTAATAG TCGAATCCCT TTATAGACCC CAGTCATTTA ATATTAAGAC

..GlyIleAla IleGlyPro ProValPheThr AspLysVal AspIleSer SerGlnIleSer·
3121   AAGGCATTGC TATCGGTCCT CCAGTCTTTA CAGATAAAGT TGATATATCA AGTCAGATAT
       TTCCGTAACG ATAGCCAGGA GGTCAGAAAT GTCTATTTCA ACTATATAGT TCAGTCTATA

..SerMetAsn GlnSerLeu GlnGlnSerLys AspTyrIle LysGluAla GlnArgLeuLeu·
3181   CCAGCATGAA TCAGTCCTTA CAACAGTCTA AGGACTATAT CAAAGAGGCT CAACGACTCC
       GGTCGTACTT AGTCAGGAAT GTTGTCAGAT TCCTGATATA GTTTCTCCGA GTTGCTGAGG

..AspThrVal AsnProSer LeuIleSerMet LeuSerMet IleIleLeu TyrValLeuSer·
3241   TTGATACTGT TAATCCATCA TTAATAAGCA TGTTGTCTAT GATCATACTG TATGTATTAT
       AACTATGACA ATTAGGTAGT AATTATTCGT ACAACAGATA CTAGTATGAC ATACATAATA
```

FIG. 5C (Continued)

```
         ..IleAlaSer LeuCysIle GlyLeuIleThr PheIleSer PheIleIle ValGluLysLys·
3301     CGATCGCATC GTTGTGTATA GGGTTGATTA CATTTATCAG TTTTATCATT GTTGAGAAAA
         GCTAGCGTAG CAACACATAT CCCAACTAAT GTAAATAGTC AAAATAGTAA CAACTCTTTT

..ArgAsnThr TyrSerArg LeuGluAspArg ArgValArg ProThrSer SerGlyAspLeu·
3361     AGAGAAACAC CTACAGCAGA TTAGAGGATA GGAGAGTCAG ACCTACAAGC AGTGGGGATC
         TCTCTTTGTG GATGTCGTCT AATCTCCTAT CCTCTCAGTC TGGATGTTCG TCACCCCTAG

⇒ C5L
         ..TyrTyrIle GlyThr (SEQ ID NO: 26)
3_1      TCTACTACAT TGGGACATAG CCCGGGTTTT TATGACTAGT TAATCACGGC CGCTTATAAA
         AGATGATGTA ACCCTGTATC GGGCCCAAAA ATACTGATCA ATTAGTGCCG GCGAATATTT

7928.DC →
3481     GATCTAAAAT GCATAATTTC TAAATAATGA AAAAAGTAC ATCATGAGCA ACGCGTTAGT
         CTAGATTTTA CGTATTAAAG ATTTATTACT TTTTTCATG TAGTACTCGT TGCGCAATCA

3541     ATATTTTACA ATGGAGATTA ACGCTCTATA CCGTTCTATG TTTATTGATT CAGATGATGT
         TATAAAATGT TACCTCTAAT TGCGAGATAT GGCAAGATAC AAATAACTAA GTCTACTACA
                                    ← 7793.SL

3601     TTTAGAAAAG AAAGTTATTG AATATGAAAA CTTAATGAA GATGAAGATG ACGACGATGA
         AAATCTTTTC TTTCAATAAC TTATACTTTT GAATTACTT CTACTTCTAC TGCTGCTACT

3661     TTATTGTTGT AAATCTGTTT TAGATGAAGA AGATGACGCG CTAAAGTATA CTATGGTTAC
         AATAACAACA TTTAGACAAA ATCTACTTCT TCTACTGCGC GATTTCATAT GATACCAATG

3721     AAAGTATAAG TCTATACTAC TAATGGCGAC TTGTGCAAGA AGGTATAGTA TAGTGAAAAT
         TTTCATATTC AGATATGATG ATTACCGCTG AACACGTTCT TCCATATCAT ATCACTTTTA

3781     GTTGTTAGAT TATGATTATG AAAAACCAAA TAAATCAGAT CCATATCTAA AGGTATCTCC
         CAACAATCTA ATACTAATAC TTTTTGGTTT ATTTAGTCTA GGTATAGATT TCCATAGAGG

3841     TTTGCACATA ATTTCATCTA TTCCTAGTTT AGAATACCTG CAGCCAAGCT TGGCACTGGC
         AAACGTGTAT TAAAGTAGAT AAGGATCAAA TCTTATGGAC GTCGGTTCGA ACCGTGACCG

3901     CGTCGTTTTA C (SEQ ID NO: 27)
         GCAGCAAAAT G (SEQ ID NO: 28)
             ← M13F
```

FIG. 5C (Continued)

SEQUENCE LISTING

```
<160> NUMBER OF SEQ ID NOS: 31

<210> SEQ ID NO 1
<211> LENGTH: 18246
<212> TYPE: DNA
<213> ORGANISM: Nipah virus

<400> SEQUENCE: 1
accaaacaag ggagaatatg gatacgttaa aatatataac gtatttttaa aacttaggaa        60
ccaagacaaa cacttttggt cttggtattg gatcctcaag aaatatatca tcatgagtga       120
tatctttgaa gaggcggcta gttttaggag ttatcaatct aagttaggga gagatgggag       180
ggctagtgca gcaactgcta cttttgacaac caagataagg atatttgtac cagctactaa       240
tagtccagag ctcagatggg aactaacatt gtttgcactt gatgtgatta gatctccgag       300
tgctgccgag tcaatgaaag ttggagctgc tttcacactc atctctatgt attcagagag       360
acccggggct ctcattagaa gtctcctcaa tgacccagac attgaagctg taataataga       420
tgttggatca atggtcaacg gaataccagt aatggagagg agaggagaca aggctcagga       480
ggagatggaa ggcttgatga gaatcctcaa aactgctcga gacagcagca agggaaaaac       540
accttttgtt gacagccgag cttacggcct acggataaca gacatgagca ccctggtctc       600
tgcagttatc accatcgagg cccagatctg gatactgatc gctaaagcag ttacagctcc       660
cgacactgcc gaggaaagtg aaactagaag atgggctaaa tacgtccaac aaaagagagt       720
caatccgttc tttgctctaa ctcagcaatg gctaacagaa atgaggaatc tgctctccca       780
gagtctatca gtaaggaagt tcatggttga gatcctcata gaagtcaaga aggaggatc       840 tgctaaaggc agagcagtag aaataatctc agacatcgga aactatgtcg aggaaactgg       900
tatggcagga ttcttcgcaa ccatcagatt cgggttggag acaaggtatc cagcacttgc       960
actcaacgaa ttccagagtg acctcaacac catcaaaagc ttgatgctac tctacagaga      1020
aattggccca agagcccctt atatggtgct tcttgaagaa tcaattcaga ctaaatttgc      1080
ccctggaggt tacccattat tgtggagctt tgccatgggt gtggctacta ctattgacag      1140
gtctatgggg gcattgaata tcaatcgtgg ttatcttgag cctatgtatt tcagactagg      1200
ccaaaaatca gcacgtcacc atgctggagg aattgatcag aacatggcaa atagactggg      1260
actaagttca gatcaagttg cagaactcgc tgctgcagtt caggaaacat cagcaggaag      1320
gcaagagagt aatgttcagg ctagagaggc aaaatttgct gcaggaggtg tgctcattgg      1380
aggcagtgat caagatatcg atgaagggga agaacctata gaacagagtg gcagacagtc      1440
```

```
agttaccttc aaaagggaga tgagtatttc atcccttgct aacagtgtgc cgagcagttc    1500
tgtgagcaca tccggtggga ccagattgac taattcatta ctaaacctca gatcaagact    1560
ggctgcaaaa gcagcaaaag aagccgcctc atccaatgca acagatgatc cagcaatcag    1620
caacagaact caaggggaat cagagaagaa gaataatcaa gacctcaaac ctgctcaaaa    1680
tgaccttgat ttcgtcagag ctgatgtgtg acgtctattt ccaatattct acagtatcca    1740
aaaatctttc tatagtacac tatcataata cgacactaag ggatcaacca tatcaaagtt    1800
acgaatcgtt ttaattatat taatcaaatg atactctttt atgggcaaac cgaagaacca    1860
atgtctacat gtaaattgag ctttggtatt gcaatcaat  acttgctcaa atcttgaac     1920
tattagtgta atttctatca tcatagagtt atcaagattt tattatataa gttggtgcag    1980
atctttggac atgaattaca cactacactc taatgaagac aaaatttaca ttacatattt    2040
aaggactatt tcctatcctt tcaatggtac ttggttatga aggtttctta atttaactaa    2100
gctactgtct ttgcactgga atatacaata cctcttacct catttcttac tttaatatca    2160
tgttatttt  ttgataagtc acttaacttg accaaggtct accaggtaat gctcgcacaa    2220
gtgaactgca atctcaactt agattaaaca taatcatgca aaatcactat tttgtactac    2280
taactcatta agaaaaactt aggatccaag agatttactc taggatctcc tattaagctt    2340
agcagtcatt agttgagagt tcaacttgca aaactctaac cttcactcta ataacaattc    2400
atccaatgga taaattggaa ctagtcaatg atggcctcaa tattattgac tttattcaga    2460
agaaccaaaa agaaatacag aagacatacg gacgatcaag tattcaacaa cccagcatca    2520
aagatcaaac aaaagcctgg gaagattttc tgcagtgcac cagtggagaa tctgaacaag    2580
ttgagggggg aatgtctaag gatgatggag atgttgaaag aagaaacttg gaggatctat    2640
ccagtacttc tcccacagat ggaactattg gaaagagagt gtcgaacacc cgtgactggg    2700
cagaaggttc agatgacata caactggacc cagtggttac agacgttgta taccatgatc    2760
atggaggaga atgtaccgga tatggattta cttcaagccc tgagagaggg tggagtgatt    2820
acacatcagg agcaaacaat gggaatgtat gtcttgtatc tgatgcaaag atgctgtcct    2880
atgctcccga aattgcagtt tctaaagaag atcgggaaac tgatctagtt catcttgaga    2940
ataaactatc tactacagga ctgaatccca cagcagtacc gttcactctg agaaacctgt    3000
ctgatcctgc aaaagactct cctgtgattg ctgaacacta ctacggacta ggagttaaag    3060
agcaaaacgt tggccctcag actagcagaa atgtcaattt ggacagcatc aaattgtaca    3120
catcagatga cgaagaggca gatcagcttg aattcgaaga tgagtttgca ggaagctcaa    3180
gtgaagtgat agtcggcatt tctcctgaag atgaagagcc ttcaagtgtt ggcggaaaac    3240
ccaatgaatc cattggacgt acaatcgaag gccaatcaat ccgagacaac cttcaagcca    3300
aggacaacaa atcaacagat gtaccaggag caggaccgaa agattcagca gtgaaggaag    3360
aaccacccca gaagaggcta cctatgttag ctgaagaatt tgagtgctct ggatcggaag    3420
acccaatcat tcgggagctg ctgaaggaga actcactcat aaattgtcag caagggaaag    3480
atgctcagcc tccatatcat tggagcatcg agaggtcaat aagcccggat aaaactgaga    3540
tcgtcaacgg tgctgtgcaa actgctgaca ggcaaagacc aggaactccg atgccaaagt    3600
cccgaggtat tccattaaaa aagggcacag acgcgaaata tccatctgct gggacggaaa    3660
acgtgcctgg gtcgaagagt ggtgcaaccc ggcatgttcg aggatcaccc ccctaccaag    3720
aaggcaagag tgtcaatgcg gagaatgtcc aactgaatgc ttccactgcg gttaaggaaa    3780
ctgataagtc agaagtaaac cccgtagacg acaacgactc acttgatgat aaatacatca    3840
```

```
tgccttcaga tgatttctca aacactttct tcccgcacga cactgatcgc ttgaattatc    3900
acgcagatca tttaggtgat tatgaccttg aaaccctgtg tgaagagtcg gttctaatgg    3960
gagtgatcaa ctctataaaa ttaattaatc tggatatgcg cttaaatcac attgaagaac    4020
aagttaaaga gatcccaaag atcatcaata agcttgagtc cattgacaga gttctggcca    4080
agactaacac cgcactctca accattgaag gacacctggt ttccatgatg ataatgatac    4140
cagggaaagg gaaaggagaa agaaagggga aaaataatcc tgagcttaaa ccagtgatag    4200
gaagagacat tctagagcag caatctcttt tttcttttga caatgtcaag aatttcagag    4260
atggatcgtt gacaaacgaa ccgtatgggg cagctgtaca gttgagagaa gatcttattc    4320
ttcctgaact taattttgag gagacaaatg catctcaatt tgttcctatg gcagatgatt    4380
catccagaga tgttatcaag acattgataa ggactcacat aaagataga gagttgagat     4440 cagaactgat tggttacctg aataaagcgg aaaatgatga ggaaattcag gagatagcga    4500
acactgtcaa tgacatcatt gacggtaata tttgatcact gaattgtcag cagaaataca    4560
atgatctaac aacaatctcc cacaagtaga caatggtttc aggtcaataa taacaacctc    4620
aatactaatc tttcacataa gcattactca ttccagccct cagacgataa cacaatactt    4680
gatacatgtt tattgaagtg tatgtagcat gattgaacta ttcaataact gtatttctca    4740
ctcttgctct tagttagtca ttgtgtctaa taattattat tacagtacaa ggtattatga    4800
attcaaagat acgcaataaa tctgatatca gcatagagta gaaaattgtt gttttgtca    4860 tgatcattcg aagatttaac aatgatgtca actttcatac ctaaacataa taacataaaa    4920
tggtcgattt gtattgtaga tctctcacgc attttagtgt catgaattag tgtttcaaat    4980
cagttgcata tcaattaaga aaacttagg agacaggtat agaacctctc tttcagataa    5040
ctggtcaatt aaggacagaa attctgtttc tcaaatccgc tagcctttgt caaagaggac    5100
acaagcaatg gagccggaca tcaagagtat ttcaagtgag tcaatggaag gagtatctga    5160
tttcagccct agttcttggg agcatggtgg gtatcttgat aaggttgaac cagaaattga    5220
tgaaaatggc agtatgattc caaaatacaa gatctatacc ccaggagcta acgagaggaa    5280
atacaacaac tacatgtacc ttatatgtta cggctttgtt gaagatgttg agagaacccc    5340
agagacaggg aaacgcaaga agatcaggac aattgctgcc taccctctgg gtgttggtaa    5400
gagtgcctct catccccaag atcttctgga ggaactctgt tccctcaaag ttactgtgag    5460
aagaacagct ggatcaactg agaaaattgt gtttggatca tctggccctc taaatcacct    5520
cgttccgtgg aagaaagtac tgactagtgg ttcaattttt aatgcagtca aggtttgtcg    5580
gaacgttgat cagatacagc ttgacaagca tcaagctctg agaatatttt ttctcagtat    5640
cacaaagctc aatgattctg gaatctacat gattccacga accatgcttg agttcaggag    5700
aaacaatgcc attgccttca atcttctagt gtacttgaag attgatgctg atttatccaa    5760 aatgggatc cagggaagcc tcgataaaga tggcttcaag gttgcctcct tcatgctaca    5820
cttggggaac tttgtccgtc gtgcagggaa gtattactct gttgattatt gtaggaggaa    5880
gattgatagg atgaaattgc agttttcact gggttccata ggcggactaa gtctccacat    5940
taagatcaat ggtgtaatca gcaaacggct gtttgctcaa atgggattcc aaaaaaacct    6000
ttgtttctct ttgatggaca tcaatccttg gctcaacaga ttgacctgga caacagttg     6060 tgagatcagc cgagtagcag ctgtgttgca gccttctatt ccaagagagt tcatgatcta    6120
tgatgatgtc ttcattgaca atacagggag aattctaaag ggctaaacag aattcttcta    6180
aaatttaatc agtcatgagt ttagtaatca tacctagtca taatacatca cacaggacta    6240
```

```
tttacaaaag acagttaaaa aatggaataa tcatgtagta gtaattgaga acattattag    6300
aatagtataa ctaaaatgta gttttttttga gtatttgatt taaaattaga taactattac    6360
aaaaaactta ggagccaagc tcttgcctcg ttcagaaggt taaacaagca ttcttaccat    6420
tggatcaaca aaaggattgg ttttatcgtc taagaaattt attgaaaggc aaagaaattc    6480
ctggttttat gttgaatgag gtgtatcaaa ctaaggagac cttctaacag ccaggtcata    6540
ggaatataaa taaaaataag aataaaattg attccatcgg aagattcatt tcaagaagtg    6600
atcaaatcaa agcggttggc agacctacca atcatatacc acaagactcg acaatggtag    6660
ttatacttga caagagatgt tattgtaatc ttttaatatt gattttgatg atctcggagt    6720
gtagtgttgg gattctacat tatgagaaat tgagtaaaat tggacttgtc aaaggagtaa    6780
caagaaaata caagattaaa agcaatcctc tcacaaaaga cattgttata aaaatgattc    6840
cgaatgtgtc gaacatgtct cagtgcacag ggagtgtcat ggaaaattat aaaacacgat    6900
taaacggtat cttaacacct ataaagggag cgttagagat ctacaaaaac aacactcatg    6960
accttgtcgg tgatgtgaga ttagccggag ttataatggc aggagttgct attgggattg    7020
caaccgcagc tcaaatcact gcaggtgtag cactatatga ggcaatgaag aatgctgaca    7080
acatcaacaa actcaaaagc agcattgaat caactaatga agctgtcgtt aaacttcaag    7140
agactgcaga aaagacagtc tatgtgctga ctgctctaca ggattacatt aatactaatt    7200
tagtaccgac aattgacaag ataagctgca acagacaga actctcacta gatctggcat    7260
tatcaaagta cctctctgat tgcttttttg tatttggccc caaccttcaa gacccagttt    7320
ctaattcaat gactatacag gctatatctc aggcattcgg tggaaattat gaaacactgc    7380
taagaacatt gggttacgct acagaagact ttgatgatct tctagaaagt gacagcataa    7440
caggtcaaat catctatgtt gatctaagta gctactatat aattgtcagg gtttattttc    7500
ctattctgac tgaaattcaa caggcctata tccaagagtt gttaccagtg agcttcaaca    7560
atgataattc agaatggatc agtattgtcc caaatttcat attggtaagg aatacattaa    7620
tatcaaatat agagattgga ttttgcctaa ttacaaagag gagcgtgatc tgcaaccaag    7680
attatgccac acctatgacc aacaacatga gagaatgttt aacgggatcg actgagaagt    7740
gtcctcgaga gctggttgtt tcatcacatg ttcccagatt tgcactatct aacggggttc    7800
tgtttgccaa ttgcataagt gttacatgtc agtgtcaaac aacaggcagg gcaatctcac    7860
aatcaggaga acaaactctg ctgatgattg acaacaccac ctgtcctaca gccgtactcg    7920
gtaatgtgat tatcagctta gggaaatatc tggggtcagt aaattataat tctgaaggca    7980
ttgctatcgg tcctccagtc tttacagata agttgatat atcaagtcag atatccagca    8040
tgaatcagtc cttacaacag tctaaggact atatcaaaga ggctcaacga ctccttgata    8100
ctgttaatcc atcattaata agcatgttgt ctatgatcat actgtatgta ttatcgatcg    8160
catcgttgtg tataggggttg attacattta tcagtttttat cattgttgag aaaaagagaa    8220
acacctacag cagattagag gataggagag tcagacctac aagcagtggg gatctctact    8280
acattgggac atagtgtatt cagattgatg aaattatgtt agagaaatca gaaaacttct    8340
gactttcaga aatggattgt atacaattag ttagatcatc ctgaataatc gaggtgagaa    8400
cattgcaact ataaaatcag atcatgtaaa tagttgtaaa aaattaaaag cttcttttaa    8460
ttcttttgaa caataattta attaatatat aacatattct ctcacacgag cgctaaccta    8520
tacactctct actaatatt tatactcata attaatgata taatgacaaa taaggattca    8580
aattggatta tgatatagtt tcatactaca atagcatttc gaccaagaaa atatccttac    8640
```

```
aattatacaa tgtacttaac cgtgaatatg taattgataa tttcccttta gaaatttaat   8700
aaaaaactta ggacccaggt ccataactca ttggatactt aactgtatct ttctaagcta   8760
tcacatatca aaggagagat tgaatgcttt tttggagatc tagatcatta ctatatgtgt   8820
ctcctataat cacatcatag gagtgaacca taatacacat ctttgggtag gggaaggaaa   8880
gtattgttga cgtactgatt gatctgcttg agtcaaataa tcagtcataa caattcaaga   8940
aaatgccggc agaaaacaag aaagttagat tcgaaaatac tacttcagac aaagggaaaa   9000
ttcctagtaa agttattaag agctactacg gaaccatgga cattaagaaa ataaatgaag   9060
gattattgga cagcaaaata ttaagtgctt tcaacacagt aatagcattg cttggatcta   9120
tcgtgatcat agtgatgaat ataatgatca tccaaaatta cacaagatca acagacaatc   9180
aggccgtgat caaagatgcg ttgcagggta tccaacagca gatcaaaggg cttgctgaca   9240
aaatcggcac agagataggg cccaaagtat cactgattga cacatccagt accattacta   9300
tcccagctaa cattgggctg ttaggttcaa agatcagcca gtcgactgca agtataaatg   9360
agaatgtgaa tgaaaaatgc aaattcacac tgcctcccct gaaaatccac gaatgtaaca   9420
tttcttgtcc taacccactc cctttttagag agtataggcc acagacagaa ggggtgagca   9480
atctagtagg attacctaat aatatttgcc tgcaaaagac atctaatcag atattgaagc   9540
caaagctgat ttcatacact ttacccgtag tcggtcaaag tggtacctgt atcacagacc   9600
cattgctggc tatggacgag ggctattttg catatagcca cctggaaaga atcggatcat   9660
gttcaagagg ggtctccaaa caagaataag taggagttgg agaggtacta gacagaggtg   9720
atgaagttcc ttctttattt atgaccaatg tctggaccc accaaatcca aacaccgttt   9780
accactgtag tgctgtatac aacaatgaat tctattatgt actttgtgca gtgtcaactg   9840
ttggagaccc tattctgaat agcacctact ggtccggatc tctaatgatg acccgtctag   9900
ctgtgaaacc caagagtaat ggtgggggtt acaatcaaca tcaacttgcc ctacgaagta   9960
tcgagaaagg gaggtatgat aaagttatgc cgtatggacc ttcaggcatc aaacagggtg  10020
acaccctgta ttttcctgct gtaggatttt tggtcaggac agagtttaaa tacaatgatt  10080
caaattgtcc catcacgaag tgtcaataca gtaaacctga aaattgcagg ctatctatgg  10140
ggattagacc aaaacagccat tatatccttc gatctggact attaaaatac aatctatcag  10200
atggggagaa ccccaaagtt gtattcattg aaatatctga tcaaagatta tctattggat  10260
ctcctagcaa aatctatgat tctttgggtc aacctgtttt ctaccaagcg tcattttcat  10320
gggatactat gattaaattt ggagatgttc taacagtcaa ccctctggtt gtcaattggc  10380
gtaataacac ggtaatatca agacccgggc aatcacaatg ccctagattc aatacatgtc  10440
cagagatctg ctgggaagga gtttataatg atgcattcct aattgacaga atcaattgga  10500
taagcgcggg tgtattcctt gacagcaatc agaccgcaga aaatcctgtt tttactgtat  10560
tcaaagataa tgaaatactt tatagggcac aactggcttc tgaggacacc aatgcacaaa  10620
aaacaataac taattgtttt ctcttgaaga ataagatttg gtgcatatca ttggttgaga  10680
tatatgacac aggagacaat gtcataagac ccaaactatt cgcggttaag ataccagagc  10740
aatgtacata aaaatcaacc tcataattta atggattgat ctaatataat gataataatc  10800
gtacaaagac atgtgatgta aacaaaattg ttgtaattaa ataagtcctc agctgaatac  10860 tttttttaaga ttagcaatag catgtttttc cagttattgg atagttgata atataattct  10920
gaaactgggt taataaataa tcttgatcgg tgatctttga gaacaatgat atcatatagt  10980
tcatcaagtg ataatcaatt ctttatatgt acactttaga gtatatttg agacttagta  11040
```

```
ttttcggccc gaatgttaaa tttaatagtt catacataac ctaaactcaa gttctaagca    11100
taatgataac aattaatgcg aacttgtctt gatgtaagga agatttgata ttaactgaga    11160
ctccacttga tatagtagag ctgaatcttg taaataaatt ataatgaata gtttattcaa    11220
agattatcat tcatattagt gtaaattaag aaaaacttag gacccaggtc cttgattatg    11280
ccaattttct cgagaaatca ttcaattgac catagactga aagcgttgtt acctagttct    11340
tcagaagaga tcttattaga attaatttat atgatctaat tcccttaaaa actgaatacc    11400
aaaaaacaaa aatggccgat gaattatcaa tatccgacat catttaccct gaatgtcatt    11460
tggatagtcc tatagtctct ggtaaactaa tatcagctat tgaatatgct caattgagac    11520
acaatcagcc cagtgatgat aaaagactgt ctgagaatat taggttaaac cttcacggga    11580
aaagaaagag tctatacata ttaagacaat ccaaacaggg tgattacatt agaaacaaca    11640
taaaaaccct aaaggaattc atgcatattg cgtaccctga atgcaataac attctattct    11700
ccatcacatc ccaaggcatg actagcaaac ttgataacat catgaaaaag tcattcaaag    11760
catacaatat cattagtaag aaagtaattg ggatgctgca aaatatcact agaaatctca    11820
taactcaaga tagaagagat gaaataatta atatacatga gtgtaggcga ttaggggatt    11880
tagggaagaa tatgagtcaa tctaaatggt atgagtgttt tttgtttttgg tttactatca    11940 aaacagagat gcgagcagtg atcaagaatt cgcaaaagcc gaaattccgt tcagattcat    12000
gcataataca catgcgagac aaaagtactg aaataatcct aaatccgaat cttatctgca    12060
ttttcaaatc agacaaaact ggaagaagt gttattatct tacacccgaa atggttctaa    12120
tgtattgtga tgtcctagag ggaaggatga tgatggagac aacagtcaaa tcggatatca    12180
agtaccaacc tctaatctcg agatccaatg ccctctgggg gctaattgat cccttgttcc    12240
ctgtcatggg aaacagaatt tacaatatag tgtctatgat agagccttta gttcttgcac    12300
tactccaact caaggatgag gctaggatcc tgagggtgc atttctgcat cactgcataa    12360
aggaaatgca tcaagaattg agtgagtgtg gttttacaga tcagaagatt cggtctatgt    12420
ttattgatga tctttttatcc attctaaata tcgataatat acatctgttg gcagagttct    12480
tttctttctt tcgtacgttt ggccatccta ttcttgaggc taaagttgct gcagaaaaag    12540
tgagagaaca tatgttggca gataaagttc ttgaatatgc ccctataatg aaagcacatg    12600
ctatattctg cgggactata taaatgggt atagggatag acacggagga gcctggcctc    12660
ctctttacct ccccgcacat gcatctaaac atataatccg tttgaaaaat tctggggaat    12720
ctttgaccat tgatgactgt gtcaagaatt gggaatcatt ctgtgggatt caatttgatt    12780
gtttcatgga gctgaaattg gacagtgatc tgagtatgta tatgaaagat aaagctttat    12840
ctccaatcaa agacgaatgg gacagtgtat acccacgtga agtgttgagc tatacccac    12900 cgaagtcaac cgagccaaga agattggttg acgttttttgt aaatgatgaa actttgatc    12960 catacaacat gctggaatat gtcttatccg gtgcttatct cgaggatgaa caattcaatg    13020
tttcttatag cttgaaggag aaagagacga agcaagctgg acgattgttc gcaaagatga    13080
cctacaaaat gcgtgcatgt caagtcatag cagaggccct gatagcctca ggtgtcggta    13140
aatattttaa ggagaacggg atggttaagg atgagcacga acttttgaag acactcttcc    13200
aattgtctat ttcctcagtt cctcgaggga acagtcaggg taatgatcct caatccatca    13260
ataatataga aagagatttc caatacttta aggggtcac taccaatgtg aaagacaaaa    13320
agaataactc ttttaataag gttaaatctg ctctcaataa tccgtgccaa gctgacggag    13380
tccatcataa catgtcaccc aatacacgaa atcgttataa gtgtagtaat acaagtaagt    13440
```

```
cttttctcga ttatcatacc gagtttaatc ctcacaatca ctataaatca gacaatacag   13500
aggcggccgt actgtccagg tatgaggaca acactgggac aaaatttgat acagtaagtg   13560
catttcttac aactgatctt aagaaattct gtctcaattg gagatacgaa tcaatggcta   13620
tatttgctga acgtctggat gagatatacg gtttacctgg attttttaat tggatgcaca   13680
aacgactaga aagatctgtt atctatgttg cagaccctaa ttgccccccct aatattgaca   13740 aacatatgga actagaaaaa actcctgaag atgatatatt cattcattat cctaaaggcg   13800
gtattgaagg atatagccaa aaaacatgga ctatagcaac tatccccttt ttattcttga   13860
gtgcctatga gacaaacacg aggattgctg caattgtcca aggagacaat gaatcaattg   13920
ctatcactca aaaagttcat cctaatcttc cctacaaggt aaagaaagag atctgtgcaa   13980
agcaagctca gctttatttt gaaaggttaa ggatgaactt aagagccctc ggccacaatc   14040
ttaaagctac agaaactatc atcagtacac atctttttat ttattcgaag aaaattcatt   14100
atgatggtgc tgtgctgtct caggcactca atcaatgtc aagatgttgc ttttggtcag   14160
agactctggt ggatgaaact agatcagctt gtagtaacat cagcactaca atagctaaag   14220
ctatagaaaa tggggttgtca agaaatgtcg gctattgcat caatattttg aaagtaattc   14280
agcagcttct catatcaact gagtttagta ttaacgagac attgacactg gatgtgacat   14340
ctcccatttc aaataattta gattggctta taacagctgc attaatcccg gcacctattg   14400
gaggattcaa ttaccttaat ttgtctagaa tttttgttag aaatataggt gatccggtta   14460
cagcatcttt ggctgatctt aagagaatga ttgatcacag tattatgact gaaagcgtat   14520
tacaaaaagt tatgaatcaa gaacctggtg atgcgagttt cttggactgg ccagtgatc   14580 catactcggg caacttgcct gactcacaaa gcatcactaa aacaattaaa aatatcacag   14640
caaggactat actgaggaac tcaccgaacc caatgctaaa aggtttattt catgacaaat   14700
cttttgatga agatcttgaa ctagctagct tcttaatgga caggagggtt atattaccta   14760
gagccgctca tgagatactg gataattcat tgacaggtgc cagagaggaa attgctggtt   14820
tattagatac aactaaaggc ttgatcagat cagggctaag aaagagtgga cttcagccaa   14880
agttagtttc tagattatct catcatgatt ataatcaatt tttaatactg aacaaacttc   14940
tatcaaacag aagacaaaat gacttgatat catcaaatac ttgctcagtt gacttggcac   15000
gagcattgag atctcacatg tggagggaat tagcgttagg tagagtaata tacggtcttg   15060
aggtaccaga tgcacttgag gctatggtgg gaaggtatat aacagggagc ttagagtgcc   15120
aaatttgtga gcagggaaac acgatgtatg ggtggttctt tgtacctagg gattcccaat   15180
tggatcaggt agatagagag cactcatcaa taagagtacc ttatgtagga tcaagtacgg   15240
atgaaagatc ggatatcaaa ctagggaatg tcaaaagacc aactaaggcc ttgcgttctg   15300
ctatcagaat tgcgacagta tatacttggg cctatgggga caatgaagag tgttggtatg   15360
aagcttggta cctagcgtct cagagggtaa acatagactt agatgtattg aaagctataa   15420
ccccagtttc cacttcaaac aatttatccc atagattgag agataaatcc acacaattta   15480
agtttgcagg gagtgtactc aacagagttt ctagatatgt taacataagc aatgacaatc   15540
tagatttcag aattgaggga gaaaaggtag atacgaatct tatttatcaa caagcaatgc   15600
tattagggtt atcggtattg gaaggtaaat tcagattgag attagaaact gatgattaca   15660
acgggatata tcacttacac gtaaaggata attgttgtgt caaagaagtg gctgatgtag   15720
gccaagtaga cgctgagttg cctatcccag aatatactga agtggataac aatcatctta   15780
tatatgatcc agaccccgtt tcagaaatag attgcagccg tcttctaat caggagtcca   15840
```

```
aatcaagaga attagacttt cctttatggt caactgagga acttcatgat gtcctagcta   15900
agactgttgc tcagaccgtt cttgagatta aacaaaggc tgacaaggat gttttaaagc    15960
aacaccttgc aatagactct gacgataaca tcaacagctt aatcacagaa tttctaatag   16020
ttgatcctga actgtttgca ctttatctag acaatctat atcaataaaa tgggcctttg    16080
aaattcatca taggcgtcct agaggaagac atactatggt cgacctattg tcagatcttg   16140
tatcaaatac atcaaagcac acttacaaag tgttgtcaaa tgccttgtca catcctagag   16200
tattcaagag atttgtaaac tgtggcttgc tattgcctac acagggtcct taccttcatc   16260
aacaagattt tgaaaagttg tctcaaaacc ttcttgtaac atcttatatg atttatctaa   16320
tgaactggtg tgacttcaag aaatccccct ttttaatcgc cgaacaggat gaaactgtga   16380
taagtctacg agaggatata ataacatcca aacatctctg tgttataatt gacttatatg   16440
caaatcacca taaacctcct tggataatag atctaaaccc acaagaaaaa atatgtgtac   16500
tgcgtgactt tatttctaaa tctaggcatg tggacacgtc ctccagatca tggaatactt   16560
ctgacctgga ttttgtaata ttctatgcat ctttgactta tttgagaaga ggtataataa   16620
aacaattaag gataagacaa gttactgagg ttatagatac cacaacaatg ttaagggaca   16680
atataattgt agagaatcct cctattaaaa caggagtgtt agacatcaga ggttgtataa   16740
tatacaattt agaggaaatc ctgtctatga acacaaaatc agcatcaaaa aagatctttta  16800
atcttaatag taggccgtca gtggagaatc ataaatatag aaggataggt ctcaactcat   16860
catcttgtta caaggcatta aatctatcac ctctgattca aaggtatttg ccgtcgggag   16920
ctcaaaggtt gtttatagga gaaggttctg ggagcatgat gttattatat cagtctacat   16980
tggggcaatc aatttctttt tacaattcag gtatagatgg agattatata ccaggtcaaa   17040
gagaactgaa actatttccc tctgaatact caattgctga ggaagaccca tctctgacgg   17100
ggaaattgaa aggactagtg gtgccccctat tcaatggaag accagaaaca acatggatcg   17160
ggaatttaga ctcctacgag tatatcataa ataggacagc ggggcgaagt ataggtcttg   17220
tccattctga catggagtct gggattgaca aaaatgtaga ggagatacta gtagaacatt   17280
cccatctaat atctatcgcg ataaatgtta tgatggagga cggactatta gtatccaaga   17340
tagcatacac ccctggattc ccaatctcaa gattatttaa catgtacaga tcatatttcg   17400
gactagtact ggtgtgtttc ccagtatata gtaatccaga ttctactgaa gtatatcttc   17460
tttgcttaca aagacggtc aagactattg ttcccccgca aaaagtcctt gagcactcta    17520
atttgcacga tgaagtcaat gaccagggaa taacatcagt gatttttaaa atcaagaatt   17580
cacagtctaa gcagttccac gatgatctaa agaagtacta tcagattgac caaccttttt   17640
ttgtaccaac taaaatcact agtgatgaac aagtacttct ccaagcaggg ctgaaactca   17700
atgggccaga aattcttaag agtgaaatca gttatgatat cggttcagat atcaatacat   17760
taagagacac catcataatt atgttaaatg aggctatgaa ttattttgat gacaacagat   17820
caccttcaca ccacctagaa ccctatccag ttttggagag aactagaatt aaaacaataa   17880
tgaattgtgt gactaaaaaa gtgattgtct actcacttat caagttcaag gacaccaaaa   17940
gctcagaact ttatcacatc aaaaataaca tcagaagaaa agttctaatc ttagatttca   18000
gatcgaagct catgacaaag actctaccta aaggatgca agagagaaga gaaaaaaacg    18060
gtttcaaaga agtttggata gtagatttat cgaatcgaga agttaaaatc tggtggaaga   18120
taatcggata catatctatt atctgattta accttccaaa tccaagacca actgataact   18180
tatgttgatc taaggttcag ttattaagaa aaacttaata acgattcttc tttacccttg   18240
```

```
ttcggt                                                            18246
```

<210> SEQ ID NO 2
<211> LENGTH: 532
<212> TYPE: PRT
<213> ORGANISM: Nipah virus

<400> SEQUENCE: 2

Met Ser Asp Ile Phe Glu Glu Ala Ala Ser Phe Arg Ser Tyr Gln Ser
 1               5                  10                  15

Lys Leu Gly Arg Asp Gly Arg Ala Ser Ala Ala Thr Ala Thr Leu Thr
            20                  25                  30

Thr Lys Ile Arg Ile Phe Val Pro Ala Thr Asn Ser Pro Glu Leu Arg
        35                  40                  45

Trp Glu Leu Thr Leu Phe Ala Leu Asp Val Ile Arg Ser Pro Ser Ala
 50                  55                  60

Ala Glu Ser Met Lys Val Gly Ala Ala Phe Thr Leu Ile Ser Met Tyr
 65                  70                  75                  80

Ser Glu Arg Pro Gly Ala Leu Ile Arg Ser Leu Leu Asn Asp Pro Asp
                85                  90                  95

Ile Glu Ala Val Ile Ile Asp Val Gly Ser Met Val Asn Gly Ile Pro
            100                 105                 110

Val Met Glu Arg Arg Gly Asp Lys Ala Gln Glu Met Glu Gly Leu
        115                 120                 125

Met Arg Ile Leu Lys Thr Ala Arg Asp Ser Ser Lys Gly Lys Thr Pro
130                 135                 140

Phe Val Asp Ser Arg Ala Tyr Gly Leu Arg Ile Thr Asp Met Ser Thr
145                 150                 155                 160

Leu Val Ser Ala Val Ile Thr Ile Glu Ala Gln Ile Trp Ile Leu Ile
                165                 170                 175

Ala Lys Ala Val Thr Ala Pro Asp Thr Ala Glu Glu Ser Glu Thr Arg
            180                 185                 190

Arg Trp Ala Lys Tyr Val Gln Gln Lys Arg Val Asn Pro Phe Phe Ala
        195                 200                 205

Leu Thr Gln Gln Trp Leu Thr Glu Met Arg Asn Leu Leu Ser Gln Ser
210                 215                 220

Leu Ser Val Arg Lys Phe Met Val Glu Ile Leu Ile Glu Val Lys Lys
225                 230                 235                 240

Gly Gly Ser Ala Lys Gly Arg Ala Val Glu Ile Ile Ser Asp Ile Gly
                245                 250                 255

Asn Tyr Val Glu Glu Thr Gly Met Ala Gly Phe Phe Ala Thr Ile Arg
            260                 265                 270

Phe Gly Leu Glu Thr Arg Tyr Pro Ala Leu Ala Leu Asn Glu Phe Gln
        275                 280                 285

Ser Asp Leu Asn Thr Ile Lys Ser Leu Met Leu Leu Tyr Arg Glu Ile
290                 295                 300

Gly Pro Arg Ala Pro Tyr Met Val Leu Leu Glu Glu Ser Ile Gln Thr
305                 310                 315                 320

Lys Phe Ala Pro Gly Gly Tyr Pro Leu Leu Trp Ser Phe Ala Met Gly
                325                 330                 335

Val Ala Thr Thr Ile Asp Arg Ser Met Gly Ala Leu Asn Ile Asn Arg
            340                 345                 350

Gly Tyr Leu Glu Pro Met Tyr Phe Arg Leu Gly Gln Lys Ser Ala Arg
        355                 360                 365

His His Ala Gly Gly Ile Asp Gln Asn Met Ala Asn Arg Leu Gly Leu
370                 375                 380

Ser Ser Asp Gln Val Ala Glu Leu Ala Ala Ala Val Gln Glu Thr Ser
385                 390                 395                 400

Ala Gly Arg Gln Glu Ser Asn Val Gln Ala Arg Glu Ala Lys Phe Ala
            405                 410                 415

Ala Gly Gly Val Leu Ile Gly Gly Ser Asp Gln Asp Ile Asp Glu Gly
            420                 425                 430

Glu Glu Pro Ile Glu Gln Ser Gly Arg Gln Ser Val Thr Phe Lys Arg
            435                 440                 445

Glu Met Ser Ile Ser Ser Leu Ala Asn Ser Val Pro Ser Ser Ser Val
450                 455                 460

Ser Thr Ser Gly Gly Thr Arg Leu Thr Asn Ser Leu Leu Asn Leu Arg
465                 470                 475                 480

Ser Arg Leu Ala Ala Lys Ala Ala Lys Glu Ala Ala Ser Ser Asn Ala
            485                 490                 495

Thr Asp Asp Pro Ala Ile Ser Asn Arg Thr Gln Gly Glu Ser Glu Lys
            500                 505                 510

Lys Asn Asn Gln Asp Leu Lys Pro Ala Gln Asn Asp Leu Asp Phe Val
515                 520                 525

Arg Ala Asp Val
530

<210> SEQ ID NO 3
<211> LENGTH: 709
<212> TYPE: PRT
<213> ORGANISM: Nipah virus

<400> SEQUENCE: 3

Met Asp Lys Leu Glu Leu Val Asn Asp Gly Leu Asn Ile Ile Asp Phe
1               5                   10                  15

Ile Gln Lys Asn Gln Lys Glu Ile Gln Lys Thr Tyr Gly Arg Ser Ser
            20                  25                  30

Ile Gln Gln Pro Ser Ile Lys Asp Gln Thr Lys Ala Trp Glu Asp Phe
        35                  40                  45

Leu Gln Cys Thr Ser Gly Glu Ser Glu Gln Val Glu Gly Gly Met Ser
50                  55                  60

Lys Asp Asp Gly Asp Val Glu Arg Arg Asn Leu Glu Asp Leu Ser Ser
65                  70                  75                  80

Thr Ser Pro Thr Asp Gly Thr Ile Gly Lys Arg Val Ser Asn Thr Arg
                85                  90                  95

Asp Trp Ala Glu Gly Ser Asp Asp Ile Gln Leu Asp Pro Val Val Thr
            100                 105                 110

Asp Val Val Tyr His Asp His Gly Gly Glu Cys Thr Gly Tyr Gly Phe
        115                 120                 125

Thr Ser Ser Pro Glu Arg Gly Trp Ser Asp Tyr Thr Ser Gly Ala Asn
    130                 135                 140

Asn Gly Asn Val Cys Leu Val Ser Asp Ala Lys Met Leu Ser Tyr Ala
145                 150                 155                 160

Pro Glu Ile Ala Val Ser Lys Glu Asp Arg Glu Thr Asp Leu Val His
                165                 170                 175

Leu Glu Asn Lys Leu Ser Thr Gly Leu Asn Pro Thr Ala Val Pro
            180                 185                 190

Phe Thr Leu Arg Asn Leu Ser Asp Pro Ala Lys Asp Ser Pro Val Ile
        195                 200                 205

```
Ala Glu His Tyr Tyr Gly Leu Gly Val Lys Glu Gln Asn Val Gly Pro
    210                 215                 220
Gln Thr Ser Arg Asn Val Asn Leu Asp Ser Ile Lys Leu Tyr Thr Ser
225                 230                 235                 240
Asp Asp Glu Glu Ala Asp Gln Leu Glu Phe Glu Asp Glu Phe Ala Gly
                245                 250                 255
Ser Ser Ser Glu Val Ile Val Gly Ile Ser Pro Glu Asp Glu Glu Pro
            260                 265                 270
Ser Ser Val Gly Gly Lys Pro Asn Glu Ser Ile Gly Arg Thr Ile Glu
        275                 280                 285
Gly Gln Ser Ile Arg Asp Asn Leu Gln Ala Lys Asp Asn Lys Ser Thr
    290                 295                 300
Asp Val Pro Gly Ala Gly Pro Lys Asp Ser Ala Val Lys Glu Glu Pro
305                 310                 315                 320
Pro Gln Lys Arg Leu Pro Met Leu Ala Glu Glu Phe Glu Cys Ser Gly
                325                 330                 335
Ser Glu Asp Pro Ile Ile Arg Glu Leu Leu Lys Glu Asn Ser Leu Ile
            340                 345                 350
Asn Cys Gln Gln Gly Lys Asp Ala Gln Pro Pro Tyr His Trp Ser Ile
        355                 360                 365
Glu Arg Ser Ile Ser Pro Asp Lys Thr Glu Ile Val Asn Gly Ala Val
    370                 375                 380
Gln Thr Ala Asp Arg Gln Arg Pro Gly Thr Pro Met Pro Lys Ser Arg
385                 390                 395                 400
Gly Ile Pro Ile Lys Lys Gly Thr Asp Ala Lys Tyr Pro Ser Ala Gly
                405                 410                 415
Thr Glu Asn Val Pro Gly Ser Lys Ser Gly Ala Thr Arg His Val Arg
            420                 425                 430
Gly Ser Pro Pro Tyr Gln Glu Gly Lys Ser Val Asn Ala Glu Asn Val
        435                 440                 445
Gln Leu Asn Ala Ser Thr Ala Val Lys Glu Thr Asp Lys Ser Glu Val
    450                 455                 460
Asn Pro Val Asp Asp Asn Asp Ser Leu Asp Asp Lys Tyr Ile Met Pro
465                 470                 475                 480
Ser Asp Asp Phe Ser Asn Thr Phe Phe Pro His Asp Thr Asp Arg Leu
                485                 490                 495
Asn Tyr His Ala Asp His Leu Gly Asp Tyr Asp Leu Glu Thr Leu Cys
            500                 505                 510
Glu Glu Ser Val Leu Met Gly Val Ile Asn Ser Ile Lys Leu Ile Asn
        515                 520                 525
Leu Asp Met Arg Leu Asn His Ile Glu Glu Gln Val Lys Glu Ile Pro
    530                 535                 540
Lys Ile Ile Asn Lys Leu Glu Ser Ile Asp Arg Val Leu Ala Lys Thr
545                 550                 555                 560
Asn Thr Ala Leu Ser Thr Ile Glu Gly His Leu Val Ser Met Met Ile
                565                 570                 575
Met Ile Pro Gly Lys Gly Lys Gly Glu Arg Lys Gly Lys Asn Asn Pro
            580                 585                 590
Glu Leu Lys Pro Val Ile Gly Arg Asp Ile Leu Glu Gln Gln Ser Leu
        595                 600                 605
Phe Ser Phe Asp Asn Val Lys Asn Phe Arg Asp Gly Ser Leu Thr Asn
    610                 615                 620
Glu Pro Tyr Gly Ala Ala Val Gln Leu Arg Glu Asp Leu Ile Leu Pro
625                 630                 635                 640
```

```
Glu Leu Asn Phe Glu Glu Thr Asn Ala Ser Gln Phe Val Pro Met Ala
                645                 650                 655

Asp Asp Ser Ser Arg Asp Val Ile Lys Thr Leu Ile Arg Thr His Ile
            660                 665                 670

Lys Asp Arg Glu Leu Arg Ser Glu Leu Ile Gly Tyr Leu Asn Lys Ala
            675                 680                 685

Glu Asn Asp Glu Glu Ile Gln Glu Ile Ala Asn Thr Val Asn Asp Ile
        690                 695                 700

Ile Asp Gly Asn Ile
705

<210> SEQ ID NO 4
<211> LENGTH: 456
<212> TYPE: PRT
<213> ORGANISM: Nipah virus

<400> SEQUENCE: 4

Met Asp Lys Leu Glu Leu Val Asn Asp Gly Leu Asn Ile Ile Asp Phe
  1               5                  10                  15

Ile Gln Lys Asn Gln Lys Glu Ile Gln Lys Thr Tyr Gly Arg Ser Ser
                20                  25                  30

Ile Gln Gln Pro Ser Ile Lys Asp Gln Thr Lys Ala Trp Glu Asp Phe
            35                  40                  45

Leu Gln Cys Thr Ser Gly Glu Ser Glu Gln Val Glu Gly Gly Met Ser
        50                  55                  60

Lys Asp Asp Gly Asp Val Glu Arg Arg Asn Leu Glu Asp Leu Ser Ser
 65                  70                  75                  80

Thr Ser Pro Thr Asp Gly Thr Ile Gly Lys Arg Val Ser Asn Thr Arg
                85                  90                  95

Asp Trp Ala Glu Gly Ser Asp Asp Ile Gln Leu Asp Pro Val Val Thr
            100                 105                 110

Asp Val Val Tyr His Asp His Gly Glu Cys Thr Gly Tyr Gly Phe
        115                 120                 125

Thr Ser Ser Pro Glu Arg Gly Trp Ser Asp Tyr Thr Ser Gly Ala Asn
        130                 135                 140

Asn Gly Asn Val Cys Leu Val Ser Asp Ala Lys Met Leu Ser Tyr Ala
145                 150                 155                 160

Pro Glu Ile Ala Val Ser Lys Glu Asp Arg Glu Thr Asp Leu Val His
                165                 170                 175

Leu Glu Asn Lys Leu Ser Thr Thr Gly Leu Asn Pro Thr Ala Val Pro
            180                 185                 190

Phe Thr Leu Arg Asn Leu Ser Asp Pro Ala Lys Asp Ser Pro Val Ile
        195                 200                 205

Ala Glu His Tyr Tyr Gly Leu Gly Val Lys Glu Gln Asn Val Gly Pro
    210                 215                 220

Gln Thr Ser Arg Asn Val Asn Leu Asp Ser Ile Lys Leu Tyr Thr Ser
225                 230                 235                 240

Asp Asp Glu Glu Ala Asp Gln Leu Glu Phe Glu Asp Glu Phe Ala Gly
                245                 250                 255

Ser Ser Ser Glu Val Ile Val Gly Ile Ser Pro Glu Asp Glu Glu Pro
            260                 265                 270

Ser Ser Val Gly Gly Lys Pro Asn Glu Ser Ile Gly Arg Thr Ile Glu
        275                 280                 285

Gly Gln Ser Ile Arg Asp Asn Leu Gln Ala Lys Asp Asn Lys Ser Thr
    290                 295                 300
```

```
Asp Val Pro Gly Ala Gly Pro Lys Asp Ser Ala Val Lys Glu Glu Pro
305                 310                 315                 320

Pro Gln Lys Arg Leu Pro Met Leu Ala Glu Glu Phe Glu Cys Ser Gly
            325                 330                 335

Ser Glu Asp Pro Ile Ile Arg Glu Leu Leu Lys Glu Asn Ser Leu Ile
            340                 345                 350

Asn Cys Gln Gln Gly Lys Asp Ala Gln Pro Pro Tyr His Trp Ser Ile
            355                 360                 365

Glu Arg Ser Ile Ser Pro Asp Lys Thr Glu Ile Val Asn Gly Ala Val
            370                 375                 380

Gln Thr Ala Asp Arg Gln Arg Pro Gly Thr Pro Met Pro Lys Ser Arg
385                 390                 395                 400

Gly Ile Pro Ile Lys Lys Gly His Arg Arg Glu Ile Ser Ile Cys Trp
            405                 410                 415

Asp Gly Lys Arg Ala Trp Val Glu Glu Trp Cys Asn Pro Ala Cys Ser
            420                 425                 430

Arg Ile Thr Pro Leu Pro Arg Arg Gln Glu Cys Gln Cys Gly Glu Cys
            435                 440                 445

Pro Thr Glu Cys Phe His Cys Gly
    450                 455

<210> SEQ ID NO 5
<211> LENGTH: 166
<212> TYPE: PRT
<213> ORGANISM: Nipah virus

<400> SEQUENCE: 5

Met Met Ala Ser Ile Leu Leu Thr Leu Phe Arg Arg Thr Lys Lys Lys
1               5                   10                  15

Tyr Arg Arg His Thr Asp Asp Gln Val Phe Asn Asn Pro Ala Ser Lys
            20                  25                  30

Ile Lys Gln Lys Pro Gly Lys Ile Phe Cys Ser Ala Pro Val Glu Asn
            35                  40                  45

Leu Asn Lys Leu Arg Gly Glu Cys Leu Arg Met Met Glu Met Leu Lys
50                  55                  60

Glu Glu Thr Trp Arg Ile Tyr Pro Val Leu Leu Pro Gln Met Glu Leu
65                  70                  75                  80

Leu Glu Arg Glu Cys Arg Thr Pro Val Thr Gly Gln Lys Val Gln Met
            85                  90                  95

Thr Tyr Asn Trp Thr Gln Trp Leu Gln Thr Leu Tyr Thr Met Ile Met
            100                 105                 110

Glu Glu Asn Val Pro Asp Met Asp Leu Leu Gln Ala Leu Arg Glu Gly
            115                 120                 125

Gly Val Ile Thr His Gln Glu Gln Thr Met Gly Met Tyr Val Leu Tyr
            130                 135                 140

Leu Met Gln Arg Cys Cys Pro Met Leu Pro Lys Leu Gln Phe Leu Lys
145                 150                 155                 160

Lys Ile Gly Lys Leu Ile
            165

<210> SEQ ID NO 6
<211> LENGTH: 352
<212> TYPE: PRT
<213> ORGANISM: Nipah virus

<400> SEQUENCE: 6
```

```
Met Glu Pro Asp Ile Lys Ser Ile Ser Ser Glu Ser Met Glu Gly Val
 1               5                  10                  15

Ser Asp Phe Ser Pro Ser Ser Trp Glu His Gly Gly Tyr Leu Asp Lys
             20                  25                  30

Val Glu Pro Glu Ile Asp Glu Asn Gly Ser Met Ile Pro Lys Tyr Lys
             35                  40                  45

Ile Tyr Thr Pro Gly Ala Asn Glu Arg Lys Tyr Asn Asn Tyr Met Tyr
     50                  55                  60

Leu Ile Cys Tyr Gly Phe Val Glu Asp Val Glu Arg Thr Pro Glu Thr
65                  70                  75                  80

Gly Lys Arg Lys Lys Ile Arg Thr Ile Ala Ala Tyr Pro Leu Gly Val
                 85                  90                  95

Gly Lys Ser Ala Ser His Pro Gln Asp Leu Leu Glu Glu Leu Cys Ser
            100                 105                 110

Leu Lys Val Thr Val Arg Arg Thr Ala Gly Ser Thr Glu Lys Ile Val
            115                 120                 125

Phe Gly Ser Ser Gly Pro Leu Asn His Leu Val Pro Trp Lys Lys Val
    130                 135                 140

Leu Thr Ser Gly Ser Ile Phe Asn Ala Val Lys Val Cys Arg Asn Val
145                 150                 155                 160

Asp Gln Ile Gln Leu Asp Lys His Gln Ala Leu Arg Ile Phe Phe Leu
                165                 170                 175

Ser Ile Thr Lys Leu Asn Asp Ser Gly Ile Tyr Met Ile Pro Arg Thr
            180                 185                 190

Met Leu Glu Phe Arg Arg Asn Asn Ala Ile Ala Phe Asn Leu Leu Val
    195                 200                 205

Tyr Leu Lys Ile Asp Ala Asp Leu Ser Lys Met Gly Ile Gln Gly Ser
210                 215                 220

Leu Asp Lys Asp Gly Phe Lys Val Ala Ser Phe Met Leu His Leu Gly
225                 230                 235                 240

Asn Phe Val Arg Arg Ala Gly Lys Tyr Tyr Ser Val Asp Tyr Cys Arg
                245                 250                 255

Arg Lys Ile Asp Arg Met Lys Leu Gln Phe Ser Leu Gly Ser Ile Gly
            260                 265                 270

Gly Leu Ser Leu His Ile Lys Ile Asn Gly Val Ile Ser Lys Arg Leu
    275                 280                 285

Phe Ala Gln Met Gly Phe Gln Lys Asn Leu Cys Phe Ser Leu Met Asp
290                 295                 300

Ile Asn Pro Trp Leu Asn Arg Leu Thr Trp Asn Asn Ser Cys Glu Ile
305                 310                 315                 320

Ser Arg Val Ala Ala Val Leu Gln Pro Ser Ile Pro Arg Glu Phe Met
                325                 330                 335

Ile Tyr Asp Asp Val Phe Ile Asp Asn Thr Gly Arg Ile Leu Lys Gly
            340                 345                 350

<210> SEQ ID NO 7
<211> LENGTH: 546
<212> TYPE: PRT
<213> ORGANISM: Nipah virus

<400> SEQUENCE: 7

Met Val Val Ile Leu Asp Lys Arg Cys Tyr Cys Asn Leu Leu Ile Leu
 1               5                  10                  15

Ile Leu Met Ile Ser Glu Cys Ser Val Gly Ile Leu His Tyr Glu Lys
             20                  25                  30
```

```
Leu Ser Lys Ile Gly Leu Val Lys Gly Val Thr Arg Lys Tyr Lys Ile
        35                  40                  45
Lys Ser Asn Pro Leu Thr Lys Asp Ile Val Lys Met Ile Pro Asn
    50                  55                  60
Val Ser Asn Met Ser Gln Cys Thr Gly Ser Val Met Glu Asn Tyr Lys
 65                  70                  75                  80
Thr Arg Leu Asn Gly Ile Leu Thr Pro Ile Lys Gly Ala Leu Glu Ile
                    85                  90                  95
Tyr Lys Asn Asn Thr His Asp Leu Val Gly Asp Val Arg Leu Ala Gly
                100                 105                 110
Val Ile Met Ala Gly Val Ala Ile Gly Ile Ala Thr Ala Ala Gln Ile
                115                 120                 125
Thr Ala Gly Val Ala Leu Tyr Glu Ala Met Lys Asn Ala Asp Asn Ile
            130                 135                 140
Asn Lys Leu Lys Ser Ser Ile Glu Ser Thr Asn Glu Ala Val Val Lys
145                 150                 155                 160
Leu Gln Glu Thr Ala Glu Lys Thr Val Tyr Val Leu Thr Ala Leu Gln
                    165                 170                 175
Asp Tyr Ile Asn Thr Asn Leu Val Pro Thr Ile Asp Lys Ile Ser Cys
            180                 185                 190
Lys Gln Thr Glu Leu Ser Leu Asp Leu Ala Leu Ser Lys Tyr Leu Ser
            195                 200                 205
Asp Leu Leu Phe Val Phe Gly Pro Asn Leu Gln Asp Pro Val Ser Asn
    210                 215                 220
Ser Met Thr Ile Gln Ala Ile Ser Gln Ala Phe Gly Gly Asn Tyr Glu
225                 230                 235                 240
Thr Leu Leu Arg Thr Leu Gly Tyr Ala Thr Glu Asp Phe Asp Asp Leu
                245                 250                 255
Leu Glu Ser Asp Ser Ile Thr Gly Gln Ile Ile Tyr Val Asp Leu Ser
                260                 265                 270
Ser Tyr Tyr Ile Ile Val Arg Val Tyr Phe Pro Ile Leu Thr Glu Ile
        275                 280                 285
Gln Gln Ala Tyr Ile Gln Glu Leu Leu Pro Val Ser Phe Asn Asn Asp
    290                 295                 300
Asn Ser Glu Trp Ile Ser Ile Val Pro Asn Phe Ile Leu Val Arg Asn
305                 310                 315                 320
Thr Leu Ile Ser Asn Ile Glu Ile Gly Phe Cys Leu Ile Thr Lys Arg
                325                 330                 335
Ser Val Ile Cys Asn Gln Asp Tyr Ala Thr Pro Met Thr Asn Asn Met
                340                 345                 350
Arg Glu Cys Leu Thr Gly Ser Thr Glu Lys Cys Pro Arg Glu Leu Val
            355                 360                 365
Val Ser Ser His Val Pro Arg Phe Ala Leu Ser Asn Gly Val Leu Phe
    370                 375                 380
Ala Asn Cys Ile Ser Val Thr Cys Gln Cys Gln Thr Thr Gly Arg Ala
385                 390                 395                 400
Ile Ser Gln Ser Gly Glu Gln Thr Leu Leu Met Ile Asp Asn Thr Thr
                405                 410                 415
Cys Pro Thr Ala Val Leu Gly Asn Val Ile Ser Leu Gly Lys Tyr
                420                 425                 430
Leu Gly Ser Val Asn Tyr Asn Ser Glu Gly Ile Ala Ile Gly Pro Pro
            435                 440                 445
Val Phe Thr Asp Lys Val Asp Ile Ser Ser Gln Ile Ser Ser Met Asn
    450                 455                 460
```

```
Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
                485                 490                 495

Leu Tyr Val Leu Ser Ile Ala Ser Leu Cys Ile Gly Leu Ile Thr Phe
            500                 505                 510

Ile Ser Phe Ile Ile Val Glu Lys Lys Arg Asn Thr Tyr Ser Arg Leu
        515                 520                 525

Glu Asp Arg Arg Val Arg Pro Thr Ser Ser Gly Asp Leu Tyr Tyr Ile
530                 535                 540

Gly Thr
545

<210> SEQ ID NO 8
<211> LENGTH: 602
<212> TYPE: PRT
<213> ORGANISM: Nipah virus

<400> SEQUENCE: 8

Met Pro Ala Glu Asn Lys Lys Val Arg Phe Glu Asn Thr Thr Ser Asp
 1               5                  10                  15

Lys Gly Lys Ile Pro Ser Lys Val Ile Lys Ser Tyr Tyr Gly Thr Met
            20                  25                  30

Asp Ile Lys Lys Ile Asn Glu Gly Leu Leu Asp Ser Lys Ile Leu Ser
        35                  40                  45

Ala Phe Asn Thr Val Ile Ala Leu Leu Gly Ser Ile Val Ile Ile Val
    50                  55                  60

Met Asn Ile Met Ile Ile Gln Asn Tyr Thr Arg Ser Thr Asp Asn Gln
65                  70                  75                  80

Ala Val Ile Lys Asp Ala Leu Gln Gly Ile Gln Gln Gln Ile Lys Gly
                85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
                245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
        275                 280                 285
```

Glu Phe Tyr Tyr Val Leu Cys Ala Val Ser Thr Val Gly Asp Pro Ile
    290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Tyr Asn Gln His Gln Leu Ala
                325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
                405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600

<210> SEQ ID NO 9
<211> LENGTH: 2244
<212> TYPE: PRT
<213> ORGANISM: Nipah virus

<400> SEQUENCE: 9

Met Ala Asp Glu Leu Ser Ile Ser Asp Ile Ile Tyr Pro Glu Cys His
1               5                   10                  15

Leu Asp Ser Pro Ile Val Ser Gly Lys Leu Ile Ser Ala Ile Glu Tyr
            20                  25                  30

Ala Gln Leu Arg His Asn Gln Pro Ser Asp Asp Lys Arg Leu Ser Glu
        35                  40                  45

Asn Ile Arg Leu Asn Leu His Gly Lys Arg Lys Ser Leu Tyr Ile Leu
    50                  55                  60

```
Arg Gln Ser Lys Gln Gly Asp Tyr Ile Arg Asn Asn Ile Lys Asn Leu
 65                  70                  75                  80

Lys Glu Phe Met His Ile Ala Tyr Pro Glu Cys Asn Asn Ile Leu Phe
                 85                  90                  95

Ser Ile Thr Ser Gln Gly Met Thr Ser Lys Leu Asp Asn Ile Met Lys
            100                 105                 110

Lys Ser Phe Lys Ala Tyr Asn Ile Ile Ser Lys Lys Val Ile Gly Met
        115                 120                 125

Leu Gln Asn Ile Thr Arg Asn Leu Ile Thr Gln Asp Arg Arg Asp Glu
    130                 135                 140

Ile Ile Asn Ile His Glu Cys Arg Arg Leu Gly Asp Leu Gly Lys Asn
145                 150                 155                 160

Met Ser Gln Ser Lys Trp Tyr Glu Cys Phe Leu Phe Trp Phe Thr Ile
                165                 170                 175

Lys Thr Glu Met Arg Ala Val Ile Lys Asn Ser Gln Lys Pro Lys Phe
            180                 185                 190

Arg Ser Asp Ser Cys Ile Ile His Met Arg Asp Lys Ser Thr Glu Ile
        195                 200                 205

Ile Leu Asn Pro Asn Leu Ile Cys Ile Phe Lys Ser Asp Lys Thr Gly
    210                 215                 220

Lys Lys Cys Tyr Tyr Leu Thr Pro Glu Met Val Leu Met Tyr Cys Asp
225                 230                 235                 240

Val Leu Glu Gly Arg Met Met Met Glu Thr Thr Val Lys Ser Asp Ile
                245                 250                 255

Lys Tyr Gln Pro Leu Ile Ser Arg Ser Asn Ala Leu Trp Gly Leu Ile
            260                 265                 270

Asp Pro Leu Phe Pro Val Met Gly Asn Arg Ile Tyr Asn Ile Val Ser
        275                 280                 285

Met Ile Glu Pro Leu Val Leu Ala Leu Leu Gln Leu Lys Asp Glu Ala
    290                 295                 300

Arg Ile Leu Arg Gly Ala Phe Leu His His Cys Ile Lys Glu Met His
305                 310                 315                 320

Gln Glu Leu Ser Glu Cys Gly Phe Thr Asp Gln Lys Ile Arg Ser Met
                325                 330                 335

Phe Ile Asp Asp Leu Leu Ser Ile Leu Asn Ile Asp Asn Ile His Leu
            340                 345                 350

Leu Ala Glu Phe Phe Ser Phe Phe Arg Thr Phe Gly His Pro Ile Leu
        355                 360                 365

Glu Ala Lys Val Ala Ala Glu Lys Val Arg Glu His Met Leu Ala Asp
    370                 375                 380

Lys Val Leu Glu Tyr Ala Pro Ile Met Lys Ala His Ala Ile Phe Cys
385                 390                 395                 400

Gly Thr Ile Ile Asn Gly Tyr Arg Asp Arg His Gly Gly Ala Trp Pro
                405                 410                 415

Pro Leu Tyr Leu Pro Ala His Ala Ser Lys His Ile Ile Arg Leu Lys
            420                 425                 430

Asn Ser Gly Glu Ser Leu Thr Ile Asp Asp Cys Val Lys Asn Trp Glu
        435                 440                 445

Ser Phe Cys Gly Ile Gln Phe Asp Cys Phe Met Glu Leu Lys Leu Asp
    450                 455                 460

Ser Asp Leu Ser Met Tyr Met Lys Asp Lys Ala Leu Ser Pro Ile Lys
465                 470                 475                 480

Asp Glu Trp Asp Ser Val Tyr Pro Arg Glu Val Leu Ser Tyr Thr Pro
```

```
                485                 490                 495
Pro Lys Ser Thr Glu Pro Arg Arg Leu Val Asp Val Phe Val Asn Asp
                500                 505                 510

Glu Asn Phe Asp Pro Tyr Asn Met Leu Glu Tyr Val Leu Ser Gly Ala
            515                 520                 525

Tyr Leu Glu Asp Glu Gln Phe Asn Val Ser Tyr Ser Leu Lys Glu Lys
            530                 535                 540

Glu Thr Lys Gln Ala Gly Arg Leu Phe Ala Lys Met Thr Tyr Lys Met
545                 550                 555                 560

Arg Ala Cys Gln Val Ile Ala Glu Ala Leu Ile Ala Ser Gly Val Gly
                565                 570                 575

Lys Tyr Phe Lys Glu Asn Gly Met Val Lys Asp Glu His Glu Leu Leu
            580                 585                 590

Lys Thr Leu Phe Gln Leu Ser Ile Ser Ser Val Pro Arg Gly Asn Ser
            595                 600                 605

Gln Gly Asn Asp Pro Gln Ser Ile Asn Asn Ile Glu Arg Asp Phe Gln
610                 615                 620

Tyr Phe Lys Gly Val Thr Thr Asn Val Lys Asp Lys Lys Asn Asn Ser
625                 630                 635                 640

Phe Asn Lys Val Lys Ser Ala Leu Asn Asn Pro Cys Gln Ala Asp Gly
                645                 650                 655

Val His His Asn Met Ser Pro Asn Thr Arg Asn Arg Tyr Lys Cys Ser
            660                 665                 670

Asn Thr Ser Lys Ser Phe Leu Asp Tyr His Thr Glu Phe Asn Pro His
            675                 680                 685

Asn His Tyr Lys Ser Asp Asn Thr Glu Ala Ala Val Leu Ser Arg Tyr
            690                 695                 700

Glu Asp Asn Thr Gly Thr Lys Phe Asp Thr Val Ser Ala Phe Leu Thr
705                 710                 715                 720

Thr Asp Leu Lys Lys Phe Cys Leu Asn Trp Arg Tyr Glu Ser Met Ala
                725                 730                 735

Ile Phe Ala Glu Arg Leu Asp Glu Ile Tyr Gly Leu Pro Gly Phe Phe
            740                 745                 750

Asn Trp Met His Lys Arg Leu Glu Arg Ser Val Ile Tyr Val Ala Asp
            755                 760                 765

Pro Asn Cys Pro Pro Asn Ile Asp Lys His Met Glu Leu Glu Lys Thr
            770                 775                 780

Pro Glu Asp Asp Ile Phe Ile His Tyr Pro Lys Gly Gly Ile Glu Gly
785                 790                 795                 800

Tyr Ser Gln Lys Thr Trp Thr Ile Ala Thr Ile Pro Phe Leu Phe Leu
                805                 810                 815

Ser Ala Tyr Glu Thr Asn Thr Arg Ile Ala Ala Ile Val Gln Gly Asp
            820                 825                 830

Asn Glu Ser Ile Ala Ile Thr Gln Lys Val His Pro Asn Leu Pro Tyr
            835                 840                 845

Lys Val Lys Lys Glu Ile Cys Ala Lys Gln Ala Gln Leu Tyr Phe Glu
850                 855                 860

Arg Leu Arg Met Asn Leu Arg Ala Leu Gly His Asn Leu Lys Ala Thr
865                 870                 875                 880

Glu Thr Ile Ile Ser Thr His Leu Phe Ile Tyr Ser Lys Lys Ile His
                885                 890                 895

Tyr Asp Gly Ala Val Leu Ser Gln Ala Leu Lys Ser Met Ser Arg Cys
            900                 905                 910
```

```
Cys Phe Trp Ser Glu Thr Leu Val Asp Glu Thr Arg Ser Ala Cys Ser
        915                 920                 925

Asn Ile Ser Thr Thr Ile Ala Lys Ala Ile Glu Asn Gly Leu Ser Arg
        930                 935                 940

Asn Val Gly Tyr Cys Ile Asn Ile Leu Lys Val Ile Gln Gln Leu Leu
945                 950                 955                 960

Ile Ser Thr Glu Phe Ser Ile Asn Glu Thr Leu Thr Leu Asp Val Thr
                965                 970                 975

Ser Pro Ile Ser Asn Asn Leu Asp Trp Leu Ile Thr Ala Ala Leu Ile
                980                 985                 990

Pro Ala Pro Ile Gly Gly Phe Asn Tyr Leu Asn Leu Ser Arg Ile Phe
                995                1000                1005

Val Arg Asn Ile Gly Asp Pro Val Thr Ala Ser Leu Ala Asp Leu Lys
        1010                1015                1020

Arg Met Ile Asp His Ser Ile Met Thr Glu Ser Val Leu Gln Lys Val
1025                1030                1035                1040

Met Asn Gln Glu Pro Gly Asp Ala Ser Phe Leu Asp Trp Ala Ser Asp
                1045                1050                1055

Pro Tyr Ser Gly Asn Leu Pro Ser Gln Ser Ile Thr Lys Thr Ile
                1060                1065                1070

Lys Asn Ile Thr Ala Arg Thr Ile Leu Arg Asn Ser Pro Asn Pro Met
        1075                1080                1085

Leu Lys Gly Leu Phe His Asp Lys Ser Phe Asp Glu Asp Leu Glu Leu
        1090                1095                1100

Ala Ser Phe Leu Met Asp Arg Arg Val Ile Leu Pro Arg Ala Ala His
1105                1110                1115                1120

Glu Ile Leu Asp Asn Ser Leu Thr Gly Ala Arg Glu Glu Ile Ala Gly
                1125                1130                1135

Leu Leu Asp Thr Thr Lys Gly Leu Ile Arg Ser Gly Leu Arg Lys Ser
                1140                1145                1150

Gly Leu Gln Pro Lys Leu Val Ser Arg Leu Ser His His Asp Tyr Asn
        1155                1160                1165

Gln Phe Leu Ile Leu Asn Lys Leu Leu Ser Asn Arg Arg Gln Asn Asp
        1170                1175                1180

Leu Ile Ser Ser Asn Thr Cys Ser Val Asp Leu Ala Arg Ala Leu Arg
1185                1190                1195                1200

Ser His Met Trp Arg Glu Leu Ala Leu Gly Arg Val Ile Tyr Gly Leu
                1205                1210                1215

Glu Val Pro Asp Ala Leu Glu Ala Met Val Gly Arg Tyr Ile Thr Gly
                1220                1225                1230

Ser Leu Glu Cys Gln Ile Cys Glu Gln Gly Asn Thr Met Tyr Gly Trp
        1235                1240                1245

Phe Phe Val Pro Arg Asp Ser Gln Leu Asp Gln Val Asp Arg Glu His
        1250                1255                1260

Ser Ser Ile Arg Val Pro Tyr Val Gly Ser Ser Thr Asp Glu Arg Ser
1265                1270                1275                1280

Asp Ile Lys Leu Gly Asn Val Lys Arg Pro Thr Lys Ala Leu Arg Ser
                1285                1290                1295

Ala Ile Arg Ile Ala Thr Val Tyr Thr Trp Ala Tyr Gly Asp Asn Glu
                1300                1305                1310

Glu Cys Trp Tyr Glu Ala Trp Tyr Leu Ala Ser Gln Arg Val Asn Ile
        1315                1320                1325

Asp Leu Asp Val Leu Lys Ala Ile Thr Pro Val Ser Thr Ser Asn Asn
        1330                1335                1340
```

```
Leu Ser His Arg Leu Arg Asp Lys Ser Thr Gln Phe Lys Phe Ala Gly
1345                1350                1355                1360

Ser Val Leu Asn Arg Val Ser Arg Tyr Val Asn Ile Ser Asn Asp Asn
            1365                1370                1375

Leu Asp Phe Arg Ile Glu Gly Glu Lys Val Asp Thr Asn Leu Ile Tyr
        1380                1385                1390

Gln Gln Ala Met Leu Leu Gly Leu Ser Val Leu Glu Gly Lys Phe Arg
    1395                1400                1405

Leu Arg Leu Glu Thr Asp Asp Tyr Asn Gly Ile Tyr His Leu His Val
1410                1415                1420

Lys Asp Asn Cys Cys Val Lys Glu Val Ala Asp Val Gly Gln Val Asp
1425                1430                1435                1440

Ala Glu Leu Pro Ile Pro Glu Tyr Thr Glu Val Asp Asn Asn His Leu
                1445                1450                1455

Ile Tyr Asp Pro Asp Pro Val Ser Glu Ile Asp Cys Ser Arg Leu Ser
            1460                1465                1470

Asn Gln Glu Ser Lys Ser Arg Glu Leu Asp Phe Pro Leu Trp Ser Thr
        1475                1480                1485

Glu Glu Leu His Asp Val Leu Ala Lys Thr Val Ala Gln Thr Val Leu
    1490                1495                1500

Glu Ile Ile Thr Lys Ala Asp Lys Asp Val Leu Lys Gln His Leu Ala
1505                1510                1515                1520

Ile Asp Ser Asp Asp Asn Ile Asn Ser Leu Ile Thr Glu Phe Leu Ile
                1525                1530                1535

Val Asp Pro Glu Leu Phe Ala Leu Tyr Leu Gly Gln Ser Ile Ser Ile
            1540                1545                1550

Lys Trp Ala Phe Glu Ile His His Arg Arg Pro Arg Gly Arg His Thr
        1555                1560                1565

Met Val Asp Leu Leu Ser Asp Leu Val Ser Asn Thr Ser Lys His Thr
    1570                1575                1580

Tyr Lys Val Leu Ser Asn Ala Leu Ser His Pro Arg Val Phe Lys Arg
1585                1590                1595                1600

Phe Val Asn Cys Gly Leu Leu Leu Pro Thr Gln Gly Pro Tyr Leu His
                1605                1610                1615

Gln Gln Asp Phe Glu Lys Leu Ser Gln Asn Leu Leu Val Thr Ser Tyr
            1620                1625                1630

Met Ile Tyr Leu Met Asn Trp Cys Asp Phe Lys Lys Ser Pro Phe Leu
        1635                1640                1645

Ile Ala Glu Gln Asp Glu Thr Val Ile Ser Leu Arg Glu Asp Ile Ile
    1650                1655                1660

Thr Ser Lys His Leu Cys Val Ile Ile Asp Leu Tyr Ala Asn His His
1665                1670                1675                1680

Lys Pro Pro Trp Ile Ile Asp Leu Asn Pro Gln Glu Lys Ile Cys Val
                1685                1690                1695

Leu Arg Asp Phe Ile Ser Lys Ser Arg His Val Asp Thr Ser Ser Arg
            1700                1705                1710

Ser Trp Asn Thr Ser Asp Leu Asp Phe Val Ile Phe Tyr Ala Ser Leu
        1715                1720                1725

Thr Tyr Leu Arg Arg Gly Ile Ile Lys Gln Leu Arg Ile Arg Gln Val
    1730                1735                1740

Thr Glu Val Ile Asp Thr Thr Thr Met Leu Arg Asp Asn Ile Ile Val
1745                1750                1755                1760

Glu Asn Pro Pro Ile Lys Thr Gly Val Leu Asp Ile Arg Gly Cys Ile
```

```
                      1765               1770               1775
Ile Tyr Asn Leu Glu Glu Ile Leu Ser Met Asn Thr Lys Ser Ala Ser
            1780               1785               1790
Lys Lys Ile Phe Asn Leu Asn Ser Arg Pro Ser Val Glu Asn His Lys
            1795               1800               1805
Tyr Arg Arg Ile Gly Leu Asn Ser Ser Ser Cys Tyr Lys Ala Leu Asn
            1810               1815               1820
Leu Ser Pro Leu Ile Gln Arg Tyr Leu Pro Ser Gly Ala Gln Arg Leu
1825                1830               1835               1840
Phe Ile Gly Glu Gly Ser Gly Ser Met Met Leu Leu Tyr Gln Ser Thr
                1845               1850               1855
Leu Gly Gln Ser Ile Ser Phe Tyr Asn Ser Gly Ile Asp Gly Asp Tyr
            1860               1865               1870
Ile Pro Gly Gln Arg Glu Leu Lys Leu Phe Pro Ser Glu Tyr Ser Ile
            1875               1880               1885
Ala Glu Glu Asp Pro Ser Leu Thr Gly Lys Leu Lys Gly Leu Val Val
            1890               1895               1900
Pro Leu Phe Asn Gly Arg Pro Glu Thr Thr Trp Ile Gly Asn Leu Asp
1905                1910               1915               1920
Ser Tyr Glu Tyr Ile Ile Asn Arg Thr Ala Gly Arg Ser Ile Gly Leu
            1925               1930               1935
Val His Ser Asp Met Glu Ser Gly Ile Asp Lys Asn Val Glu Glu Ile
            1940               1945               1950
Leu Val Glu His Ser His Leu Ile Ser Ile Ala Ile Asn Val Met Met
            1955               1960               1965
Glu Asp Gly Leu Leu Val Ser Lys Ile Ala Tyr Thr Pro Gly Phe Pro
            1970               1975               1980
Ile Ser Arg Leu Phe Asn Met Tyr Arg Ser Tyr Phe Gly Leu Val Leu
1985                1990               1995               2000
Val Cys Phe Pro Val Tyr Ser Asn Pro Asp Ser Thr Glu Val Tyr Leu
                2005               2010               2015
Leu Cys Leu Gln Lys Thr Val Lys Thr Ile Val Pro Pro Gln Lys Val
            2020               2025               2030
Leu Glu His Ser Asn Leu His Asp Glu Val Asn Asp Gln Gly Ile Thr
            2035               2040               2045
Ser Val Ile Phe Lys Ile Lys Asn Ser Gln Ser Lys Gln Phe His Asp
            2050               2055               2060
Asp Leu Lys Lys Tyr Tyr Gln Ile Asp Gln Pro Phe Phe Val Pro Thr
2065                2070               2075               2080
Lys Ile Thr Ser Asp Glu Gln Val Leu Leu Gln Ala Gly Leu Lys Leu
                2085               2090               2095
Asn Gly Pro Glu Ile Leu Lys Ser Glu Ile Ser Tyr Asp Ile Gly Ser
            2100               2105               2110
Asp Ile Asn Thr Leu Arg Asp Thr Ile Ile Met Leu Asn Glu Ala
            2115               2120               2125
Met Asn Tyr Phe Asp Asp Asn Arg Ser Pro Ser His His Leu Glu Pro
            2130               2135               2140
Tyr Pro Val Leu Glu Arg Thr Arg Ile Lys Thr Ile Met Asn Cys Val
2145                2150               2155               2160
Thr Lys Lys Val Ile Val Tyr Ser Leu Ile Lys Phe Lys Asp Thr Lys
                2165               2170               2175
Ser Ser Glu Leu Tyr His Ile Leu Asn Asn Ile Arg Arg Lys Val Leu
            2180               2185               2190
```

```
Ile Leu Asp Phe Arg Ser Lys Leu Met Thr Lys Thr Leu Pro Lys Gly
        2195                2200                2205

Met Gln Glu Arg Arg Glu Lys Asn Gly Phe Lys Glu Val Trp Ile Val
    2210                2215                2220

Asp Leu Ser Asn Arg Glu Val Lys Ile Trp Trp Lys Ile Ile Gly Tyr
2225                2230                2235                2240

Ile Ser Ile Ile

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Met Pro Ala Glu Asn Lys Lys Val Val Lys Ile Pro Glu Gln Cys Thr
1               5                   10                  15

<210> SEQ ID NO 11
<211> LENGTH: 88
<212> TYPE: DNA
<213> ORGANISM: Artificial Sequence
<220> FEATURE:
<221> NAME/KEY: CDS
<222> LOCATION: (30)..(77)
<220> FEATURE:
<223> OTHER INFORMATION: Description of Artificial Sequence: Synthetic
      oligonucleotide

<400> SEQUENCE: 11
atcgcgatat ccgttaagtt tgtatcgta atg ccg gca gaa aac aag aaa gtt         53
                                 Met Pro Ala Glu Asn Lys Lys Val
                                  1               5 gtt aag ata cca gag caa tgt aca taactcgagc g                            88
Val Lys Ile Pro Glu Gln Cys Thr
     10              15

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggcagtgtcg ggagctgtaa                                                   20

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
cgctcgagtt atgtacattg ctctggtatc ttaac                                  35

<210> SEQ ID NO 14
<211> LENGTH: 602
<212> TYPE: PRT
<213> ORGANISM: Artificial Sequence
<220> FEATURE:
<223> OTHER INFORMATION: Description of Artificial Sequence: Synthetic
``` plasmid pSL-6802-1-4

<400> SEQUENCE: 14

```
Met Pro Ala Glu Asn Lys Lys Val Arg Phe Glu Asn Thr Thr Ser Asp
  1               5                  10                  15
Lys Gly Lys Ile Pro Ser Lys Val Ile Lys Ser Tyr Tyr Gly Thr Met
             20                  25                  30
Asp Ile Lys Lys Ile Asn Glu Gly Leu Leu Asp Ser Lys Ile Leu Ser
         35                  40                  45
Ala Phe Asn Thr Val Ile Ala Leu Leu Gly Ser Ile Val Ile Ile Val
     50                  55                  60
Met Asn Ile Met Ile Ile Gln Asn Tyr Thr Arg Ser Thr Asp Asn Gln
 65                  70                  75                  80
Ala Val Ile Lys Asp Ala Leu Gln Gly Ile Gln Gln Ile Lys Gly
                 85                  90                  95
Leu Ala Asp Lys Ile Gly Thr Glu Ile Gly Pro Lys Val Ser Leu Ile
                100                 105                 110
Asp Thr Ser Ser Thr Ile Thr Ile Pro Ala Asn Ile Gly Leu Leu Gly
            115                 120                 125
Ser Lys Ile Ser Gln Ser Thr Ala Ser Ile Asn Glu Asn Val Asn Glu
        130                 135                 140
Lys Cys Lys Phe Thr Leu Pro Pro Leu Lys Ile His Glu Cys Asn Ile
145                 150                 155                 160
Ser Cys Pro Asn Pro Leu Pro Phe Arg Glu Tyr Arg Pro Gln Thr Glu
                165                 170                 175
Gly Val Ser Asn Leu Val Gly Leu Pro Asn Asn Ile Cys Leu Gln Lys
            180                 185                 190
Thr Ser Asn Gln Ile Leu Lys Pro Lys Leu Ile Ser Tyr Thr Leu Pro
        195                 200                 205
Val Val Gly Gln Ser Gly Thr Cys Ile Thr Asp Pro Leu Leu Ala Met
    210                 215                 220
Asp Glu Gly Tyr Phe Ala Tyr Ser His Leu Glu Arg Ile Gly Ser Cys
225                 230                 235                 240
Ser Arg Gly Val Ser Lys Gln Arg Ile Ile Gly Val Gly Glu Val Leu
                245                 250                 255
Asp Arg Gly Asp Glu Val Pro Ser Leu Phe Met Thr Asn Val Trp Thr
            260                 265                 270
Pro Pro Asn Pro Asn Thr Val Tyr His Cys Ser Ala Val Tyr Asn Asn
        275                 280                 285
Glu Phe Tyr Tyr Val Leu Cys Ala Val Ser Thr Val Gly Asp Pro Ile
    290                 295                 300
Leu Asn Ser Thr Tyr Trp Ser Gly Ser Leu Met Met Thr Arg Leu Ala
305                 310                 315                 320
Val Lys Pro Lys Ser Asn Gly Gly Tyr Asn Gln His Gln Leu Ala
                325                 330                 335
Leu Arg Ser Ile Glu Lys Gly Arg Tyr Asp Lys Val Met Pro Tyr Gly
            340                 345                 350
Pro Ser Gly Ile Lys Gln Gly Asp Thr Leu Tyr Phe Pro Ala Val Gly
        355                 360                 365
Phe Leu Val Arg Thr Glu Phe Lys Tyr Asn Asp Ser Asn Cys Pro Ile
    370                 375                 380
Thr Lys Cys Gln Tyr Ser Lys Pro Glu Asn Cys Arg Leu Ser Met Gly
385                 390                 395                 400
Ile Arg Pro Asn Ser His Tyr Ile Leu Arg Ser Gly Leu Leu Lys Tyr
```

```
                   405                 410                 415
Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
    450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
                485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
    530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
                565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
        595                 600

<210> SEQ ID NO 15
<211> LENGTH: 4067
<212> TYPE: DNA
<213> ORGANISM: Artificial Sequence
<220> FEATURE:
<221> NAME/KEY: CDS
<222> LOCATION: (1770)..(3575)
<220> FEATURE:
<223> OTHER INFORMATION: Description of Artificial Sequence: Synthetic
      plasmid pSL-6802-1-4

<400> SEQUENCE: 15
gcggccgcat tctgaatgtt aaatgttata ctttggatga agctataaat atgcattgga    60
aaaataatcc atttaaagaa aggattcaaa tactacaaaa cctaagcgat aatatgttaa   120
ctaagcttat tcttaacgac gctttaaata tacacaaata acataatttt ttgtataacc   180
taacaaataa ctaaaacata aaaataataa aaggaaatgt aatatcgtaa ttattttact   240 cagganatggg gttaaatatt tatatcacgt gtatatctat actgttatcg tatactcttt   300
acaattacta ttacgaatat gcaagagata ataagattac gtatttaaga gaatcttgtc   360
atgataattg ggtacgacat agtgataaat gctatttcgc atcgttacat aaagtcagtt   420
ggaaagatgg atttgacaga tgtaacttaa taggtgcaaa aatgttaaat aacagcattc   480
tatcggaaga taggatacca gttatattat acaaaaatca ctggttggat aaaacagatt   540
ctgcaatatt cgtaaaagat gaagattact gcgaatttgt aaactatgac aataaaaagc   600
catttatctc aacgacatcg tgtaattctt ccatgtttta tgtatgtgtt tcagatatta   660
tgagattact ataaactttt tgtatactta tattccgtaa actatattaa tcatgaagaa   720
aatgaaaaag tatagaagct gttcacgagc ggttgttgaa acaacaaaa ttatacattc    780 aagatggctt acatatacgt ctgtgaggct atcatggata atgacaatgc atctctaaat   840
```

| | |
|---|---|
| aggttttttgg acaatggatt cgaccctaac acggaatatg gtactctaca atctcctctt | 900 |
| gaaatggctg taatgttcaa gaataccgag gctataaaaa tcttgatgag gtatggagct | 960 |
| aaacctgtag ttactgaatg cacaacttct tgtctgcatg atgcggtgtt gagagacgac | 1020 |
| tacaaaatag tgaaagatct gttgaagaat aactatgtaa acaatgttct ttacagcgga | 1080 |
| ggctttactc ctttgtgttt ggcagcttac cttaacaaag ttaatttggt taaacttcta | 1140 |
| ttggctcatt cggcggatgt agatatttca aacacggatc ggttaactcc tctacatata | 1200 |
| gccgtatcaa ataaaaattt aacaatggtt aaacttctat tgaacaaagg tgctgatact | 1260 |
| gacttgctgg ataacatggg acgtactcct ttaatgatcg ctgtacaatc tggaaatatt | 1320 |
| gaaatatgta gcacactact taaaaaaaat aaaatgtcca gaactgggaa aaattgatct | 1380 |
| tgccagctgt aattcatggt agaaaagaag tgctcaggct acttttcaac aaaggagcag | 1440 |
| atgtaaacta catctttgaa agaaatggaa aatcatatac tgttttggaa ttgattaaag | 1500 |
| aaagttactc tgagacacaa aagaggtagc tgaagtggta ctctcaaagg tacgtgacta | 1560 |
| attagctata aaaaggatcc gggttaatta attagtcatc aggcagggcg agaacgagac | 1620 |
| tatctgctcg ttaattaatt agagcttctt tattctatac ttaaaaagtg aaaataaata | 1680 |
| caaaggttct tgagggttgt gttaaattga agcgagaaa taatcataaa ttatttcatt | 1740 |
| atcgcgatat ccgttaagtt tgtatcgta atg ccg gca gaa aac aag aaa gtt | 1793 |
|                                                Met Pro Ala Glu Asn Lys Lys Val<br>                                                  1                5 | |
| aga ttc gaa aat act act tca gac aaa ggg aaa att cct agt aaa gtt<br>Arg Phe Glu Asn Thr Thr Ser Asp Lys Gly Lys Ile Pro Ser Lys Val<br> 10                              15                             20 | 1841 |
| att aag agc tac tac gga acc atg gac att aag aaa ata aat gaa gga<br>Ile Lys Ser Tyr Tyr Gly Thr Met Asp Ile Lys Lys Ile Asn Glu Gly<br>25                            30                            35                            40 | 1889 |
| tta ttg gac agc aaa ata tta agt gct ttc aac aca gta ata gca ttg<br>Leu Leu Asp Ser Lys Ile Leu Ser Ala Phe Asn Thr Val Ile Ala Leu<br>                        45                            50                            55 | 1937 |
| ctt gga tct atc gtg atc ata gtg atg aat ata atg atc caa aat<br>Leu Gly Ser Ile Val Ile Ile Val Met Asn Ile Met Ile Ile Gln Asn<br>     60                           65                            70 | 1985 |
| tac aca aga tca aca gac aat cag gcc gtg atc aaa gat gcg ttg cag<br>Tyr Thr Arg Ser Thr Asp Asn Gln Ala Val Ile Lys Asp Ala Leu Gln<br>75                            80                            85 | 2033 |
| ggt atc caa cag cag atc aaa ggg ctt gct gac aaa atc ggc aca gag<br>Gly Ile Gln Gln Gln Ile Lys Gly Leu Ala Asp Lys Ile Gly Thr Glu<br>         90                           95                          100 | 2081 |
| ata ggg ccc aaa gta tca ctg att gac aca tcc agt acc att act atc<br>Ile Gly Pro Lys Val Ser Leu Ile Asp Thr Ser Ser Thr Ile Thr Ile<br>105                         110                          115                        120 | 2129 |
| cca gct aac att ggg ctg tta ggt tca aag atc agc cag tcg act gca<br>Pro Ala Asn Ile Gly Leu Leu Gly Ser Lys Ile Ser Gln Ser Thr Ala<br>                        125                          130                          135 | 2177 |
| agt ata aat gag aat gtg aat gaa aaa tgc aaa ttc aca ctg cct ccc<br>Ser Ile Asn Glu Asn Val Asn Glu Lys Cys Lys Phe Thr Leu Pro Pro<br>                   140                          145                          150 | 2225 |
| ttg aaa atc cac gaa tgt aac att tct tgt cct aac cca ctc cct ttt<br>Leu Lys Ile His Glu Cys Asn Ile Ser Cys Pro Asn Pro Leu Pro Phe<br>               155                          160                          165 | 2273 |
| aga gag tat agg cca cag aca gaa ggg gtg agc aat cta gta gga tta<br>Arg Glu Tyr Arg Pro Gln Thr Glu Gly Val Ser Asn Leu Val Gly Leu<br>         170                           175                          180 | 2321 |
| cct aat aat att tgc ctg caa aag aca tct aat cag ata ttg aag cca<br>Pro Asn Asn Ile Cys Leu Gln Lys Thr Ser Asn Gln Ile Leu Lys Pro | 2369 |

-continued

```
              185                 190                 195                 200
aag ctg att tca tac act tta ccc gta gtc ggt caa agt ggt acc tgt          2417
Lys Leu Ile Ser Tyr Thr Leu Pro Val Val Gly Gln Ser Gly Thr Cys
                    205                 210                 215 atc aca gac cca ttg ctg gct atg gac gag ggc tat ttt gca tat agc          2465
Ile Thr Asp Pro Leu Leu Ala Met Asp Glu Gly Tyr Phe Ala Tyr Ser
                220                 225                 230 cac ctg gaa aga atc gga tca tgt tca aga ggg gtc tcc aaa caa aga          2513
His Leu Glu Arg Ile Gly Ser Cys Ser Arg Gly Val Ser Lys Gln Arg
            235                 240                 245 ata ata gga gtt gga gag gta cta gac aga ggt gat gaa gtt cct tct          2561
Ile Ile Gly Val Gly Glu Val Leu Asp Arg Gly Asp Glu Val Pro Ser
        250                 255                 260 tta ttt atg acc aat gtc tgg acc cca cca aat cca aac acc gtt tac          2609
Leu Phe Met Thr Asn Val Trp Thr Pro Pro Asn Pro Asn Thr Val Tyr
265                 270                 275                 280 cac tgt agt gct gta tac aac aat gaa ttc tat tat gta ctt tgt gca          2657
His Cys Ser Ala Val Tyr Asn Asn Glu Phe Tyr Tyr Val Leu Cys Ala
                285                 290                 295 gtg tca act gtt gga gac cct att ctg aat agc acc tac tgg tcc gga          2705
Val Ser Thr Val Gly Asp Pro Ile Leu Asn Ser Thr Tyr Trp Ser Gly
                300                 305                 310 tct cta atg atg acc cgt cta gct gtg aaa ccc aag agt aat ggt ggg          2753
Ser Leu Met Met Thr Arg Leu Ala Val Lys Pro Lys Ser Asn Gly Gly
            315                 320                 325 ggt tac aat caa cat caa ctt gcc cta cga agt atc gag aaa ggg agg          2801
Gly Tyr Asn Gln His Gln Leu Ala Leu Arg Ser Ile Glu Lys Gly Arg
        330                 335                 340 tat gat aaa gtt atg ccg tat gga cct tca ggc atc aaa cag ggt gac          2849
Tyr Asp Lys Val Met Pro Tyr Gly Pro Ser Gly Ile Lys Gln Gly Asp
345                 350                 355                 360 acc ctg tat ttt cct gct gta gga ttt ttg gtc agg aca gag ttt aaa          2897
Thr Leu Tyr Phe Pro Ala Val Gly Phe Leu Val Arg Thr Glu Phe Lys
                365                 370                 375 tac aat gat tca aat tgt ccc atc acg aag tgt caa tac agt aaa cct          2945
Tyr Asn Asp Ser Asn Cys Pro Ile Thr Lys Cys Gln Tyr Ser Lys Pro
                380                 385                 390 gaa aat tgc agg cta tct atg ggg att aga cca aac agc cat tat atc          2993
Glu Asn Cys Arg Leu Ser Met Gly Ile Arg Pro Asn Ser His Tyr Ile
            395                 400                 405 ctt cga tct gga cta tta aaa tac aat cta tca gat ggg gag aac ccc          3041
Leu Arg Ser Gly Leu Leu Lys Tyr Asn Leu Ser Asp Gly Glu Asn Pro
        410                 415                 420 aaa gtt gta ttc att gaa ata tct gat caa aga tta tct att gga tct          3089
Lys Val Val Phe Ile Glu Ile Ser Asp Gln Arg Leu Ser Ile Gly Ser
425                 430                 435                 440 cct agc aaa atc tat gat tct ttg ggt caa cct gtt ttc tac caa gcg          3137
Pro Ser Lys Ile Tyr Asp Ser Leu Gly Gln Pro Val Phe Tyr Gln Ala
                445                 450                 455 tca ttt tca tgg gat act atg att aaa ttt gga gat gtt cta aca gtc          3185
Ser Phe Ser Trp Asp Thr Met Ile Lys Phe Gly Asp Val Leu Thr Val
                460                 465                 470 aac cct ctg gtt gtc aat tgg cgt aat aac acg gta ata tca aga ccc          3233
Asn Pro Leu Val Val Asn Trp Arg Asn Asn Thr Val Ile Ser Arg Pro
            475                 480                 485 ggg caa tca caa tgc cct aga ttc aat aca tgt cca gag atc tgc tgg          3281
Gly Gln Ser Gln Cys Pro Arg Phe Asn Thr Cys Pro Glu Ile Cys Trp
        490                 495                 500 gaa gga gtt tat aat gat gca ttc cta att gac aga atc aat tgg ata          3329
Glu Gly Val Tyr Asn Asp Ala Phe Leu Ile Asp Arg Ile Asn Trp Ile
```

|  |  |  |  |  |  |  |  |  |  |  |  |  |
|---|---|---|---|---|---|---|---|---|---|---|---|---|
| | | 505 | | | | 510 | | | | 515 | | 520 |

```
agc gcg ggt gta ttc ctt gac agc aat cag acc gca gaa aat cct gtt    3377
Ser Ala Gly Val Phe Leu Asp Ser Asn Gln Thr Ala Glu Asn Pro Val
                525                 530                 535 ttt act gta ttc aaa gat aat gaa ata ctt tat agg gca caa ctg gct    3425
Phe Thr Val Phe Lys Asp Asn Glu Ile Leu Tyr Arg Ala Gln Leu Ala
            540                 545                 550 tct gag gac acc aat gca caa aaa aca ata act aat tgt ttt ctc ttg    3473
Ser Glu Asp Thr Asn Ala Gln Lys Thr Ile Thr Asn Cys Phe Leu Leu
        555                 560                 565 aag aat aag att tgg tgc ata tca ttg gtt gag ata tat gac aca gga    3521
Lys Asn Lys Ile Trp Cys Ile Ser Leu Val Glu Ile Tyr Asp Thr Gly
    570                 575                 580 gac aat gtc ata aga ccc aaa cta ttc gcg gtt aag ata cca gag caa    3569
Asp Asn Val Ile Arg Pro Lys Leu Phe Ala Val Lys Ile Pro Glu Gln
585                 590                 595                 600 tgt aca taactcgagt ctagaatcga tcccgggttt tatgactag ttaatcacgg      3625
Cys Thr ccgcttataa agatctaaaa tgcataattt ctaaataatg aaaaaaagta catcatgagc   3685
aacgcgttag tatattttac aatggagatt aacgctctat accgttctat gtttattgat   3745
tcagatgatg ttttagaaaa gaaagttatt gaatatgaaa actttaatga agatgaagat   3805
gacgacgatg attattgttg taaatctgtt ttagatgaag aagatgacgc gctaaagtat   3865
actatggtta caaagtataa gtctatacta ctaatggcga cttgtgcaag aaggtatagt   3925
atagtgaaaa tgttgttaga ttatgattat gaaaaaccaa ataaatcaga tccatatcta   3985
aaggtatctc ctttgcacat aatttcatct attcctagtt tagaatacct gcagccaagc   4045
ttggcactgg ccgtcgtttt ac                                           4067
```

<210> SEQ ID NO 16
<211> LENGTH: 4067
<212> TYPE: DNA
<213> ORGANISM: Artificial Sequence
<220> FEATURE:
<223> OTHER INFORMATION: Description of Artificial Sequence: Synthetic plasmid pSL-6802-1-4

<400> SEQUENCE: 16

```
gtaaaacgac ggccagtgcc aagcttggct gcaggtattc taaactagga atagatgaaa     60
ttatgtgcaa aggagatacc tttagatatg gatctgattt atttggtttt tcataatcat    120
aatctaacaa cattttcact atactatacc ttcttgcaca gtcgccatt agtagtatag     180 acttatactt tgtaaccata gtatacttta gcgcgtcatc ttcttcatct aaaacagatt    240
tacaacaata atcatcgtcg tcatcttcat cttcattaaa gttttcatat tcaataactt    300
tcttttctaa aacatcatct gaatcaataa acatagaacg gtatagagcg ttaatctcca    360
ttgtaaaata tactaacgcg ttgctcatga tgtactttt tcattatttt agaaattatg    420
cattttagat ctttataagc ggccgtgatt aactagtcat aaaaacccgg gatcgattct    480
agactcgagt tatgtacatt gctctggtat cttaaccgcg aatagtttgg gtcttatgac    540
attgtctcct gtgtcatata tctcaaccaa tgatatgcac caaatcttat tcttcaagag    600
aaaacaatta gttattgttt tttgtgcatt ggtgtcctca gaagccagtt gtgccctata    660
aagtatttca ttatctttga atacagtaaa aacaggattt tctgcggtct gattgctgtc    720
aaggaataca cccgcgctta tccaattgat tctgtcaatt aggaatgcat cattataaac    780
tccttcccag cagatctctg gacatgtatt gaatctaggg cattgtgatt gcccgggtct    840
```

```
tgatattacc gtgttattac gccaattgac aaccagaggg ttgactgtta gaacatctcc    900
aaatttaatc atagtatccc atgaaaatga cgcttggtag aaaacaggtt gacccaaaga    960
atcatagatt ttgctaggag atccaataga taatctttga tcagatattt caatgaatac   1020
aactttgggg ttctccccat ctgatagatt gtattttaat agtccagatc gaaggatata   1080
atggctgttt ggtctaatcc ccatagatag cctgcaattt tcaggtttac tgtattgaca   1140
cttcgtgatg ggacaatttg aatcattgta tttaaactct gtcctgacca aaaatcctac   1200
agcaggaaaa tacagggtgt caccctgttt gatgcctgaa ggtccatacg cataacttt    1260
atcatacctc cctttctcga tacttcgtag ggcaagttga tgttgattgt aaccccacc    1320
attactcttg ggtttcacag ctagacgggt catcattaga gatccggacc agtaggtgct   1380
attcagaata gggtctccaa cagttgacac tgcacaaagt acataataga attcattgtt   1440
gtatacagca ctacagtggt aaacggtgtt tggatttggt ggggtccaga cattggtcat   1500
aaataaagaa ggaacttcat cacctctgtc tagtacctct ccaactccta ttattctttg   1560
tttggagacc cctcttgaac atgatccgat tctttccagg tggctatatg caaaatagcc   1620
ctcgtccata gccagcaatg ggtctgtgat acaggtacca ctttgaccga ctacgggtaa   1680
agtgtatgaa atcagctttg gcttcaatat ctgattagat gtcttttgca ggcaaatatt   1740
attaggtaat cctactagat tgctcacccc ttctgtctgt ggcctatact ctctaaaagg   1800
gagtgggtta ggacaagaaa tgttacattc gtggattttc aagggaggca gtgtgaattt   1860
gcatttttca ttcacattct catttatact tgcagtcgac tggctgatct ttgaacctaa   1920
cagcccaatg ttagctggga tagtaatggt actggatgtg tcaatcagtg atactttggg   1980
ccctatctct gtgccgattt tgtcagcaag ccctttgatc tgctgttgga tacccctgcaa  2040
cgcatctttg atcacggcct gattgtctgt tgatcttgtg taattttgga tgatcattat   2100
attcatcact atgatcacga tagatccaag caatgctatt actgtgttga aagcacttaa   2160
tattttgctg tccaataatc cttcatttat tttcttaatg tccatggttc cgtagtagct   2220
cttaataact ttactaggaa ttttcccttt gtctgaagta gtattttcga atctaacttt   2280
cttgttttct gccggcatta cgatacaaac ttaacggata tcgcgataat gaaataattt   2340
atgattattt ctcgctttca atttaacaca accctcaaga accttgtat ttattttcac    2400
tttttaagta tagaataaag aagctctaat taattaacga gcagatagtc tcgttctcgc   2460
cctgcctgat gactaattaa ttaacccgga tcctttttat agctaattag tcacgtacct   2520
ttgagagtac cacttcagct acctcttttg tgtctcagag taactttctt taatcaattc   2580
caaaacagta tatgattttc catttctttc aaagatgtag tttacatctg ctcctttgtt   2640
gaaaagtagc ctgagcactt cttttctacc atgaattaca gctggcaaga tcaatttttc   2700
ccagttctgg acatttatt ttttttaagt agtgtgctac atatttcaat atttccagat    2760
tgtacagcga tcattaaagg agtacgtccc atgttatcca gcaagtcagt atcagcacct   2820
ttgttcaata gaagtttaac cattgttaaa tttttatttg atacggctat atgtagagga   2880
gttaaccgat ccgtgtttga aatatctaca tccgccgaat gagccaatag aagtttaacc   2940
aaattaactt tgttaaggta agctgccaaa cacaaggag taaagcctcc gctgtaaaga    3000
acattgttta catagttatt cttcaacaga tctttcacta ttttgtagtc gtctctcaac   3060
accgcatcat gcagacaaga agttgtgcat tcagtaacta caggtttagc tccataccct   3120
atcaagattt ttatagcctc ggtattcttg aacattacag ccatttcaag aggagattgt   3180
agagtaccat attccgtgtt agggtcgaat ccattgtcca aaaacctatt tagagatgca   3240
```

-continued

```
ttgtcattat ccatgatagc ctcacagacg tatatgtaag ccatcttgaa tgtataattt    3300
tgttgttttc aacaaccgct cgtgaacagc ttctatactt tttcattttc ttcatgatta    3360
atatagttta cggaatataa gtatacaaaa agtttatagt aatctcataa tatctgaaac    3420
acatacataa aacatggaag aattacacga tgtcgttgag ataaatggct ttttattgtc    3480
atagtttaca aattcgcagt aatcttcatc ttttacgaat attgcagaat ctgttttatc    3540
caaccagtga tttttgtata atataactgg tatcctatct tccgatagaa tgctgttatt    3600
taacattttt gcacctatta agttacatct gtcaaatcca tctttccaac tgactttatg    3660
taacgatgcg aaatagcatt tatcactatg tcgtacccaa ttatcatgac aagattctct    3720
taaatacgta atcttattat ctcttgcata ttcgtaatag taattgtaaa gagtatacga    3780
taacagtata gatatacacg tgatataaat atttaaccc attcctgagt aaaataatta    3840
cgatattaca tttcctttta ttattttat gttttagtta tttgttaggt tatacaaaaa    3900
ttatgtttat ttgtgtatat ttaaagcgtc gttaagaata agcttagtta acatattatc    3960
gcttaggttt tgtagtattt gaatcctttc tttaaatgga ttattttcc aatgcatatt    4020 tatagcttca tccaaagtat aacatttaac attcagaatg cggccgc                  4067
```

<210> SEQ ID NO 17
<211> LENGTH: 602
<212> TYPE: PRT
<213> ORGANISM: Artificial Sequence
<220> FEATURE:
<223> OTHER INFORMATION: Description of Artificial Sequence: Synthetic plasmid pSL-6802-2-5

<400> SEQUENCE: 17

```
Met Pro Ala Glu Asn Lys Lys Val Arg Phe Glu Asn Thr Thr Ser Asp
 1               5                  10                  15

Lys Gly Lys Ile Pro Ser Lys Val Ile Lys Ser Tyr Tyr Gly Thr Met
             20                  25                  30

Asp Ile Lys Lys Ile Asn Glu Gly Leu Leu Asp Ser Lys Ile Leu Ser
         35                  40                  45

Ala Phe Asn Thr Val Ile Ala Leu Leu Gly Ser Ile Val Ile Val
     50                  55                  60

Met Asn Ile Met Ile Ile Gln Asn Tyr Thr Arg Ser Thr Asp Asn Gln
 65                  70                  75                  80

Ala Val Ile Lys Asp Ala Leu Gln Gly Ile Gln Gln Ile Lys Gly
                 85                  90                  95

Leu Ala Asp Lys Ile Gly Thr Glu Ile Gly Pro Lys Val Ser Leu Ile
            100                 105                 110

Asp Thr Ser Ser Thr Ile Thr Ile Pro Ala Asn Ile Gly Leu Leu Gly
        115                 120                 125

Ser Lys Ile Ser Gln Ser Thr Ala Ser Ile Asn Glu Asn Val Asn Glu
    130                 135                 140

Lys Cys Lys Phe Thr Leu Pro Pro Leu Lys Ile His Glu Cys Asn Ile
145                 150                 155                 160

Ser Cys Pro Asn Pro Leu Pro Phe Arg Glu Tyr Arg Pro Gln Thr Glu
                165                 170                 175

Gly Val Ser Asn Leu Val Gly Leu Pro Asn Asn Ile Cys Leu Gln Lys
            180                 185                 190

Thr Ser Asn Gln Ile Leu Lys Pro Lys Leu Ile Ser Tyr Thr Leu Pro
        195                 200                 205

Val Val Gly Gln Ser Gly Thr Cys Ile Thr Asp Pro Leu Leu Ala Met
    210                 215                 220
```

Asp Glu Gly Tyr Phe Ala Tyr Ser His Leu Glu Arg Ile Gly Ser Cys
225                 230                 235                 240

Ser Arg Gly Val Ser Lys Gln Arg Ile Ile Gly Val Gly Glu Val Leu
            245                 250                 255

Asp Arg Gly Asp Glu Val Pro Ser Leu Phe Met Thr Asn Val Trp Thr
            260                 265                 270

Pro Pro Asn Pro Asn Thr Val Tyr His Cys Ser Ala Val Tyr Asn Asn
            275                 280                 285

Glu Phe Tyr Tyr Val Leu Cys Ala Val Ser Thr Val Gly Asp Pro Ile
290                 295                 300

Leu Asn Ser Thr Tyr Trp Ser Gly Ser Leu Met Met Thr Arg Leu Ala
305                 310                 315                 320

Val Lys Pro Lys Ser Asn Gly Gly Tyr Asn Gln His Gln Leu Ala
            325                 330                 335

Leu Arg Ser Ile Glu Lys Gly Arg Tyr Asp Lys Val Met Pro Tyr Gly
            340                 345                 350

Pro Ser Gly Ile Lys Gln Gly Asp Thr Leu Tyr Phe Pro Ala Val Gly
        355                 360                 365

Phe Leu Val Arg Thr Glu Phe Lys Tyr Asn Asp Ser Asn Cys Pro Ile
370                 375                 380

Thr Lys Cys Gln Tyr Ser Lys Pro Glu Asn Cys Arg Leu Ser Met Gly
385                 390                 395                 400

Ile Arg Pro Asn Ser His Tyr Ile Leu Arg Ser Gly Leu Leu Lys Tyr
            405                 410                 415

Asn Leu Ser Asp Gly Glu Asn Pro Lys Val Val Phe Ile Glu Ile Ser
            420                 425                 430

Asp Gln Arg Leu Ser Ile Gly Ser Pro Ser Lys Ile Tyr Asp Ser Leu
        435                 440                 445

Gly Gln Pro Val Phe Tyr Gln Ala Ser Phe Ser Trp Asp Thr Met Ile
450                 455                 460

Lys Phe Gly Asp Val Leu Thr Val Asn Pro Leu Val Val Asn Trp Arg
465                 470                 475                 480

Asn Asn Thr Val Ile Ser Arg Pro Gly Gln Ser Gln Cys Pro Arg Phe
            485                 490                 495

Asn Thr Cys Pro Glu Ile Cys Trp Glu Gly Val Tyr Asn Asp Ala Phe
            500                 505                 510

Leu Ile Asp Arg Ile Asn Trp Ile Ser Ala Gly Val Phe Leu Asp Ser
        515                 520                 525

Asn Gln Thr Ala Glu Asn Pro Val Phe Thr Val Phe Lys Asp Asn Glu
530                 535                 540

Ile Leu Tyr Arg Ala Gln Leu Ala Ser Glu Asp Thr Asn Ala Gln Lys
545                 550                 555                 560

Thr Ile Thr Asn Cys Phe Leu Leu Lys Asn Lys Ile Trp Cys Ile Ser
            565                 570                 575

Leu Val Glu Ile Tyr Asp Thr Gly Asp Asn Val Ile Arg Pro Lys Leu
            580                 585                 590

Phe Ala Val Lys Ile Pro Glu Gln Cys Thr
            595                 600

<210> SEQ ID NO 18
<211> LENGTH: 4998
<212> TYPE: DNA
<213> ORGANISM: Artificial Sequence
<220> FEATURE:
<221> NAME/KEY: CDS
<222> LOCATION: (1693)..(3498)
<220> FEATURE:
<223> OTHER INFORMATION: Description of Artificial Sequence: Synthetic plasmid pSL-6802-2-5

<400> SEQUENCE: 18

```
gtaaaacgac ggccagtgaa ttgtaatacg actcactata gggcgaattg ggtgacccTT    60
tacaagaata aaagaagaaa caactgtgaa atagtttata atgtaattc gtatgcagaa    120 aacgataata tattttggta tgagaaatct aaaggagaca tagtttgtat agacatgcgc    180
tcttccgatg agatattcga tgcttttcta atgtatcata tagctacaag atatgcctat    240
catgatgatg atatatatct acaaatagtg ttatattatt ctaataatca aaatgttata    300
tcttatatta cgaaaaataa atacgttaag tatataagaa ataaaactag agacgatatt    360
cataaagtaa aaatattagc tctagaagac tttacaacgg aagaaatata ttgttggatt    420
agtaatatat aacagcgtag ctgcacggtt ttgatcattt ccaacaata taaaccaatg     480 aaggaggacg actcatcaaa cataaataac attcacggaa atattcagt atcagattta     540 tcacaagatg attatgttat tgaatgtata gacggatctt ttgattcgat caagtataga     600
gatataaagg ttataataat gaagaataac ggttacgtta attgtagtaa attatgtaaa    660
atgcggaata aatactttc tagatggttg cgtctttcta cttctaaagc attattagac     720
atttacaata ataagtcagt agataatgct attgttaaag tctatggtaa aggtaagaaa    780
cttattataa caggatttta tctcaaacaa aatatgatac gttatgttat tgagtggata    840
ggggatgatt ttacaaacga tatatacaaa atgattaatt tctataatgc gttattcggt    900
aacgatgaat taaaaatagt atcctgtgaa acactctat gcccgtttat agaacttggt      960
agatgctatt atggtaaaaa atgtaagtat atacacggag atcaatgtga tatctgtggt    1020
ctatatatac tcaccctac cgatattaac caacgagttt ctcacaagaa aacttgttta    1080
gtagatagag attctttgat tgtgtttaaa agaagtacca gtaaaaagtg tggcatatgc    1140
atagaagaaa taaacaaaaa acatatttcc gaacagtatt ttggaattct cccaagttgt    1200
aaacatattt tttgcctatc atgtataaga cgttgggcag atactaccag aaatacagat    1260
actgaaaata cgtgtcctga atgtagaata gttttttcctt tcataatacc cagtaggtat    1320
tggatagata taaatatga taaaaaaata ttatataata gatataagaa aatgatttt    1380 acaaaaatac ctataagaac aataaaaata taattacatt tacggaaaat agctggtttt    1440
agtttaccaa cttagagtaa ttatcatatt gaatctatat tgctaattag ctaataaaaa    1500
cccgggttaa ttaattagtc atcaggcagg gcgagaacga gactatctgc tcgttaatta    1560
attagagctt ctttattcta tacttaaaaa gtgaaaataa atacaaaggt tcttgagggt    1620
tgtgttaaat tgaaagcgag aaataatcat aaattatttc attatcgcga tatccgttaa    1680
gtttgtatcg ta atg ccg gca gaa aac aag aaa gtt aga ttc gaa aat act     1731
              Met Pro Ala Glu Asn Lys Lys Val Arg Phe Glu Asn Thr
               1                5                  10 act tca gac aaa ggg aaa att cct agt aaa gtt att aag agc tac tac         1779
Thr Ser Asp Lys Gly Lys Ile Pro Ser Lys Val Ile Lys Ser Tyr Tyr
     15                  20                  25 gga acc atg gac att aag aaa ata aat gaa gga tta ttg gac agc aaa         1827
Gly Thr Met Asp Ile Lys Lys Ile Asn Glu Gly Leu Leu Asp Ser Lys
 30                  35                  40                  45 ata tta agt gct ttc aac aca gta ata gca ttg ctt gga tct atc gtg         1875
Ile Leu Ser Ala Phe Asn Thr Val Ile Ala Leu Leu Gly Ser Ile Val
                 50                  55                  60 atc ata gtg atg aat ata atg atc atc caa aat tac aca aga tca aca         1923
```

-continued

```
Ile Ile Val Met Asn Ile Met Ile Ile Gln Asn Tyr Thr Arg Ser Thr
            65                  70                  75 gac aat cag gcc gtg atc aaa gat gcg ttg cag ggt atc caa cag cag      1971
Asp Asn Gln Ala Val Ile Lys Asp Ala Leu Gln Gly Ile Gln Gln Gln
            80                  85                  90 atc aaa ggg ctt gct gac aaa atc ggc aca gag ata ggg ccc aaa gta      2019
Ile Lys Gly Leu Ala Asp Lys Ile Gly Thr Glu Ile Gly Pro Lys Val
 95                 100                 105 tca ctg att gac aca tcc agt acc att act atc cca gct aac att ggg      2067
Ser Leu Ile Asp Thr Ser Ser Thr Ile Thr Ile Pro Ala Asn Ile Gly
110                 115                 120                 125 ctg tta ggt tca aag atc agc cag tcg act gca agt ata aat gag aat      2115
Leu Leu Gly Ser Lys Ile Ser Gln Ser Thr Ala Ser Ile Asn Glu Asn
                130                 135                 140 gtg aat gaa aaa tgc aaa ttc aca ctg cct ccc ttg aaa atc cac gaa      2163
Val Asn Glu Lys Cys Lys Phe Thr Leu Pro Pro Leu Lys Ile His Glu
                145                 150                 155 tgt aac att tct tgt cct aac cca ctc cct ttt aga gag tat agg cca      2211
Cys Asn Ile Ser Cys Pro Asn Pro Leu Pro Phe Arg Glu Tyr Arg Pro
                160                 165                 170 cag aca gaa ggg gtg agc aat cta gta gga tta cct aat aat att tgc      2259
Gln Thr Glu Gly Val Ser Asn Leu Val Gly Leu Pro Asn Asn Ile Cys
175                 180                 185 ctg caa aag aca tct aat cag ata ttg aag cca aag ctg att tca tac      2307
Leu Gln Lys Thr Ser Asn Gln Ile Leu Lys Pro Lys Leu Ile Ser Tyr
190                 195                 200                 205 act tta ccc gta gtc ggt caa agt ggt acc tgt atc aca gac cca ttg      2355
Thr Leu Pro Val Val Gly Gln Ser Gly Thr Cys Ile Thr Asp Pro Leu
                210                 215                 220 ctg gct atg gac gag ggc tat ttt gca tat agc cac ctg gaa aga atc      2403
Leu Ala Met Asp Glu Gly Tyr Phe Ala Tyr Ser His Leu Glu Arg Ile
                225                 230                 235 gga tca tgt tca aga ggg gtc tcc aaa caa aga ata ata gga gtt gga      2451
Gly Ser Cys Ser Arg Gly Val Ser Lys Gln Arg Ile Ile Gly Val Gly
                240                 245                 250 gag gta cta gac aga ggt gat gaa gtt cct tct tta ttt atg acc aat      2499
Glu Val Leu Asp Arg Gly Asp Glu Val Pro Ser Leu Phe Met Thr Asn
255                 260                 265 gtc tgg acc cca cca aat cca aac acc gtt tac cac tgt agt gct gta      2547
Val Trp Thr Pro Pro Asn Pro Asn Thr Val Tyr His Cys Ser Ala Val
270                 275                 280                 285 tac aac aat gaa ttc tat tat gta ctt tgt gca gtg tca act gtt gga      2595
Tyr Asn Asn Glu Phe Tyr Tyr Val Leu Cys Ala Val Ser Thr Val Gly
                290                 295                 300 gac cct att ctg aat agc acc tac tgg tcc gga tct cta atg atg acc      2643
Asp Pro Ile Leu Asn Ser Thr Tyr Trp Ser Gly Ser Leu Met Met Thr
                305                 310                 315 cgt cta gct gtg aaa ccc aag agt aat ggt ggg ggt tac aat caa cat      2691
Arg Leu Ala Val Lys Pro Lys Ser Asn Gly Gly Gly Tyr Asn Gln His
                320                 325                 330 caa ctt gcc cta cga agt atc gag aaa ggg agg tat gat aaa gtt atg      2739
Gln Leu Ala Leu Arg Ser Ile Glu Lys Gly Arg Tyr Asp Lys Val Met
335                 340                 345 ccg tat gga cct tca ggc atc aaa cag ggt gac acc ctg tat ttt cct      2787
Pro Tyr Gly Pro Ser Gly Ile Lys Gln Gly Asp Thr Leu Tyr Phe Pro
350                 355                 360                 365 gct gta gga ttt ttg gtc agg aca gag ttt aaa tac aat gat tca aat      2835
Ala Val Gly Phe Leu Val Arg Thr Glu Phe Lys Tyr Asn Asp Ser Asn
                370                 375                 380 tgt ccc atc acg aag tgt caa tac agt aaa cct gaa aat tgc agg cta      2883
```

```
                Cys Pro Ile Thr Lys Cys Gln Tyr Ser Lys Pro Glu Asn Cys Arg Leu
                            385                 390                 395 tct atg ggg att aga cca aac agc cat tat atc ctt cga tct gga cta              2931
Ser Met Gly Ile Arg Pro Asn Ser His Tyr Ile Leu Arg Ser Gly Leu
        400                 405                 410 tta aaa tac aat cta tca gat ggg gag aac ccc aaa gtt gta ttc att              2979
Leu Lys Tyr Asn Leu Ser Asp Gly Glu Asn Pro Lys Val Val Phe Ile
    415                 420                 425 gaa ata tct gat caa aga tta tct att gga tct cct agc aaa atc tat              3027
Glu Ile Ser Asp Gln Arg Leu Ser Ile Gly Ser Pro Ser Lys Ile Tyr
430                 435                 440                 445 gat tct ttg ggt caa cct gtt ttc tac caa gcg tca ttt tca tgg gat              3075
Asp Ser Leu Gly Gln Pro Val Phe Tyr Gln Ala Ser Phe Ser Trp Asp
                450                 455                 460 act atg att aaa ttt gga gat gtt cta aca gtc aac cct ctg gtt gtc              3123
Thr Met Ile Lys Phe Gly Asp Val Leu Thr Val Asn Pro Leu Val Val
            465                 470                 475 aat tgg cgt aat aac acg gta ata tca aga ccc ggg caa tca caa tgc              3171
Asn Trp Arg Asn Asn Thr Val Ile Ser Arg Pro Gly Gln Ser Gln Cys
        480                 485                 490 cct aga ttc aat aca tgt cca gag atc tgc tgg gaa gga gtt tat aat              3219
Pro Arg Phe Asn Thr Cys Pro Glu Ile Cys Trp Glu Gly Val Tyr Asn
    495                 500                 505 gat gca ttc cta att gac aga atc aat tgg ata agc gcg ggt gta ttc              3267
Asp Ala Phe Leu Ile Asp Arg Ile Asn Trp Ile Ser Ala Gly Val Phe
510                 515                 520                 525 ctt gac agc aat cag acc gca gaa aat cct gtt ttt act gta ttc aaa              3315
Leu Asp Ser Asn Gln Thr Ala Glu Asn Pro Val Phe Thr Val Phe Lys
                530                 535                 540 gat aat gaa ata ctt tat agg gca caa ctg gct tct gag gac acc aat              3363
Asp Asn Glu Ile Leu Tyr Arg Ala Gln Leu Ala Ser Glu Asp Thr Asn
            545                 550                 555 gca caa aaa aca ata act aat tgt ttt ctc ttg aag aat aag att tgg              3411
Ala Gln Lys Thr Ile Thr Asn Cys Phe Leu Leu Lys Asn Lys Ile Trp
        560                 565                 570 tgc ata tca ttg gtt gag ata tat gac aca gga gac aat gtc ata aga              3459
Cys Ile Ser Leu Val Glu Ile Tyr Asp Thr Gly Asp Asn Val Ile Arg
    575                 580                 585 ccc aaa cta ttc gcg gtt aag ata cca gag caa tgt aca taactcgagt              3508
Pro Lys Leu Phe Ala Val Lys Ile Pro Glu Gln Cys Thr
590                 595                 600 ttttattgac tagttaatca taagataaat aatatacagc attgtaacca tcgtcatccg            3568
ttatcggggg aataatatta ccatacagta ttattaaatt ttcttacgaa gaatatagat            3628
cggtatttat cgttagttta ttttacattt attaattaaa catgtctact attacctgtt            3688
atggaaatga caaatttagt tatataattt atgataaaat taagataata ataatgaaat            3748
caaataatta tgtaaatgct actagattat gtgaattacg aggaagaaag tttacgaact            3808
ggaaaaaatt aagtgaatct aaaatattag tcgataatgt aaaaaaaata aatgataaaa            3868
ctaaccagtt aaaaacggat atgattatat acgttaagga tattgatcat aaaggaagag            3928
atacttgcgg ttactatgta caccaagatc tggtatcttc tatatcaaat tggatatctc            3988
cgttattcgc cgttaaggta aataaaatta ttaactatta tatatgtaat gaatatgata            4048
tacgacttag cgaaatggaa tctgatatga cagaagtaat agatgtagtt gataaattag            4108
taggaggata caatgatgaa atagcagaaa taatatattt gtttaataaa tttatagaaa            4168
aatatattgc taacatatcg ttatcaactg aattatctag tatattaaat aattttataa            4228
attttaataa aaaatacaat aacgacataa aagatattaa atctttaatt cttgatctga            4288
```

```
aaaacacatc tataaaacta gataaaaagt tattcgataa agataataat gaatcgaacg    4348
atgaaaaatt ggaaacagaa gttgataagc taattttttt catctaaata gtattatttt    4408
attgaagtac gaagttttac gttagataaa taataaaggt cgattttat tttgttaaat     4468 atcaaatatg tcattatctg ataaagatac aaaaacacac ggtgattatc aaccatctaa    4528
cgaacagata ttacaaaaaa tacgtcggac tatggaaaac gaagctgata gcctcaatag    4588
aagaagcatt aaagaaattg ttgtagatgt tatgaagaat tgggatcatc ctctcaacga    4648
agaaatagat aaagttctaa actggaaaaa tgatacatta aacgatttag atcatctaaa    4708
tacagatgat aatattaagg aaatcataca atgtctgatt agagaatttg cgtttaaaaa    4768
gatcaattct attatgtata gttatgctat ggtaaaactc aattcagata acgaaacatt    4828
gaaagataaa attaaggatt atttttataga aactattctt aaagacaaac gtggttataa    4888
acaaaagcca ttaccctaga gcggccgcca ccgcggtgga gctccagctt ttgttccctt    4948
tagtgagggt taatttcgag cttggcgtaa tcatggtcat agctgtttcc               4998

<210> SEQ ID NO 19
<211> LENGTH: 4998
<212> TYPE: DNA
<213> ORGANISM: Artificial Sequence
<220> FEATURE:
<223> OTHER INFORMATION: Description of Artificial Sequence: Synthetic
      plasmid pSL-6802-2-5

<400> SEQUENCE: 19
ggaaacagct atgaccatga ttacgccaag ctcgaaatta accctcacta aagggaacaa      60
aagctggagc tccaccgcgg tggcggccgc tctagggtaa tggcttttgt ttataaccac     120
gtttgtcttt aagaatagtt tctataaaat aatccttaat tttatctttc aatgtttcgt     180
tatctgaatt gagttttacc atagcataac tatacataat agaattgatc ttttaaacg      240 caaattctct aatcagacat tgtatgattt ccttaatatt atcatctgta tttagatgat     300
ctaaatcgtt taatgtatca ttttccagt ttagaacttt atctatttct tcgttgagag      360
gatgatccca attcttcata acatctacaa caatttcttt aatgcttctt ctattgaggc     420
tatcagcttc gttttccata gtccgacgta ttttttgtaa tatctgttcg ttagatggtt    480
gataatcacc gtgtgttttt gtatctttat cagataatga catatttgat atttaacaaa    540
ataaaaatcg acctttatta tttatctaac gtaaaacttc gtacttcaat aaaataatac    600
tatttagatg aaaaaaatta gcttatcaac ttctgttttcc aattttttcat cgttcgattc   660 attattatct ttatcgaata acttttttatc tagttttata gatgtgtttt tcagatcaag   720
aattaaagat ttaatatctt ttatgtcgtt attgtatttt ttattaaaat ttataaaatt    780
atttaatata ctagataatt cagttgataa cgatatgtta gcaatatatt tttctataaa    840
tttattaaac aaatatatta tttctgctat ttcatcattg tatcctccta ctaattttatc   900 aactacatct attacttctg tcatatcaga ttccatttcg ctaagtcgta tatcatattc    960
attacatata taatagttaa taattttatt taccttaacg gcgaataacg gagatatcca   1020
atttgatata gaagatacca gatcttggtg tacatagtaa ccgcaagtat ctcttccttt   1080
atgatcaata tccttaacgt atataatcat atccgttttt aactggttag ttttatcatt   1140 tattttttt acattatcga ctaatatttt agattcactt aattttttcc agttcgtaaa    1200
ctttcttcct cgtaattcac ataatctagt agcatttaca taattatttg atttcattat   1260
tattatctta attttatcat aaattatata actaaatttg tcatttccat aacaggtaat   1320
```

```
agtagacatg tttaattaat aaatgtaaaa taaactaacg ataaataccg atctatattc    1380
ttcgtaagaa aatttaataa tactgtatgg taatattatt ccccgtataa cggatgacga    1440
tggttacaat gctgtatatt atttatctta tgattaacta gtcaataaaa actcgagtta    1500
tgtacattgc tctggtatct taaccgcgaa tagtttgggt cttatgacat tgtctcctgt    1560
gtcatatatc tcaaccaatg atatgcacca aatcttattc ttcaagagaa aacaattagt    1620
tattgttttt tgtgcattgg tgtcctcaga agccagttgt gccctataaa gtatttcatt    1680
atctttgaat acagtaaaaa caggattttc tgcggtctga ttgctgtcaa ggaatacacc    1740
cgcgcttatc caattgattc tgtcaattag gaatgcatca ttataaactc cttcccagca    1800
gatctctgga catgtattga atctagggca ttgtgattgc ccgggtcttg atattaccgt    1860
gttattacgc caattgacaa ccagagggtt gactgttaga acatctccaa atttaatcat    1920
agtatcccat gaaaatgacg cttggtagaa aacaggttga cccaaagaat catagatttt    1980
gctaggagat ccaatagata atctttgatc agatatttca atgaatacaa ctttggggtt    2040
ctccccatct gatagattgt atttttaatag tccagatcga aggatataat ggctgtttgg    2100
tctaatcccc atagatagcc tgcaattttc aggtttactg tattgacact tcgtgatggg    2160
acaatttgaa tcattgtatt taaactctgt cctgaccaaa aatcctacag caggaaaata    2220
cagggtgtca ccctgtttga tgcctgaagg tccatacggc ataactttat catacctccc    2280
tttctcgata cttcgtaggg caagttgatg ttgattgtaa cccccaccat tactcttggg    2340
tttcacagct agacgggtca tcattagaga tccggaccag taggtgctat tcagaatagg    2400
gtctccaaca gttgacactg cacaaagtac ataatagaat tcattgttgt atacagcact    2460
acagtggtaa acgtgtttg gatttggtgg ggtccagaca ttggtcataa ataaagaagg     2520
aacttcatca cctctgtcta gtacctctcc aactcctatt attctttgtt tggagacccc    2580
tcttgaacat gatccgattc tttccaggtg gctatatgca aaatagccct cgtccatagc    2640
cagcaatggg tctgtgatac aggtaccact ttgaccgact acgggtaaag tgtatgaaat    2700
cagctttggc ttcaatatct gattagatgt cttttgcagg caaatattat taggtaatcc    2760
tactagattg ctcaccccctt ctgtctgtgg cctatactct ctaaaaggga gtgggttagg    2820
acaagaaatg ttacattcgt ggattttcaa gggaggcagt gtgaatttgc attttttcatt   2880 cacattctca tttatacttg cagtcgactg gctgatcttt gaacctaaca gcccaatgtt    2940
agctgggata gtaatggtac tggatgtgtc aatcagtgat actttgggcc ctatctctgt    3000
gccgattttg tcagcaagcc ctttgatctg ctgttggata ccctgcaacg catctttgat    3060
cacggcctga ttgtctgttg atcttgtgta attttggatg atcattatat tcatcactat    3120
gatcacgata gatccaagca atgctattac tgtgttgaaa gcacttaata ttttgctgtc    3180
caataatcct tcatttattt tcttaatgtc catggttccg tagtagctct taataacttt    3240
actaggaatt ttccctttgt ctgaagtagt atttttcgaat ctaactttct tgttttctgc   3300
cggcattacg atacaaactt aacggatatc gcgataatga aataatttat gattatttct    3360
cgctttcaat ttaacacaac cctcaagaac ctttgtattt attttcactt tttaagtata    3420
gaataaagaa gctctaatta attaacgagc agatagtctc gttctcgccc tgcctgatga    3480
ctaattaatt aacccgggtt tttattagct aattagcaat atagattcaa tatgataatt    3540
actctaagtt ggtaaactaa aaccagctat tttccgtaaa tgtaattata tttttattgt    3600
tcttataggt atttttgtaa aaatcatttt cttatatcta ttatataata ttttttttatc   3660 atatttatta tctatccaat acctactggg tattatgaaa ggaaaaacta ttctacattc    3720
```

-continued

```
aggacacgta ttttcagtat ctgtatttct ggtagtatct gcccaacgtc ttatacatga    3780
taggcaaaaa atatgtttac aacttgggag aattccaaaa tactgttcgg aaatatgttt    3840
tttgtttatt tcttctatgc atatgccaca cttttactg  gtacttcttt taaacacaat    3900
caaagaatct ctatctacta aacaagtttt cttgtgagaa actcgttggt taatatcggt    3960
agggtgtagt atatatagac cacagatatc acattgatct ccgtgtatat acttacattt    4020
tttaccataa tagcatctac caagttctat aaacgggcat agagtgtttt cacaggatac    4080
tatttttaat tcatcgttac cgaataacgc attatagaaa ttaatcattt tgtatatatc    4140
gtttgtaaaa tcatcccta  tccactcaat aacataacgt atcatatttt gtttgagata    4200
aaatcctgtt ataataagtt tcttaccttt accatagact ttaacaatag cattatctac    4260
tgacttatta ttgtaaatgt ctaataatgc tttagaagta gaaagacgca accatctaga    4320
aaagtattta ttccgcattt tacataattt actacaatta acgtaaccgt tattcttcat    4380
tattataacc tttatatctc tatacttgat cgaatcaaaa gatccgtcta tacattcaat    4440
aacataatca tcttgtgata aatctgatac tgaatatttt ccgtgaatgt tatttatgtt    4500
tgatgagtcg tcctccttca ttggtttata ttgttggaaa atgatcaaaa ccgtgcagct    4560
acgctgttat atattactaa tccaacaata tatttcttcc gttgtaaagt cttctagagc    4620 taatatttt  actttatgaa tatcgtctct agtttattt  cttatatact taacgtattt    4680 attttttcgta atataagata taacattttg attattagaa taatataaca ctatttgtag    4740
atatatatca tcatcatgat aggcatatct tgtagctata tgatacatta gaaaagcatc    4800
gaatatctca tcggaagagc gcatgtctat acaaactatg tctcctttag atttctcata    4860
ccaaaatata ttatcgtttt ctgcatacga attacattta taaactatt  cacagttgtt    4920 tcttcttta  ttcttgtaaa gggtcaccca attcgccca  tagtgagtcg tattacaatt    4980
cactggccgt cgttttac                                                  4998
```

```
<210> SEQ ID NO 20
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Met Val Val Ile Leu Asp Lys Arg Asp Leu Leu Phe Val Phe Gly Pro
 1               5                  10                  15

Asn Leu Gly Asp Leu Tyr Tyr Ile Gly Thr
            20                  25

<210> SEQ ID NO 21
<211> LENGTH: 111
<212> TYPE: DNA
<213> ORGANISM: Artificial Sequence
<220> FEATURE:
<221> NAME/KEY: CDS
<222> LOCATION: (31)..(108)
<220> FEATURE:
<223> OTHER INFORMATION: Description of Artificial Sequence: Synthetic
      oligonucleotide

<400> SEQUENCE: 21
tatcgcgata tccgttaagt ttgtatcgta atg gta gtt ata ctt gac aag aga    54
                                Met Val Val Ile Leu Asp Lys Arg
                                 1               5 gat ttg ctt ttt gta ttt ggc ccc aac ctt ggg gat ctc tac tac att    102
```

```
Asp Leu Leu Phe Val Phe Gly Pro Asn Leu Gly Asp Leu Tyr Tyr Ile
    10                  15                  20 ggg aca tag                                                                      111
Gly Thr
25

<210> SEQ ID NO 22
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
gcggatcccg ggctatgtcc caatgtagta gagatcccc                                        39

<210> SEQ ID NO 23
<211> LENGTH: 546
<212> TYPE: PRT
<213> ORGANISM: Artificial Sequence
<220> FEATURE:
<223> OTHER INFORMATION: Description of Artificial Sequence: Synthetic
      plasmid pSL-6839-1

<400> SEQUENCE: 23

Met Val Val Ile Leu Asp Lys Arg Cys Tyr Cys Asn Leu Leu Ile Leu
 1               5                  10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
```

```
                260                265                270
Ser Tyr Tyr Ile Ile Val Arg Val Tyr Phe Pro Ile Leu Thr Glu Ile
            275                280                285
Gln Gln Ala Tyr Ile Gln Glu Leu Leu Pro Val Ser Phe Asn Asn Asp
        290                295                300
Asn Ser Glu Trp Ile Ser Ile Val Pro Asn Phe Ile Leu Val Arg Asn
305                310                315                320
Thr Leu Ile Ser Asn Ile Glu Ile Gly Phe Cys Leu Ile Thr Lys Arg
                325                330                335
Ser Val Ile Cys Asn Gln Asp Tyr Ala Thr Pro Met Thr Asn Asn Met
            340                345                350
Arg Glu Cys Leu Thr Gly Ser Thr Glu Lys Cys Pro Arg Glu Leu Val
        355                360                365
Val Ser Ser His Val Pro Arg Phe Ala Leu Ser Asn Gly Val Leu Phe
    370                375                380
Ala Asn Cys Ile Ser Val Thr Cys Gln Cys Gln Thr Thr Gly Arg Ala
385                390                395                400
Ile Ser Gln Ser Gly Glu Gln Thr Leu Leu Met Ile Asp Asn Thr Thr
                405                410                415
Cys Pro Thr Ala Val Leu Gly Asn Val Ile Ile Ser Leu Gly Lys Tyr
            420                425                430
Leu Gly Ser Val Asn Tyr Asn Ser Glu Gly Ile Ala Ile Gly Pro Pro
        435                440                445
Val Phe Thr Asp Lys Val Asp Ile Ser Ser Gln Ile Ser Ser Met Asn
450                455                460
Gln Ser Leu Gln Gln Ser Lys Asp Tyr Ile Lys Glu Ala Gln Arg Leu
465                470                475                480
Leu Asp Thr Val Asn Pro Ser Leu Ile Ser Met Leu Ser Met Ile Ile
                485                490                495
Leu Tyr Val Leu Ser Ile Ala Ser Leu Cys Ile Gly Leu Ile Thr Phe
            500                505                510
Ile Ser Phe Ile Ile Val Glu Lys Lys Arg Asn Thr Tyr Ser Arg Leu
        515                520                525
Glu Asp Arg Arg Val Arg Pro Thr Ser Ser Gly Asp Leu Tyr Tyr Ile
    530                535                540
Gly Thr
545

<210> SEQ ID NO 24
<211> LENGTH: 4840
<212> TYPE: DNA
<213> ORGANISM: Artificial Sequence
<220> FEATURE:
<221> NAME/KEY: CDS
<222> LOCATION: (1693)..(3330)
<220> FEATURE:
<223> OTHER INFORMATION: Description of Artificial Sequence: Synthetic
      plasmid pSL-6839-1

<400> SEQUENCE: 24
gtaaaacgac ggccagtgaa ttgtaatacg actcactata gggcgaattg ggtgacccctt    60 tacaagaata aaagaagaaa caactgtgaa atagtttata aatgtaattc gtatgcagaa   120
aacgataata tattttggta tgagaaatct aaaggagaca tagtttgtat agacatgcgc   180
tcttccgatg agatattcga tgcttttcta atgtatcata tagctacaag atatgcctat   240
catgatgatg atatatatct acaaatagtg ttatattatt ctaataatca aaatgttata   300
```

```
tcttatatta cgaaaaataa atacgttaag tatataagaa ataaaactag agacgatatt      360
cataaagtaa aaatattagc tctagaagac tttacaacgg aagaaatata ttgttggatt      420
agtaatatat aacagcgtag ctgcacggtt ttgatcattt tccaacaata taaaccaatg      480
aaggaggacg actcatcaaa cataaataac attcacggaa atattcagt atcagattta       540 tcacaagatg attatgttat tgaatgtata gacggatctt ttgattcgat caagtataga      600
gatataaagg ttataataat gaagaataac ggttacgtta attgtagtaa attatgtaaa      660
atgcggaata aatactttc tagatggttg cgtctttcta cttctaaagc attattagac       720
atttacaata ataagtcagt agataatgct attgttaaag tctatggtaa aggtaagaaa      780
cttattataa caggatttta tctcaaacaa aatatgatac gttatgttat tgagtggata      840
ggggatgatt ttacaaacga tatatacaaa atgattaatt tctataatgc gttattcggt      900
aacgatgaat taaaaatagt atcctgtgaa acactctat gcccgtttat agaacttggt       960
agatgctatt atggtaaaaa atgtaagtat atacacggag atcaatgtga tatctgtggt     1020
ctatatatac tacaccctac cgatattaac caacgagttt ctcacaagaa aacttgttta     1080
gtagatagag attctttgat tgtgtttaaa agaagtacca gtaaaaagtg tggcatatgc     1140
atagaagaaa taaacaaaaa acatatttcc gaacagtatt ttggaattct cccaagttgt     1200
aaacatattt tttgcctatc atgtataaga cgttgggcag atactaccag aaatacagat     1260
actgaaaata cgtgtcctga atgtagaata gttttccctt tcataatacc cagtaggtat     1320
tggatagata ataaatatga taaaaaaata ttatataata gatataagaa aatgattttt     1380
acaaaaatac ctataagaac aataaaaata taattacatt tacggaaaat agctggtttt     1440
agtttaccaa cttagagtaa ttatcatatt gaatctatat tgctaattag ctaataaaaa     1500
cccgggttaa ttaattagtc atcaggcagg gcgagaacga gactatctgc tcgttaatta     1560
attagagctt ctttattcta tacttaaaaa gtgaaaataa atacaaaggt tcttgagggt     1620
tgtgttaaat tgaaagcgag aaataatcat aaattatttc attatcgcga tatccgttaa     1680
gtttgtatcg ta atg gta gtt ata ctt gac aag aga tgt tat tgt aat ctt     1731
              Met Val Val Ile Leu Asp Lys Arg Cys Tyr Cys Asn Leu
                1               5                  10 tta ata ttg att ttg atg atc tcg gag tgt agt gtt ggg att cta cat      1779
Leu Ile Leu Ile Leu Met Ile Ser Glu Cys Ser Val Gly Ile Leu His
 15                  20                  25 tat gag aaa ttg agt aaa att gga ctt gtc aaa gga gta aca aga aaa      1827
Tyr Glu Lys Leu Ser Lys Ile Gly Leu Val Lys Gly Val Thr Arg Lys
 30              35                  40                  45 tac aag att aaa agc aat cct ctc aca aaa gac att gtt ata aaa atg      1875
Tyr Lys Ile Lys Ser Asn Pro Leu Thr Lys Asp Ile Val Ile Lys Met
             50                  55                  60 att ccg aat gtg tcg aac atg tct cag tgc aca ggg agt gtc atg gaa      1923
Ile Pro Asn Val Ser Asn Met Ser Gln Cys Thr Gly Ser Val Met Glu
         65                  70                  75 aat tat aaa aca cga tta aac ggt atc tta aca cct ata aag gga gcg      1971
Asn Tyr Lys Thr Arg Leu Asn Gly Ile Leu Thr Pro Ile Lys Gly Ala
     80                  85                  90 tta gag atc tac aaa aac aac act cat gac ctt gtc ggt gat gtg aga      2019
Leu Glu Ile Tyr Lys Asn Asn Thr His Asp Leu Val Gly Asp Val Arg
 95                 100                 105 tta gcc gga gtt ata atg gca gga gtt gct att ggg att gca acc gca      2067
Leu Ala Gly Val Ile Met Ala Gly Val Ala Ile Gly Ile Ala Thr Ala
110                 115                 120                 125 gct caa atc act gca ggt gta gca cta tat gag gca atg aag aat gct      2115
Ala Gln Ile Thr Ala Gly Val Ala Leu Tyr Glu Ala Met Lys Asn Ala
```

-continued

```
                    130                 135                 140
gac aac atc aac aaa ctc aaa agc agc att gaa tca act aat gaa gct    2163
Asp Asn Ile Asn Lys Leu Lys Ser Ser Ile Glu Ser Thr Asn Glu Ala
            145                 150                 155 gtc gtt aaa ctt caa gag act gca gaa aag aca gtc tat gtg ctg act    2211
Val Val Lys Leu Gln Glu Thr Ala Glu Lys Thr Val Tyr Val Leu Thr
        160                 165                 170 gct cta cag gat tac att aat act aat tta gta ccg aca att gac aag    2259
Ala Leu Gln Asp Tyr Ile Asn Thr Asn Leu Val Pro Thr Ile Asp Lys
    175                 180                 185 ata agc tgc aaa cag aca gaa ctc tca cta gat ctg gca tta tca aag    2307
Ile Ser Cys Lys Gln Thr Glu Leu Ser Leu Asp Leu Ala Leu Ser Lys
190                 195                 200                 205 tac ctc tct gat ttg cta ttc gta ttt ggg ccc aac ctt caa gac cca    2355
Tyr Leu Ser Asp Leu Leu Phe Val Phe Gly Pro Asn Leu Gln Asp Pro
                210                 215                 220 gtt tct aat tca atg act ata cag gct ata tct cag gca ttc ggt gga    2403
Val Ser Asn Ser Met Thr Ile Gln Ala Ile Ser Gln Ala Phe Gly Gly
            225                 230                 235 aat tat gaa aca ctg cta aga aca ttg ggt tac gct aca gaa gac ttt    2451
Asn Tyr Glu Thr Leu Leu Arg Thr Leu Gly Tyr Ala Thr Glu Asp Phe
        240                 245                 250 gat gat ctt cta gaa agt gac agc ata aca ggt caa atc atc tat gtt    2499
Asp Asp Leu Leu Glu Ser Asp Ser Ile Thr Gly Gln Ile Ile Tyr Val
    255                 260                 265 gat cta agt agc tac tat ata att gtc agg gtt tat ttt cct att ctg    2547
Asp Leu Ser Ser Tyr Tyr Ile Ile Val Arg Val Tyr Phe Pro Ile Leu
270                 275                 280                 285 act gaa att caa cag gcc tat atc caa gag ttg tta cca gtg agc ttc    2595
Thr Glu Ile Gln Gln Ala Tyr Ile Gln Glu Leu Leu Pro Val Ser Phe
                290                 295                 300 aac aat gat aat tca gaa tgg atc agt att gtc cca aat ttc ata ttg    2643
Asn Asn Asp Asn Ser Glu Trp Ile Ser Ile Val Pro Asn Phe Ile Leu
            305                 310                 315 gta agg aat aca tta ata tca aat ata gag att gga ttt tgc cta att    2691
Val Arg Asn Thr Leu Ile Ser Asn Ile Glu Ile Gly Phe Cys Leu Ile
        320                 325                 330 aca aag agg agc gtg atc tgc aac caa gat tat gcc aca cct atg acc    2739
Thr Lys Arg Ser Val Ile Cys Asn Gln Asp Tyr Ala Thr Pro Met Thr
    335                 340                 345 aac aac atg aga gaa tgt tta acg gga tcg act gag aag tgt cct cga    2787
Asn Asn Met Arg Glu Cys Leu Thr Gly Ser Thr Glu Lys Cys Pro Arg
350                 355                 360                 365 gag ctg gtt gtt tca tca cat gtt ccc aga ttt gca cta tct aac ggg    2835
Glu Leu Val Val Ser Ser His Val Pro Arg Phe Ala Leu Ser Asn Gly
                370                 375                 380 gtt ctg ttt gcc aat tgc ata agt gtt aca tgt cag tgt caa aca aca    2883
Val Leu Phe Ala Asn Cys Ile Ser Val Thr Cys Gln Cys Gln Thr Thr
            385                 390                 395 ggc agg gca atc tca caa tca gga gaa caa act ctg ctg atg att gac    2931
Gly Arg Ala Ile Ser Gln Ser Gly Glu Gln Thr Leu Leu Met Ile Asp
        400                 405                 410 aac acc acc tgt cct aca gcc gta ctc ggt aat gtg att atc agc tta    2979
Asn Thr Thr Cys Pro Thr Ala Val Leu Gly Asn Val Ile Ile Ser Leu
    415                 420                 425 ggg aaa tat ctg ggg tca gta aat tat aat tct gaa ggc att gct atc    3027
Gly Lys Tyr Leu Gly Ser Val Asn Tyr Asn Ser Glu Gly Ile Ala Ile
430                 435                 440                 445 ggt cct cca gtc ttt aca gat aaa gtt gat ata tca agt cag ata tcc    3075
Gly Pro Pro Val Phe Thr Asp Lys Val Asp Ile Ser Ser Gln Ile Ser
```

|     |     |     |     |     |     |     |     |     |     |     |     |     |     |     |     |     |
| --- | --- | --- | --- | --- | --- | --- | --- | --- | --- | --- | --- | --- | --- | --- | --- | --- |
|     |     |     | 450 |     |     |     | 455 |     |     |     | 460 |     |     |     |     |     |
| agc | atg | aat | cag | tcc | tta | caa | cag | tct | aag | gac | tat | atc | aaa | gag | gct | 3123 |
| Ser | Met | Asn | Gln | Ser | Leu | Gln | Gln | Ser | Lys | Asp | Tyr | Ile | Lys | Glu | Ala |     |
|     |     |     | 465 |     |     |     | 470 |     |     |     | 475 |     |     |     |     |     |
| caa | cga | ctc | ctt | gat | act | gtt | aat | cca | tca | tta | ata | agc | atg | ttg | tct | 3171 |
| Gln | Arg | Leu | Leu | Asp | Thr | Val | Asn | Pro | Ser | Leu | Ile | Ser | Met | Leu | Ser |     |
|     |     | 480 |     |     |     |     | 485 |     |     |     |     | 490 |     |     |     |     |
| atg | atc | ata | ctg | tat | gta | tta | tcg | atc | gca | tcg | ttg | tgt | ata | ggg | ttg | 3219 |
| Met | Ile | Ile | Leu | Tyr | Val | Leu | Ser | Ile | Ala | Ser | Leu | Cys | Ile | Gly | Leu |     |
|     | 495 |     |     |     |     | 500 |     |     |     |     | 505 |     |     |     |     |     |
| att | aca | ttt | atc | agt | ttt | atc | att | gtt | gag | aaa | aag | aga | aac | acc | tac | 3267 |
| Ile | Thr | Phe | Ile | Ser | Phe | Ile | Ile | Val | Glu | Lys | Lys | Arg | Asn | Thr | Tyr |     |
| 510 |     |     |     |     | 515 |     |     |     |     | 520 |     |     |     |     | 525 |     |
| agc | aga | tta | gag | gat | agg | aga | gtc | aga | cct | aca | agc | agt | ggg | gat | ctc | 3315 |
| Ser | Arg | Leu | Glu | Asp | Arg | Arg | Val | Arg | Pro | Thr | Ser | Ser | Gly | Asp | Leu |     |
|     |     |     |     | 530 |     |     |     |     | 535 |     |     |     |     | 540 |     |     |
| tac | tac | att | ggg | aca | tagcccggga | tccctcgagt | ttttattgac | tagttaatca |     |     |     |     |     |     |     | 3370 |
| Tyr | Tyr | Ile | Gly | Thr |     |     |     |     |     |     |     |     |     |     |     |     |
|     |     |     |     | 545 |     |     |     |     |     |     |     |     |     |     |     |     |

```
taagataaat aatatacagc attgtaacca tcgtcatccg ttatacgggg aataatatta    3430
ccatacagta ttattaaatt ttcttacgaa gaatatagat cggtatttat cgttagttta    3490
ttttacattt attaattaaa catgtctact attacctgtt atggaaatga caaatttagt    3550
tatataattt atgataaaat taagataata ataatgaaat caaataatta tgtaaatgct    3610
actagattat gtgaattacg aggaagaaag tttacgaact ggaaaaaatt aagtgaatct    3670
aaaatattag tcgataatgt aaaaaaaata aatgataaaa ctaaccagtt aaaaacggat    3730
atgattatat acgttaagga tattgatcat aaaggaagag atacttgcgg ttactatgta    3790
caccaagatc tggtatcttc tatatcaaat tggatatctc cgttattcgc cgttaaggta    3850
aataaaatta ttaactatta tatatgtaat gaatatgata tacgacttag cgaaatggaa    3910
tctgatatga cagaagtaat agatgtagtt gataaattag taggaggata caatgatgaa    3970
atagcagaaa taatatattt gtttaataaa tttatagaaa aatatattgc taacatatcg    4030
ttatcaactg aattatctag tatattaaat aatttttataa attttaataa aaaatacaat    4090
aacgacataa aagatattaa atctttaatt cttgatctga aaaacacatc tataaaacta    4150
gataaaaagt tattcgataa agataataat gaatcgaacg atgaaaaatt ggaaacagaa    4210
gttgataagc taatttttttt catctaaata gtattatttt attgaagtac gaagttttac    4270
gttagataaa taataaaggt cgattttttat tttgttaaat atcaaatatg tcattatctg    4330
ataaagatac aaaaacacac ggtgattatc aaccatctaa cgaacagata ttacaaaaaa    4390
tacgtcggac tatggaaaac gaagctgata gcctcaatag aagaagcatt aagagaattg    4450
ttgtagatgt tatgaagaat tgggatcatc ctctcaacga gaaatagat aaagttctaa    4510 actggaaaaa tgatacatta aacgatttag atcatctaaa tacagatgat aatattaagg    4570
aaatcataca atgtctgatt agagaatttg cgtttaaaaa gatcaattct attatgtata    4630
gttatgctat ggtaaaactc aattcagata acgaaacatt gaaagataaa attaaggatt    4690
attttataga aactattctt aaagacaaac gtggttataa acaaaagcca ttaccctaga    4750
gcggccgcca ccgcggtgga gctccagctt ttgttccctt tagtgagggt taatttcgag    4810
cttggcgtaa tcatggtcat agctgttttcc                                   4840
```

<210> SEQ ID NO 25
<211> LENGTH: 4840
<212> TYPE: DNA

<213> ORGANISM: Artificial Sequence
<220> FEATURE:
<223> OTHER INFORMATION: Description of Artificial Sequence: Synthetic plasmid pSL-6839-1

<400> SEQUENCE: 25

```
ggaaacagct atgaccatga ttacgccaag ctcgaaatta accctcacta aagggaacaa        60
aagctggagc tccaccgcgg tggcggccgc tctagggtaa tggcttttgt ttataaccac       120
gtttgtcttt aagaatagtt tctataaaat aatccttaat tttatctttc aatgtttcgt       180
tatctgaatt gagttttacc atagcataac tatacataat agaattgatc tttttaaacg       240
caaattctct aatcagacat tgtatgattt ccttaatatt atcatctgta tttagatgat       300
ctaaatcgtt taatgtatca tttttccagt ttagaacttt atctatttct tcgttgagag       360
gatgatccca attcttcata acatctacaa caatttcttt aatgcttctt ctattgaggc       420
tatcagcttc gttttccata gtccgacgta tttttttgtaa tatctgttcg ttagatggtt      480
gataatcacc gtgtgttttt gtatctttat cagataatga catatttgat atttaacaaa       540
ataaaaatcg acctttatta tttatctaac gtaaaacttc gtacttcaat aaaataatac       600
tatttagatg aaaaaaatta gcttatcaac ttctgttttcc aatttttcat cgttcgattc      660
attattatct ttatcgaata acttttttatc tagttttata gatgtgtttt tcagatcaag      720
aattaaagat ttaatatctt ttatgtcgtt attgtatttt ttattaaaat ttataaaatt       780
atttaatata ctagataatt cagttgataa cgatatgtta gcaatatatt tttctataaa       840
tttattaaac aaatatatta tttctgctat tcatcattg tatcctccta ctaatttatc       900
aactacatct attacttctg tcatatcaga ttccatttcg ctaagtcgta tatcatattc       960
attacatata taatagttaa taattttatt taccttaacg gcgaataacg gagatatcca      1020
atttgatata gaagatacca gatcttggtg tacatagtaa ccgcaagtat ctcttccttt      1080
atgatcaata tccttaacgt atataatcat atccgttttt aactggttag ttttatcatt      1140
tattttttt acattatcga ctaatatttt agattcactt aatttttcc agttcgtaaa       1200
ctttcttcct cgtaattcac ataatctagt agcatttaca taattatttg atttcattat      1260
tattatctta atttatcat aaattatata actaaattg tcatttccat aacaggtaat       1320
agtagacatg tttaattaat aaatgtaaaa taaactaacg ataaataccg atctatattc      1380
ttcgtaagaa aatttaataa tactgtatgg taatattatt ccccgtataa cggatgacga      1440
tggttacaat gctgtatatt atttatctta tgattaacta gtcaataaaa actcgaggga      1500
tcccgggcta tgtcccaatg tagtagagat ccccactgct tgtaggtctg actctcctat      1560
cctctaatct gctgtaggtg tttctctttt tctcaacaat gataaaactg ataaatgtaa      1620
tcaaccctat acacaacgat gcgatcgata atacatacag tatgatcata gacaacatgc      1680
ttattaatga tggattaaca gtatcaagga gtcgttgagc ctctttgata tagtccttag      1740
actgttgtaa ggactgattc atgctggata tctgacttga tatatcaact ttatctgtaa      1800
agactggagg accgatagca atgccttcag aattataatt tactgacccc agatatttcc      1860
ctaagctgat aatcacatta ccgagtacgg ctgtaggaca ggtggtgttg tcaatcatca      1920
gcagagtttg ttctcctgat tgtgagattg ccctgcctgt tgtttgacac tgacatgtaa      1980
cacttatgca attggcaaac agaaccccgt tagatagtgc aaatctggga acatgtgatg      2040
aaacaaccag ctctcgagga cacttctcag tcgatcccgt taaacattct ctcatgttgt      2100
tggtcatagg tgtggcataa tcttggttgc agatcacgct cctctttgta attaggcaaa      2160
atccaatctc tatatttgat attaatgtat tccttaccaa tatgaaattt gggacaatac      2220
```

```
tgatccattc tgaattatca ttgttgaagc tcactggtaa caactcttgg atataggcct    2280
gttgaatttc agtcagaata ggaaaataaa ccctgacaat tatatagtag ctacttagat    2340
caacatagat gatttgacct gttatgctgt cactttctag aagatcatca aagtcttctg    2400
tagcgtaacc caatgttctt agcagtgttt cataatttcc accgaatgcc tgagatatag    2460
cctgtatagt cattgaatta gaaactgggt cttgaaggtt gggcccaaat acgaatagca    2520
aatcagagag gtactttgat aatgccagat ctagtgagag ttctgtctgt ttgcagctta    2580
tcttgtcaat tgtcggtact aaattagtat taatgtaatc ctgtagagca gtcagcacat    2640
agactgtctt ttctgcagtc tcttgaagtt taacgacagc ttcattagtt gattcaatgc    2700
tgcttttgag tttgttgatg ttgtcagcat tcttcattgc ctcatatagt gctacacctg    2760
cagtgatttg agctgcggtt gcaatcccaa tagcaactcc tgccattata actccggcta    2820
atctcacatc accgacaagg tcatgagtgt tgttttgta gatctctaac gctcccttta    2880
taggtgttaa gataccgttt aatcgtgttt tataattttc catgacactc cctgtgcact    2940
gagacatgtt cgacacattc ggaatcattt ttataacaat gtcttttgtg agaggattgc    3000
ttttaatctt gtattttctt gttactcctt tgacaagtcc aatttactc aatttctcat    3060 aatgtagaat cccaacacta cactccgaga tcatcaaaat caatattaaa agattacaat    3120
aacatctctt gtcaagtata actaccatta cgatacaaac ttaacggata tcgcgataat    3180
gaaataattt atgattattt ctcgctttca atttaacaca accctcaaga acctttgtat    3240
ttattttcac tttttaagta tagaataaag aagctctaat taattaacga gcagatagtc    3300
tcgttctcgc cctgcctgat gactaattaa ttaacccggg tttttattag ctaattagca    3360
atatagattc aatatgataa ttactctaag ttggtaaact aaaaccagct attttccgta    3420
aatgtaatta tattttatt gttcttatag gtattttgt aaaaatcatt tcttatatc    3480 tattatataa tattttttta tcatatttat tatctatcca ataccactg ggtattatga    3540 aaggaaaaac tattctacat tcaggacacg tattttcagt atctgtattt ctggtagtat    3600
ctgcccaacg tctttacat gataggcaaa aaatatgttt acaacttggg agaattccaa    3660
aatactgttc ggaaatatgt ttttttgttta tttcttctat gcatatgcca cacttttac    3720 tggtacttct tttaaacaca atcaaagaat ctctatctac taaacaagtt ttcttgtgag    3780
aaactcgttg gttaatatcg gtagggtgta gtatatatag accacagata tcacattgat    3840
ctccgtgtat atacttacat tttttaccat aatagcatct accaagttct ataaacgggc    3900
atagagtgtt ttcacaggat actatttta attcatcgtt accgaataac gcattataga    3960
aattaatcat tttgtatata tcgttttgaa aatcatcccc tatccactca ataacataac    4020
gtatcatatt ttgtttgaga taaatcctg ttataataag tttcttacct ttaccataga    4080
ctttaacaat agcattatct actgacttat tattgtaaat gtctaataat gctttagaag    4140
tagaaagacg caaccatcta gaaaagtatt tattccgcat tttacataat ttactacaat    4200
taacgtaacc gttattcttc attattataa cctttatatc tctatacttg atcgaatcaa    4260
aagatccgtc tatacattca ataacataat catcttgtga taaatctgat actgaatatt    4320
ttccgtgaat gttatttatg tttgatgagt cgtcctcctt cattggttta tattgttgga    4380
aaatgatcaa aaccgtgcag ctacgctgtt atatattact aatccaacaa tatatttctt    4440
ccgttgtaaa gtcttctaga gctaatattt ttactttatg aatatcgtct ctagttttat    4500
ttcttatata cttaacgtat ttatttttcg taatataaga tataacattt tgattattag    4560
aataatataa cactatttgt agatatatat catcatcatg ataggcatat cttgtagcta    4620
```

```
tatgatacat tagaaaagca tcgaatatct catcggaaga gcgcatgtct atacaaacta    4680
tgtctccttt agatttctca taccaaaata tattatcgtt ttctgcatac gaattacatt    4740
tataaactat ttcacagttg tttcttcttt tattcttgta aagggtcacc caattcgccc    4800
tatagtgagt cgtattacaa ttcactggcc gtcgttttac                          4840
```

<210> SEQ ID NO 26
<211> LENGTH: 546
<212> TYPE: PRT
<213> ORGANISM: Artificial Sequence
<220> FEATURE:
<223> OTHER INFORMATION: Description of Artificial Sequence: Synthetic
      plasmid pSL-6851-29

<400> SEQUENCE: 26

```
Met Val Val Ile Leu Asp Lys Arg Cys Tyr Cys Asn Leu Leu Ile Leu
 1               5                  10                  15

Ile Leu Met Ile Ser Glu Cys Ser Val Gly Ile Leu His Tyr Glu Lys
            20                  25                  30

Leu Ser Lys Ile Gly Leu Val Lys Gly Val Thr Arg Lys Tyr Lys Ile
        35                  40                  45

Lys Ser Asn Pro Leu Thr Lys Asp Ile Val Ile Lys Met Ile Pro Asn
    50                  55                  60

Val Ser Asn Met Ser Gln Cys Thr Gly Ser Val Met Glu Asn Tyr Lys
65                  70                  75                  80

Thr Arg Leu Asn Gly Ile Leu Thr Pro Ile Lys Gly Ala Leu Glu Ile
                85                  90                  95

Tyr Lys Asn Asn Thr His Asp Leu Val Gly Asp Val Arg Leu Ala Gly
            100                 105                 110

Val Ile Met Ala Gly Val Ala Ile Gly Ile Ala Thr Ala Ala Gln Ile
        115                 120                 125

Thr Ala Gly Val Ala Leu Tyr Glu Ala Met Lys Asn Ala Asp Asn Ile
    130                 135                 140

Asn Lys Leu Lys Ser Ser Ile Glu Ser Thr Asn Glu Ala Val Val Lys
145                 150                 155                 160

Leu Gln Glu Thr Ala Glu Lys Thr Val Tyr Val Leu Thr Ala Leu Gln
                165                 170                 175

Asp Tyr Ile Asn Thr Asn Leu Val Pro Thr Ile Asp Lys Ile Ser Cys
            180                 185                 190

Lys Gln Thr Glu Leu Ser Leu Asp Leu Ala Leu Ser Lys Tyr Leu Ser
        195                 200                 205

Asp Leu Leu Phe Val Phe Gly Pro Asn Leu Gln Asp Pro Val Ser Asn
    210                 215                 220

Ser Met Thr Ile Gln Ala Ile Ser Gln Ala Phe Gly Gly Asn Tyr Glu
225                 230                 235                 240

Thr Leu Leu Arg Thr Leu Gly Tyr Ala Thr Glu Asp Phe Asp Asp Leu
                245                 250                 255

Leu Glu Ser Asp Ser Ile Thr Gly Gln Ile Ile Tyr Val Asp Leu Ser
            260                 265                 270

Ser Tyr Tyr Ile Ile Val Arg Val Tyr Phe Pro Ile Leu Thr Glu Ile
        275                 280                 285

Gln Gln Ala Tyr Ile Gln Glu Leu Leu Pro Val Ser Phe Asn Asn Asp
    290                 295                 300

Asn Ser Glu Trp Ile Ser Ile Val Pro Asn Phe Ile Leu Val Arg Asn
305                 310                 315                 320
```

```
Thr Leu Ile Ser Asn Ile Glu Ile Gly Phe Cys Leu Ile Thr Lys Arg
            325                 330                 335

Ser Val Ile Cys Asn Gln Asp Tyr Ala Thr Pro Met Thr Asn Asn Met
        340                 345                 350

Arg Glu Cys Leu Thr Gly Ser Thr Glu Lys Cys Pro Arg Glu Leu Val
    355                 360                 365

Val Ser Ser His Val Pro Arg Phe Ala Leu Ser Asn Gly Val Leu Phe
370                 375                 380

Ala Asn Cys Ile Ser Val Thr Cys Gln Cys Gln Thr Thr Gly Arg Ala
385                 390                 395                 400

Ile Ser Gln Ser Gly Glu Gln Thr Leu Leu Met Ile Asp Asn Thr Thr
            405                 410                 415

Cys Pro Thr Ala Val Leu Gly Asn Val Ile Ser Leu Gly Lys Tyr
        420                 425                 430

Leu Gly Ser Val Asn Tyr Asn Ser Glu Gly Ile Ala Ile Gly Pro Pro
    435                 440                 445

Val Phe Thr Asp Lys Val Asp Ile Ser Ser Gln Ile Ser Ser Met Asn
450                 455                 460

Gln Ser Leu Gln Gln Ser Lys Asp Tyr Ile Lys Glu Ala Gln Arg Leu
465                 470                 475                 480

Leu Asp Thr Val Asn Pro Ser Leu Ile Ser Met Leu Ser Met Ile Ile
            485                 490                 495

Leu Tyr Val Leu Ser Ile Ala Ser Leu Cys Ile Gly Leu Ile Thr Phe
        500                 505                 510

Ile Ser Phe Ile Ile Val Glu Lys Lys Arg Asn Thr Tyr Ser Arg Leu
    515                 520                 525

Glu Asp Arg Arg Val Arg Pro Thr Ser Ser Gly Asp Leu Tyr Tyr Ile
530                 535                 540

Gly Thr
545

<210> SEQ ID NO 27
<211> LENGTH: 3911
<212> TYPE: DNA
<213> ORGANISM: Artificial Sequence
<220> FEATURE:
<221> NAME/KEY: CDS
<222> LOCATION: (1800)..(3437)
<220> FEATURE:
<223> OTHER INFORMATION: Description of Artificial Sequence: Synthetic
      plasmid pSL-6851-29

<400> SEQUENCE: 27
ggaaacagct atgaccatga ttacgaattg cggccgcaat tctgaatgtt aaatgttata      60
ctttggatga agctataaat atgcattgga aaataatcc atttaaagaa aggattcaaa     120
tactacaaaa cctaagcgat aatatgttaa ctaagcttat tcttaacgac gctttaaata     180
tacacaaata aacataattt ttgtataacc taacaaataa ctaaaacata aaataataa     240 aaggaaatgt aatatcgtaa ttattttact caggaatggg gttaaatatt tatatcacgt     300
gtatatctat actgttatcg tatactcttt acaattacta ttcgaatat gcaagagata     360 ataagattac gtatttaaga gaatcttgtc atgataattg ggtacgacat agtgataaat     420
gctatttcgc atcgttacat aaagtcagtt ggaaagatgg atttgacaga tgtaacttaa     480
taggtgcaaa aatgttaaat aacagcattc tatcggaaga taggatacca gttatattat     540
acaaaaatca ctggttggat aaaacagatt ctgcaatatt cgtaaagat gaagattact     600 gcgaatttgt aaactatgac aataaaaagc catttatctc aacgacatcg tgtaattctt     660
```

```
ccatgtttta tgtatgtgtt tcagatatta tgagattact ataaacttttt tgtatactta    720 tattccgtaa actatattaa tcatgaagaa aatgaaaaag tatagaagct gttcacgagc    780
ggttgttgaa acaacaaaa ttatacattc aagatggctt acatatacgt ctgtgaggct    840
atcatggata atgacaatgc atctctaaat aggttttttgg acaatggatt cgaccctaac    900
acggaatatg gtactctaca atctcctctt gaaatggctg taatgttcaa gaataccgag    960
gctataaaaa tcttgatgag gtatggagct aaacctgtag ttactgaatg cacaacttct   1020
tgtctgcatg atgcggtgtt gagagacgac tacaaaatag tgaaagatct gttgaagaat   1080
aactatgtaa acaatgttct ttacagcgga ggctttactc ctttgtgttt ggcagcttac   1140
cttaacaaag ttaatttggt taaacttcta ttggctcatt cggcggatgt agatatttca   1200
aacacggatc ggttaactcc tctacatata gccgtatcaa ataaaaattt aacaatggtt   1260
aaacttctat tgaacaaagg tgctgatact gacttgctgg ataacatggg acgtactcct   1320
ttaatgatcg ctgtacaatc tggaaatatt gaaatatgta gcacactact taaaaaaaat   1380
aaaatgtcca gaactgggaa aaattgatct tgccagctgt aattcatggt agaaaagaag   1440
tgctcaggct acttttcaac aaaggagcag atgtaaacta catctttgaa agaaatggaa   1500
aatcatatac tgttttggaa ttgattaaag aaagttactc tgagacacaa agaggtagc   1560 tgaagtggta ctctcaaagg tacgtgacta attagctata aaaaggatcc gggttaatta   1620
attagtcatc aggcagggcg agaacgagac tatctgctcg ttaattaatt agagcttctt   1680
tattctatac ttaaaaagtg aaaataaata caaaggttct tgagggttgt gttaaattga   1740
aagcgagaaa taatcataaa ttatttcatt atcgcgatat ccgttaagtt tgtatcgta    1799 atg gta gtt ata ctt gac aag aga tgt tat tgt aat ctt tta ata ttg   1847
Met Val Val Ile Leu Asp Lys Arg Cys Tyr Cys Asn Leu Leu Ile Leu
 1               5                  10                  15 att ttg atg atc tcg gag tgt agt gtt ggg att cta cat tat gag aaa   1895
Ile Leu Met Ile Ser Glu Cys Ser Val Gly Ile Leu His Tyr Glu Lys
             20                  25                  30 ttg agt aaa att gga ctt gtc aaa gga gta aca aga aaa tac aag att   1943
Leu Ser Lys Ile Gly Leu Val Lys Gly Val Thr Arg Lys Tyr Lys Ile
         35                  40                  45 aaa agc aat cct ctc aca aaa gac att gtt ata aaa atg att ccg aat   1991
Lys Ser Asn Pro Leu Thr Lys Asp Ile Val Ile Lys Met Ile Pro Asn
 50                  55                  60 gtg tcg aac atg tct cag tgc aca ggg agt gtc atg gaa aat tat aaa   2039
Val Ser Asn Met Ser Gln Cys Thr Gly Ser Val Met Glu Asn Tyr Lys
 65                  70                  75                  80 aca cga tta aac ggt atc tta aca cct ata aag gga gcg tta gag atc   2087
Thr Arg Leu Asn Gly Ile Leu Thr Pro Ile Lys Gly Ala Leu Glu Ile
                 85                  90                  95 tac aaa aac aac act cat gac ctt gtc ggt gat gtg aga tta gcc gga   2135
Tyr Lys Asn Asn Thr His Asp Leu Val Gly Asp Val Arg Leu Ala Gly
             100                 105                 110 gtt ata atg gca gga gtt gct att ggg att gca acc gca gct caa atc   2183
Val Ile Met Ala Gly Val Ala Ile Gly Ile Ala Thr Ala Ala Gln Ile
         115                 120                 125 act gca ggt gta gca cta tat gag gca atg aag aat gct gac aac atc   2231
Thr Ala Gly Val Ala Leu Tyr Glu Ala Met Lys Asn Ala Asp Asn Ile
 130                 135                 140 aac aaa ctc aaa agc agc att gaa tca act aat gaa gct gtc gtt aaa   2279
Asn Lys Leu Lys Ser Ser Ile Glu Ser Thr Asn Glu Ala Val Val Lys
145                 150                 155                 160 ctt caa gag act gca gaa aag aca gtc tat gtg ctg act gct cta cag   2327
Leu Gln Glu Thr Ala Glu Lys Thr Val Tyr Val Leu Thr Ala Leu Gln
```

-continued

| | | |
|---|---|---|
| Leu Gln Glu Thr Ala Glu Lys Thr Val Tyr Val Leu Thr Ala Leu Gln<br>                   165                   170                175 | | |
| gat tac att aat act aat tta gta ccg aca att gac aag ata agc tgc<br>Asp Tyr Ile Asn Thr Asn Leu Val Pro Thr Ile Asp Lys Ile Ser Cys<br>                   180                   185                190 | | 2375 |
| aaa cag aca gaa ctc tca cta gat ctg gca tta tca aag tac ctc tct<br>Lys Gln Thr Glu Leu Ser Leu Asp Leu Ala Leu Ser Lys Tyr Leu Ser<br>               195                   200                205 | | 2423 |
| gat ttg cta ttc gta ttt ggg ccc aac ctt caa gac cca gtt tct aat<br>Asp Leu Leu Phe Val Phe Gly Pro Asn Leu Gln Asp Pro Val Ser Asn<br>     210                   215                   220 | | 2471 |
| tca atg act ata cag gct ata tct cag gca ttc ggt gga aat tat gaa<br>Ser Met Thr Ile Gln Ala Ile Ser Gln Ala Phe Gly Gly Asn Tyr Glu<br>225                   230                   235                240 | | 2519 |
| aca ctg cta aga aca ttg ggt tac gct aca gaa gac ttt gat gat ctt<br>Thr Leu Leu Arg Thr Leu Gly Tyr Ala Thr Glu Asp Phe Asp Asp Leu<br>               245                   250                255 | | 2567 |
| cta gaa agt gac agc ata aca ggt caa atc atc tat gtt gat cta agt<br>Leu Glu Ser Asp Ser Ile Thr Gly Gln Ile Ile Tyr Val Asp Leu Ser<br>               260                   265                270 | | 2615 |
| agc tac tat ata att gtc agg gtt tat ttt cct att ctg act gaa att<br>Ser Tyr Tyr Ile Ile Val Arg Val Tyr Phe Pro Ile Leu Thr Glu Ile<br>             275                   280                285 | | 2663 |
| caa cag gcc tat atc caa gag ttg tta cca gtg agc ttc aac aat gat<br>Gln Gln Ala Tyr Ile Gln Glu Leu Leu Pro Val Ser Phe Asn Asn Asp<br>     290                   295                   300 | | 2711 |
| aat tca gaa tgg atc agt att gtc cca aat ttc ata ttg gta agg aat<br>Asn Ser Glu Trp Ile Ser Ile Val Pro Asn Phe Ile Leu Val Arg Asn<br>305                   310                   315                320 | | 2759 |
| aca tta ata tca aat ata gag att gga ttt tgc cta att aca aag agg<br>Thr Leu Ile Ser Asn Ile Glu Ile Gly Phe Cys Leu Ile Thr Lys Arg<br>                     325                   330                335 | | 2807 |
| agc gtg atc tgc aac caa gat tat gcc aca cct atg acc aac aac atg<br>Ser Val Ile Cys Asn Gln Asp Tyr Ala Thr Pro Met Thr Asn Asn Met<br>             340                   345                350 | | 2855 |
| aga gaa tgt tta acg gga tcg act gag aag tgt cct cga gag ctg gtt<br>Arg Glu Cys Leu Thr Gly Ser Thr Glu Lys Cys Pro Arg Glu Leu Val<br>               355                   360                365 | | 2903 |
| gtt tca tca cat gtt ccc aga ttt gca cta tct aac ggg gtt ctg ttt<br>Val Ser Ser His Val Pro Arg Phe Ala Leu Ser Asn Gly Val Leu Phe<br>     370                   375                   380 | | 2951 |
| gcc aat tgc ata agt gtt aca tgt cag tgt caa aca aca ggc agg gca<br>Ala Asn Cys Ile Ser Val Thr Cys Gln Cys Gln Thr Thr Gly Arg Ala<br>385                   390                   395                400 | | 2999 |
| atc tca caa tca gga gaa caa act ctg ctg atg att gac aac acc acc<br>Ile Ser Gln Ser Gly Glu Gln Thr Leu Leu Met Ile Asp Asn Thr Thr<br>                     405                   410                415 | | 3047 |
| tgt cct aca gcc gta ctc ggt aat gtg att atc agc tta ggg aaa tat<br>Cys Pro Thr Ala Val Leu Gly Asn Val Ile Ile Ser Leu Gly Lys Tyr<br>             420                   425                430 | | 3095 |
| ctg ggg tca gta aat tat aat tct gaa ggc att gct atc ggt cct cca<br>Leu Gly Ser Val Asn Tyr Asn Ser Glu Gly Ile Ala Ile Gly Pro Pro<br>               435                   440                445 | | 3143 |
| gtc ttt aca gat aaa gtt gat ata tca agt cag ata tcc agc atg aat<br>Val Phe Thr Asp Lys Val Asp Ile Ser Ser Gln Ile Ser Ser Met Asn<br>     450                   455                   460 | | 3191 |
| cag tcc tta caa cag tct aag gac tat atc aaa gag gct caa cga ctc<br>Gln Ser Leu Gln Gln Ser Lys Asp Tyr Ile Lys Glu Ala Gln Arg Leu<br>465                   470                   475                480 | | 3239 |
| ctt gat act gtt aat cca tca tta ata agc atg ttg tct atg atc ata | | 3287 |

-continued

```
Leu Asp Thr Val Asn Pro Ser Leu Ile Ser Met Leu Ser Met Ile Ile
        485                 490                 495 ctg tat gta tta tcg atc gca tcg ttg tgt ata ggg ttg att aca ttt    3335
Leu Tyr Val Leu Ser Ile Ala Ser Leu Cys Ile Gly Leu Ile Thr Phe
        500                 505                 510 atc agt ttt atc att gtt gag aaa aag aga aac acc tac agc aga tta    3383
Ile Ser Phe Ile Ile Val Glu Lys Lys Arg Asn Thr Tyr Ser Arg Leu
        515                 520                 525 gag gat agg aga gtc aga cct aca agc agt ggg gat ctc tac tac att    3431
Glu Asp Arg Arg Val Arg Pro Thr Ser Ser Gly Asp Leu Tyr Tyr Ile
    530                 535                 540 ggg aca tagcccgggt ttttatgact agtaatcac ggccgcttat aaagatctaa     3487
Gly Thr
545 aatgcataat ttctaaataa tgaaaaaaag tacatcatga gcaacgcgtt agtatatttt    3547
acaatggaga ttaacgctct ataccgttct atgtttattg attcagatga tgttttagaa    3607
aagaaagtta ttgaatatga aactttaat gaagatgaag atgacgacga tgattattgt    3667
tgtaaatctg ttttagatga agaagatgac gcgctaaagt atactatggt tacaaagtat    3727
aagtctatac tactaatggc gacttgtgca agaaggtata gtagtgaa atgttgtta     3787
gattatgatt atgaaaaacc aaataaatca gatccatatc taaaggtatc tcctttgcac    3847
ataattcat ctattcctag tttagaatac ctgcagccaa gcttggcact ggccgtcgtt    3907
ttac                                                                 3911
```

<210> SEQ ID NO 28
<211> LENGTH: 3911
<212> TYPE: DNA
<213> ORGANISM: Artificial Sequence
<220> FEATURE:
<223> OTHER INFORMATION: Description of Artificial Sequence: Synthetic plasmid pSL-6851-29

<400> SEQUENCE: 28

```
gtaaaacgac ggccagtgcc aagcttggct gcaggtattc taaactagga atagatgaaa      60
ttatgtgcaa aggagatacc tttagatatg gatctgattt atttggtttt tcataatcat     120
aatctaacaa cattttcact atactatacc ttcttgcaca agtcgccatt agtagtatag     180
acttatactt tgtaaccata gtacacttta gcgcgtcatc ttcttcatct aaaacagatt     240
tacaacaata atcatcgtcg tcatcttcat cttcattaaa gttttcatat tcaataactt     300
tcttttctaa aacatcatct gaatcaataa acatagaacg gtatagagcg ttaatctcca     360
ttgtaaaata tactaacgcg ttgctcatga tgtactttt ttcattattt agaaattatg      420
cattttagat ctttataagc ggccgtgatt aactagtcat aaaaacccgg gctatgtccc     480
aatgtagtag agatccccac tgcttgtagg tctgactctc ctatcctcta atctgctgta     540
ggtgtttctc ttttttctcaa caatgataaa actgataaat gtaatcaacc ctatacacaa     600
cgatgcgatc gataatacat acagtatgat catagacaac atgcttatta atgatggatt      660
aacagtatca aggagtcgtt gagcctcttt gatatagtcc ttagactgtt gtaaggactg      720
attcatgctg gatatctgac ttgatatatc aactttatct gtaaagactg gaggaccgat      780
agcaatgcct tcagaattat aatttactga ccccagatat ttccctaagc tgataatcac      840
attaccgagt acggctgtag acaggtggt gttgtcaatc atcagcagag tttgttctcc       900
tgattgtgag attgccctgc ctgttgtttg acactgacat gtaacactta tgcaattggc      960
aaacagaacc ccgttagata gtgcaaatct gggaacatgt gatgaaacaa ccagctctcg    1020
```

```
aggacacttc tcagtcgatc ccgttaaaca ttctctcatg ttgttggtca taggtgtggc   1080
ataatcttgg ttgcagatca cgctcctctt tgtaattagg caaaatccaa tctctatatt   1140
tgatattaat gtattcctta ccaatatgaa atttgggaca atactgatcc attctgaatt   1200
atcattgttg aagctcactg gtaacaactc ttggatatag gcctgttgaa tttcagtcag   1260
aataggaaaa taaaccctga caattatata gtagctactt agatcaacat agatgatttg   1320
acctgttatg ctgtcacttt ctagaagatc atcaaagtct tctgtagcgt aacccaatgt   1380
tcttagcagt gtttcataat ttccaccgaa tgcctgagat atagcctgta tagtcattga   1440
attagaaact gggtcttgaa ggttgggccc aaatacgaat agcaaatcag agaggtactt   1500
tgataatgcc agatctagtg agagttctgt ctgtttgcag cttatcttgt caattgtcgg   1560
tactaaatta gtattaatgt aatcctgtag agcagtcagc acatagactg tcttttctgc   1620
agtctcttga agtttaacga cagcttcatt agttgattca atgctgcttt tgagtttgtt   1680
gatgttgtca gcattcttca ttgcctcata tagtgctaca cctgcagtga tttgagctgc   1740
ggttgcaatc ccaatagcaa ctcctgccat tataactccg gctaatctca catcaccgac   1800
aaggtcatga gtgttgtttt tgtagatctc taacgctccc tttataggtg ttaagatacc   1860
gtttaatcgt gttttataat tttccatgac actccctgtg cactgagaca tgttcgacac   1920
attcggaatc attttttataa caatgtcttt tgtgagagga ttgcttttaa tcttgtattt   1980
tcttgttact cctttgacaa gtccaatttt actcaatttc tcataatgta gaatcccaac   2040
actacactcc gagatcatca aaatcaatat taaaagatta caataacatc tcttgtcaag   2100
tataactacc attacgatac aaacttaacg gatatcgcga taatgaaata atttatgatt   2160
atttctcgct ttcaatttaa cacaaccctc aagaaccttt gtatttattt tcacttttta   2220
agtatagaat aaagaagctc taattaatta acgagcagat agtctcgttc tcgccctgcc   2280
tgatgactaa ttaattaacc cggatccttt ttatagctaa ttagtcacgt accttttgaga   2340 gtaccacttc agctacctct tttgtgtctc agagtaactt tctttaatca attccaaaac   2400
agtatatgat tttccatttc tttcaaagat gtagtttaca tctgctccctt tgttgaaaag   2460 tagcctgagc acttcttttc taccatgaat tacagctggc aagatcaatt tttcccagtt   2520
ctggacattt tattttttt aagtagtgtg ctacatattt caatatttcc agattgtaca   2580
gcgatcatta aaggagtacg tcccatgtta tccagcaagt cagtatcagc acctttgttc   2640
aatagaagtt taaccattgt taaatttta tttgatacgg ctatatgtag aggagttaac   2700
cgatccgtgt ttgaaatatc tacatccgcc gaatgagcca atagaagttt aaccaaatta   2760
actttgttaa ggtaagctgc caaacacaaa ggagtaaagc ctccgctgta agaacattg   2820 tttacatagt tattcttcaa cagatctttc actattttgt agtcgtctct caacaccgca   2880
tcatgcagac aagaagttgt gcattcagta actacaggtt tagctccata cctcatcaag   2940 attttttatag cctcggtatt cttgaacatt acagccattt caagaggaga ttgtagagta   3000
ccatattccg tgttagggtc gaatccattg tccaaaaacc tatttagaga tgcattgtca   3060
ttatccatga tagcctcaca gacgtatatg taagccatct tgaatgtata attttgttgt   3120
tttcaacaac cgctcgtgaa cagcttctat acttttcat tttcttcatg attaatatag   3180
tttacggaat ataagtatac aaaaagttta gtaatctc ataatatctg aaacacatac   3240
ataaaacatg gaagaattac acgatgtcgt tgagataaat ggctttttat tgtcatagtt   3300
tacaaattcg cagtaatctt catctttac gaatattgca gaatctgttt tatccaacca   3360 gtgattttg tataatataa ctggtatcct atcttccgat agaatgctgt tatttaacat   3420
```

-continued

```
ttttgcacct attaagttac atctgtcaaa tccatctttc caactgactt tatgtaacga   3480
tgcgaaatag catttatcac tatgtcgtac ccaattatca tgacaagatt ctcttaaata   3540
cgtaatctta ttatctcttg catattcgta atagtaattg taaagagtat acgataacag   3600
tatagatata cacgtgatat aaatatttaa ccccattcct gagtaaaata attacgatat   3660
tacatttcct tttattattt ttatgtttta gttatttgtt aggttataca aaaattatgt   3720
ttatttgtgt atatttaaag cgtcgttaag aataagctta gttaacatat tatcgcttag   3780
gttttgtagt atttgaatcc tttctttaaa tggattattt ttccaatgca tatttatagc   3840
ttcatccaaa gtataacatt taacattcag aattgcggcc gcaattcgta atcatggtca   3900
tagctgtttc c                                                        3911

<210> SEQ ID NO 29
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gcacttgatg tgattaga                                                   18

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
gatttgctat tcgtatttgg gcccaacctt                                      30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
aaggttgggc ccaaatacga atagcaaatc                                      30
```

NIPAH VIRUS VACCINES

CROSS-REFERENCE TO RELATED APPLICATIONS

This application is a continuation of U.S. application Ser. No. 11/404,534 filed on Apr. 14, 2006, now U.S. Pat. No. 7,803,612, which claims priority from U.S. Provisional Application Ser. No. 60/674,583, filed Apr. 25, 2005.

INCORPORATION BY REFERENCE

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to recombinant vaccines against Nipah virus and the administration of such vaccines.

BACKGROUND OF THE INVENTION

Nipah virus is a member of the Paramyxoviridae family and is related to the Hendra virus (formerly called equine morbillivirus). The Nipah virus was initially isolated in 1999 upon examining samples from an outbreak of encephalitis and respiratory illness among adult men in Malaysia and Singapore (see, e.g., Chua et al., Lancet. 1999 Oct. 9; 354 (9186):1257-9 and Paton et al., Lancet. 1999 Oct. 9; 354 (9186):1253-6). The host for Nipah virus is still unknown, but flying foxes (bats of the *Pteropus* genus) are suspected to be the natural host.

Because of changes in ecological conditions, flying foxes are increasingly coming into contact with humans and domesticated animals. Therefore, it is conceivable that the viruses in flying foxes may infect domesticated animals and humans, which could result in a more virulent, possibly fatal, disease. Nipah virus caused a relatively mild disease in pigs in Malaysia and Singapore and the virus was transmitted to humans, cats and dogs through close contact with infected pigs.

Infectious with Nipah virus in humans has been associated with an encephalitis characterized by fever and drowsiness and more serious central nervous system disease, such as coma, seizures and inability to maintain breathing (see, e.g., Lee et al., Ann Neurol. 1999 September; 46(3):428-32). Illness with Nipah virus begins with 3-14 days of fever and headache, followed by drowsiness and disorientation characterized by mental confusion. These signs and symptoms can progress to coma within 24-48 hours. Some patients have had a respiratory illness during the early part of their infections. Serious nervous disease with Nipah virus encephalitis has been marked by some sequelae, such as persistent convulsions and personality changes. During the Nipah virus disease outbreak in 1998-1999, about 40% of the patients with serious nervous disease who entered hospitals died from the illness (see, e.g., Lam & Chua, Clin Infect Dis. 2002 May 1; 34 Suppl 2:S48-51).

Accordingly, a goal of animal health is the betterment of human health by preventing disease transmission between animals and/or humans.

Nipah virus infection can be prevented by avoiding animals that are known to be infected and using appropriate personal protective equipment devices when it is necessary to come into contact with potentially infected animals. The drug ribavirin has been shown to be effective against the Nipah virus in vitro, however, controlled drug investigations have not been performed and the clinical usefulness is uncertain.

If an efficient program to prevent or treat Nipah virus infection is to be developed, it will be necessary to define the viral antigens which are important in inducing protective responses and to formulate potential immunoprophylactic treatments. The attachment (G) and fusion (F) glycoproteins of Nipah virus have been implicated as viral antigens (see, e.g., Bossart et al., J. Virol. 2002 November; 76(22):11186-98 and Guillaume et al., J. Virol. 2004 January; 78(2):834-40). The Nipah virus glycoproteins (G and F) when expressed as vaccinia virus recombinants have induced an immune response in hamsters which protected against a lethal challenge by Nipah virus (see, e.g., Guillaume et al., J. Virol. 2004 January; 78(2):834-40). However, it was observed that in both active and passive immunization, the antibody response to Nipah virus was strongly stimulated, suggesting that the efficacy of the immunization is related to the capability of the vector to replicate.

Accordingly, there is a need in the art for an efficacious and reliable Nipah virus vaccine where heterologous proteins are expressed with limited or no productive replication.

Citation or identification of any document in this application is not an admission that such document is available as prior art to the present invention.

SUMMARY OF THE INVENTION

The invention is based, in part, on the development of an efficacious recombinant vaccine that immunizes pigs against Nipah virus with an attenuated canarypox or attenuated fowlpox vector encoding a Nipah virus glycoprotein so there can be expression of the heterologous proteins with limited or no productive replication.

The invention may comprise an avipox expression vector encompassing a polynucleotide that encodes a Nipah virus glycoprotein. In one embodiment, the Nipah virus glycoprotein may be the attachment (G) protein. Advantageously, the polynucleotide may comprise the nucleotide base sequence of nucleotide 8943 to nucleotide 10751 of SEQ ID NO: 1 or the polynucleotide encodes the peptide of SEQ ID NO: 8. In another embodiment, the Nipah virus glycoprotein may be the fusion (F) protein. Advantageously, the polynucleotide may comprise the nucleotide base sequence of nucleotide 6654 to nucleotide 8294 of SEQ ID NO: 1 or the polynucleotide encodes the peptide of SEQ ID NO: 7. In yet another embodiment, the Nipah virus glycoprotein may be the attachment (G) protein and the fusion (F) protein. Advantageously, the polynucleotide may comprise the nucleotide base sequence of nucleotide 6654 to nucleotide 8294 and the nucleotide base sequence of nucleotide 8943 to nucleotide 10751 of SEQ ID NO: 1 or the polynucleotide encodes the peptide of SEQ ID NO: 7 and SEQ ID NO: 8.

The avipox expression vector may be an attenuated avipox expression vector. In one embodiment, the avipox expression vector may be a canarypox vector. Advantageously, the canarypox vector may be ALVAC. In another embodiment, the avipox expression vector may be a fowlpox vector. Advantageously, the fowlpox vector may be TROVAC.

The invention encompasses a formulation for delivery and expression of a Nipah virus glycoprotein, wherein the formulation may comprise any one of the vectors described above and a pharmaceutically or veterinarily acceptable carrier, vehicle or excipient. In one embodiment, the carrier, vehicle or excipient may facilitate infection and/or improves preservation of the vector. The invention also encompasses method of delivering a Nipah virus glycoprotein to an animal, comprising administering the above formulation of paragraph to an animal. Advantageously, the animal is a pig.

The invention also encompasses a method of eliciting an immune response in an animal that may comprise administering a composition that may comprise any one of the vectors described above in an effective amount for eliciting an immune response. The invention also relates to a method of eliciting an immune response in an animal that may comprise administering a composition that may comprise a cell, wherein the cell may comprise any one of the vectors described above in an effective amount for eliciting an immune response. Advantageously, the animal is a pig.

The invention further encompasses a method of inducing an immunological or protective response in an animal that may comprise administering a composition that may comprise any one of the vectors described above in an effective amount for eliciting an immune response. The invention further relates to a method of inducing an immunological or protective response in an animal that may comprise administering a composition that may comprise a cell, wherein the cell may comprise any one of the vectors described above in an effective amount for eliciting an immune response. Advantageously, the animal is a pig.

The invention also provides for a kit for performing any of the above described methods comprising the any of the above described compositions and optionally, instructions for performing the method.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 1 illustrates Nipah virus nucleotide (FIG. 1A) and amino acid (FIG. 1B) sequences. See, e.g., GenBank Accession No. NC_002728, Chua et al., Science. 2000 May 26; 288(5470):1432-5; Harcourt et al., Virology. 2001 Aug. 15; 287(1):192-201; Chan et al., J Gen Virol. 2001 September; 82(Pt 9):2151-5 and Chua et al., Microbes Infect. 2002 February; 4(2):145-51, the disclosures of which are incorporated by reference in their entireties.

FIG. 2 illustrates the construction of the plasmid pSL-6802-1-4. FIG. 2A is a map of the Nipah virus coding regions. FIG. 2B illustrates the PCR oligonucleotides for the amplification of the Nipah G gene. FIG. 2D is the nucleotide sequence of the left and right arms and the expression cassette with translation of the Nipah virus G gene.

FIG. 3 illustrates the construction of the plasmid pSL-6802-2-5. FIG. 3C is the nucleotide sequence of the left and right arms and the expression cassette with translation of the Nipah virus G gene.

FIG. 4 illustrates the construction of the plasmid pSL-6839-1. FIG. 4A is a map of the Nipah virus and vaccine antigen. FIG. 4B illustrates the PCR oligonucleotides for the amplification of the Nipah F gene. FIG. 4D is the nucleotide sequence of left and right arms and the expression cassette with translation of the Nipah virus F gene.

FIG. 5 illustrates the construction of the plasmid pSL-6851-29. FIG. 5A illustrates the PCR oligonucleotides from the amplification of the Nipah F gene. FIG. 5C is the nucleotide sequence of the left and right arms and the expression cassette with translation of the Nipah virus F gene.

FIG. 7 illustrates a Nipah F immunoblot.

DETAILED DESCRIPTION

Figure 2C:
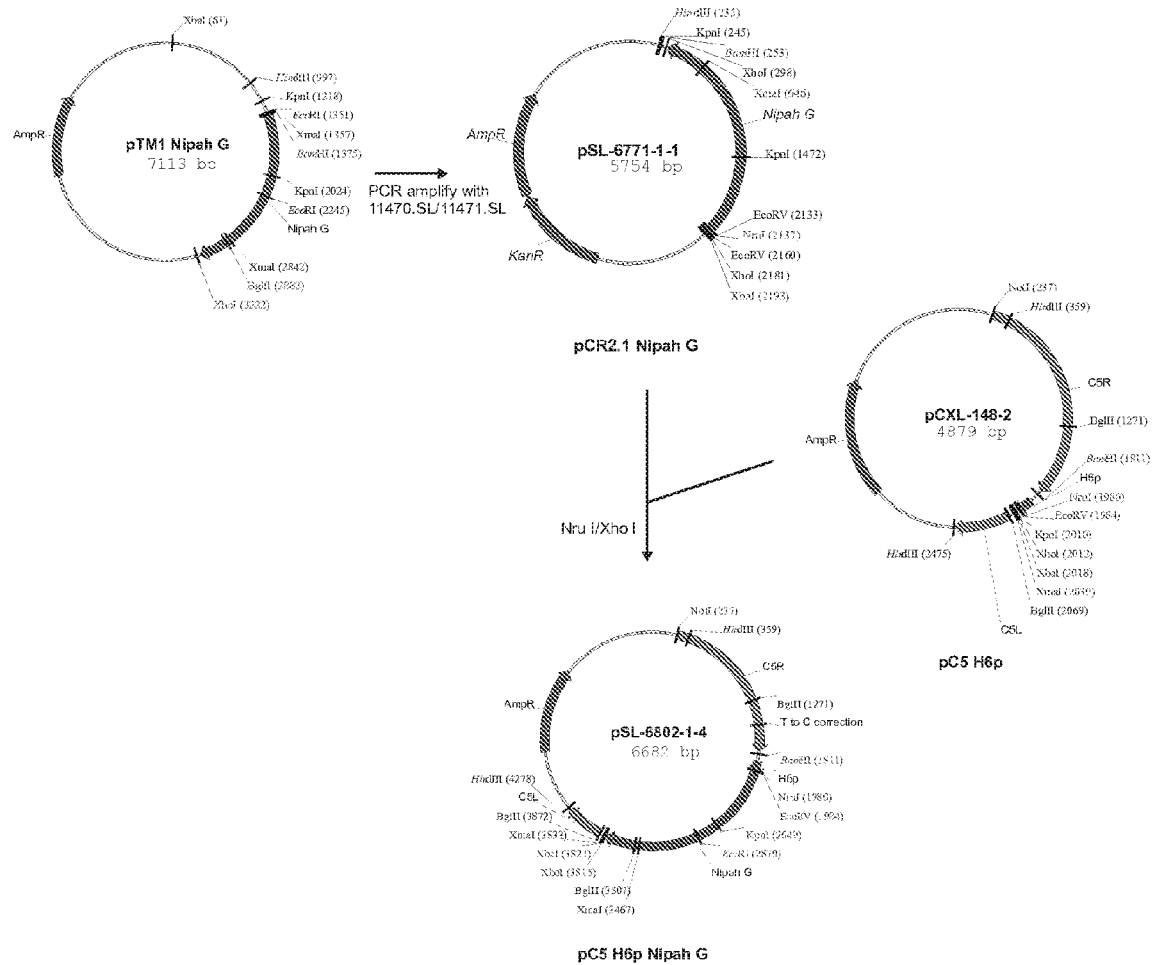
FIG. 2C illustrates the construction of pSL-6802-1-4.

The invention is based, in part, on the development of an efficacious recombinant vaccine against Nipah virus. Therefore, the invention encompasses, in part, a recombinant vaccine against Nipah virus.

In an embodiment of the invention, a Nipah virus gene is encoded into an expression vector. In an advantageous embodiment, the Nipah virus gene encodes a glycoprotein. In a particularly advantageous embodiment, the Nipah virus gene encodes the attachment (G) glycoprotein. In another particularly advantageous embodiment, the Nipah virus gene encodes the fusion (F) glycoprotein.

In an advantageous embodiment, the expression vector is a viral vector. In a particularly advantageous embodiment, the viral vector is an avipox vector. In a more advantageous embodiment, the avipox vector is a canarypox vector or a fowlpox vector. More advantageously, the avipox vector is an attenuated avipox vector. In a particularly advantageous embodiment, the attenuated avipox vector is an attenuated canarypox or an attenuated fowlpox vector. Advantageously, the attenuated canarypox vector is ALVAC and the attenuated fowlpox vector is TROVAC.

In another embodiment, the Nipah virus protein is any Nipah virus protein with a known protein sequence, or a fragment thereof. In an advantageous embodiment, the Nipah virus protein is a glycoprotein. In a particularly advantageous embodiment, the Nipah virus protein is the attachment (G) glycoprotein, advantageously with the sequence of SEQ ID NO: 8. In another particularly advantageous embodiment, the Nipah virus protein is the fusion (F) glycoprotein, advantageously with the sequence of SEQ ID NO: 7.

In a particularly advantageous embodiment of the invention, the recombinant constructs are the ALVAC construct expressing Nipah G designated as vCP2199, the ALVAC construct expressing Nipah F designated as vCP2208, the TROVAC construct expressing Nipah G designated as vFP2200 and the TROVAC construct expressing Nipah F designated as vFP2207.

In another embodiment of the invention, the Nipah virus protein includes, but is not limited to, nucleocapsid protein (advantageously SEQ ID NO.: 2), phosphoprotein (advantageously SEQ ID NO: 3), V protein (advantageously SEQ ID NO: 4), C protein (advantageously SEQ ID NO: 5), matrix protein (advantageously SEQ ID NO: 6) or polymerase (advantageously SEQ ID NO: 9).

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

In another embodiment, the Nipah virus gene is any Nipah virus gene with a known nucleotide sequence. In an advantageous embodiment, the Nipah virus gene encodes a glycoprotein. In a particularly advantageous embodiment, the Nipah virus gene encodes the attachment (G) glycoprotein, advantageously nucleotides 8943 to 10751 of SEQ ID NO: 1. In another particularly advantageous embodiment, the Nipah virus gene encodes the fusion (F) glycoprotein, advantageously nucleotides 6654 to 8294 of SEQ ID NO: 1.

In another embodiment of the invention, the Nipah virus gene may encode a nucleocapsid protein (advantageously nucleotides 113 to 1711 of SEQ ID NO: 1), phosphoprotein (advantageously nucleotides 2406 to 4535 of SEQ ID NO: 1), V protein (advantageously nucleotides 2406 to 3775 of SEQ ID NO: 1), C protein (advantageously nucleotides 2428 to 2928 of SEQ ID NO: 1), matrix protein (advantageously nucleotides 5108 to 6166 of SEQ ID NO: 1) or polymerase (advantageously nucleotides 11259 to 18213 of SEQ ID NO: 1).

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

The invention further comprises a complementary strand to a Nipah virus polynucleotide, advantageously to a Nipah virus glycoprotein polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of Nipah virus polypeptides and functionally equivalent fragments thereof which may enhance, decrease or not significantly affect properties of the polypeptides encoded thereby. These functionally equivalent variants, derivatives, and fragments display the ability to retain the activity of a Nipah virus polypeptide, advantageously a Nipah virus glycoprotein. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

For the purposes of the present invention, sequence identity or homology is determined by comparing the sequences when aligned so as to maximize overlap and identity while minimizing sequence gaps. In particular, sequence identity may be determined using any of a number of mathematical algorithms. A nonlimiting example of a mathematical algorithm used for comparison of two sequences is the algorithm of Karlin & Altschul, Proc. Natl. Acad. Sci. USA 1990; 87:

2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as $(N_{ref}-N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence identity of 75% with the sequence AATCAATC ($N_{ref}=8$; $N_{dif}=2$).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being considered equal to uracil (U) in RNA sequences.

And, without undue experimentation, the skilled artisan can consult with many other programs or references for determining percent homology.

The invention further encompasses a Nipah virus protein, advantageously a Nipah virus glycoprotein, contained in a vector molecule or an expression vector and operably linked to an enhancer and/or a promoter element if necessary. In an advantageous embodiment, the promoter is a cytomegalovirus (CMV) promoter. In another embodiment, the enhancers and/or promoters include various cell or tissue specific promoters, various viral promoters and enhancers and various Nipah virus DNA sequences isogenically specific for each animal species.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, enhancer, ribosome binding sites, polyadenylation sites, transcription terminator, additional transcription units under control of the same or a different promoter, sequences that permit cloning, expression, homologous recombination, and transformation of a host cell, and any such construct as may be desirable to provide embodiments of this invention.

Elements for the expression of a Nipah virus protein, advantageously a Nipah virus glycoprotein, are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses and a transcription terminator for poxviruses. When the polynucleotide encodes a polyprotein fragment, e.g. a Nipah virus protein, advantageously, in the vector, an ATG is placed at 5' of the reading frame and a stop codon is placed at 3'. Other elements for controlling expression may be present, such as enhancer sequences, stabilizing sequences and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6; 312,683; U.S. patent application Ser. No. 920,197, filed Oct. 16, 1986; WO 90/01543; W091/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Felgner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-Nipah virus proteins or fragments thereof, e.g., non-Nipah virus proteins or fragments thereof, cytokines, etc. to be expressed by vector or vectors in, or included in, the compositions of the invention.

The cytokine or cytokines can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The cytokine(s) can be chosen from: interleukin 18 (IL-18), interleukin 12 (IL-12), interleukin 15 (IL-15), MIP-1α (macrophage inflammatory protein 1α; Marshall E. et al., Br. J. Cancer, 1997, 75 (12), 1715-1720), GM-CSF (Granulocyte-Macrophage Colony-Stimulating Factor. Preferably, use is made of cytokines of the species to be vaccinated; that is, advantageously, the cytokine is matched to the target or host species, and, note for example, porcine GM-CSF (S. Inumaru et al. Immunol. Cell Biol. 1995, 73(5), 474-476), canine GM-CSF (example 8 of WO00/77043), feline GM-CSF (example 9 of WO00/77043).

WO00/77210 provides the nucleotide sequence and the amino acid sequence corresponding to equine GM-CSF, the in vitro GM-CSF production and the construction of vectors (e.g., plasmids and viral vectors) permitting in vivo equine GM-CSF expression The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of Nipah virus polynucleotides and, advantageously, the vector contains and expresses a polynucleotide that includes, consists essentially of, or consists of a coding region encoding a Nipah virus protein, advantageously a Nipah virus glycoprotein, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of a Nipah virus glycoprotein, or a fragment thereof.

According to another embodiment, the vector or vectors in the preparation comprise, or consist essentially of, or consist of polynucleotide(s) encoding one or more proteins or fragment(s) thereof of a Nipah virus protein, advantageously a Nipah virus glycoprotein. The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different Nipah virus isolates encoding the same proteins and/or for different proteins, but advantageously for the same proteins. As to preparations containing one or more vectors containing, consisting essentially of or consisting of polynucleotides encoding, and advantageously expressing, advantageously in vivo, a Nipah virus protein, advantageously a Nipah virus glycoprotein, or an epitope thereof, it is advantageous that the expression products be from two, three or more different Nipah virus isolates, advantageously strains. The invention is also directed at mixtures of vectors that contain, consist essentially of, or consist of coding for, and express, different Nipah virus proteins.

In an advantageous embodiment, the vector is a viral vector, advantageously an avipox vector containing Nipah virus gene, advantageously a Nipah virus glycoprotein gene. In a particularly advantageous embodiment, the avipox vector is a canary pox vector, advantageously, an attenuated canarypox vector such as ALVAC. Attenuated canarypox viruses are described in U.S. Pat. No. 5,756,103 (ALVAC) and WO01/05934. In another particularly advantageous embodiment, the avipox vector is a fowlpox vector, advantageously an attenuated fowlpox vector such as TROVAC. Reference is also made to U.S. Pat. No. 5,766,599 which pertains to the attenuated fowlpox strain TROVAC.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494, 807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the atenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766, 599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

Advantageously, for the vaccination of mammals the expression vector is a canarypox or a fowlpox. In this way, there can be expression of the heterologous proteins with limited or no productive replication.

According to one embodiment of the invention, the expression vector is a viral vector, in particular an in vivo expression vector. In an advantageous embodiment, the expression vector is an adenovirus vector, such as a human adenovirus (HAV) or a canine adenovirus (CAV). Advantageously, the adenovirus is a human Ad5 vector, an E1-deleted and/or disrupted adenovirus, an E3-deleted and/or disrupted adenovirus or an E1- and E3-deleted and/or disrupted adenovirus. Optionally, E4 may be deleted and/or disrupted from any of the adenoviruses described above. For example, the human Ad5 vectors described in Yarosh et al. and Lutze-Wallace et al. can be used to express a Nipah virus glycoprotein gene according to the methods of the invention (see, e.g., Yarosh et al., Vaccine. 1996 September; 14(13):1257-64 and Lutze-Wallace et al., Biologicals. 1995 December; 23(4):271-7).

In one embodiment the viral vector is a human adenovirus, in particular a serotype 5 adenovirus, rendered incompetent for replication by a deletion in the E1 region of the viral genome. The deleted adenovirus is propagated in E1-expressing 293 cells or PER cells, in particular PER.C6 (F. Falloux et al Human Gene Therapy 1998, 9, 1909-1917). The human adenovirus can be deleted in the E3 region eventually in combination with a deletion in the E1 region (see, e.g. J. Shriver et al. Nature, 2002, 415, 331-335, F. Graham et al Methods in Molecular Biology Vol 0.7: Gene Transfer and Expression Protocols Edited by E. Murray, The Human Press Inc, 1991, p 109-128; Y. Ilan et al Proc. Natl. Acad. Sci. 1997, 94, 2587-2592; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter). The CMV-IE promoter is advantageously of murine or human origin. The promoter of the elongation factor 1α can also be used. In one particular embodiment a promoter regulated by hypoxia, e.g. the promoter HRE described in K. Boast et al Human Gene Therapy 1999, 13, 2197-2208), can be used. A muscle specific promoter can also be used (X. Li et al Nat. Biotechnol. 1999, 17, 241-245). Strong promoters are also discussed herein in relation to plasmid vectors. A poly(A) sequence and terminator sequence can be inserted downstream the polynucleotide to be expressed, e.g. a bovine growth hormone gene or a rabbit β-globin gene polyadenylation signal.

In another embodiment the viral vector is a canine adenovirus, in particular a CAV-2 (see, e.g. L. Fischer et al. Vaccine, 2002, 20, 3485-3497; U.S. Pat. No. 5,529,780; U.S. Pat. No. 5,688,920; PCT Application No. WO95/14102). For CAV, the insertion sites can be in the E3 region and/or in the region located between the E4 region and the right ITR region (see U.S. Pat. No. 6,090,393; U.S. Pat. No. 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to a yet further embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention.

Each plasmid comprises or contains or consists essentially of, in addition to the polynucleotide encoding a Nipah virus protein, advantageously a Nipah virus glycoprotein, variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell, 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Advantageously, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. Protein production can take place by the transfection of mammalian cells by plasmids, by replication or expression without productive replication of viral vectors on mammal cells or avian cells, or by Baculovirus replication (see, e.g., U.S. Pat. No. 4,745,051; Vialard J. et al., J. Virol., 1990 64 (1), 37-50; Verne A., Virology, 1988, 167, 56-71), e.g. *Autographa californica* Nuclear Polyhedrosis Virus AcNPV, on insect cells (e.g. Sf9 *Spodoptera frugiperda* cells, ATCC CRL 1711; see also U.S. Pat. Nos. 6,228,846, 6,103,526). Mammalian cells which can be used are advantageously hamster cells (e.g. CHO or BHK-21) or monkey cells (e.g. COS or VERO). The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

It is understood to one of skill in the art that conditions for culturing a host cell varies according to the particular gene and that routine experimentation is necessary at times to determine the optimal conditions for culturing a Nipah virus protein, advantageously a Nipah virus glycoprotein, depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of a Nipah virus protein, advantageously a Nipah virus glycoprotein, in a target cell. Determination of the therapeutically effective amount is routine experimentation for one of ordinary skill in the art. In one embodiment, the formulation comprises an expression vector comprising a polynucleotide that expresses a Nipah virus protein, advantageously a Nipah virus glycoprotein, and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

$$R_1\text{—}O\text{—}CH_2\text{—}\underset{OR_1}{CH}\text{—}CH_2\text{—}\underset{CH_3}{\overset{CH_3}{\overset{+}{N}}}\text{—}R_2\text{—}X$$

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

In a specific embodiment, the pharmaceutical composition is directly administered in vivo, and the encoded product is expressed by the vector in the host. The methods of in vivo delivery a vector encoding Nipah virus protein, advantageously a Nipah virus glycoprotein (see, e.g., U.S. Pat. No. 6,423,693; patent publications EP 1052286, EP 1205551, U.S. patent publication 20040057941, WO 9905300 and Draghia-Akli et al., Mol Ther. 2002 December; 6(6):830-6; the disclosures of which are incorporated by reference in their entireties) can be modified to deliver a Nipah virus protein, advantageously a Nipah virus glycoprotein, of the present invention. The in vivo delivery of a vector encoding a Nipah virus protein, advantageously a Nipah virus glycoprotein, described herein can be accomplished by one of ordinary skill in the art given the teachings of the above-mentioned references.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

The immunogenic compositions and vaccines according to the invention may comprise or consist essentially of one or more adjuvants. Particularly suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman D. M. et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, (5) cytokines, (6) aluminum hydroxide or aluminum phosphate or (7) other adjuvants discussed in any document cited and incorporated by reference into the instant application, or (8) any combinations or mixtures thereof.

The oil in water emulsion (3), which is especially appropriate for viral vectors, can be based on:
light liquid paraffin oil (European pharmacopoeia type),
isoprenoid oil such as squalane, squalene,
oil resulting from the oligomerization of alkenes, e.g. isobutene or decene,
esters of acids or alcohols having a straight-chain alkyl group, such as vegetable oils, ethyl oleate, propylene glycol, di(caprylate/caprate), glycerol tri(caprylate/caprate) and propylene glycol dioleate, or
esters of branched, fatty alcohols or acids, especially isostearic acid esters.

The oil is used in combination with emulsifiers to form an emulsion. The emulsifiers may be nonionic surfactants, such as:

esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, polyoxypropylene-polyoxyethylene copolymer blocks, such as Pluronic, e.g., L121.

Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., $$----\overset{R_1}{\underset{COOH}{C}}-(CH_2)_{\overline{x}}\overset{R_2}{\underset{COOH}{C}}-(CH_2)_{\overline{y}}-$$

Nature 186: 778-780, Jun. 4, 1960.

With regard to structure, the acrylic or methacrylic acid polymers and EMA are preferably formed by basic units having the following formula:

in which:

$R_1$ and $R_2$, which can be the same or different, represent H or $CH_3$ x=0 or 1, preferably x=1 y=1 or 2, with x+y=2.

For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

One skilled in the art can determine the effective plasmid dose to be used for each immunization or vaccination protocol and species from this disclosure and the knowledge in the art.

In an advantageous embodiment, the pharmaceutical and/or therapeutic compositions and/or formulations according to the invention are administered by injection, such as, but not limited to, intramuscular (IM), intradermal (ID) or subcutaneous (SC) injection.

Also in connection with such a therapeutic composition, from the disclosure herein and the knowledge in the art, the skilled artisan can determine the number of administrations, the administration route, and the doses to be used for each injection protocol, without any undue experimentation.

In an advantageous embodiment, the recombinant vaccine can be administered to a pig or infected or transfected into cells in an amount of about at least $10^3$ pfu; more preferably about $10^4$ pfu to about $10^{10}$ pfu, e.g., about $10^5$ pfu to about $10^9$ pfu, for instance about $10^6$ pfu to about $10^8$ pfu, per dose, for example, per 2 ml dose. In a particularly advantageous embodiment, the dose is about $10^8$ pfu per dose.

The method includes at least one administration to an animal of an efficient amount of the therapeutic composition according to the invention. The animal may be male, female, pregnant female and newborn. This administration may be notably done by intramuscular (IM), intradermal (ID) or subcutaneous (SC) injection or via intranasal or oral administration. In an advantageous embodiment, the therapeutic composition according to the invention can be administered by a syringe or a needleless apparatus (like, for example Pigjet, Biojector or Vitajet (Bioject, Oreg., USA)). Another approach to administer plasmid is to use electroporation see, e.g. S. Tollefsen et al. Vaccine, 2002, 20, 3370-3378; S. Tollefsen et al. Scand. J. Immunol., 2003, 57, 229-238; S. Babiuk et al., Vaccine, 2002, 20, 3399-3408; PCT Application No. WO99/01158.

The invention relates to the use of the pharmaceutical compositions for vaccinating in animals against Nipah virus infection. The invention relates to the use of the pharmaceutical compositions for vaccinating in animals against Hendra virus infection. In a particular embodiment, the pharmaceutical compositions comprising Nipah F and Nipah G according to the present invention are used for vaccinating in animals against infections caused by Nipah or Hendra viruses. In an advantageous embodiment, the animal is a pig. In other advantageous embodiments, the animal is a cat, dog, horse or human.

The invention also provides for a method for preventing Nipah virus transmission between a first animal and a second animal comprising immunizing or eliciting an immune response in a first animal using any of the methods described herein to prevent disease transmission to the second animal. The invention also provides for a method for preventing Hendra virus transmission from an infected animal to another animal comprising immunizing or eliciting an immune response in a first animal using any of the methods described herein to prevent disease transmission to the second animal. In a particular embodiment, the pharmaceutical compositions comprising Nipah F and Nipah G according to the present invention are used for vaccinating said first animals against infections caused by Nipah or Hendra viruses. In an advantageous embodiment, wherein the first animal is a pig. The second animal is a cat a dog, or a horse, advantageously a human.

The invention also provides for a kit for performing any of the above described methods comprising the any of the above described compositions and optionally, instructions for performing the method.

The invention will now be further described by way of the following non-limiting examples.

EXAMPLES

Example 1

Constructs

Construction of the Plasmid pSL-6802-1-4.

pSL-6802-1-4 comprises the flanking sequences of the C5 locus, H6 vaccinia promoter and G Nipah virus gene to generate VCP2199. The Nipah virus was isolated from human CSF. The Nipah G gene was PCR amplified and inserted into plasmid pTM1, generating pTM1 Nipah G. The purpose was to construct a pC5 H6p Nipah G donor plasmid for generation of an ALVAC canarypox virus recombinant expressing Nipah G. The plasmid name was pC5 H6p Nipah G, pSL-6802-1-4. The plasmid backbone was pCXL-148-2, pC5 H6p comprising the H6 vaccinia promoter, the left and the right arms corresponding to the C5 locus of insertion. The plasmid pCXL-148-2 is derived from the plasmid pNVQH6C5LSP-18 by a single base mutation from T to C in the C5 right arm. The plasmid pNVQH6C5LSP-18 is described in S. Loosmore et al US2005/0031641.

The Nipah G gene was PCR amplified using pTM1 Nipah G as template and primers 11470.SL and 11471.SL (FIG. 2B). The ~1.8 kb PCR fragment was cloned into pCR2.1, generating clone pSL-6771-1-1 (pCR2.1H6p Nipah G), which was confirmed by sequence analysis (FIG. 2C). The ~1.8 kb Nru I-Xho I H6p Nipah G fragment from pSL-6771-1-1 was cloned into pCXL-148-2 (pC5 H6p), generating pSL-6802-1-4 (pC5 H6p Nipah G), which was confirmed by sequence analysis (FIGS. 2C AND 2D).

Construction of the Plasmid pSL-6802-2-5.

pSL-6802-2-5 comprises the flanking sequences of the F8 locus, H6 vaccinia promoter and G Nipah virus gene to generate VFP2200. The Nipah virus was isolated from human CSF. The Nipah G gene was PCR amplified and inserted into plasmid pTM1, generating pTM1 Nipah G. The purpose was to construct a pF8 H6p Nipah G donor plasmid for generation of a fowlpox recombinant expressing Nipah G. The plasmid name was pF8 H6p Nipah G, pSL-6802-2-5. The plasmid backbone was pSL-6427-2-1, pF8 H6p comprising the H6 promoter, the left and the right arms of the F8 locus of insertion. The plasmid pSL-6427-2-1 is derived from the plasmid pSL-5440-5-1 by a single base mutation from C to T in the F8 left arm. The plasmid pSL-5440-5-1 is described in S. Loosmore et al US2005/0031641.

Figures 3A, 3B:
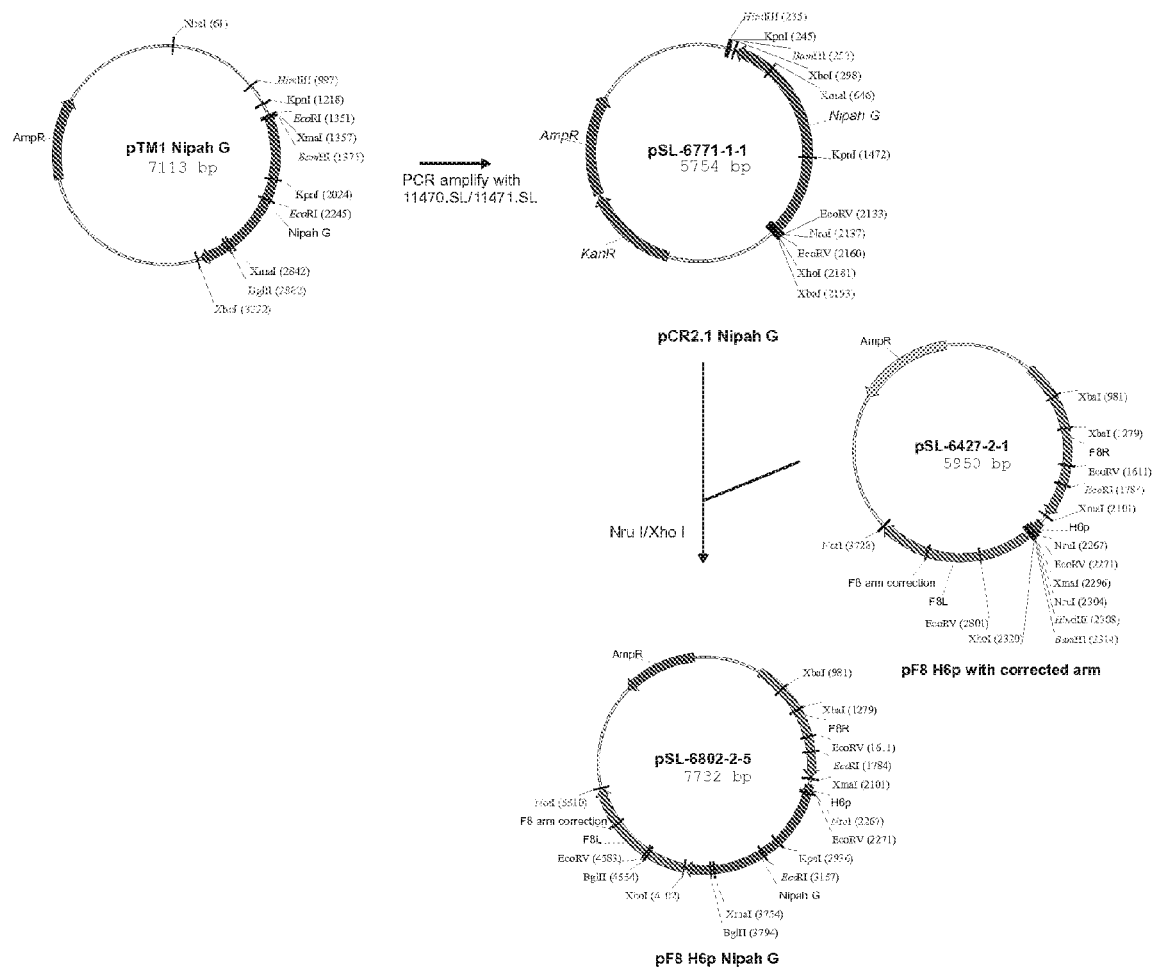
FIG. 3A illustrates the PCR oligonucleotides for the amplification of the Nipah G gene.
FIG. 3B illustrates the construction of pSL-6802-2-5.

The Nipah G gene was PCR amplified using pTM1 Nipah G as template and primers 11470.SL and 11471.SL (FIG. 3A). The ~1.8 kb PCR fragment was cloned into pCR2.1, generating clone pSL-6771-1-1 (pCR2.1H6p Nipah G), which was confirmed by sequence analysis (FIG. 3 B). The ~1.8 kb Nru I-Xho I H6p Nipah G fragment from pSL-6771-1-1 was cloned into pSL-6427-2-1 (pF8 H6p), generating pSL-6802-2-5 (pF8 H6p Nipah G), which was confirmed by sequence analysis (FIGS. 3B AND 3C).

Construction of the Plasmid pSL-6839-1.

pSL-6839-1 comprises the flanking sequences of the F8 locus, H6 vaccinia promoter and F Nipah virus gene to generate VFP2207. The Nipah virus was isolated from human CSF. The Nipah F gene was PCR amplified and inserted into plasmid pTM1, generating pTM1 Nipah F. The purpose was to construct a pF8 H6p Nipah F donor plasmid for generation of a fowlpox recombinant expressing Nipah F. The plasmid name: pF8 H6p Nipah F, pSL-6839-1. The plasmid backbone was pSL-6427-2-1, pF8 H6p comprising the H6 vaccinia promoter, the left and the right arms of the F8 locus of insertion.

Figure 4C:
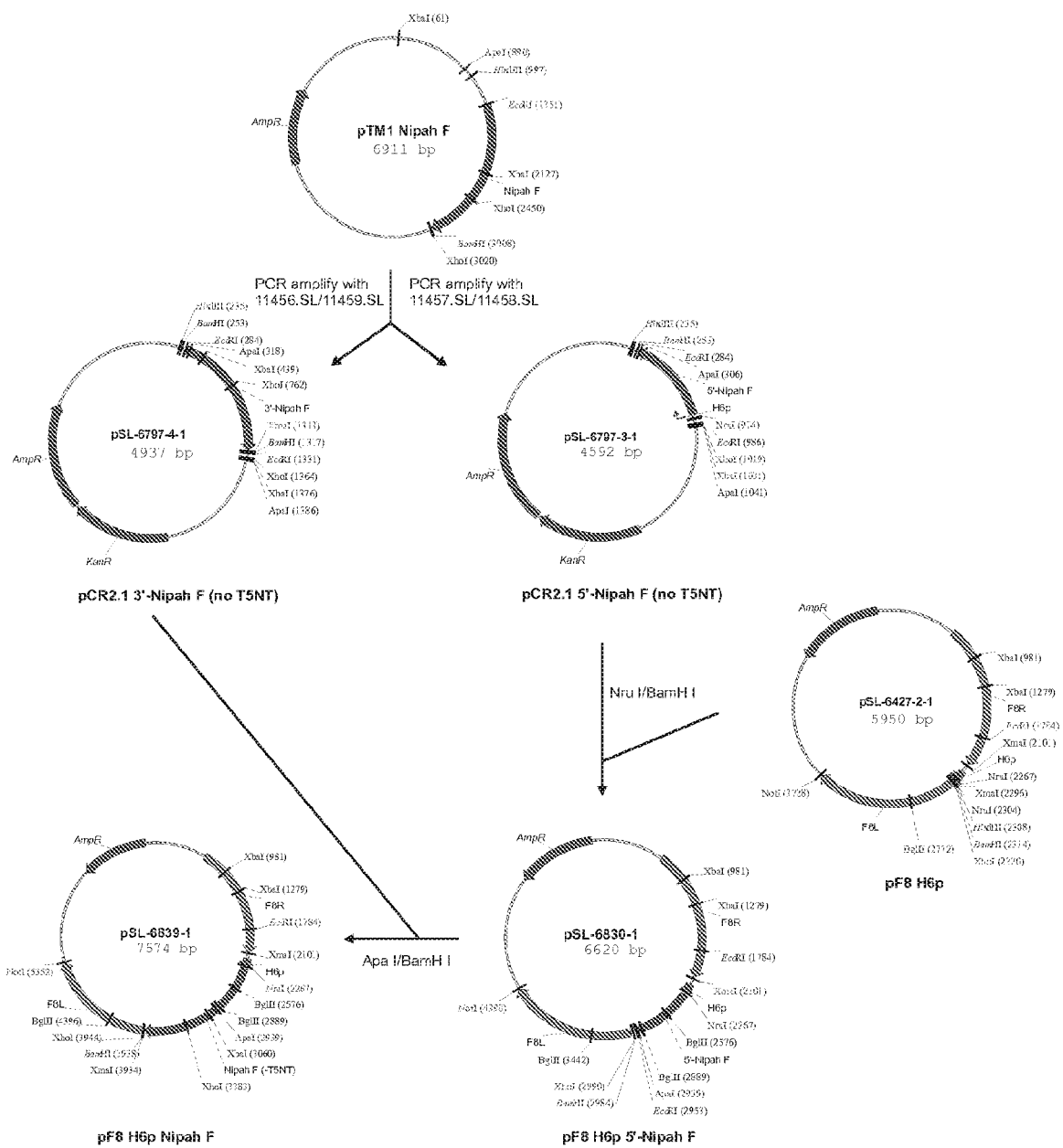
FIG. 4C illustrates the construction of pSL-6839-1.

There was an internal T5NT sequence in Nipah F that was removed by site-directed mutagenesis. A fragment encoding the 3'-end of the H6 promoter and the 5'-end of the Nipah Fgene was PCR amplified using primers 11457.SL and 11458.SL. In the amplified fragment the T5NT sequence was removed and an Apa I site was introduced for cloning purposes (FIG. 4B). The fragment was cloned into pCR2.1, generating pSL-6797-3-1 (pCR2.1H6p 5'-Nipah F, no T5NT), which was confirmed by sequence analysis (FIG. 4C). The 3'-Nipah F fragment was PCR amplified using primers 11456.SL and 11459.SL. In the amplified fragment the T5NT sequence was removed and an Apa I site was introduced for cloning purposes (FIG. 4B). The fragment was cloned into pCR2.1, generating pSL-6797-4-1 (pCR2.1 3'-Nipah F, no T5NT), which was confirmed by sequence analysis (FIG. 4C). The ~0.7 kb Nru I-BamH I H6p 5'-Nipah F fragment from pSL-6797-3-1 was inserted into pSL-6427-2-1 (pF8 H6p), generating pSL-6830-1 (pF8 H6p 5'-Nipah F). The ~1.0 kb Apa I-BamH I 3'-Nipah F fragment from pSL-6797-4-1 was inserted between Apa I and Bam H I of pSL-6830-1, generating pSL-6839-1 (pF8 H6p Nipah F), which was confirmed by sequence analysis (FIGS. 4C and 4D).

Construction of the Plasmid pSL-6851-29.

pSL-6851-29 comprises the flanking sequences of the C5 locus, H6 vaccinia promoter and F Nipah virus gene to generate VCP2208. The Nipah virus was isolated from human CSF. The Nipah F gene was PCR amplified and inserted into plasmid pTM1, generating pTM1 Nipah F. The purpose was to construct a pC5 H6p Nipah F donor plasmid to generate an ALVAC canarypoxvirus recombinant expressing Nipah F. The plasmid name was pSL-6851-29, pC5 H6p Nipah F. The plasmid backbone was pCXL-148-2, pC5 H6p comprising the H6 vaccinia promoter, the left arm and the right arm of the C5 locus of insertion.

Figure 5B:
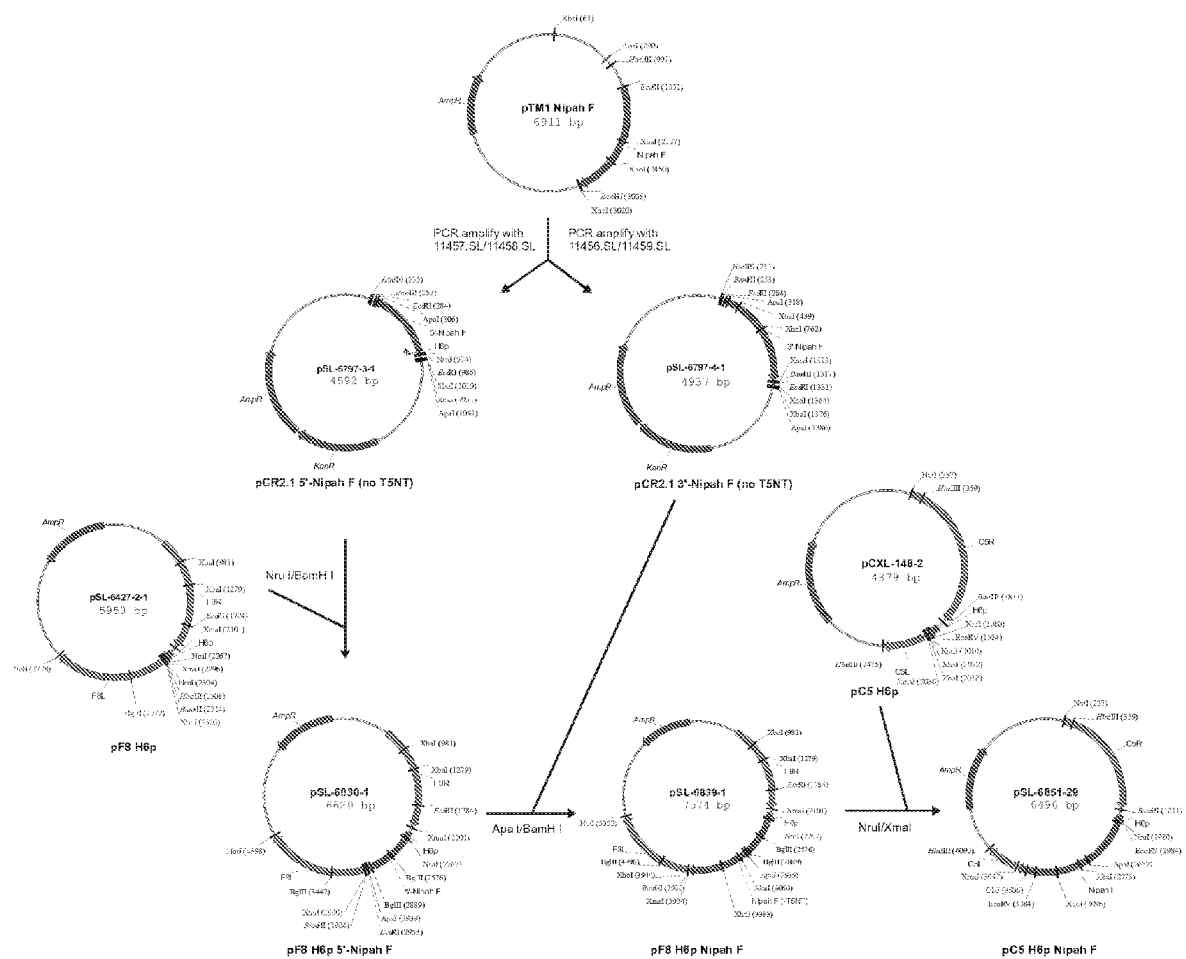
FIG. 5B is a plasmid diagram of pSL-6851-29.

There was an internal T5NT sequence in Nipah F that was removed by site-directed mutagenesis. A fragment encoding the 3'-end of the H6 promoter and the 5'-end of the Nipah F gene was PCR amplified using primers 11457.SL and 11458.SL. In the amplified fragment the T5NT sequence was remove and an Apa I site was introduced for cloning purposes (FIG. 5A). The fragment was cloned into pCR2.1, generating pSL-6797-3-1 (pCR2.1H6p 5'-Nipah F, no T5NT), which was confirmed by sequence analysis (FIG. 5B). The 3'-Nipah F fragment was PCR amplified using primers 11456.SL and 11459.SL. In the amplified fragment the T5NT sequence was removed and an Apa I site was introduced for cloning purposes (FIG. 5A). The fragment was cloned into pCR2.1, generating pSL-6797-4-1 (pCR2.1 3'-Nipah F, no T5NT), which was confirmed by sequence analysis (FIG. 5B). The ~0.7 kb Nru I-BamH I H6p 5'-Nipah F fragment from pSL-6797-3-1 was inserted into pSL-6427-2-1 (pF8 H6p), generating pSL-6830-1 (pF8 H6p 5'-Nipah F). The ~1.0 kb Apa I-BamH I 3'-Nipah F fragment from pSL-6797-4-1 was inserted between Apa I and Bam H I of pSL-6830-1, generating pSL-6839-1 (pF8 H6p Nipah F), which was confirmed by sequence analysis. The 1.7 kb Nru I-Xma I H6p Nipah F fragment from pSL-6839-1 was inserted into pCXL-148-2 (pC5 H6p) to generate pSL-6851-29 (pC5 H6p Nipah F), which was confirmed by sequence analysis (FIGS. 5B and 5C).

Construction of the Fowlpox-Recombinant Expressing Nipah F, vFP2207.

The gene was Nipah F. The donor plasmid was pSL-6839-1. The insertion site was the F8 locus of Fowl pox. The promoters was the vaccinia virus H6 promoter. The cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL-6839-1 (20 ug). The transfected cells were subsequently infected with Fowlpox as rescue virus at MOI of 10. After 48 h, the transfected-infected cells were harvested, sonicated and used for recombinant virus screening. Recombinant plaques were screened based on the plaque lift hybridization method using a Nipah F specific probe, which was labeled with horseradish peroxidase. After four sequential rounds of plaque purification, the recombinant designated as vFP2207 was generated and confirmed by hybridization as 100% positive for the insert and 100% negative for the F8 ORF.

Construction of the Canarypox Recombinant Expressing Nipah G, vCP2199.

The gene was Nipah G. The donor plasmid was pSL-6802-1-4. The insertion site was C5. The promoter was the H6 promoter. The cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL-6802-1-4 (15 ug) The transfected cells were subsequently infected with ALVAC as rescue virus at MOI of 10 After 24 h, the transfected-infected cells were harvested, sonicated and used for recombinant virus screening. Recombinant plaques were screened based on the plaque lift hybridization method using Nipah G-specific probe which was labeled with horse radish peroxidase After five sequential rounds of plaque purification, the recombinant designated as vCP2199 was generated and confirmed by hybridization as 100% positive for the Nipah G insert and 100% negative for the C5 ORF.

Construction of the Fowlpox Recombinant Expressing, Nipah G, vFP2200.

The genes was Nipah G. The donor plasmid was pSL6802-2-5. The insertion site was F8. The promoter was the H6 promoter. The cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL6802-2-5 (15 ug). The transfected cells were subsequently infected with fowlpox as rescue virus at MOI of 8. After 48 h, the transfected-infected cells were harvested, sonicated and used for recombinant virus screening. Recombinant plaques were screened based on the plaque lift hybridization method using Nipah G-specific probe which was labeled with horse radish peroxidase. After four sequential rounds of plaque purification, the recombinant designated as vFP2200—was generated They were confirmed by hybridization as 100% positive for the Nipah G insert and 100% negative for the F8 ORF.

Construction of the Canarypox Recombinant Expressing Nipah F, vCP2208.

The gene was Nipah F. The donor plasmid was pSL6851.29 (pC5 H6p Nipha F). The insertion site was C5. The promoter was the vaccinia H6 promoter. Cells for in vitro recombination were primary chicken embryo fibroblast cells (1° CEF) grown in 10% FBS, DMEM.

The in vitro recombination was performed by transfection of 1° CEF cells with Not I-linearized donor plasmid pSL6851.29 (10 ug). The transfected cells were subsequently infected with the ALVAC as rescue virus at MOI of 10. After 24 h, the transfected-infected cells were harvested, sonicated and used for recombinant virus screening. Recombinant plaques were screened based on the plaque lift hybridization method using a Nipah F-specific probe which was labeled with horse radish peroxidase. After four sequential rounds of plaque purification, the recombinant designated as vCP2208 was generated and confirmed by hybridization as 100% positive for the Nipah F insert and 100% negative for the C5 ORF.

Example 2

Expression

Figure 6:
FIG. 6 illustrates a Nipah G western blot. Lane 1 was the ALVAC supt, lane 2 was the vCP2199 supt (ALVAC Nipah G), lane 3 was the vCP2199 supt (ALVAC Nipah G), lane 4 was the fowlpox supt, lane 5 was the vFP2200 supt (fowlpox Nipah G), lane 6 was the vFP2200 supt (fowlpox Nipah G), lane 7 was the markers (177.6, 113.9, 81.2, 60.7, 47.4, 36.1, 25.3, 19.0, 14.7, 6.1 kDa, lane 8 was the ALVAC pellet, lane 9 was vCP2199 pellet, lane 10 was the vCP2199 pellet, lane 11 was the fowlpox pellet, lane 12 was the vFP2200 pellet and lane 13 was the vFP2200 pellet.

Western blot of Fowlpox Nipah G, vFP2200 (FIG. 6).

Primary CEF cells were infected with vCP2199 (ALVAC C5 H6p Nipah G) and vFP2200 (Fowlpox F8 H6p Nipah G) at MOI of 10 and incubated at 37° C. for 24 hrs. The cells and culture supernatant were then harvested. Sample proteins were separated on a 10% SDS-PAGE gel, transferred to Immobilon nylon membrane. The guinea pig antiserum and chemiluminescence system were used. Nipah G was expressed in cell pellets for vCP2199 and vFP2200. It did not show up in supernatant.

Figure 7A:
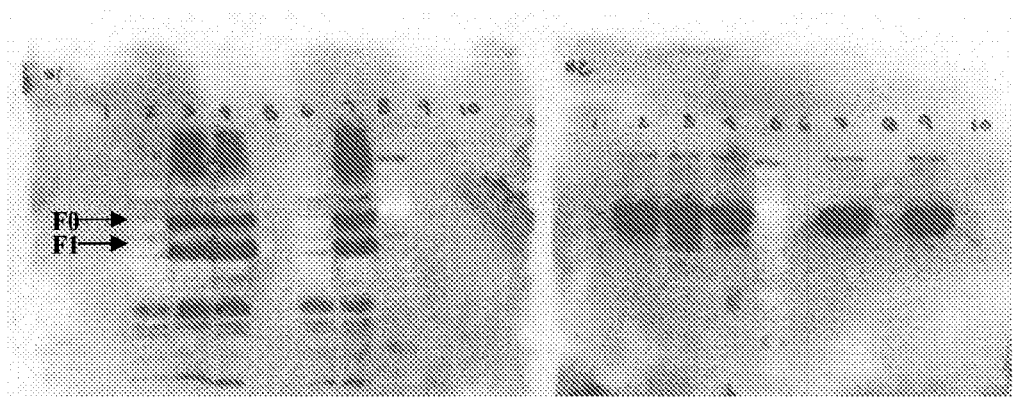
FIG. 7A was blotted with guinea pig antiserum.
Figure 7B:
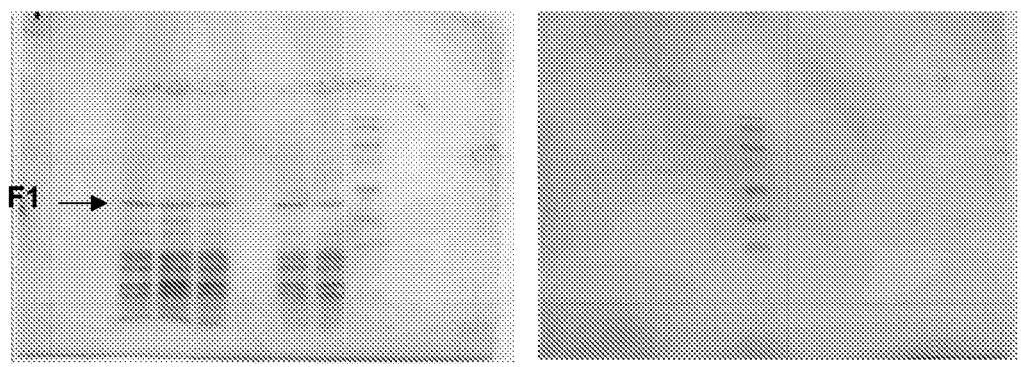
FIG. 7B was blotted with porcine antiserum. Gel #1 was the Nipah F recombinants (pellets only). Lane 1 was a space, lane 2 was Fowlpox, lane 3 was vFP2207, lane 4 was vFP2207, lane 5 was a space, lane 6 was ALVAC, lane 7 was cvCP2208, lane 8 was marker 170, 130, 100, 72, 55, 40, 33, 24 kDa and lanes 9 and 10 were spaces. Gel #2 was the Nipah F recombinants (supernant only). Lane 1 was a space, lane 2 was Fowlpox, lane 3 was vFP2207, lane 4 was vFP2207, lane 5 was Marker 170, 130, 100, 72, 55, 40, 33, 24 kDa, lane 6 was a space, lane 7 was ALVAC, lane 8 was a space, lane 9 was vCP2208 and lane 10 was a space.

Western Blot of ALVAC Nipah F, vCP2208 (FIGS. 7A and 7B).

Primary CEF cells were infected with vCP2208. (ALVAC C5 H6p Nipah F) s at MOI of 10 and incubated for 24 hours. The supernatant was harvested and clarified. The cells were harvested and suspended in water to lyse. Lysate and supernatant were separated by 10% SDS-PAGE. The protein was transferred to nylon membrane and blocked with Western blocking buffer. Using guinea pig antiserum and chemiluminescence developing system it was shown expressions of F protein from vCP2208 (ALVAC C5 H6p Nipah F). Using porcine antiserum and horseradish peroxidase system it was shown also expression of the F protein from vCP2208 but with a lower intensity.

Western blot of ALVAC Nipah G, vCP2199 (FIG. 6).

Primary CEF cells were infected with vCP2199 (ALVAC C5 H6p Nipah G) and vFP2200 (Fowlpox F8 H6p Nipah G) at MOI of 10 and incubated at 37° C. for 24 hrs. The cells and culture supernatant were then harvested. Sample proteins were separated on a 10% SDS-PAGE gel, transferred to Immobilon nylon membrane. The guinea pig antiserum and chemiluminescence system were used. Nipah G was expressed in cell pellets for vCP2199 and vFP2200. It did not show up in supernatant.

Western blot of Fowlpox Nipah F, vFP2207 (FIGS. 7A and 7B).

Primary CEF cells were infected with vFP2207 (Fowlpox F8 H6p Nipah F) at MOI of 10 and incubated for 24 hours. The supernatant was harvested and clarified. The cells were harvested and suspended in water to lyse. Lysate and supernatant were separated by 10% SDS-PAGE. The protein was transferred to nylon membrane and blocked with Western blocking buffer. Using guinea pig antiserum and chemiluminescence developing system shown expressions of F protein from vFP2207 (Fowlpox F8 H6p Nipah F). Using porcine antiserum and horseradish peroxidase system it was shown also expression of the F protein from vFP2207 but with a lower intensity.

Example 3

Serology and Protection

Sixteen pigs were allocated randomly into four groups. Group F animals were immunized with $10^8$ pfu/dose of VCP2208 expressing Nipah virus F protein. Group G animals were immunized with $10^8$ pfu/dose of VCP2199 expressing Nipah virus G protein. Group G+F animals were immunized with a mixture containing $10^8$ pfu/dose of VCP2199 and $10^8$ pfu/dose of VCP 2208 expressing respectively Nipah virus G and F proteins. Group challenge animals were unvaccinated control animals.

The pigs were injected by intramuscular route on Day 0 and Day 14. The pigs were challenged by intranasal inoculation of $2.5 \times 10^5$ pfu of Nipah virus on Day 28. Seven days post challenge the presence of virus is identified by RT-PCR or virus isolation in various organs and in nasal swabs. Blood samples are collected on D0, D7, D14, D21, D28, D29, D30, D31, D32, D34, and D35 after the first injection and antibody titers are measured by IgG indirect ELISA or seroneutralisation assay. The neutralizing antibodies were determined in microtiter plaque reduction neutralization assay (mPRNT) as previously described (H. Weingartl et al. Can. J. Vet. Rrs. 2003, 67, 128-132), using Vero V-76 cells and 1% carboxymethylcellulose overlay. Wells with 90% plaque reduction were considered positive for presence of Nipah virus neutralizing antibodies. ELISA and neutralizing titers (NT) data are presented in Table 1. The combined Nipah F/G induced the highest neutralizing titer prior to challenge, followed closely by G vaccine. The F vaccine induced lower neutralizing antibodies.

Virus Plaque Assay:

Virus plaque assay was performed in 12-well plates (Costar, Corning, N.Y.) with either Vero 76 or PT-K75 confluent monolayers. Virus inoculum (400 µl/well) was incubated on cells for 1 h at 33° C., 5% $CO_2$, and then replaced with 2 ml of 2% carboxymethyl-cellulose, sodium salt, medium viscosity/DMEM (Sigma Chemical, St. Louis, Mo.)/2% FBS overlay, and incubated at 33° C., 5% $CO_2$. The cells were fixed after 5 days with 4% formaldehyde and stained with 0.5% of crystal violet/80% methanol/PBS. Real time RT-PCR was performed on serum/plasma and PMBC samples only, according to V. Guillaume et al J. Virol. Method. 2004, 120, 229-237, using a SmartCycler (Cepheid), Quantitech kit (Qiagen), and primers and probe (Applied Biosystems International) located within the N gene. Forward primer GCA CTT GAT GTG ATT AGA (SEQ ID NO: 29) and reverse primer GGC AGT GTC GGG AGC TGT AA (SEQ ID NO: 30), located within the N gene, yielding a 395 by amplicon. The real time RT-PCR was standardized using Nipah virus N gene cloned in to the pSHAME2a plasmid with sensitivity of 300 copies/reaction in 100 µl sample. Samples becoming positive at 35 cycles were considered negative.

Nipah virus was isolated at very low titer in trigeminal ganglion of pig #33 (one plaque), #35 (one plaque) and #36. In control animals Nipah virus could be reisolated from a number of tissues up to 10e3 pfu/ml: pig #39 positive in turbinates, trachea, olfactory bulbs, trigeminal ganglion, bronchiolar lymph node and submandibular lymph nodes (LN); pig #40 positive in turbinates, trachea, olfactory bulb, meninges, trigeminal ganglion, bronchiolar LN, submandibular LN and brain. The RT-PCR results are provided in Tables 2 and 3. The figures are threshold cycle numbers. No RNA is detected in immunized pigs plasma, serum or the PBMC of the pigs immunized with F/G vaccine.

These results show a clear protection with recombinant expressing either Nipah virus F or G proteins and a full protection with the combination of Nipah virus F+G proteins.

Example 4

Cross-Neutralization

Eighteen pigs were allocated randomly into four groups. Group F of 4 animals were immunized with $10^8$ pfu/dose of vCP2208 expressing Nipah virus F protein. Group G of 4 animals were immunized with $10^8$ pfu/dose of vCP2199 expressing Nipah virus G protein. Group G+F of 4 animals were immunized with a mixture containing $10^8$ pfu/dose of vCP2199 and $10^8$ pfu/dose of vCP 2208 expressing respectively Nipah virus G and F proteins. As unvaccinated control group, 6 animals were naturally infected with Nipah viruses and carried up to 28 days post infection (dpi). This group was named "long term infection".

The pigs of groups F, G and G+F were injected by intramuscular route on Day 0 and Day 14. Blood samples are collected on D27 after the vaccination (dpv or day post vaccination) and antibody titers are measured by seroneutralisation assay. The neutralizing antibodies were determined in microtiter plaque reduction neutralization assay (mPRNT) as previously described (H. Weingartl et al. Can. J. Vet. Rrs. 2003, 67, 128-132), using Vero V-76 cells seeded in 96 well plate at $1.2 \times 10^5$ cells/$cm^2$ (40,000 cells per well) incubated in 5% $CO_2$ 37° C., with DMEM medium supplemented with 10% FBS.

100 µL of serial two-fold sera dilutions (1/10-1/1280) was incubated for 1 hour 5% $CO_2$ 37° C. with 100 µL of either Hendra or Nipah virus adjusted to contain 1000 PFU per 100 µL. All the dilutions were made in DMEM.

After incubation 100 µL of the above mixture was transferred onto V76 cells monolayer. The plate with inoculum was incubated for 1 hour at 5% $CO_2$ 37° C.

After 1 hour inoculum was removed and replaced with 100 µL of 2% carboxymethylcellulose solution in DMEM supplemented with 2% FBS. The plates were incubated at 5% $CO_2$ 37° C. for 72 hours.

Back titration for the Nipah virus gave the result that the working dilution was 500 PFU/well, and for Hendra virus: 625 PFU/well.

Note: Sera from the pigs vaccinated with F protein were diluted two-fold from 1/50 to 1/2400.

Wells with 90% plaque reduction were considered positive for presence of Nipah virus neutralizing antibodies or for presence of Hendra virus neutralizing antibodies. Neutralizing titers data are presented in Table 4. The combined Nipah F/G induced a synergistic effect for the production of antibodies against the Hendra virus, which are not produced during a natural infection with Nipah viruses (see results of long term infection group). The G vaccine or the F vaccine alone induced no or lower neutralizing antibodies against Hendra viruses than the F+G vaccine. There is not correlation between the levels of antibody titer against Nipah viruses and those against Hendra viruses.

TABLE 1

| | | ELISA and NT Data | | | | | | | | | | | | | | | |
|---|---|---|---|---|---|---|---|---|---|---|---|---|---|---|---|---|---|
| | | N4 F | | | | N4 G | | | | N4 Challenge | | | | N4 G + F | | | |
| | Pig # | 31 | 32 | 33 | 34 | 35 | 36 | 37 | 38 | 39 | 40 | 41 | 42 | 43 | 44 | 45 | 46 |
| ELISA Data | | | | | | | | | | | | | | | | | |
| pre vac | | 0 | 0 | 0 | 0 | 0 | 0 | 0 | 0 | | | | | 0 | 0 | 0 | 0 |
| 7 dpv | | 0 | 0 | 0 | 0 | | | | | | | | | 0 | 0 | 0 | 0 |
| 14 dpv | Boost | 0 | 0 | 0 | 0 | 0 | 0 | 0 | 0 | | | | | 100 | 0 | 0 | 100 |
| 21 dpv | | 0 | 0 | 0 | 0 | 1600 | 3200 | 3200 | 1600 | | | | | 1600 | 6400 | 1600 | 6400 |
| | Pre chal | 0 | 0 | 0 | 0 | 1600 | 3200 | 3200 | 3200 | 0 | 100? | 0 | 0 | 800 | 3200 | 800 | 3200 |
| 1 dpi | | 0 | 100 | | | 400 | | | | 100 | 0 | | | 800 | 800 | | |
| 2 dpi | | | | 100 | 0 | | | 1600 | 800 | | | 0 | 100 | | | 400 | 800 |
| 3 dpi | | 0 | 0 | | | 800 | 800 | | | 0 | 0 | | | 800 | 1600 | | |
| 4 dpi | | | | 0 | 0 | | | 1600 | 3200 | | | 0 | 0 | | | 200 | 800 |
| 5 dpi | | | | | | | | | | | | | | | | | |
| 6 dpi | | 0 | 0 | | | 400 | 400 | | | 100 | 100 | | | | 1600 | | 800 |
| 7 dpi | | | | 0 | 0 | | | 1600 | 800 | | | 200 | 400 | 800 | | 200 | |
| 8 dpi | | | | | | | | | | | | | | | | | |
| NT Data | | | | | | | | | | | | | | | | | |
| pre vac | | <20 | <20 | <20 | <20 | <20 | <20 | <20 | <20 | | | | | <20 | <20 | <20 | <20 |
| 7 dpv | | <20 | <20 | <20 | 20 | x | x | x | x | | | | | 20 | 20 | <20 | <20 |
| 14 dpv | Boost | x | x | x | x | 40 | 30 | 40 | <20 | | | | | 40 | 20 | 40 | 40 |
| 21 dpv | | 80 | <160 | 80 | <320 | 1280 | <320 | 1280 | 1280 | | | | | 1280 | 1280 | 320 | 640 |
| | Pre chal | 80 | 80 | 80 | 160 | 640 | 1280 | 640 | 320 | <20 | <20 | <20 | <20 | 1280 | 2560 | 640 | 1280 |
| 1 dpi | | 80 | 80 | | | 640 | 640 | | | <20 | <20 | | | 640 | 2560 | | |
| 2 dpi | | | | 160 | 160 | | | <640 | 160 | | | <20 | <20 | | | 640 | 1280 |
| 3 dpi | | 80 | 80 | | | 320 | 640 | | | <20 | <20 | | | 320 | 640 | | |
| 4 dpi | | | | 80 | 160 | | | 640 | 320 | | | <20 | <20 | | | 320 | 640 |
| 5 dpi | | | | | | | | | | | | | | | | | |
| 6 dpi | | 20 | 40 | | | 320 | 1280 | | | <20 | <20 | | | | 1280 | | 320 |
| 7 dpi | | | | 20 | 80 | | | 640 | 640 | | | <20 | <20 | 1280 | | 1280 | |
| 8 dpi | | | | | | | | | | | | | | | | | |

(dpv = days post vaccination, dpi = days post infection)

TABLE 2

| | Real time RT-PCR in tissues | | | | | | | | | | | | | | |
|---|---|---|---|---|---|---|---|---|---|---|---|---|---|---|---|
| | sample | | | | | | | | | | | | | | |
| | 31 | 32 | 33 F | 34 | 35 | 36 | 37 G | 38 | 39 RT | 40 RT challenge | 41 RT | 42 RT | 43 | 44 F + G | 45 | 46 |
| hind brain | — | — | — | — | — | — | — | — | 28 31 | 24 24.8 | 24.3 24.8 | — | — | — | — | — |
| CSF | — | — | — | — | — | — | — | — | nd | 0 | 29.3 29.6 | 30.5 28.9 | — | — | — | — |
| olfactory bulb | —/ 32 | — | — | — | 30 | — | — | — | 25 | 18 19 | 23.5 23.8 | nd | — | — | — | — |
| trigeminal ganglion | — | — | 28.5 | 30 | 32 | — | — | — | 26 | 18 19 | 25.1 25 | 18.8 23.8 | — | — | — | — |
| turbinate | — | — | — | — | — | — | — | — | 19 20 | 18 | 27.6 30.8 | 25.6 29 | — | — | — | — |
| trachea | — | — | — | 29 | — | — | 31 | 31 | 18 19.7 | 19 | 29 28.2 | 0- | — | — | — | — |
| lung | — | — | — | — | — | — | — | — | 0 | — | — | — | — | — | — | — |
| submandibular LN | — | — | — | — | — | — | — | — | 23 21.5 | 23 | -? nd saliv? | — | — | — | — | — |
| bronchiolar LN | — | — | — | — | — | — | — | — | 22.5 21.7 | 24 | — | — | — | — | — | — |
| spleen | — | — | — | — | — | — | — | — | 0 | — | — | — | — | — | — | — |

(CSF = cerebrospinal fluid, LN = lymph node)

TABLE 3

Real time RT-PCR, pharyngeal swabs

| | sample | | | | | | | | | | | | | | | |
|---|---|---|---|---|---|---|---|---|---|---|---|---|---|---|---|---|
| | 31 | 32 F | 33 | 34 | 35 | 36 G | 37 | 38 | 39 RT | 40 RT | 41 RT challenge | 42 RT | 43 | 44 F + G | 45 | 46 |
| pharyngeal swab 1 dpi | — | — | | | | — | — | | — | — | | | | — | — | |
| pharyngeal swab 2 dpi | | | — | — | | | | — | — | | | | — | | — | — |
| pharyngeal swab 3 dpi | — | 28 27.5 | | | | | | | 31.3 31.8 | 29.4 27.7 | | | — | — | | |
| pharyngeal swab 4 dpi | | | — | — | | — | — | | — | — | | | | | — | — |
| pharyngeal swab 6 dpi | — | — | | | | | | — | 25.3 27.3 | 28.5 28.3 | | | — | — | | |
| pharyngeal swab 7 dpi | | | — | — | | — | — | | | | 27.3 24.8 | 24.6 25.8 | | | — | — |
| | 31 | 32 | 33 | 34 | 35 | 36 | 37 | 38 | 39 | 40 | 41 | 42 | 43 | 44 | 45 | 46 |

TABLE 4

Neutralization titers

| Groups | Long term infection | | | | | | F vaccinated | | | | G vaccinated | | | | G + F vaccinated | | | |
|---|---|---|---|---|---|---|---|---|---|---|---|---|---|---|---|---|---|---|
| dpi | 23 | 11 | 29 | 27 | 24 | 28 | 0 | 0 | 0 | 0 | 0 | 0 | 0 | 0 | 0 | 0 | 0 | 0 |
| dpv | — | — | — | — | — | — | 27 | 27 | 27 | 27 | 27 | 27 | 27 | 27 | 27 | 27 | 27 | 27 |
| Nipah virus titration | 320 | 320 | 640 | 640 | 640 | 1280 | 200 | 200 | 200 | 400 | 640 | 1280 | 2560 | 1280 | 1280 | 1280 | 640 | 1280 |
| Hendra virus titration | 0 | 0 | 0 | 0 | 0 | 0 | 0 | 0 | 20 | 0 | 0 | 20 | 0 | 0 | 80 | 80 | 80 | 80 |

The invention is further described by the following numbered paragraphs:

1. An avipox expression vector comprising a polynucleotide that encodes a Nipah virus glycoprotein.
2. The avipox expression vector of paragraph 1 wherein the Nipah virus glycoprotein is the attachment (G) protein.
3. The avipox expression vector of paragraph 1 wherein the Nipah virus glycoprotein is the fusion (F) protein.
4. The avipox expression vector of paragraph 1 wherein the Nipah virus glycoprotein is the attachment (G) protein and the fusion (F) protein.
5. The avipox expression vector of paragraph 2 wherein the polynucleotide comprises the nucleotide base sequence of nucleotide 8943 to nucleotide 10751 of SEQ ID NO: 1.
6. The avipox expression vector of paragraph 3 wherein the polynucleotide comprises the nucleotide base sequence of nucleotide 6654 to nucleotide 8294 of SEQ ID NO: 1.
7. The avipox expression vector of paragraph 4 wherein the polynucleotide encodes the peptide of SEQ ID NO: 8.
8. The avipox expression vector of paragraph 2 wherein the polynucleotide encodes the peptide of SEQ ID NO: 7.
9. The avipox expression vector of paragraph 3 wherein the polynucleotide encodes the peptide of SEQ ID NO: 7 and the peptide of SEQ ID NO: 8.
10. The avipox expression vector of paragraph 5 wherein the polynucleotide comprises the nucleotide base sequence of nucleotide 6654 to nucleotide 10751 of SEQ ID NO: 1.
11. The avipox expression vector of paragraphs 1 to 10 wherein the avipox expression vector is an attenuated avipox expression vector.
12. The avipox expression vector of paragraphs 1 to 11 wherein the avipox expression vector is a canarypox vector.
13. The canarypox vector of paragraph 12 wherein the canarypox vector is ALVAC.
14. The avipox expression vector of paragraphs 1 to 11 wherein the avipox expression vector is a fowlpox vector.
15. The fowlpox vector of paragraph 14 wherein the fowlpox vector is TROVAC.
16. An expression vector wherein the expression vector is vCP2199.
17. An expression vector wherein the expression vector is vCP2208.
18. An expression vector wherein the expression vector is vFP2200.
19. An expression vector wherein the expression vector is vVP2207.
20. A formulation for delivery and expression of a Nipah virus glycoprotein, wherein the formulation comprises the vector of any one of paragraphs 1 to 19 and a pharmaceutically or veterinarily acceptable carrier, vehicle or excipient.
21. The formulation of paragraph 20, wherein the carrier, vehicle or excipient facilitates transfection and/or improves preservation of the vector.
22. A method of delivering a Nipah virus glycoprotein to an animal, comprising administering the formulation of paragraph 21 or 22 to the animal.
23. The method of paragraph 22 wherein the animal is a pig.
24. A method of eliciting an immune response in an animal comprising administering a composition comprising the vector of any one of paragraphs 1 to 19 in an effective amount for eliciting an immune response.
25. A method of eliciting an immune response in an animal comprising administering a composition comprising a cell, wherein the cell comprises the vector of any one of paragraphs 1 to 19 in an effective amount for eliciting an immune response.

26. A method of inducing an immunological or protective response in an animal comprising administering a composition comprising the vector of any one of paragraphs 1 to 19 in an effective amount for eliciting an immune response.

27. A method of inducing an immunological or protective response in an animal comprising administering a composition comprising a cell, wherein the cell comprises the vector of any one of paragraphs 1 to 19 in an effective amount for eliciting an immune response.

28. The method of any one of paragraphs 24 to 27 wherein the animal is a pig.

29. A method for preventing Nipah virus transmission between a first animal and a second animal comprising the method of any one of paragraphs 24 to 27 wherein the animal of any one of paragraphs 24 to 27 is the first animal.

30. The method of paragraph 29 wherein the first animal is a pig.

31. The method of paragraph 29 or 30 wherein the second animal is a human.

32. The method of paragraph 29 or 30 wherein the second animal is a cat or a dog.

33. A kit for performing the method of any one of paragraphs 22 to 32 comprising the vectors of any one of paragraphs 1 to 19 or the formulations of any one of paragraphs 20 or 21 and instructions for performing the method.

Having thus described in detail advantageous embodiments of the present invention, it is to be understood that the invention defined by the above paragraphs is not to be limited to particular details set forth in the above description as many apparent variations thereof are possible without departing from the spirit or scope of the present invention.

What is claimed is:

1. A canarypox expression vector comprising a polynucleotide having the sequence as set forth in SEQ ID NO:15 or SEQ ID NO:16.

2. A fowlpox expression vector comprising a polynucleotide having the sequence as set forth in SEQ ID NO:18 or SEQ ID NO:19.

3. A formulation comprising the expression vector of claim 1 or 2 and a pharmaceutically or veterinarily acceptable carrier, vehicle or excipient.

4. The formulation of claim 3, wherein the formulation further comprises an avipox expression vector comprising a polynucleotide having the sequence as set forth in SEQ ID NO:24, 25, 27 or 28.

5. A method of inducing an immunological or protective response in an animal comprising administering the avipox expression vector of claim 1 or 2.

6. The method of claim 5, wherein the animal is selected from the group consisting of pig, cat, dog, and horse.

* * * * *